(12) United States Patent
Choi

(10) Patent No.: US 11,243,206 B2
(45) Date of Patent: Feb. 8, 2022

(54) GENDER-SPECIFIC MARKERS FOR DIAGNOSING PROGNOSIS AND DETERMINING TREATMENT STRATEGY FOR RENAL CANCER PATIENTS

(71) Applicant: THE CATHOLIC UNIVERSITY OF KOREA INDUSTRY-ACADEMIC COOPERATION FOUNDATION, Seoul (KR)

(72) Inventor: Yeong Jin Choi, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 593 days.

(21) Appl. No.: 15/779,108

(22) PCT Filed: Sep. 27, 2017

(86) PCT No.: PCT/KR2017/010741
§ 371 (c)(1),
(2) Date: May 25, 2018

(87) PCT Pub. No.: WO2018/062862
PCT Pub. Date: Apr. 5, 2018

(65) Prior Publication Data
US 2018/0348225 A1    Dec. 6, 2018

(30) Foreign Application Priority Data

Sep. 28, 2016  (KR) .................. 10-2016-0124785
Sep. 25, 2017  (KR) .................. 10-2017-0123572

(51) Int. Cl.
| | | |
|---|---|---|
| C12Q 1/68 | (2018.01) | |
| G01N 33/574 | (2006.01) | |
| C12Q 1/6886 | (2018.01) | |

(52) U.S. Cl.
CPC ..... *G01N 33/57438* (2013.01); *C12Q 1/6886* (2013.01); *C12Q 2600/158* (2013.01); *G01N 2800/52* (2013.01)

(58) Field of Classification Search
CPC .................. C12Q 2600/118; C12Q 1/6886
See application file for complete search history.

(56) References Cited

U.S. PATENT DOCUMENTS 10,280,468 B2 *  5/2019  Harkin ................. A61P 35/00
2018/0348225 A1  12/2018  Choi

FOREIGN PATENT DOCUMENTS

| KR | 10-1267580 B1 | 5/2013 |
| KR | 10-1446626 B1 | 10/2014 |
| KR | 10-2061814 B1 | 1/2020 |

OTHER PUBLICATIONS

Brannon et al. (Eur Urol, 2012, 61:258-268, plus supplementary Tables) (Year: 2012).*
Huang et al. (Int Urol Nephrol 2014, 46:539-553) (Year: 2014).*
Brannon et al. (Eur Urol, 2012, 61: p. 258-268).*
Brannon et al., "Meta-analysis of Clear Cell Renal Cell Carcinoma Gene Expression Defines a Variant Subgroup and Identifies Gender Influences on Tumor Biology", European Urology, 2012, vol. 61, pp. 258-268.
Brugarolas, "Molecular Genetics of Clear-Cell Renal Cell Carcinoma", Journal of clinical Oncology, 2014, vol. 32, No. 18, pp. 1968-1976.
Huang et al., "Key pathways and genes controlling the development and progression of clear cell renal cell carcinoma (ccRCC) based on gene set enrichment analysis", International Urology and Nephrology, 2014, vol. 46, pp. 539-553.
Ricketts et al., Gender Specific Mutation Incidence and Survival Associations in Clear Cell Renal Cell Carcinoma (CCRCC), PLOS ONE, 2015, vol. 10, No. 10, e0140257, pp. 1-10.
The Office Action dated Jan. 14, 2020 for the corresponding Korean patent application 10-2019-0175405, 4 pages.

* cited by examiner

*Primary Examiner* — Stephanie K Mummert
(74) *Attorney, Agent, or Firm* — Vorys. Sater, Seymour and Pease LLP; Mih Suhn Koh

(57) ABSTRACT

The present invention relates to markers for diagnosing the difference in effects of renal cancer treatment or the prognosis of renal cancer patients, according to the gender of renal cancer patients. The survival rate and recurrence rate of renal cancer of a particular gender respectively relate to the mutation of genes, of the present invention, in renal cancer patients, and thus the mutated genes of the present invention can be used as markers in predicting, on the basis of gender, the difference in effects of renal cancer treatment or the prognosis of renal cancer patients.

6 Claims, 10 Drawing Sheets

Specification includes a Sequence Listing.

【Figure 1】
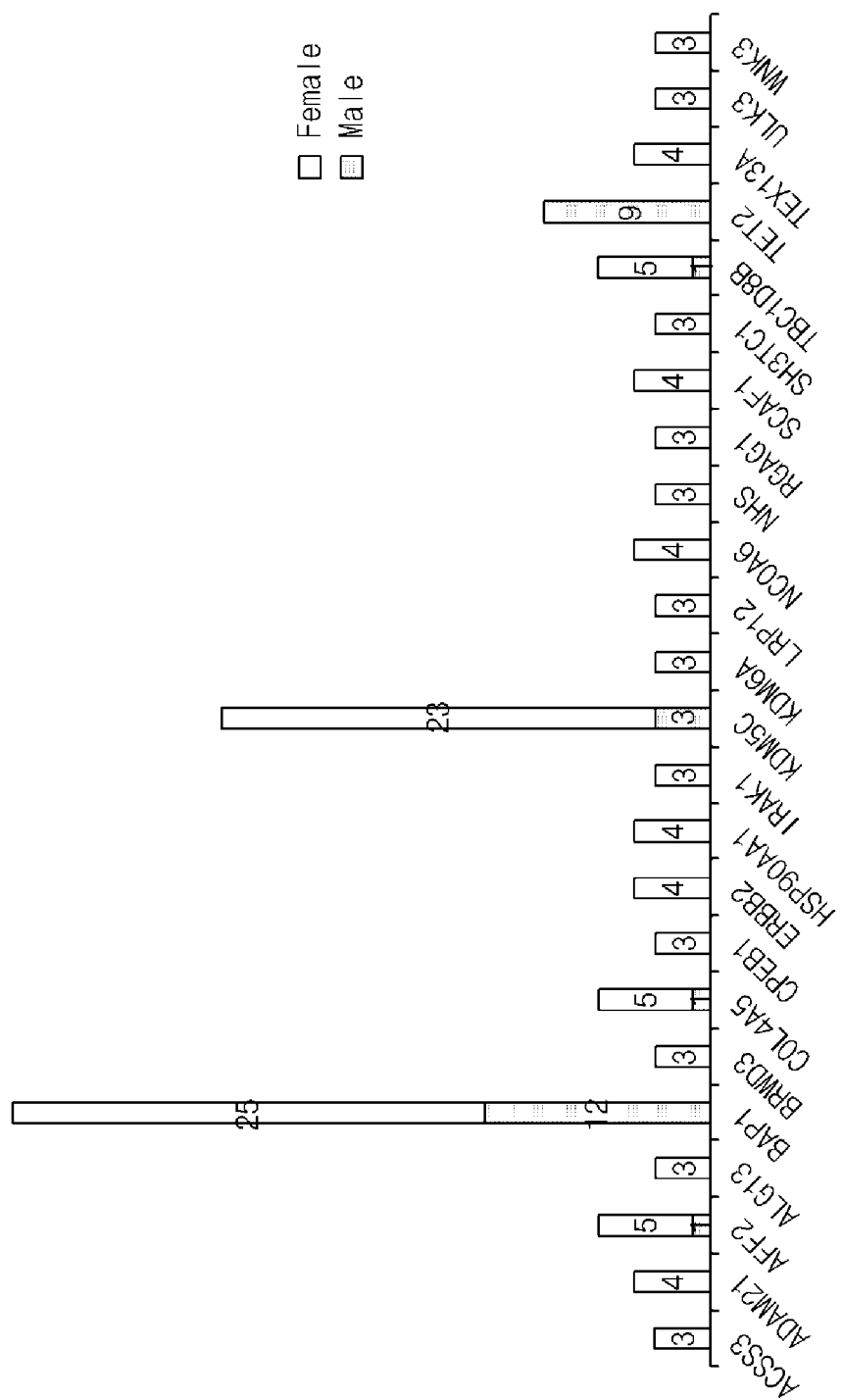

【Figure 2】
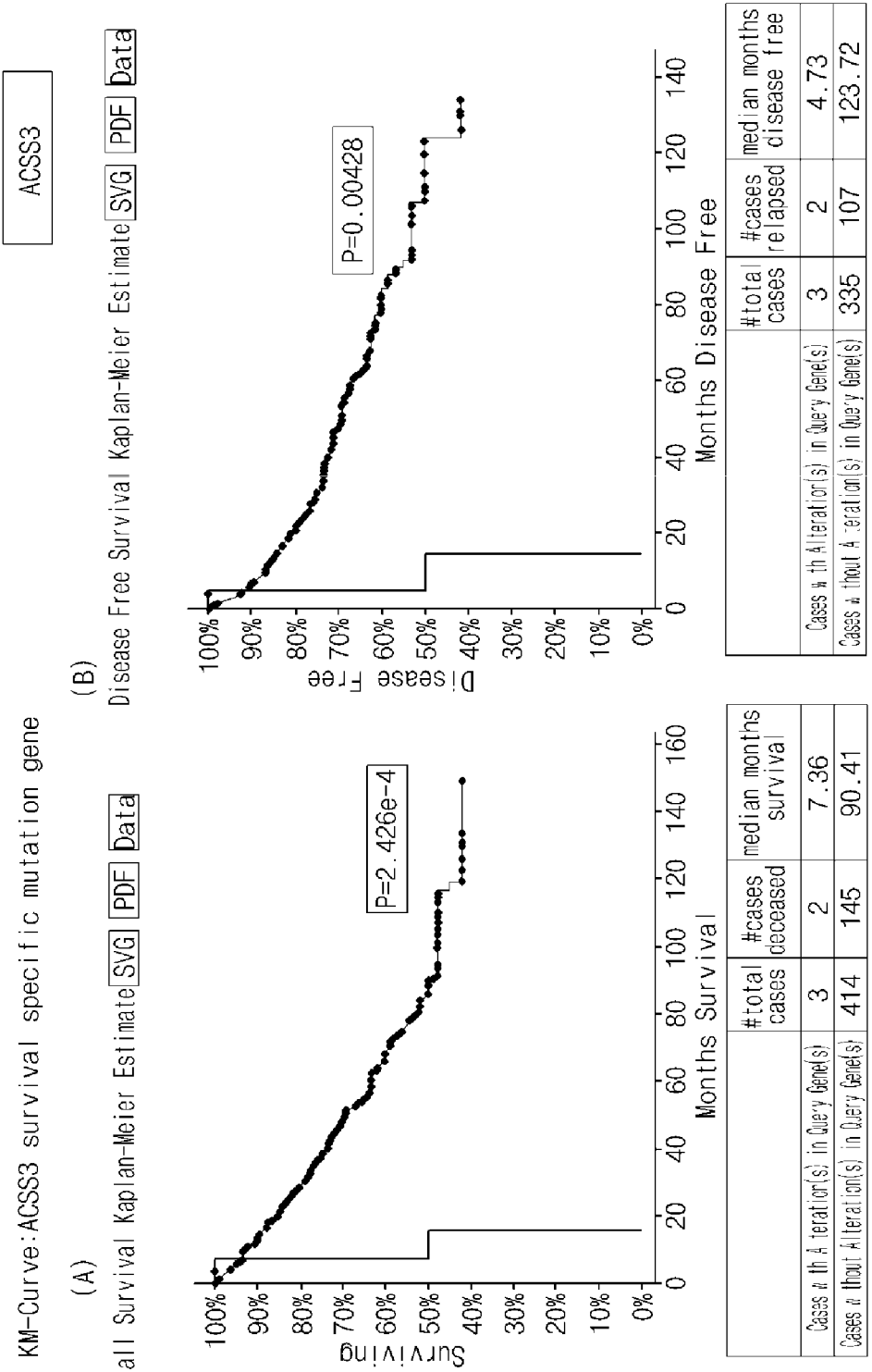

[Figure 3]
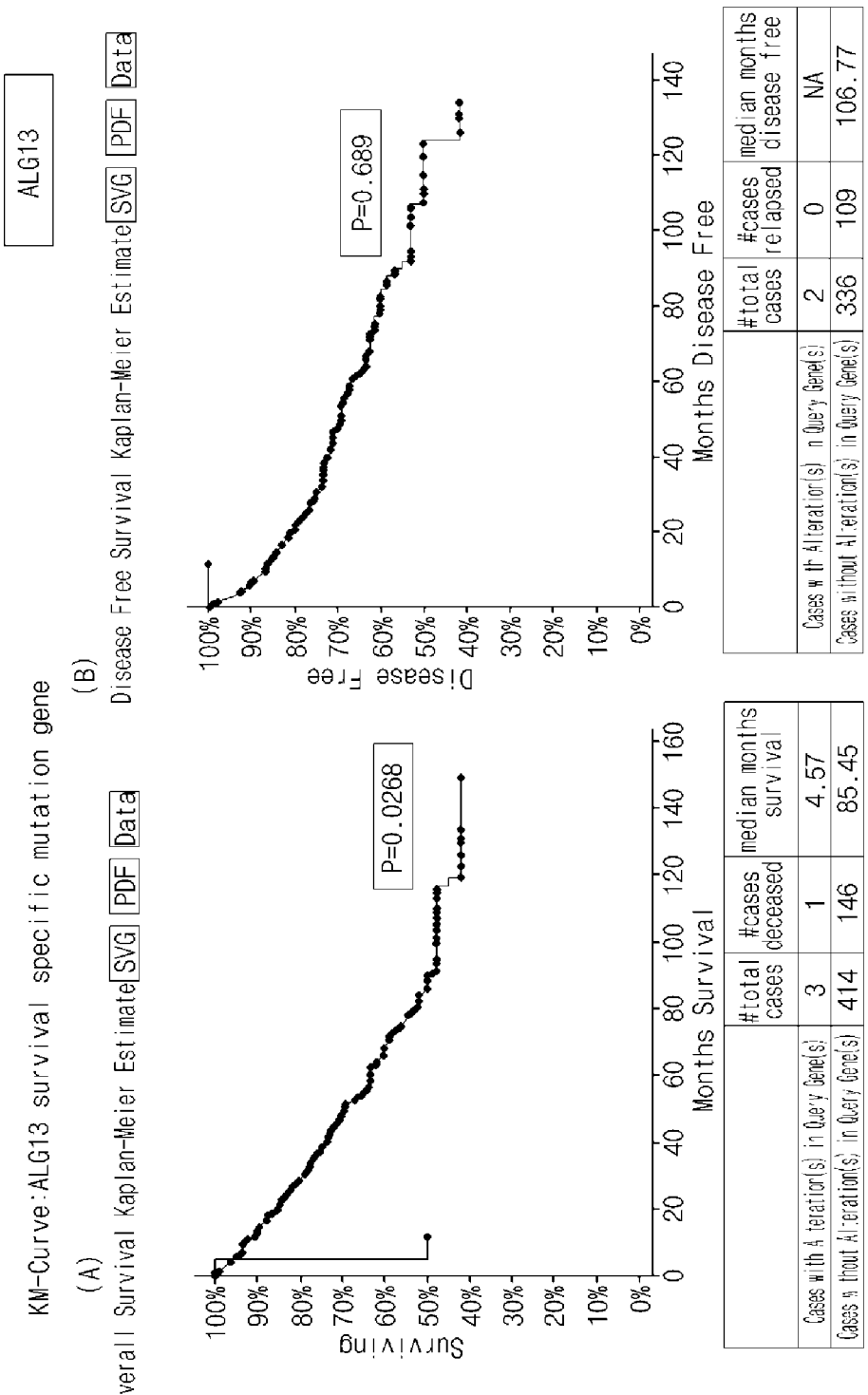

[Figure 4]
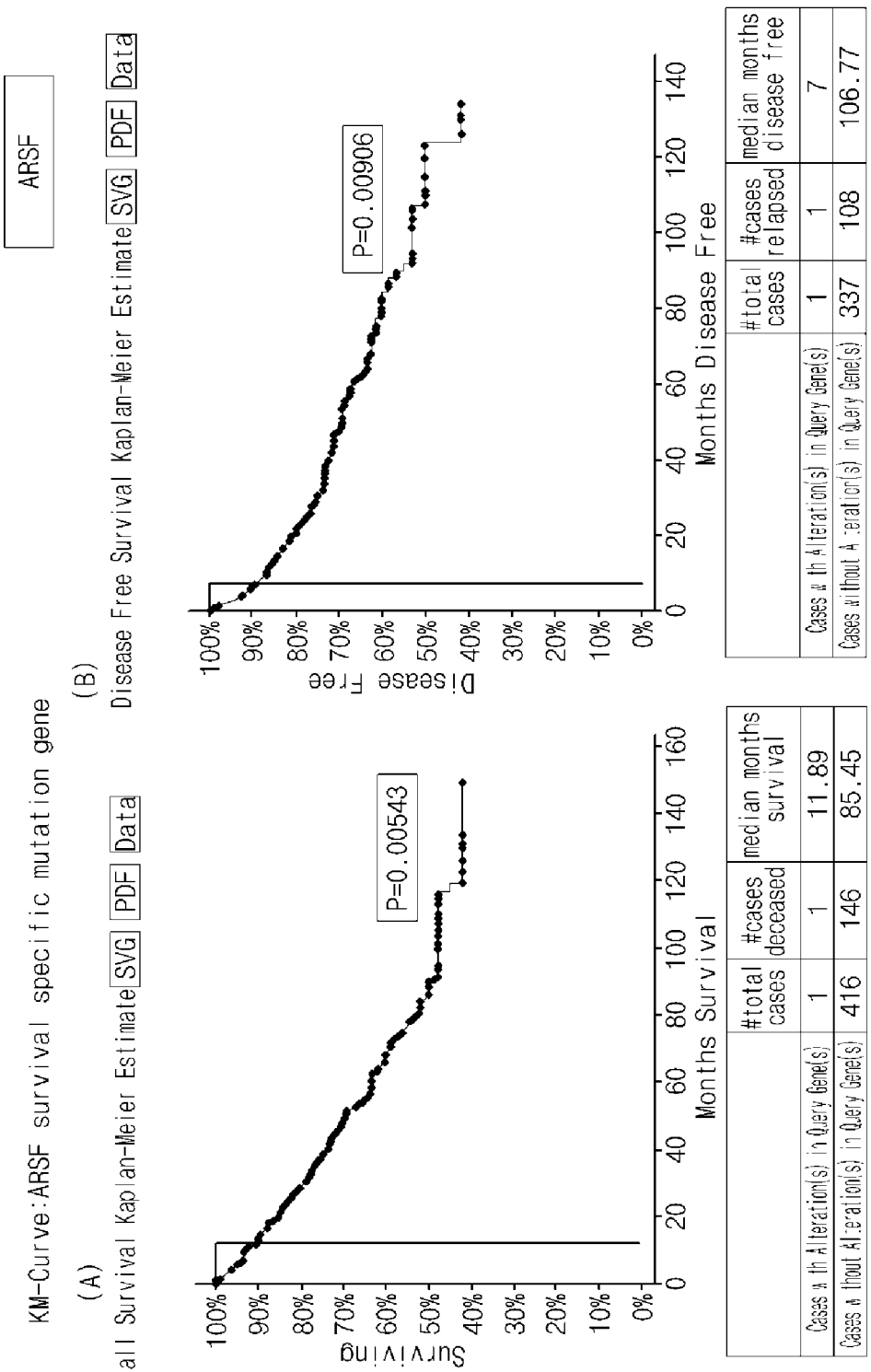

[Figure 5]
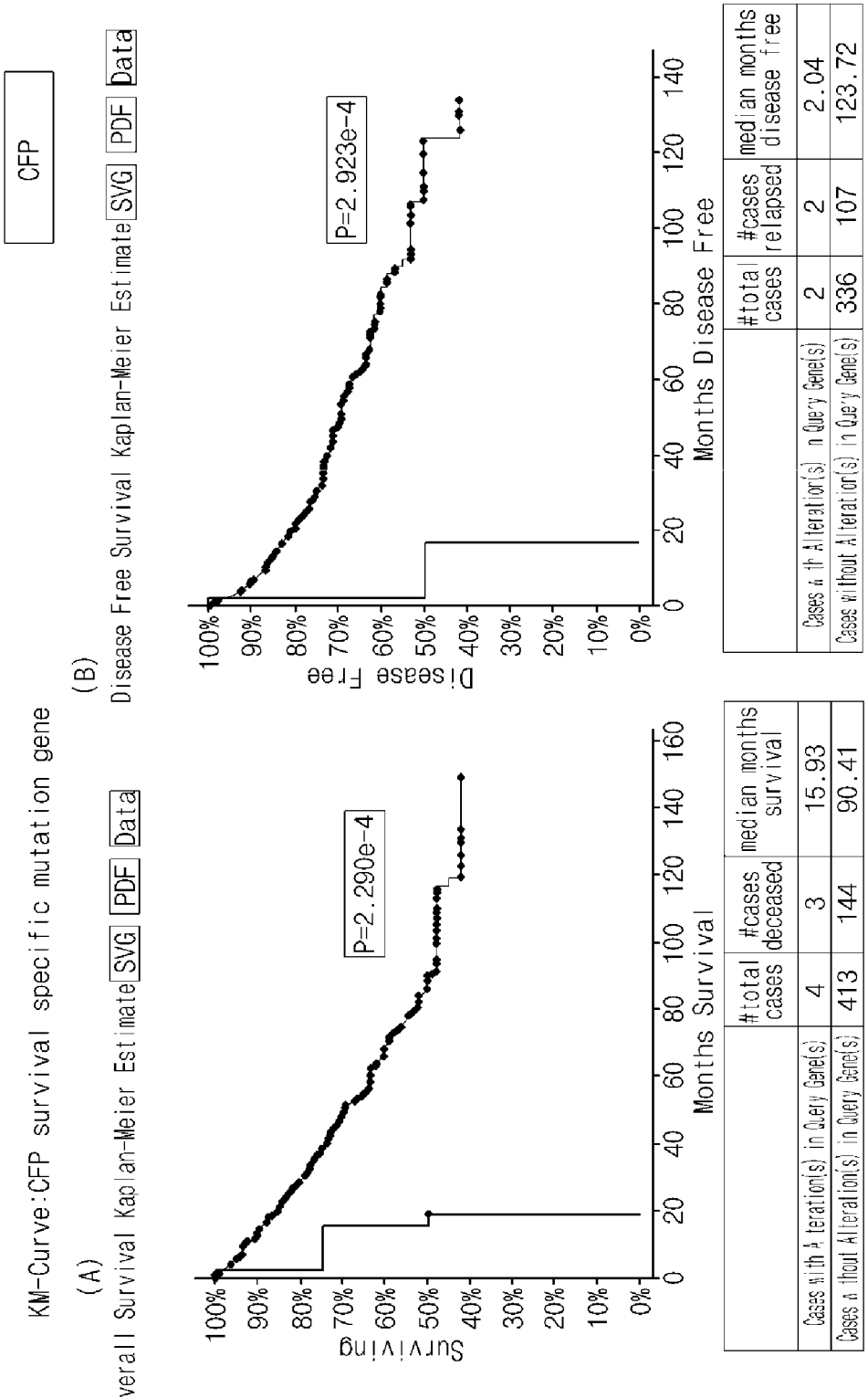

[Figure 6]
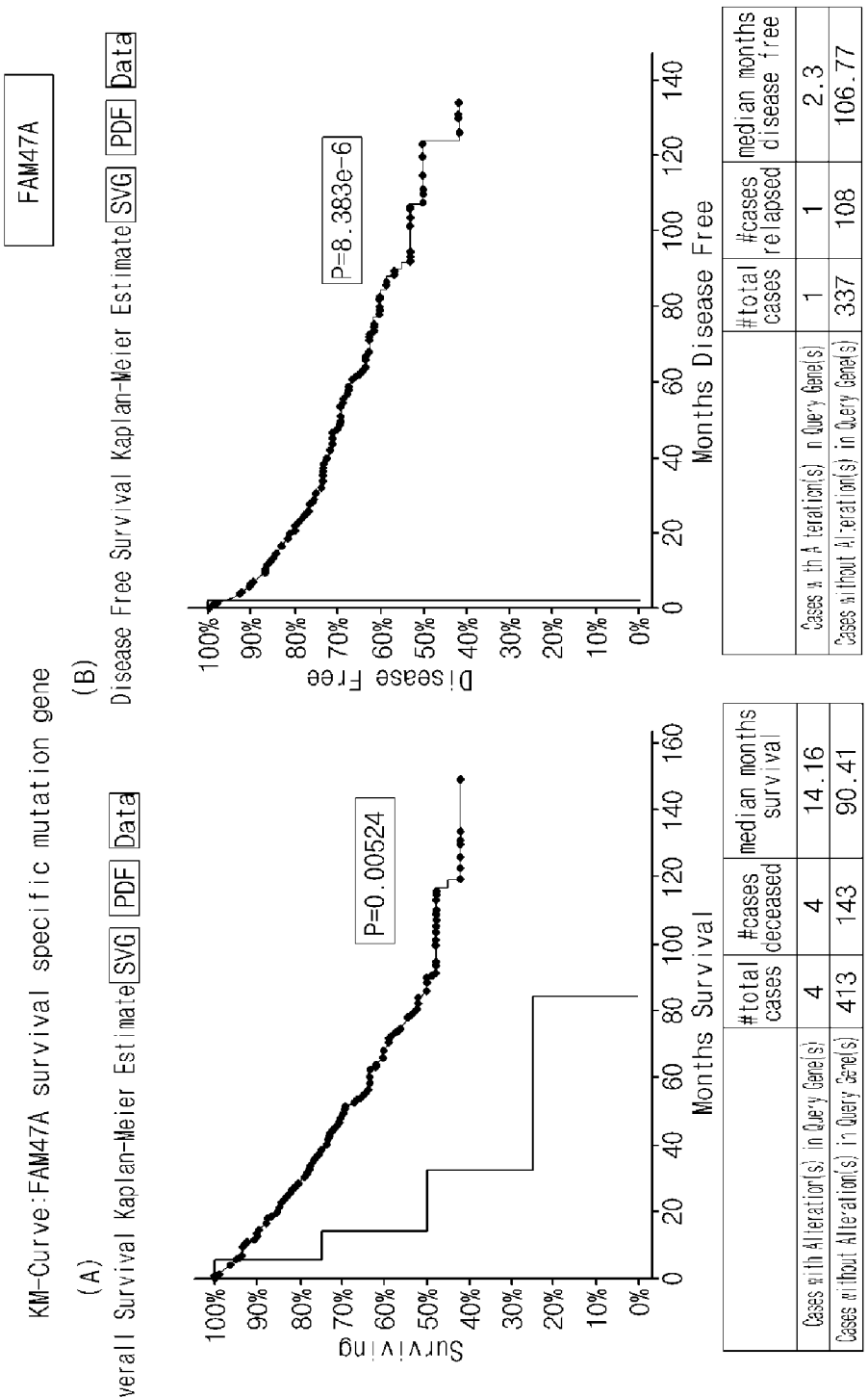

[Figure 7]
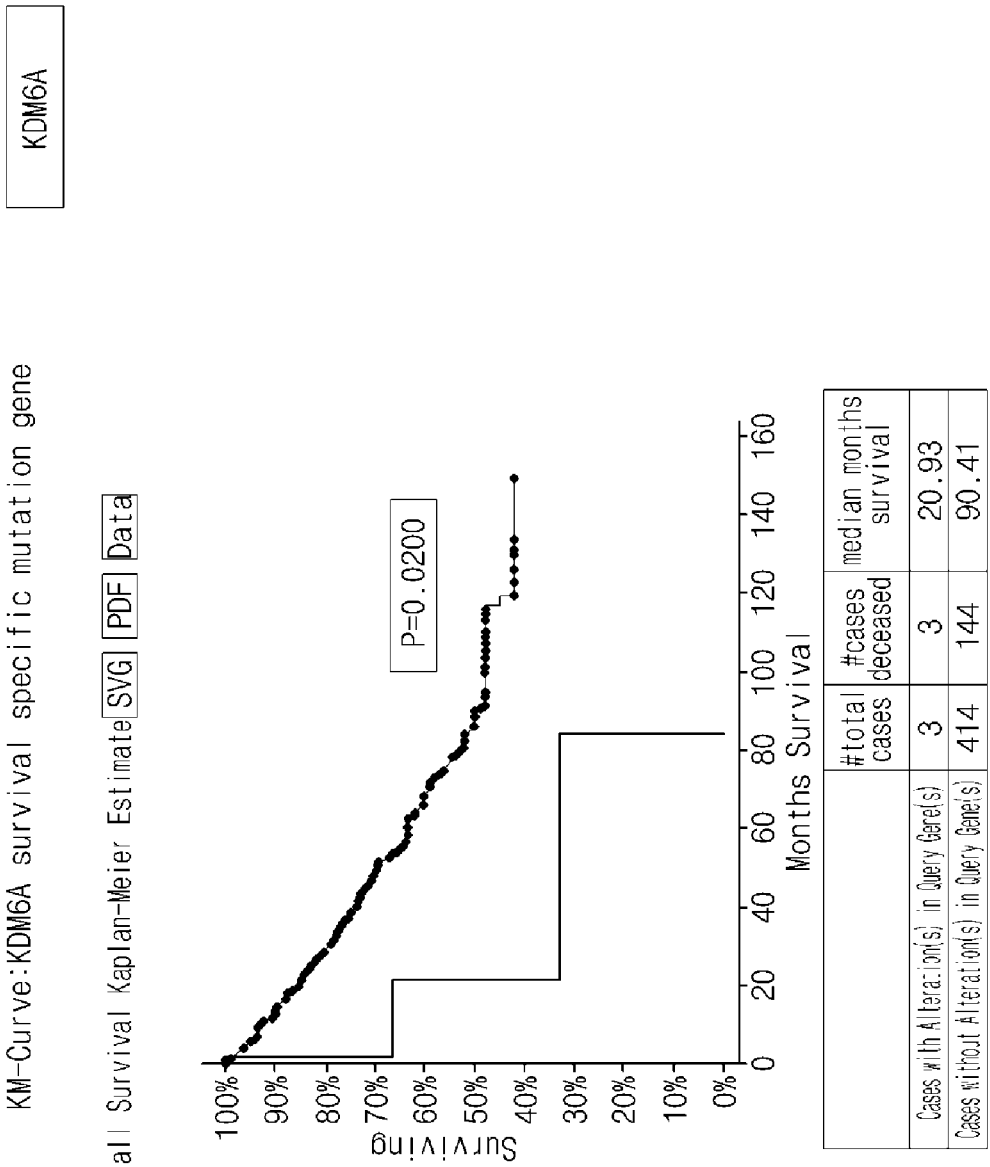

[Figure 8]
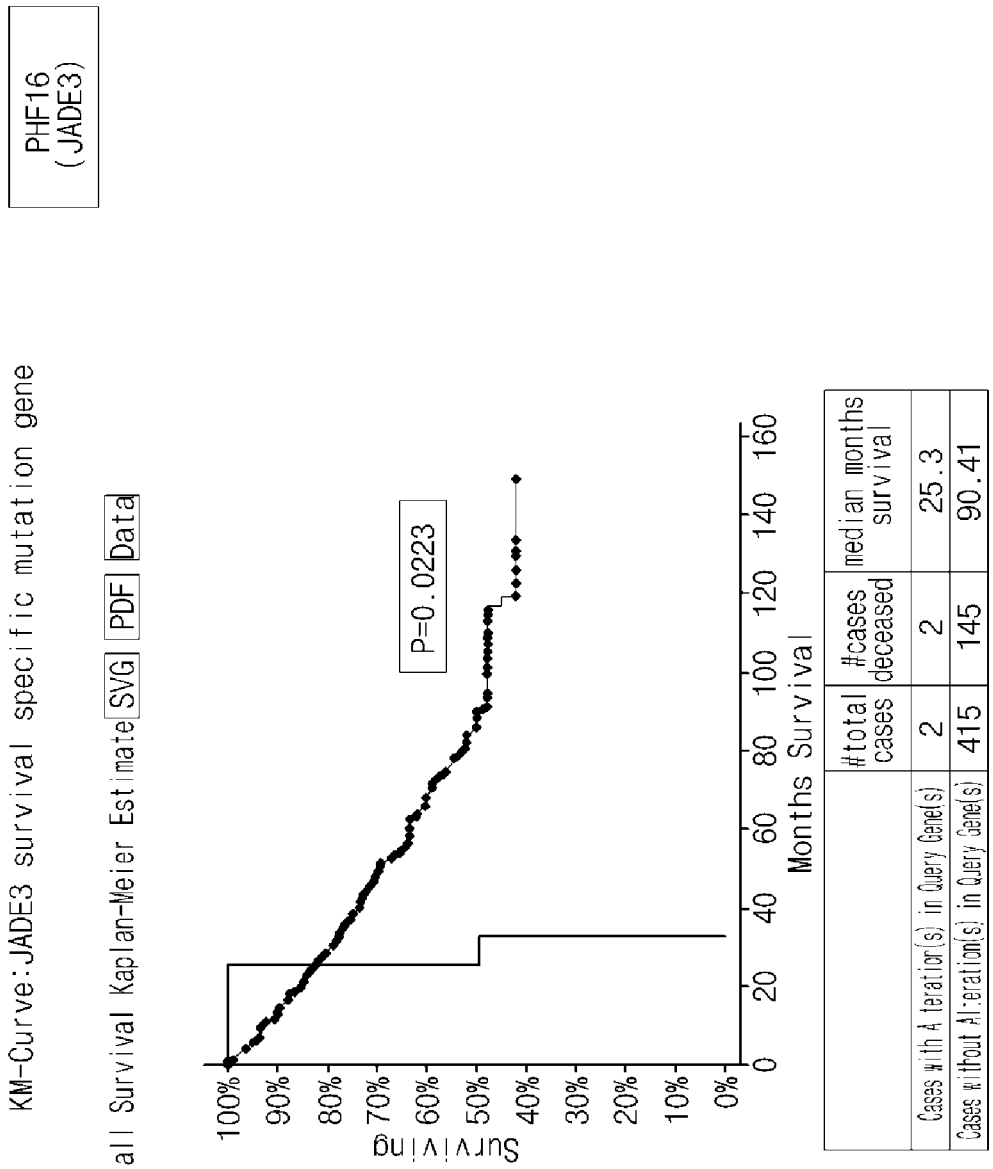

[Figure 9]
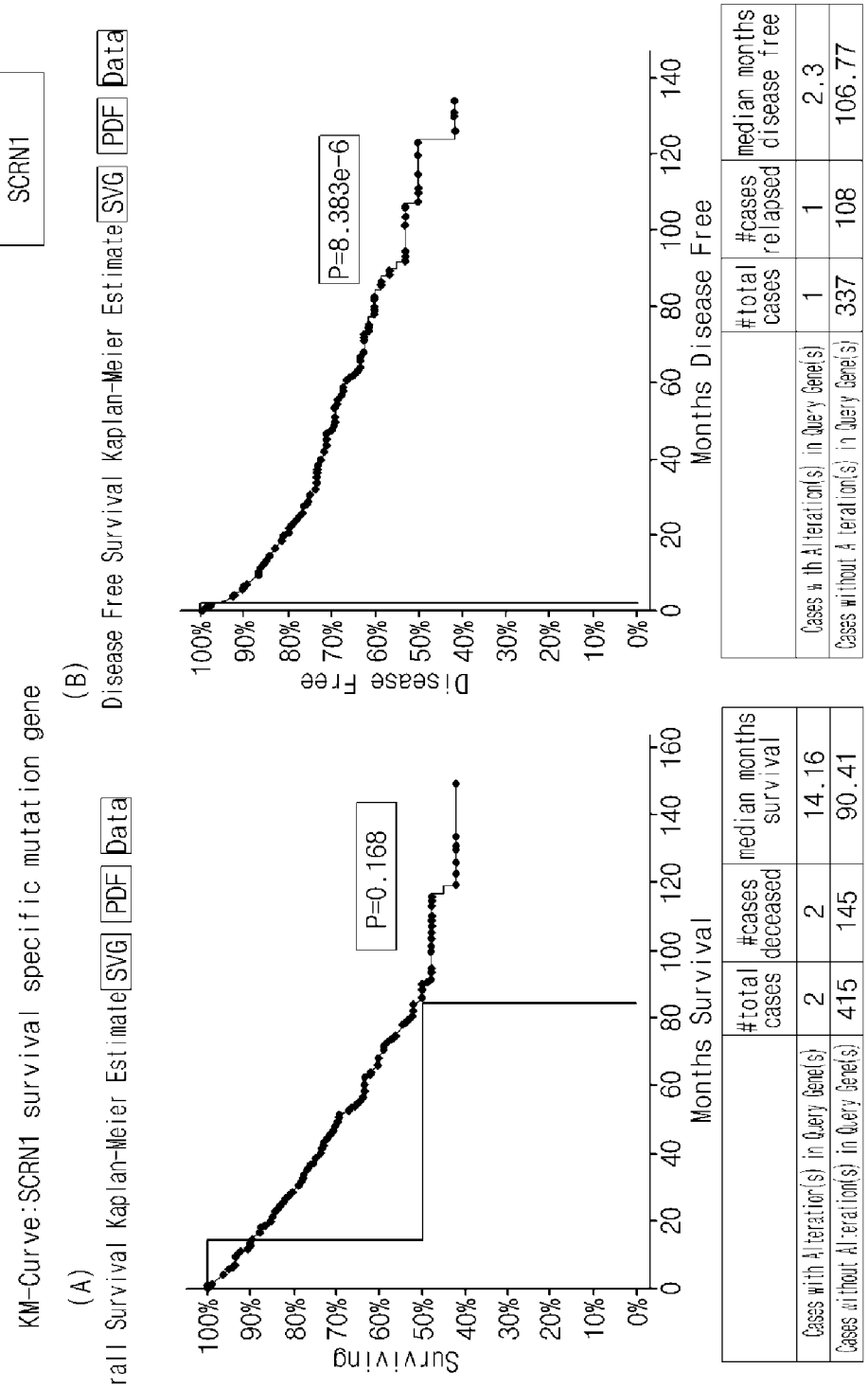

【Figure 10】
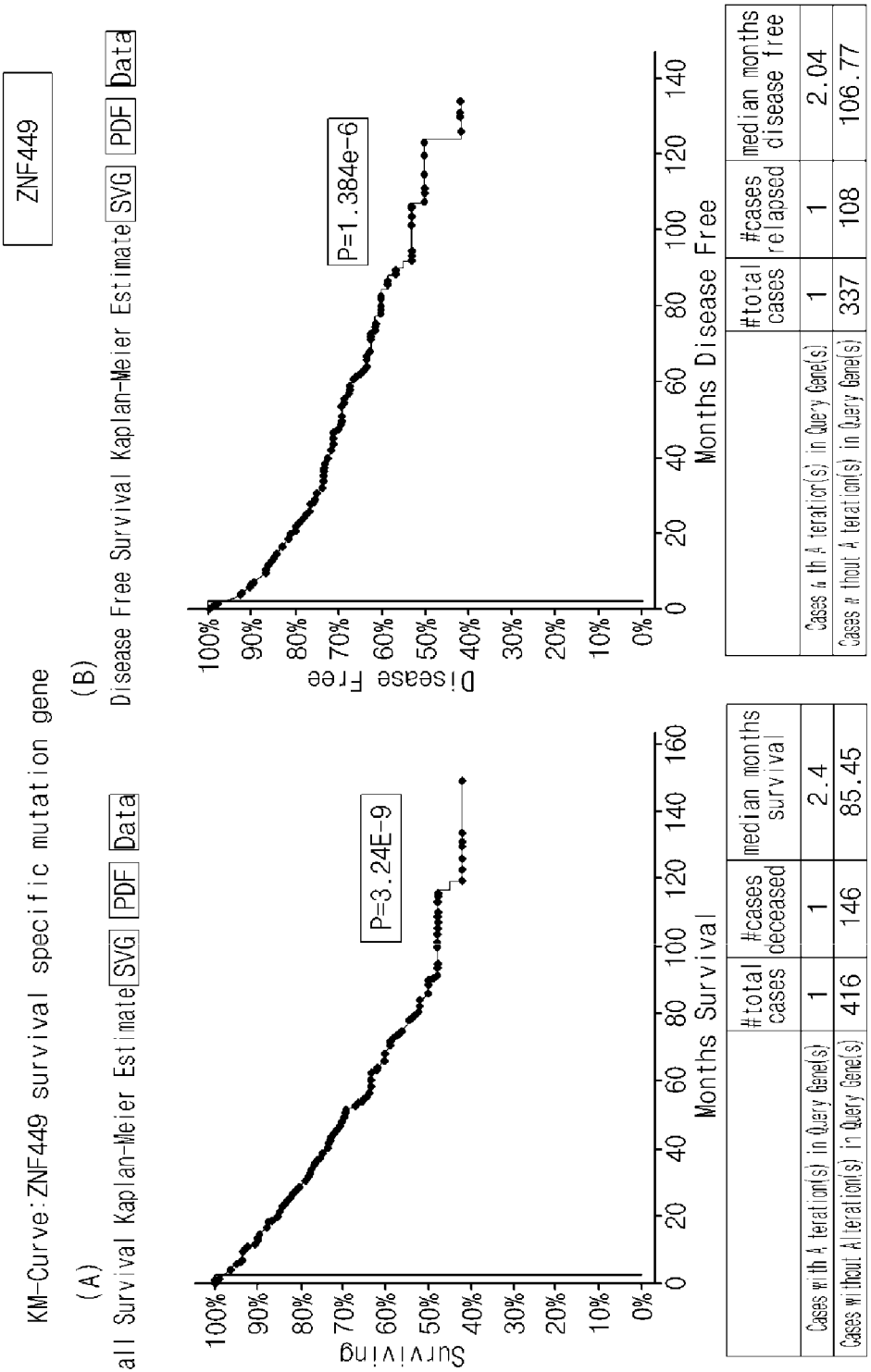

```
                    SEQUENCE LISTING

<160> NUMBER OF SEQ ID NOS: 282

<210> SEQ ID NO 1
<211> LENGTH: 686
<212> TYPE: PRT
<213> ORGANISM: Homo sapiens

<400> SEQUENCE: 1

Met Lys Pro Ser Trp Leu Gln Cys Arg Lys Val Thr Ser Ala Gly Gly
1               5                   10                  15

Leu Gly Gly Pro Leu Pro Gly Ser Ser Pro Ala Arg Gly Ala Gly Ala
            20                  25                  30

Ala Leu Arg Ala Leu Val Val Pro Gly Pro Arg Gly Gly Leu Gly Gly
        35                  40                  45

Arg Gly Cys Arg Ala Leu Ser Ser Gly Ser Gly Ser Glu Tyr Lys Thr
    50                  55                  60

His Phe Ala Ala Ser Val Thr Asp Pro Glu Arg Phe Trp Gly Lys Ala
65                  70                  75                  80

Ala Glu Gln Ile Ser Trp Tyr Lys Pro Trp Thr Lys Thr Leu Glu Asn
                85                  90                  95

Lys His Ser Pro Ser Thr Arg Trp Phe Val Glu Gly Met Leu Asn Ile
            100                 105                 110

Cys Tyr Asn Ala Val Asp Arg His Ile Glu Asn Gly Lys Gly Asp Lys
        115                 120                 125

Ile Ala Ile Ile Tyr Asp Ser Pro Val Thr Asn Thr Lys Ala Thr Phe
    130                 135                 140

Thr Tyr Lys Glu Val Leu Glu Gln Val Ser Lys Leu Ala Gly Val Leu
145                 150                 155                 160

Val Lys His Gly Ile Lys Lys Gly Asp Thr Val Val Ile Tyr Met Pro
                165                 170                 175

Met Ile Pro Gln Ala Met Tyr Thr Met Leu Ala Cys Ala Arg Ile Gly
```

```
            180                 185                 190
Ala Ile His Ser Leu Ile Phe Gly Gly Phe Ala Ser Lys Glu Leu Ser
                195                 200                 205

Ser Arg Ile Asp His Val Lys Pro Lys Val Val Thr Ala Ser Phe
    210                 215                 220

Gly Ile Glu Pro Gly Arg Arg Val Glu Tyr Val Pro Leu Val Glu Glu
225                 230                 235                 240

Ala Leu Lys Ile Gly Gln His Lys Pro Asp Lys Ile Leu Ile Tyr Asn
                245                 250                 255

Arg Pro Asn Met Glu Ala Val Pro Leu Ala Pro Gly Arg Asp Leu Asp
                260                 265                 270

Trp Asp Glu Glu Met Ala Lys Ala Gln Ser His Asp Cys Val Pro Val
            275                 280                 285

Leu Ser Glu His Pro Leu Tyr Ile Leu Tyr Thr Ser Gly Thr Thr Gly
            290                 295                 300

Leu Pro Lys Gly Val Ile Arg Pro Thr Gly Gly Tyr Ala Val Met Leu
305                 310                 315                 320

His Trp Ser Met Ser Ser Ile Tyr Gly Leu Gln Pro Gly Glu Val Trp
                325                 330                 335

Trp Ala Ala Ser Asp Leu Gly Trp Val Val Gly His Ser Tyr Ile Cys
                340                 345                 350

Tyr Gly Pro Leu Leu His Gly Asn Thr Thr Val Leu Tyr Glu Gly Lys
            355                 360                 365

Pro Val Gly Thr Pro Asp Ala Gly Ala Tyr Phe Arg Val Leu Ala Glu
            370                 375                 380

His Gly Val Ala Ala Leu Phe Thr Ala Pro Thr Ala Ile Arg Ala Ile
385                 390                 395                 400

Arg Gln Gln Asp Pro Gly Ala Ala Leu Gly Lys Gln Tyr Ser Leu Thr
                405                 410                 415

Arg Phe Lys Thr Leu Phe Val Ala Gly Glu Arg Cys Asp Val Glu Thr
            420                 425                 430

Leu Glu Trp Ser Lys Asn Val Phe Arg Val Pro Val Leu Asp His Trp
            435                 440                 445

Trp Gln Thr Glu Thr Gly Ser Pro Ile Thr Ala Ser Cys Val Gly Leu
    450                 455                 460

Gly Asn Ser Lys Thr Pro Pro Gly Gln Ala Gly Lys Ser Val Pro
465                 470                 475                 480

Gly Tyr Asn Val Met Ile Leu Asp Asp Asn Met Gln Lys Leu Lys Ala
                485                 490                 495

Arg Cys Leu Gly Asn Ile Val Val Lys Leu Pro Leu Pro Pro Gly Ala
                500                 505                 510

Phe Ser Gly Leu Trp Lys Asn Gln Glu Ala Phe Lys His Leu Tyr Phe
            515                 520                 525

Glu Lys Phe Pro Gly Tyr Tyr Asp Thr Met Asp Ala Gly Tyr Met Asp
            530                 535                 540

Glu Glu Gly Tyr Leu Tyr Val Met Ser Arg Val Asp Asp Val Ile Asn
545                 550                 555                 560

Val Ala Gly His Arg Ile Ser Ala Gly Ala Ile Glu Glu Ser Ile Leu
                565                 570                 575

Ser His Gly Thr Val Ala Asp Cys Ala Val Val Gly Lys Glu Asp Pro
            580                 585                 590

Leu Lys Gly His Val Pro Leu Ala Leu Cys Val Leu Arg Lys Asp Ile
            595                 600                 605
```

Asn Ala Thr Glu Glu Gln Val Leu Glu Glu Ile Val Lys His Val Arg
            610                 615                 620

Gln Asn Ile Gly Pro Val Ala Ala Phe Arg Asn Ala Val Phe Val Lys
625                 630                 635                 640

Gln Leu Pro Lys Thr Arg Ser Gly Lys Ile Pro Arg Ser Ala Leu Ser
            645                 650                 655

Ala Ile Val Asn Gly Lys Pro Tyr Lys Ile Thr Ser Thr Ile Glu Asp
            660                 665                 670

Pro Ser Ile Phe Gly His Val Glu Glu Met Leu Lys Gln Ala
            675                 680                 685

<210> SEQ ID NO 2
<211> LENGTH: 722
<212> TYPE: PRT
<213> ORGANISM: Homo sapiens

<400> SEQUENCE: 2

Met Ala Val Asp Gly Thr Leu Val Tyr Ile Arg Val Thr Leu Leu Leu
1               5                   10                  15

Leu Trp Leu Gly Val Phe Leu Ser Ile Ser Gly Tyr Cys Gln Ala Gly
            20                  25                  30

Pro Ser Gln His Phe Thr Ser Pro Glu Val Val Ile Pro Leu Lys Val
            35                  40                  45

Ile Ser Arg Gly Arg Ser Ala Lys Ala Pro Gly Trp Leu Ser Tyr Ser
        50                  55                  60

Leu Arg Phe Gly Gly Gln Lys His Val Val His Met Arg Val Lys Lys
65                  70                  75                  80

Leu Leu Val Ser Arg His Leu Pro Val Phe Thr Tyr Thr Asp Asp Arg
                85                  90                  95

Ala Leu Leu Glu Asp Gln Leu Phe Ile Pro Asp Asp Cys Tyr Tyr His
            100                 105                 110

Gly Tyr Val Glu Ala Ala Pro Glu Ser Leu Val Val Phe Ser Ala Cys
        115                 120                 125

Phe Gly Gly Phe Arg Gly Val Leu Lys Ile Ser Gly Leu Thr Tyr Glu
130                 135                 140

Ile Glu Pro Ile Arg His Ser Ala Thr Phe Glu His Leu Val Tyr Lys
145                 150                 155                 160

Ile Asn Ser Asn Glu Thr Gln Phe Pro Ala Met Arg Cys Gly Leu Thr
                165                 170                 175

Glu Lys Glu Val Ala Arg Gln Gln Leu Glu Phe Glu Glu Ala Glu Asn
            180                 185                 190

Ser Ala Leu Glu Pro Lys Ser Ala Gly Asp Trp Trp Thr His Ala Trp
        195                 200                 205

Phe Leu Glu Leu Val Val Val Asn His Asp Phe Phe Ile Tyr Ser
210                 215                 220

Gln Ser Asn Ile Ser Lys Val Gln Glu Asp Val Phe Leu Val Val Asn
225                 230                 235                 240

Ile Val Asp Ser Met Tyr Lys Gln Leu Gly Thr Tyr Ile Ile Leu Ile
                245                 250                 255

Gly Ile Glu Ile Trp Asn Gln Gly Asn Val Phe Pro Met Thr Ser Ile
            260                 265                 270

Glu Gln Val Leu Asn Asp Phe Ser Gln Trp Lys Gln Ile Ser Leu Ser
        275                 280                 285

Gln Leu Gln His Asp Ala Ala His Met Phe Ile Lys Asn Ser Leu Ile

```
              290                 295                 300
Ser Ile Leu Gly Leu Ala Tyr Val Ala Gly Ile Cys Arg Pro Ile
305                 310                 315                 320

Asp Cys Gly Val Asp Asn Phe Gln Gly Asp Thr Trp Ser Leu Phe Ala
                    325                 330                 335

Asn Thr Val Ala His Glu Leu Gly His Thr Leu Gly Met Gln His Asp
                340                 345                 350

Glu Glu Phe Cys Phe Cys Gly Glu Arg Gly Cys Ile Met Asn Thr Phe
            355                 360                 365

Arg Val Pro Ala Glu Lys Phe Thr Asn Cys Ser Tyr Ala Asp Phe Met
        370                 375                 380

Lys Thr Thr Leu Asn Gln Gly Ser Cys Leu His Asn Pro Pro Arg Leu
385                 390                 395                 400

Gly Glu Ile Phe Met Leu Lys Arg Cys Gly Asn Gly Val Val Glu Arg
                    405                 410                 415

Glu Glu Gln Cys Asp Cys Gly Ser Val Gln Gln Cys Glu Gln Asp Ala
                420                 425                 430

Cys Cys Leu Leu Asn Cys Thr Leu Arg Pro Gly Ala Ala Cys Ala Phe
            435                 440                 445

Gly Leu Cys Cys Lys Asp Cys Lys Phe Met Pro Ser Gly Glu Leu Cys
        450                 455                 460

Arg Gln Glu Val Asn Glu Cys Asp Leu Pro Glu Trp Cys Asn Gly Thr
465                 470                 475                 480

Ser His Gln Cys Pro Glu Asp Arg Tyr Val Gln Asp Gly Ile Pro Cys
                    485                 490                 495

Ser Asp Ser Ala Tyr Cys Tyr Gln Lys Arg Cys Asn Asn His Asp Gln
                500                 505                 510

His Cys Arg Glu Ile Phe Gly Lys Asp Ala Lys Ser Ala Ser Gln Asn
            515                 520                 525

Cys Tyr Lys Glu Ile Asn Ser Gln Gly Asn Arg Phe Gly His Cys Gly
        530                 535                 540

Ile Asn Gly Thr Thr Tyr Leu Lys Cys His Ile Ser Asp Val Phe Cys
545                 550                 555                 560

Gly Arg Val Gln Cys Glu Asn Val Arg Asp Ile Pro Leu Leu Gln Asp
                    565                 570                 575

His Phe Thr Leu Gln His Thr His Ile Asn Gly Val Thr Cys Trp Gly
                580                 585                 590

Ile Asp Tyr His Leu Arg Met Asn Ile Ser Asp Ile Gly Glu Val Lys
            595                 600                 605

Asp Gly Thr Val Cys Gly Pro Gly Lys Ile Cys Ile His Lys Lys Cys
        610                 615                 620

Val Ser Leu Ser Val Leu Ser His Val Cys Leu Pro Glu Thr Cys Asn
625                 630                 635                 640

Met Lys Gly Ile Cys Asn Asn Lys His His Cys His Cys Gly Tyr Gly
                    645                 650                 655

Trp Ser Pro Pro Tyr Cys Gln His Arg Gly Tyr Gly Gly Ser Ile Asp
                660                 665                 670

Ser Gly Pro Ala Ser Ala Lys Arg Gly Val Phe Leu Pro Leu Ile Val
            675                 680                 685

Ile Pro Ser Leu Ser Val Leu Thr Phe Leu Phe Thr Val Gly Leu Leu
        690                 695                 700

Met Tyr Leu Arg Gln Cys Ser Gly Pro Lys Glu Thr Lys Ala His Ser
705                 710                 715                 720
```

Ser Gly

<210> SEQ ID NO 3
<211> LENGTH: 1311
<212> TYPE: PRT
<213> ORGANISM: Homo sapiens

<400> SEQUENCE: 3

```
Met Asp Leu Phe Asp Phe Phe Arg Asp Trp Asp Leu Glu Gln Gln Cys
1               5                   10                  15

His Tyr Glu Gln Asp Arg Ser Ala Leu Lys Lys Arg Glu Trp Glu Arg
                20                  25                  30

Arg Asn Gln Glu Val Gln Glu Asp Asp Leu Phe Ser Ser Gly Phe
                35                  40                  45

Asp Leu Phe Gly Glu Pro Tyr Lys Val Ala Glu Tyr Thr Asn Lys Gly
    50                  55                  60

Asp Ala Leu Ala Asn Arg Val Gln Asn Thr Leu Gly Asn Tyr Asp Glu
65                  70                  75                  80

Met Lys Asn Leu Leu Thr Asn His Ser Asn Gln Asn His Leu Val Gly
                85                  90                  95

Ile Pro Lys Asn Ser Val Pro Gln Asn Pro Asn Lys Asn Glu Pro
                100                 105                 110

Ser Phe Phe Pro Glu Gln Lys Asn Arg Ile Ile Pro Pro His Gln Asp
            115                 120                 125

Asn Thr His Pro Ser Ala Pro Met Pro Pro Ser Val Val Ile Leu
    130                 135                 140

Asn Ser Thr Leu Ile His Ser Asn Arg Lys Ser Lys Pro Glu Trp Ser
145                 150                 155                 160

Arg Asp Ser His Asn Pro Ser Thr Val Leu Ala Ser Gln Ala Ser Gly
                165                 170                 175

Gln Pro Asn Lys Met Gln Thr Leu Thr Gln Asp Gln Ser Gln Ala Lys
            180                 185                 190

Leu Glu Asp Phe Phe Val Tyr Pro Ala Glu Gln Pro Gln Ile Gly Glu
        195                 200                 205

Val Glu Glu Ser Asn Pro Ser Ala Lys Glu Asp Ser Asn Pro Asn Ser
    210                 215                 220

Ser Gly Glu Asp Ala Phe Lys Glu Ile Phe Gln Ser Asn Ser Pro Glu
225                 230                 235                 240

Glu Ser Glu Phe Ala Val Gln Ala Pro Gly Ser Pro Leu Val Ala Ser
                245                 250                 255

Ser Leu Leu Ala Pro Ser Ser Gly Leu Ser Val Gln Asn Phe Pro Pro
            260                 265                 270

Gly Leu Tyr Cys Lys Thr Ser Met Gly Gln Gln Lys Pro Thr Ala Tyr
        275                 280                 285

Val Arg Pro Met Asp Gly Gln Asp Gln Ala Pro Asp Ile Ser Pro Thr
    290                 295                 300

Leu Lys Pro Ser Ile Glu Phe Glu Asn Ser Phe Gly Asn Leu Ser Phe
305                 310                 315                 320

Gly Thr Leu Leu Asp Gly Lys Pro Ser Ala Ala Ser Ser Lys Thr Lys
                325                 330                 335

Leu Pro Lys Phe Thr Ile Leu Gln Thr Ser Glu Val Ser Leu Pro Ser
            340                 345                 350

Asp Pro Ser Cys Val Glu Glu Ile Leu Arg Glu Met Thr His Ser Trp
        355                 360                 365
```

```
Pro Thr Pro Leu Thr Ser Met His Thr Ala Gly His Ser Glu Gln Ser
    370                 375                 380

Thr Phe Ser Ile Pro Gly Gln Glu Ser Gln His Leu Thr Pro Gly Phe
385                 390                 395                 400

Thr Leu Gln Lys Trp Asn Asp Pro Thr Thr Arg Ala Ser Thr Lys Ser
                405                 410                 415

Val Ser Phe Lys Ser Met Leu Glu Asp Asp Leu Lys Leu Ser Ser Asp
            420                 425                 430

Glu Asp Asp Leu Glu Pro Val Lys Thr Leu Thr Thr Gln Cys Thr Ala
        435                 440                 445

Thr Glu Leu Tyr Gln Ala Val Glu Lys Ala Lys Pro Arg Asn Asn Pro
    450                 455                 460

Val Asn Pro Pro Leu Ala Thr Pro Gln Pro Pro Ala Val Gln Ala
465                 470                 475                 480

Ser Gly Gly Ser Gly Ser Ser Glu Ser Glu Ser Ser Glu Ser
                485                 490                 495

Asp Ser Asp Thr Glu Ser Ser Thr Thr Asp Ser Glu Ser Asn Glu Ala
                500                 505                 510

Pro Arg Val Ala Thr Pro Glu Pro Glu Pro Pro Ser Thr Asn Lys Trp
            515                 520                 525

Gln Leu Asp Lys Trp Leu Asn Lys Val Thr Ser Gln Asn Lys Ser Phe
530                 535                 540

Ile Cys Gly Gln Asn Glu Thr Pro Met Glu Thr Ile Ser Leu Pro Pro
545                 550                 555                 560

Pro Ile Ile Gln Pro Met Glu Val Gln Met Lys Val Lys Thr Asn Ala
                565                 570                 575

Ser Gln Val Pro Ala Glu Pro Lys Glu Arg Pro Leu Leu Ser Leu Ile
            580                 585                 590

Arg Glu Lys Ala Arg Pro Arg Pro Thr Gln Lys Ile Pro Glu Thr Lys
                595                 600                 605

Ala Leu Lys His Lys Leu Ser Thr Thr Ser Glu Thr Val Ser Gln Arg
    610                 615                 620

Thr Ile Gly Lys Lys Gln Pro Lys Lys Val Glu Lys Asn Thr Ser Thr
625                 630                 635                 640

Asp Glu Phe Thr Trp Pro Lys Pro Asn Ile Thr Ser Ser Thr Pro Lys
                645                 650                 655

Glu Lys Glu Ser Val Glu Leu His Asp Pro Pro Arg Gly Arg Asn Lys
                660                 665                 670

Ala Thr Ala His Lys Pro Ala Pro Arg Lys Glu Pro Arg Pro Asn Ile
        675                 680                 685

Pro Leu Ala Pro Glu Lys Lys Lys Tyr Arg Gly Pro Gly Lys Ile Val
    690                 695                 700

Pro Lys Ser Arg Glu Phe Ile Glu Thr Asp Ser Ser Thr Ser Asp Ser
705                 710                 715                 720

Asn Thr Asp Gln Glu Glu Thr Leu Gln Ile Lys Val Leu Pro Pro Cys
                725                 730                 735

Ile Ile Ser Gly Gly Asn Thr Ala Lys Ser Lys Glu Ile Cys Gly Ala
                740                 745                 750

Ser Leu Thr Leu Ser Thr Leu Met Ser Ser Gly Ser Asn Asn Asn
        755                 760                 765

Leu Ser Ile Ser Asn Glu Glu Pro Thr Phe Ser Pro Ile Pro Val Met
    770                 775                 780
```

```
Gln Thr Glu Ile Leu Ser Pro Leu Arg Asp His Glu Asn Leu Lys Asn
785                 790                 795                 800

Leu Trp Val Lys Ile Asp Leu Asp Leu Leu Ser Arg Val Pro Gly His
                805                 810                 815

Ser Ser Leu His Ala Ala Pro Ala Lys Pro Asp His Lys Glu Thr Ala
            820                 825                 830

Thr Lys Pro Lys Arg Gln Thr Ala Val Thr Ala Val Glu Lys Pro Ala
        835                 840                 845

Pro Lys Gly Lys Arg Lys His Lys Pro Ile Glu Val Ala Glu Lys Ile
    850                 855                 860

Pro Glu Lys Lys Gln Arg Leu Glu Glu Ala Thr Thr Ile Cys Leu Leu
865                 870                 875                 880

Pro Pro Cys Ile Ser Pro Ala Pro Pro His Lys Pro Pro Asn Thr Arg
                885                 890                 895

Glu Asn Asn Ser Ser Arg Arg Ala Asn Arg Arg Lys Glu Glu Lys Leu
            900                 905                 910

Phe Pro Pro Pro Leu Ser Pro Leu Pro Glu Asp Pro Arg Arg Arg
        915                 920                 925

Asn Val Ser Gly Asn Asn Gly Pro Phe Gly Gln Asp Lys Asn Ile Ala
    930                 935                 940

Met Thr Gly Gln Ile Thr Ser Thr Lys Pro Lys Arg Thr Glu Gly Lys
945                 950                 955                 960

Phe Cys Ala Thr Phe Lys Gly Ile Ser Val Asn Glu Gly Asp Thr Pro
                965                 970                 975

Lys Lys Ala Ser Ser Ala Thr Ile Thr Val Thr Asn Thr Ala Ile Ala
            980                 985                 990

Thr Ala Thr Val Thr Ala Thr Ala  Ile Val Thr Thr Thr  Val Thr Ala
        995                 1000                1005

Thr Ala  Thr Ala Thr Ala Thr  Thr Thr Thr Thr  Thr Thr Ile
    1010                1015                1020

Ser Thr  Ile Thr Ser Thr Ile  Thr Thr Gly Leu Met  Asp Ser Ser
    1025                1030                1035

His Leu  Glu Met Thr Ser Trp  Ala Ala Leu Pro Leu  Leu Ser Ser
    1040                1045                1050

Ser Ser  Thr Asn Val Arg Arg  Pro Lys Leu Thr Phe  Asp Asp Ser
    1055                1060                1065

Val His  Asn Ala Asp Tyr Tyr  Met Gln Glu Ala Lys  Lys Leu Lys
    1070                1075                1080

His Lys  Ala Asp Ala Leu Phe  Glu Lys Phe Gly Lys  Ala Val Asn
    1085                1090                1095

Tyr Ala  Asp Ala Ala Leu Ser  Phe Thr Glu Cys Gly  Asn Ala Met
    1100                1105                1110

Glu Arg  Asp Pro Leu Glu Ala  Lys Ser Pro Tyr Thr  Met Tyr Ser
    1115                1120                1125

Glu Thr  Val Glu Leu Leu Arg  Tyr Ala Met Arg Leu  Lys Asn Phe
    1130                1135                1140

Ala Ser  Pro Leu Ala Ser Asp  Gly Asp Lys Lys Leu  Ala Val Leu
    1145                1150                1155

Cys Tyr  Arg Cys Leu Ser Leu  Leu Tyr Leu Arg Met  Phe Lys Leu
    1160                1165                1170

Lys Lys  Asp His Ala Met Lys  Tyr Ser Arg Ser Leu  Met Glu Tyr
    1175                1180                1185

Phe Lys  Gln Asn Ala Ser Lys  Val Ala Gln Ile Pro  Ser Pro Trp
```

```
            1190                1195                1200

Val Ser Asn Gly Lys Asn Thr Pro Ser Pro Val Ser Leu Asn Asn
    1205                1210                1215

Val Ser Pro Ile Asn Ala Met Gly Asn Cys Asn Asn Gly Pro Val
    1220                1225                1230

Thr Ile Pro Gln Arg Ile His His Met Ala Ala Ser His Val Asn
    1235                1240                1245

Ile Thr Ser Asn Val Leu Arg Gly Tyr Glu His Trp Asp Met Ala
    1250                1255                1260

Asp Lys Leu Thr Arg Glu Asn Lys Glu Phe Phe Gly Asp Leu Asp
    1265                1270                1275

Thr Leu Met Gly Pro Leu Thr Gln His Ser Ser Met Thr Asn Leu
    1280                1285                1290

Val Arg Tyr Val Arg Gln Gly Leu Cys Trp Leu Arg Ile Asp Ala
    1295                1300                1305

His Leu Leu
    1310

<210> SEQ ID NO 4
<211> LENGTH: 1137
<212> TYPE: PRT
<213> ORGANISM: Homo sapiens

<400> SEQUENCE: 4

Met Lys Cys Val Phe Val Thr Val Gly Thr Thr Ser Phe Asp Asp Leu
1               5                   10                  15

Ile Ala Cys Val Ser Ala Pro Asp Ser Leu Gln Lys Ile Glu Ser Leu
                20                  25                  30

Gly Tyr Asn Arg Leu Ile Leu Gln Ile Gly Arg Gly Thr Val Val Pro
            35                  40                  45

Glu Pro Phe Ser Thr Glu Ser Phe Thr Leu Asp Val Tyr Arg Tyr Lys
        50                  55                  60

Asp Ser Leu Lys Glu Asp Ile Gln Lys Ala Asp Leu Val Ile Ser His
65                  70                  75                  80

Ala Gly Ala Gly Ser Cys Leu Glu Thr Leu Glu Lys Gly Lys Pro Leu
                85                  90                  95

Val Val Val Ile Asn Glu Lys Leu Met Asn Asn His Gln Leu Glu Leu
                100                 105                 110

Ala Lys Gln Leu His Lys Glu Gly His Leu Phe Tyr Cys Thr Cys Arg
            115                 120                 125

Val Leu Thr Cys Pro Gly Gln Ala Lys Ser Ile Ala Ser Ala Pro Gly
        130                 135                 140

Lys Cys Gln Asp Ser Ala Ala Leu Thr Ser Thr Ala Phe Ser Gly Leu
145                 150                 155                 160

Asp Phe Gly Leu Leu Ser Gly Tyr Leu His Lys Gln Ala Leu Val Thr
                165                 170                 175

Ala Thr His Pro Thr Cys Thr Leu Leu Phe Pro Ser Cys His Ala Phe
            180                 185                 190

Phe Pro Leu Pro Leu Thr Pro Thr Leu Tyr Lys Met His Lys Gly Trp
        195                 200                 205

Lys Asn Tyr Cys Ser Gln Lys Ser Leu Asn Glu Ala Ser Met Asp Glu
    210                 215                 220

Tyr Leu Gly Ser Leu Gly Leu Phe Arg Lys Leu Thr Ala Lys Asp Ala
225                 230                 235                 240
```

-continued

Ser Cys Leu Phe Arg Ala Ile Ser Glu Gln Leu Phe Cys Ser Gln Val
            245                 250                 255
His His Leu Glu Ile Arg Lys Ala Cys Val Ser Tyr Met Arg Glu Asn
        260                 265                 270
Gln Gln Thr Phe Glu Ser Tyr Val Glu Gly Ser Phe Glu Lys Tyr Leu
        275                 280                 285
Glu Arg Leu Gly Asp Pro Lys Glu Ser Ala Gly Gln Leu Glu Ile Arg
        290                 295                 300
Ala Leu Ser Leu Ile Tyr Asn Arg Asp Phe Ile Leu Tyr Arg Phe Pro
305                 310                 315                 320
Gly Lys Pro Pro Thr Tyr Val Thr Asp Asn Gly Tyr Glu Asp Lys Ile
                325                 330                 335
Leu Leu Cys Tyr Ser Ser Ser Gly His Tyr Asp Ser Val Tyr Ser Lys
                340                 345                 350
Gln Phe Gln Ser Ser Ala Ala Val Cys Gln Ala Val Leu Tyr Glu Ile
            355                 360                 365
Leu Tyr Lys Asp Val Phe Val Val Asp Glu Glu Leu Lys Thr Ala
            370                 375                 380
Ile Lys Leu Phe Arg Ser Gly Ser Lys Asn Arg Asn Asn Ala Val
385                 390                 395                 400
Thr Gly Ser Glu Asp Ala His Thr Asp Tyr Lys Ser Ser Asn Gln Asn
                405                 410                 415
Arg Met Glu Glu Trp Gly Ala Cys Tyr Asn Ala Glu Asn Ile Pro Glu
            420                 425                 430
Gly Tyr Asn Lys Gly Thr Glu Thr Lys Ser Pro Glu Asn Pro Ser
            435                 440                 445
Lys Met Pro Phe Pro Tyr Lys Val Leu Lys Ala Leu Asp Pro Glu Ile
        450                 455                 460
Tyr Arg Asn Val Glu Phe Asp Val Trp Leu Asp Ser Arg Lys Glu Leu
465                 470                 475                 480
Gln Lys Ser Asp Tyr Met Glu Tyr Ala Gly Arg Gln Tyr Tyr Leu Gly
                485                 490                 495
Asp Lys Cys Gln Val Cys Leu Glu Ser Glu Gly Arg Tyr Tyr Asn Ala
                500                 505                 510
His Ile Gln Glu Val Gly Asn Glu Asn Asn Ser Val Thr Val Phe Ile
            515                 520                 525
Glu Glu Leu Ala Glu Lys His Val Val Pro Leu Ala Asn Leu Lys Pro
            530                 535                 540
Val Thr Gln Val Met Ser Val Pro Ala Trp Asn Ala Met Pro Ser Arg
545                 550                 555                 560
Lys Gly Arg Gly Tyr Gln Lys Met Pro Gly Gly Tyr Val Pro Glu Ile
                565                 570                 575
Val Ile Ser Glu Met Asp Ile Lys Gln Gln Lys Lys Met Phe Lys Lys
            580                 585                 590
Ile Arg Gly Lys Glu Val Tyr Met Thr Met Ala Tyr Gly Lys Gly Asp
            595                 600                 605
Pro Leu Leu Pro Pro Arg Leu Gln His Ser Met His Tyr Gly His Asp
        610                 615                 620
Pro Pro Met His Tyr Ser Gln Thr Ala Gly Asn Val Met Ser Asn Glu
625                 630                 635                 640
His Phe His Pro Gln His Pro Ser Pro Arg Gln Gly Arg Gly Tyr Gly
                645                 650                 655
Met Pro Arg Asn Ser Ser Arg Phe Ile Asn Arg His Asn Met Pro Gly

-continued

```
                660                 665                 670
Pro Lys Val Asp Phe Tyr Pro Gly Pro Gly Lys Arg Cys Cys Gln Ser
            675                 680                 685

Tyr Asp Asn Phe Ser Tyr Arg Ser Arg Ser Phe Arg Arg Ser His Arg
        690                 695                 700

Gln Met Ser Cys Val Asn Lys Glu Ser Gln Tyr Gly Phe Thr Pro Gly
705                 710                 715                 720

Asn Gly Gln Met Pro Arg Gly Leu Glu Glu Thr Ile Thr Phe Tyr Glu
                725                 730                 735

Val Glu Glu Gly Asp Glu Thr Ala Tyr Pro Thr Leu Pro Asn His Gly
            740                 745                 750

Gly Pro Ser Thr Met Val Pro Ala Thr Ser Gly Tyr Cys Val Gly Arg
        755                 760                 765

Arg Gly His Ser Ser Gly Lys Gln Thr Leu Asn Leu Glu Glu Gly Asn
    770                 775                 780

Gly Gln Ser Glu Asn Gly Arg Tyr His Glu Glu Tyr Leu Tyr Arg Ala
785                 790                 795                 800

Glu Pro Asp Tyr Glu Thr Ser Gly Val Tyr Ser Thr Thr Ala Ser Thr
                805                 810                 815

Ala Asn Leu Ser Leu Gln Asp Arg Lys Ser Cys Ser Met Ser Pro Gln
            820                 825                 830

Asp Thr Val Thr Ser Tyr Asn Tyr Pro Gln Lys Met Met Gly Asn Ile
        835                 840                 845

Ala Ala Val Ala Ala Ser Cys Ala Asn Asn Val Pro Ala Pro Val Leu
    850                 855                 860

Ser Asn Gly Ala Ala Asn Gln Ala Ile Ser Thr Thr Ser Val Ser
865                 870                 875                 880

Ser Gln Asn Ala Ile Gln Pro Leu Phe Val Ser Pro Thr His Gly
            885                 890                 895

Arg Pro Val Ile Ala Ser Pro Ser Tyr Pro Cys His Ser Ala Ile Pro
        900                 905                 910

His Ala Gly Ala Ser Leu Pro Pro Pro Pro Pro Pro Pro Pro Pro Pro
    915                 920                 925

Pro Pro Pro Pro Pro Pro Pro Pro Pro Pro Pro Pro Pro Pro Pro Pro
930                 935                 940

Pro Ala Leu Asp Val Gly Glu Thr Ser Asn Leu Gln Pro Pro Pro Pro
945                 950                 955                 960

Leu Pro Pro Pro Tyr Ser Cys Asp Pro Ser Gly Ser Asp Leu Pro
            965                 970                 975

Gln Asp Thr Lys Val Leu Gln Tyr Tyr Phe Asn Leu Gly Leu Gln Cys
        980                 985                 990

Tyr Tyr His Ser Tyr Trp His Ser Met Val Tyr Val Pro Gln Met Gln
    995                 1000                1005

Gln Gln Leu His Val Glu Asn Tyr Pro Val Tyr Thr Glu Pro Pro
    1010                1015                1020

Leu Val Asp Gln Thr Val Pro Gln Cys Tyr Ser Glu Val Arg Arg
    1025                1030                1035

Glu Asp Gly Ile Gln Ala Glu Ala Ser Ala Asn Asp Thr Phe Pro
    1040                1045                1050

Asn Ala Asp Ser Ser Ser Val Pro His Gly Ala Val Tyr Tyr Pro
    1055                1060                1065

Val Met Ser Asp Pro Tyr Gly Gln Pro Pro Leu Pro Gly Phe Asp
    1070                1075                1080
```

```
Ser Cys Leu Pro Val Val Pro Asp Tyr Ser Cys Val Pro Pro Trp
    1085                1090                1095

His Pro Val Gly Thr Ala Tyr Gly Gly Ser Ser Gln Ile His Gly
    1100                1105                1110

Ala Ile Asn Pro Gly Pro Ile Gly Cys Ile Ala Pro Ser Pro Pro
    1115                1120                1125

Ala Ser His Tyr Val Pro Gln Gly Met
    1130                1135

<210> SEQ ID NO 5
<211> LENGTH: 729
<212> TYPE: PRT
<213> ORGANISM: Homo sapiens

<400> SEQUENCE: 5

Met Asn Lys Gly Trp Leu Glu Leu Glu Ser Asp Pro Gly Leu Phe Thr
1               5                   10                  15

Leu Leu Val Glu Asp Phe Gly Val Lys Gly Val Gln Val Glu Glu Ile
            20                  25                  30

Tyr Asp Leu Gln Ser Lys Cys Gln Gly Pro Val Tyr Gly Phe Ile Phe
        35                  40                  45

Leu Phe Lys Trp Ile Glu Glu Arg Arg Ser Arg Arg Lys Val Ser Thr
    50                  55                  60

Leu Val Asp Asp Thr Ser Val Ile Asp Asp Ile Val Asn Asn Met
65                  70                  75                  80

Phe Phe Ala His Gln Leu Ile Pro Asn Ser Cys Ala Thr His Ala Leu
                85                  90                  95

Leu Ser Val Leu Leu Asn Cys Ser Ser Val Asp Leu Gly Pro Thr Leu
            100                 105                 110

Ser Arg Met Lys Asp Phe Thr Lys Gly Phe Ser Pro Glu Ser Lys Gly
        115                 120                 125

Tyr Ala Ile Gly Asn Ala Pro Glu Leu Ala Lys Ala His Asn Ser His
    130                 135                 140

Ala Arg Pro Glu Pro Arg His Leu Pro Glu Lys Gln Asn Gly Leu Ser
145                 150                 155                 160

Ala Val Arg Thr Met Glu Ala Phe His Phe Val Ser Tyr Val Pro Ile
                165                 170                 175

Thr Gly Arg Leu Phe Glu Leu Asp Gly Leu Lys Val Tyr Pro Ile Asp
            180                 185                 190

His Gly Pro Trp Gly Asp Glu Glu Trp Thr Asp Lys Ala Arg Arg
        195                 200                 205

Val Ile Met Glu Arg Ile Gly Leu Ala Thr Ala Gly Glu Pro Tyr His
    210                 215                 220

Asp Ile Arg Phe Asn Leu Met Ala Val Val Pro Asp Arg Ile Lys
225                 230                 235                 240

Tyr Glu Ala Arg Leu His Val Leu Lys Val Asn Arg Gln Thr Val Leu
                245                 250                 255

Glu Ala Leu Gln Gln Leu Ile Arg Val Thr Gln Pro Glu Leu Ile Gln
            260                 265                 270

Thr His Lys Ser Gln Glu Ser Gln Leu Pro Glu Glu Ser Lys Ser Ala
        275                 280                 285

Ser Asn Lys Ser Pro Leu Val Leu Glu Ala Asn Arg Ala Pro Ala Ala
    290                 295                 300

Ser Glu Gly Asn His Thr Asp Gly Ala Glu Glu Ala Ala Gly Ser Cys
```

```
305                 310                 315                 320
Ala Gln Ala Pro Ser His Ser Pro Pro Asn Lys Pro Lys Leu Val Val
                325                 330                 335

Lys Pro Pro Gly Ser Ser Leu Asn Gly Val His Pro Asn Pro Thr Pro
                340                 345                 350

Ile Val Gln Arg Leu Pro Ala Phe Leu Asp Asn His Asn Tyr Ala Lys
                355                 360                 365

Ser Pro Met Gln Glu Glu Glu Asp Leu Ala Ala Gly Val Gly Arg Ser
        370                 375                 380

Arg Val Pro Val Arg Pro Pro Gln Gln Tyr Ser Asp Asp Glu Asp Asp
385                 390                 395                 400

Tyr Glu Asp Asp Glu Asp Asp Val Gln Asn Thr Asn Ser Ala Leu
                405                 410                 415

Arg Tyr Lys Gly Lys Gly Thr Gly Lys Pro Gly Ala Leu Ser Gly Ser
                420                 425                 430

Ala Asp Gly Gln Leu Ser Val Leu Gln Pro Asn Thr Ile Asn Val Leu
            435                 440                 445

Ala Glu Lys Leu Lys Glu Ser Gln Lys Asp Leu Ser Ile Pro Leu Ser
        450                 455                 460

Ile Lys Thr Ser Ser Gly Ala Gly Ser Pro Ala Val Ala Val Pro Thr
465                 470                 475                 480

His Ser Gln Pro Ser Pro Thr Pro Ser Asn Glu Ser Thr Asp Thr Ala
                485                 490                 495

Ser Glu Ile Gly Ser Ala Phe Asn Ser Pro Leu Arg Ser Pro Ile Arg
            500                 505                 510

Ser Ala Asn Pro Thr Arg Pro Ser Ser Pro Val Thr Ser His Ile Ser
        515                 520                 525

Lys Val Leu Phe Gly Glu Asp Asp Ser Leu Leu Arg Val Asp Cys Ile
        530                 535                 540

Arg Tyr Asn Arg Ala Val Arg Asp Leu Gly Pro Val Ile Ser Thr Gly
545                 550                 555                 560

Leu Leu His Leu Ala Glu Asp Gly Val Leu Ser Pro Leu Ala Leu Thr
                565                 570                 575

Glu Gly Gly Lys Gly Ser Ser Pro Ser Ile Arg Pro Ile Gln Gly Ser
            580                 585                 590

Gln Gly Ser Ser Ser Pro Val Glu Lys Glu Val Val Glu Ala Thr Asp
        595                 600                 605

Ser Arg Glu Lys Thr Gly Met Val Arg Pro Gly Glu Pro Leu Ser Gly
610                 615                 620

Glu Lys Tyr Ser Pro Lys Glu Leu Leu Ala Leu Leu Lys Cys Val Glu
625                 630                 635                 640

Ala Glu Ile Ala Asn Tyr Glu Ala Cys Leu Lys Glu Val Glu Lys
                645                 650                 655

Arg Lys Lys Phe Lys Ile Asp Asp Gln Arg Arg Thr His Asn Tyr Asp
                660                 665                 670

Glu Phe Ile Cys Thr Phe Ile Ser Met Leu Ala Gln Glu Gly Met Leu
            675                 680                 685

Ala Asn Leu Val Glu Gln Asn Ile Ser Val Arg Arg Gln Gly Val
            690                 695                 700

Ser Ile Gly Arg Leu His Lys Gln Arg Lys Pro Asp Arg Arg Lys Arg
705                 710                 715                 720

Ser Arg Pro Tyr Lys Ala Lys Arg Gln
                725
```

-continued

<210> SEQ ID NO 6
<211> LENGTH: 1802
<212> TYPE: PRT
<213> ORGANISM: Homo sapiens

<400> SEQUENCE: 6

```
Met Ala Ala Ala Pro Thr Gln Ile Glu Ala Glu Leu Tyr Tyr Leu Ile
1               5                   10                  15

Ala Arg Phe Leu Gln Ser Gly Pro Cys Asn Lys Ser Ala Gln Val Leu
            20                  25                  30

Val Gln Glu Leu Glu Glu His Gln Leu Ile Pro Arg Arg Leu Asp Trp
        35                  40                  45

Glu Gly Lys Glu His Arg Arg Ser Phe Glu Asp Leu Val Ala Ala Asn
    50                  55                  60

Ala His Ile Pro Pro Asp Tyr Leu Leu Lys Ile Cys Glu Arg Ile Gly
65                  70                  75                  80

Pro Leu Leu Asp Lys Glu Ile Pro Gln Ser Val Pro Gly Val Gln Thr
                85                  90                  95

Leu Leu Gly Val Gly Arg Gln Ser Leu Leu Arg Asp Ala Lys Asp Cys
            100                 105                 110

Lys Ser Thr Leu Trp Asn Gly Ser Ala Phe Ala Ala Leu His Arg Gly
        115                 120                 125

Arg Pro Pro Glu Leu Pro Val Asn Tyr Val Lys Pro Pro Asn Val Val
    130                 135                 140

Asn Ile Thr Ser Ala Arg Gln Leu Thr Gly Cys Ser Arg Phe Gly His
145                 150                 155                 160

Ile Phe Pro Ser Ser Ala Tyr Gln His Ile Lys Met His Lys Arg Ile
                165                 170                 175

Leu Gly His Leu Ser Ser Val Tyr Cys Val Ala Phe Asp Arg Ser Gly
            180                 185                 190

Arg Arg Ile Phe Thr Gly Ser Asp Asp Cys Leu Val Lys Ile Trp Ala
        195                 200                 205

Thr Asp Asp Gly Arg Leu Leu Ala Thr Leu Arg Gly His Ser Ala Glu
    210                 215                 220

Ile Ser Asp Met Ala Val Asn Tyr Glu Asn Thr Leu Ile Ala Ala Gly
225                 230                 235                 240

Ser Cys Asp Lys Val Val Arg Val Trp Cys Leu Arg Thr Cys Ala Pro
                245                 250                 255

Val Ala Val Leu Gln Gly His Ser Ala Ser Ile Thr Ser Ile Gln Phe
            260                 265                 270

Cys Pro Ser Thr Lys Gly Thr Asn Arg Tyr Leu Thr Ser Thr Gly Ala
        275                 280                 285

Asp Gly Thr Ile Cys Phe Trp Gln Trp His Val Lys Thr Met Lys Phe
    290                 295                 300

Arg Asp Arg Pro Val Lys Phe Thr Glu Arg Ser Arg Pro Gly Val Gln
305                 310                 315                 320

Ile Ser Cys Ser Ser Phe Ser Ser Gly Gly Met Phe Ile Thr Thr Gly
                325                 330                 335

Ser Thr Asp His Val Ile Arg Ile Tyr Tyr Leu Gly Ser Glu Val Pro
            340                 345                 350

Glu Lys Ile Ala Glu Leu Glu Ser His Thr Asp Lys Val Val Ala Val
        355                 360                 365

Gln Phe Cys Asn Asn Gly Asp Ser Leu Arg Phe Val Ser Gly Ser Arg
```

```
            370                 375                 380
Asp Gly Thr Ala Arg Ile Trp Gln Tyr Gln Gln Glu Trp Lys Ser
385                 390                 395                 400

Ile Val Leu Asp Met Ala Thr Lys Met Thr Gly Asn Asn Leu Pro Ser
                405                 410                 415

Gly Glu Asp Lys Ile Thr Lys Leu Lys Val Thr Met Val Ala Trp Asp
                420                 425                 430

Arg Tyr Asp Thr Thr Val Ile Thr Ala Val Asn Asn Phe Leu Leu Lys
            435                 440                 445

Val Trp Asn Ser Ile Thr Gly Gln Leu Leu His Thr Leu Ser Gly His
            450                 455                 460

Asp Asp Glu Val Phe Val Leu Glu Ala His Pro Phe Asp Gln Arg Ile
465                 470                 475                 480

Ile Leu Ser Ala Gly His Asp Gly Asn Ile Phe Ile Trp Asp Leu Asp
                485                 490                 495

Arg Gly Thr Lys Ile Arg Asn Tyr Phe Asn Met Ile Glu Gly Gln Gly
                500                 505                 510

His Gly Ala Val Phe Asp Cys Lys Phe Ser Pro Asp Gly Asn His Phe
                515                 520                 525

Ala Cys Thr Asp Ser His Gly His Leu Leu Leu Phe Gly Phe Gly Cys
            530                 535                 540

Ser Lys Tyr Tyr Glu Lys Ile Pro Asp Gln Met Phe Phe His Thr Asp
545                 550                 555                 560

Tyr Arg Pro Leu Ile Arg Asp Ala Asn Asn Tyr Val Leu Asp Glu Gln
                565                 570                 575

Thr Gln Gln Ala Pro His Leu Met Pro Pro Phe Leu Val Asp Val
            580                 585                 590

Asp Gly Asn Pro His Pro Thr Lys Phe Gln Arg Leu Val Pro Gly Arg
            595                 600                 605

Glu Asn Cys Lys Asp Glu Gln Leu Ile Pro Gln Leu Gly Tyr Val Ala
            610                 615                 620

Asn Gly Asp Gly Glu Val Val Glu Gln Val Ile Gly Gln Gln Thr Asn
625                 630                 635                 640

Asp Gln Asp Glu Ser Ile Leu Asp Gly Ile Ile Arg Glu Leu Gln Arg
                645                 650                 655

Glu Gln Asp Leu Arg Leu Ile Asn Glu Gly Asp Val Pro His Leu Pro
            660                 665                 670

Val Asn Arg Ala Tyr Ser Val Asn Gly Ala Leu Arg Ser Pro Asn Met
            675                 680                 685

Asp Ile Ser Ser Ser Pro Asn Ile Arg Leu Arg His Ser Ser Gln
690                 695                 700

Ile Glu Gly Val Arg Gln Met His Asn Asn Ala Pro Arg Ser Gln Met
705                 710                 715                 720

Ala Thr Glu Arg Asp Leu Met Ala Trp Ser Arg Arg Val Val Asn
            725                 730                 735

Glu Leu Asn Asn Gly Val Ser Arg Val Gln Glu Glu Cys Arg Thr Ala
                740                 745                 750

Lys Gly Asp Ile Glu Ile Ser Leu Tyr Thr Val Glu Lys Lys Lys
            755                 760                 765

Pro Ser Tyr Thr Thr Gln Arg Asn Asp Tyr Glu Pro Ser Cys Gly Arg
            770                 775                 780

Ser Leu Arg Arg Thr Gln Arg Lys Arg Gln His Thr Tyr Gln Thr Arg
785                 790                 795                 800
```

-continued

Ser Asn Ile Glu His Asn Ser Gln Ala Ser Cys Gln Asn Ser Gly Val
                805                 810                 815

Gln Glu Asp Ser Asp Ser Ser Glu Asp Glu Thr Val Gly Thr
            820                 825                 830

Ser Asp Ala Ser Val Glu Asp Pro Val Val Glu Trp Gln Ser Glu Ser
            835                 840                 845

Ser Ser Ser Asp Ser Ser Ser Glu Tyr Ser Asp Trp Thr Ala Asp Ala
            850                 855                 860

Gly Ile Asn Leu Gln Pro Pro Lys Arg Gln Thr Arg Gln Thr Thr Arg
865                 870                 875                 880

Lys Ile Cys Ser Ser Ser Asp Glu Glu Asn Leu Lys Ser Leu Glu Glu
                885                 890                 895

Arg Gln Lys Lys Pro Lys Gln Thr Arg Lys Lys Lys Gly Gly Leu Val
                900                 905                 910

Ser Ile Ala Gly Glu Pro Asn Glu Glu Trp Phe Ala Pro Gln Trp Ile
                915                 920                 925

Leu Asp Thr Ile Pro Arg Arg Ser Pro Phe Val Pro Gln Met Gly Asp
            930                 935                 940

Glu Leu Ile Tyr Phe Arg Gln Gly His Glu Ala Tyr Val Arg Ala Val
945                 950                 955                 960

Arg Lys Ser Lys Ile Tyr Ser Val Asn Leu Gln Lys Gln Pro Trp Asn
                965                 970                 975

Lys Met Asp Leu Arg Glu Gln Glu Phe Val Lys Ile Val Gly Ile Lys
                980                 985                 990

Tyr Glu Val Gly Pro Pro Thr Leu Cys Cys Leu Lys Leu Ala Phe Leu
                995                 1000                1005

Asp Pro Ile Ser Gly Lys Met Thr Gly Glu Ser Phe Ser Ile Lys
    1010                1015                1020

Tyr His Asp Met Pro Asp Val Ile Asp Phe Leu Val Leu His Gln
    1025                1030                1035

Phe Tyr Asn Glu Ala Lys Glu Arg Asn Trp Gln Ile Gly Asp Arg
    1040                1045                1050

Phe Arg Ser Ile Ile Asp Asp Ala Trp Trp Phe Gly Thr Val Glu
    1055                1060                1065

Ser Gln Gln Pro Phe Gln Pro Glu Tyr Pro Asp Ser Ser Phe Gln
    1070                1075                1080

Cys Tyr Ser Val His Trp Asp Asn Asn Glu Arg Glu Lys Met Ser
    1085                1090                1095

Pro Trp Asp Met Glu Pro Ile Pro Glu Gly Thr Ala Phe Pro Asp
    1100                1105                1110

Glu Val Gly Ala Gly Val Pro Val Ser Gln Glu Glu Leu Thr Ala
    1115                1120                1125

Leu Leu Tyr Lys Pro Gln Glu Gly Glu Trp Gly Ala His Ser Arg
    1130                1135                1140

Asp Glu Glu Cys Glu Arg Val Ile Gln Gly Ile Asn His Leu Leu
    1145                1150                1155

Ser Leu Asp Phe Ala Ser Pro Phe Ala Val Pro Val Asp Leu Ser
    1160                1165                1170

Ala Tyr Pro Leu Tyr Cys Thr Val Val Ala Tyr Pro Thr Asp Leu
    1175                1180                1185

Asn Thr Ile Arg Arg Arg Leu Glu Asn Arg Phe Tyr Arg Arg Ile
    1190                1195                1200

-continued

| | | | | | | | | | |
|---|---|---|---|---|---|---|---|---|---|
| Ser | Ala | Leu | Met | Trp | Glu | Val | Arg | Tyr | Ile | Glu | His | Asn | Ala | Arg |
| 1205 | | | | | 1210 | | | | | 1215 | | | | |
| Thr | Phe | Asn | Glu | Pro | Asp | Ser | Pro | Ile | Val | Lys | Ala | Ala | Lys | Ile |
| 1220 | | | | | 1225 | | | | | 1230 | | | | |
| Val | Thr | Asp | Val | Leu | Leu | Arg | Phe | Ile | Gly | Asp | Gln | Ser | Cys | Thr |
| 1235 | | | | | 1240 | | | | | 1245 | | | | |
| Asp | Ile | Leu | Asp | Thr | Tyr | Asn | Lys | Ile | Lys | Ala | Glu | Glu | Arg | Asn |
| 1250 | | | | | 1255 | | | | | 1260 | | | | |
| Ser | Thr | Asp | Ala | Glu | Glu | Asp | Thr | Glu | Ile | Val | Asp | Leu | Asp | Ser |
| 1265 | | | | | 1270 | | | | | 1275 | | | | |
| Asp | Gly | Pro | Gly | Thr | Ser | Ser | Gly | Arg | Arg | Val | Lys | Cys | Arg | Gly |
| 1280 | | | | | 1285 | | | | | 1290 | | | | |
| Arg | Arg | Gln | Ser | Leu | Lys | Cys | Asn | Pro | Asp | Ala | Trp | Lys | Lys | Gln |
| 1295 | | | | | 1300 | | | | | 1305 | | | | |
| Cys | Lys | Glu | Leu | Leu | Ser | Leu | Ile | Tyr | Glu | Arg | Glu | Asp | Ser | Glu |
| 1310 | | | | | 1315 | | | | | 1320 | | | | |
| Pro | Phe | Arg | Gln | Pro | Ala | Asp | Leu | Leu | Ser | Tyr | Pro | Gly | His | Gln |
| 1325 | | | | | 1330 | | | | | 1335 | | | | |
| Glu | Gln | Glu | Gly | Glu | Ser | Ser | Glu | Ser | Val | Val | Pro | Glu | Arg | Gln |
| 1340 | | | | | 1345 | | | | | 1350 | | | | |
| Gln | Asp | Ser | Ser | Leu | Ser | Glu | Asp | Tyr | Gln | Asp | Val | Ile | Asp | Thr |
| 1355 | | | | | 1360 | | | | | 1365 | | | | |
| Pro | Val | Asp | Phe | Ser | Thr | Val | Lys | Glu | Thr | Leu | Glu | Ala | Gly | Asn |
| 1370 | | | | | 1375 | | | | | 1380 | | | | |
| Tyr | Gly | Ser | Pro | Leu | Glu | Phe | Tyr | Lys | Asp | Val | Arg | Gln | Ile | Phe |
| 1385 | | | | | 1390 | | | | | 1395 | | | | |
| Asn | Asn | Ser | Lys | Ala | Tyr | Thr | Ser | Asn | Lys | Lys | Ser | Arg | Ile | Tyr |
| 1400 | | | | | 1405 | | | | | 1410 | | | | |
| Ser | Met | Met | Leu | Arg | Leu | Ser | Ala | Leu | Phe | Glu | Ser | His | Ile | Lys |
| 1415 | | | | | 1420 | | | | | 1425 | | | | |
| Asn | Ile | Ile | Ser | Glu | Tyr | Lys | Ser | Ala | Ile | Gln | Ser | Gln | Lys | Arg |
| 1430 | | | | | 1435 | | | | | 1440 | | | | |
| Arg | Arg | Pro | Arg | Tyr | Arg | Lys | Arg | Leu | Arg | Ser | Ser | Ser | Ser | Ser |
| 1445 | | | | | 1450 | | | | | 1455 | | | | |
| Leu | Ser | Ser | Ser | Gly | Ala | Pro | Ser | Pro | Lys | Gly | Lys | Gln | Lys | Gln |
| 1460 | | | | | 1465 | | | | | 1470 | | | | |
| Met | Lys | Leu | Gln | Pro | Lys | Asn | Asp | Gln | Asn | Thr | Ser | Val | Ser | His |
| 1475 | | | | | 1480 | | | | | 1485 | | | | |
| Ala | Arg | Thr | Ser | Ser | Pro | Phe | Ser | Ser | Pro | Val | Ser | Asp | Ala | Ala |
| 1490 | | | | | 1495 | | | | | 1500 | | | | |
| Glu | Gly | Leu | Ser | Leu | Tyr | Leu | Leu | Asp | Asp | Glu | Pro | Asp | Gly | Pro |
| 1505 | | | | | 1510 | | | | | 1515 | | | | |
| Phe | Ser | Ser | Ser | Ser | Phe | Gly | Gly | Tyr | Ser | Arg | Ser | Gly | Asn | Ser |
| 1520 | | | | | 1525 | | | | | 1530 | | | | |
| His | Asp | Pro | Gly | Lys | Ala | Lys | Ser | Phe | Arg | Ala | Asn | Arg | Val | Leu | Pro |
| 1535 | | | | | 1540 | | | | | 1545 | | | | |
| Val | Lys | Gln | Asp | His | Ser | Leu | Asp | Gly | Pro | Leu | Thr | Asn | Gly | Asp |
| 1550 | | | | | 1555 | | | | | 1560 | | | | |
| Gly | Arg | Glu | Pro | Arg | Thr | Gly | Ile | Lys | Arg | Lys | Leu | Leu | Ser | Ala |
| 1565 | | | | | 1570 | | | | | 1575 | | | | |
| Ser | Glu | Glu | Asp | Glu | Asn | Met | Gly | Gly | Glu | Asp | Lys | Glu | Lys | Lys |
| 1580 | | | | | 1585 | | | | | 1590 | | | | |
| Glu | Thr | Lys | Glu | Lys | Ser | His | Leu | Ser | Thr | Ser | Glu | Ser | Gly | Glu |

```
                    1595                1600                1605

Leu Gly Ser Ser Leu Ser Ser Glu Ser Thr Cys Gly Ser Asp Ser
        1610                1615                1620

Asp Ser Glu Ser Thr Ser Arg Thr Asp Gln Asp Tyr Val Asp Gly
    1625                1630                1635

Asp His Asp Tyr Ser Lys Phe Ile Gln Thr Arg Pro Lys Arg Lys
    1640                1645                1650

Leu Arg Lys Gln His Gly Asn Gly Lys Arg Asn Trp Lys Thr Arg
    1655                1660                1665

Gly Thr Gly Gly Arg Gly Arg Trp Gly Arg Trp Gly Arg Trp Ser
    1670                1675                1680

Arg Gly Gly Arg Gly Arg Gly Gly Arg Gly Arg Gly Ser Arg Gly
    1685                1690                1695

Arg Gly Gly Gly Thr Arg Gly Arg Gly Arg Gly Arg Gly Gly
    1700                1705                1710

Arg Gly Ala Ser Arg Gly Ala Thr Arg Ala Lys Arg Ala Arg Ile
    1715                1720                1725

Ala Asp Asp Glu Phe Asp Thr Met Phe Ser Gly Arg Phe Ser Arg
    1730                1735                1740

Leu Pro Arg Ile Lys Thr Arg Asn Gln Gly Arg Arg Thr Val Leu
    1745                1750                1755

Tyr Asn Asp Asp Ser Asp Asn Asp Asn Phe Val Ser Thr Glu Asp
    1760                1765                1770

Pro Leu Asn Leu Gly Thr Ser Arg Ser Gly Arg Val Arg Lys Met
    1775                1780                1785

Thr Glu Lys Ala Arg Val Ser His Leu Met Gly Trp Asn Tyr
    1790                1795                1800

<210> SEQ ID NO 7
<211> LENGTH: 1685
<212> TYPE: PRT
<213> ORGANISM: Homo sapiens

<400> SEQUENCE: 7

Met Lys Leu Arg Gly Val Ser Leu Ala Ala Gly Leu Phe Leu Leu Ala
1               5                   10                  15

Leu Ser Leu Trp Gly Gln Pro Ala Glu Ala Ala Ala Cys Tyr Gly Cys
            20                  25                  30

Ser Pro Gly Ser Lys Cys Asp Cys Ser Gly Ile Lys Gly Glu Lys Gly
        35                  40                  45

Glu Arg Gly Phe Pro Gly Leu Glu Gly His Pro Gly Leu Pro Gly Phe
    50                  55                  60

Pro Gly Pro Glu Gly Pro Pro Gly Pro Arg Gly Gln Lys Gly Asp Asp
65                  70                  75                  80

Gly Ile Pro Gly Pro Pro Gly Pro Lys Gly Ile Arg Gly Pro Pro Gly
                85                  90                  95

Leu Pro Gly Phe Pro Gly Thr Pro Gly Leu Pro Gly Met Pro Gly His
            100                 105                 110

Asp Gly Ala Pro Gly Pro Gln Gly Ile Pro Gly Cys Asn Gly Thr Lys
        115                 120                 125

Gly Glu Arg Gly Phe Pro Gly Ser Pro Gly Phe Pro Gly Leu Gln Gly
    130                 135                 140

Pro Pro Gly Pro Pro Gly Ile Pro Gly Met Lys Gly Glu Pro Gly Ser
145                 150                 155                 160
```

```
Ile Ile Met Ser Ser Leu Pro Gly Pro Lys Gly Asn Pro Gly Tyr Pro
                165                 170                 175

Gly Pro Pro Gly Ile Gln Gly Leu Pro Gly Pro Thr Gly Ile Pro Gly
            180                 185                 190

Pro Ile Gly Pro Pro Gly Pro Pro Gly Leu Met Gly Pro Pro Gly Pro
        195                 200                 205

Pro Gly Leu Pro Gly Pro Lys Gly Asn Met Gly Leu Asn Phe Gln Gly
    210                 215                 220

Pro Lys Gly Glu Lys Gly Glu Gln Gly Leu Gln Gly Pro Pro Gly Pro
225                 230                 235                 240

Pro Gly Gln Ile Ser Glu Gln Lys Arg Pro Ile Asp Val Glu Phe Gln
                245                 250                 255

Lys Gly Asp Gln Gly Leu Pro Gly Asp Arg Gly Pro Pro Gly Pro Pro
            260                 265                 270

Gly Ile Arg Gly Pro Pro Gly Pro Pro Gly Gly Glu Lys Gly Glu Lys
        275                 280                 285

Gly Glu Gln Gly Glu Pro Gly Lys Arg Gly Lys Pro Gly Lys Asp Gly
        290                 295                 300

Glu Asn Gly Gln Pro Gly Ile Pro Gly Leu Pro Gly Asp Pro Gly Tyr
305                 310                 315                 320

Pro Gly Glu Pro Gly Arg Asp Gly Glu Lys Gly Gln Lys Gly Asp Thr
                325                 330                 335

Gly Pro Pro Gly Pro Pro Gly Leu Val Ile Pro Arg Pro Gly Thr Gly
            340                 345                 350

Ile Thr Ile Gly Glu Lys Gly Asn Ile Gly Leu Pro Gly Leu Pro Gly
        355                 360                 365

Glu Lys Gly Glu Arg Gly Phe Pro Gly Ile Gln Gly Pro Pro Gly Leu
        370                 375                 380

Pro Gly Pro Pro Gly Ala Ala Val Met Gly Pro Pro Gly Pro Pro Gly
385                 390                 395                 400

Phe Pro Gly Glu Arg Gly Gln Lys Gly Asp Glu Gly Pro Pro Gly Ile
                405                 410                 415

Ser Ile Pro Gly Pro Pro Gly Leu Asp Gly Gln Pro Gly Ala Pro Gly
            420                 425                 430

Leu Pro Gly Pro Pro Gly Pro Ala Gly Pro His Ile Pro Pro Ser Asp
        435                 440                 445

Glu Ile Cys Glu Pro Gly Pro Pro Gly Pro Pro Gly Ser Pro Gly Asp
        450                 455                 460

Lys Gly Leu Gln Gly Glu Gln Gly Val Lys Gly Asp Lys Gly Asp Thr
465                 470                 475                 480

Cys Phe Asn Cys Ile Gly Thr Gly Ile Ser Gly Pro Pro Gly Gln Pro
                485                 490                 495

Gly Leu Pro Gly Leu Pro Gly Pro Gly Ser Leu Gly Phe Pro Gly
            500                 505                 510

Gln Lys Gly Glu Lys Gly Gln Ala Gly Ala Thr Gly Pro Lys Gly Leu
        515                 520                 525

Pro Gly Ile Pro Gly Ala Pro Gly Ala Pro Gly Phe Pro Gly Ser Lys
        530                 535                 540

Gly Glu Pro Gly Asp Ile Leu Thr Phe Pro Gly Met Lys Gly Asp Lys
545                 550                 555                 560

Gly Glu Leu Gly Ser Pro Gly Ala Pro Gly Leu Pro Gly Leu Pro Gly
                565                 570                 575

Thr Pro Gly Gln Asp Gly Leu Pro Gly Leu Pro Gly Pro Lys Gly Glu
```

-continued

```
                580                 585                 590
    Pro Gly Gly Ile Thr Phe Lys Gly Glu Arg Gly Pro Pro Gly Asn Pro
                    595                 600                 605

Gly Leu Pro Gly Leu Pro Gly Asn Ile Gly Pro Met Gly Pro Pro Gly
    610                 615                 620

Phe Gly Pro Pro Gly Pro Val Gly Glu Lys Gly Ile Gln Gly Val Ala
    625                 630                 635                 640

Gly Asn Pro Gly Gln Pro Gly Ile Pro Gly Lys Gly Asp Pro Gly
                    645                 650                 655

Gln Thr Ile Thr Gln Pro Gly Lys Pro Gly Leu Pro Gly Asn Pro Gly
                    660                 665                 670

Arg Asp Gly Asp Val Gly Leu Pro Gly Asp Pro Gly Leu Pro Gly Gln
                    675                 680                 685

Pro Gly Leu Pro Gly Ile Pro Gly Ser Lys Gly Glu Pro Gly Ile Pro
                    690                 695                 700

Gly Ile Gly Leu Pro Gly Pro Gly Pro Lys Gly Phe Pro Gly Ile
    705                 710                 715                 720

Pro Gly Pro Pro Gly Ala Pro Gly Thr Pro Gly Arg Ile Gly Leu Glu
                    725                 730                 735

Gly Pro Pro Gly Pro Pro Gly Phe Pro Gly Pro Lys Gly Glu Pro Gly
                    740                 745                 750

Phe Ala Leu Pro Gly Pro Pro Gly Pro Pro Gly Leu Pro Gly Phe Lys
                    755                 760                 765

Gly Ala Leu Gly Pro Lys Gly Asp Arg Gly Phe Pro Gly Pro Pro Gly
    770                 775                 780

Pro Pro Gly Arg Thr Gly Leu Asp Gly Leu Pro Gly Pro Lys Gly Asp
    785                 790                 795                 800

Val Gly Pro Asn Gly Gln Pro Gly Pro Met Gly Pro Pro Gly Leu Pro
                    805                 810                 815

Gly Ile Gly Val Gln Gly Pro Pro Gly Pro Pro Gly Ile Pro Gly Pro
                    820                 825                 830

Ile Gly Gln Pro Gly Leu His Gly Ile Pro Gly Glu Lys Gly Asp Pro
                    835                 840                 845

Gly Pro Pro Gly Leu Asp Val Pro Gly Pro Pro Gly Glu Arg Gly Ser
    850                 855                 860

Pro Gly Ile Pro Gly Ala Pro Gly Pro Ile Gly Pro Pro Gly Ser Pro
    865                 870                 875                 880

Gly Leu Pro Gly Lys Ala Gly Ala Ser Gly Phe Pro Gly Thr Lys Gly
                    885                 890                 895

Glu Met Gly Met Met Gly Pro Pro Gly Pro Pro Gly Pro Leu Gly Ile
                    900                 905                 910

Pro Gly Arg Ser Gly Val Pro Gly Leu Lys Gly Asp Asp Gly Leu Gln
                    915                 920                 925

Gly Gln Pro Gly Leu Pro Gly Pro Thr Gly Glu Lys Gly Ser Lys Gly
                    930                 935                 940

Glu Pro Gly Leu Pro Gly Pro Pro Gly Pro Met Asp Pro Asn Leu Leu
    945                 950                 955                 960

Gly Ser Lys Gly Glu Lys Gly Glu Pro Gly Leu Pro Gly Ile Pro Gly
                    965                 970                 975

Val Ser Gly Pro Lys Gly Tyr Gln Gly Leu Pro Gly Asp Pro Gly Gln
                    980                 985                 990

Pro Gly Leu Ser Gly Gln Pro Gly  Leu Pro Gly Pro  Gly Pro Lys
                    995                 1000                1005
```

```
Gly Asn Pro Gly Leu Pro Gly Gln Pro Gly Leu Ile Gly Pro Pro
    1010            1015                1020

Gly Leu Lys Gly Thr Ile Gly Asp Met Gly Phe Pro Gly Pro Gln
    1025            1030                1035

Gly Val Glu Gly Pro Pro Gly Pro Ser Gly Val Pro Gly Gln Pro
    1040            1045                1050

Gly Ser Pro Gly Leu Pro Gly Gln Lys Gly Asp Lys Gly Asp Pro
    1055            1060                1065

Gly Ile Ser Ser Ile Gly Leu Pro Gly Leu Pro Gly Pro Lys Gly
    1070            1075                1080

Glu Pro Gly Leu Pro Gly Tyr Pro Gly Asn Pro Gly Ile Lys Gly
    1085            1090                1095

Ser Val Gly Asp Pro Gly Leu Pro Gly Leu Pro Gly Thr Pro Gly
    1100            1105                1110

Ala Lys Gly Gln Pro Gly Leu Pro Gly Phe Pro Gly Thr Pro Gly
    1115            1120                1125

Pro Pro Gly Pro Lys Gly Ile Ser Gly Pro Pro Gly Asn Pro Gly
    1130            1135                1140

Leu Pro Gly Glu Pro Gly Pro Val Gly Gly Gly His Pro Gly
    1145            1150                1155

Gln Pro Gly Pro Pro Gly Glu Lys Gly Lys Pro Gly Gln Asp Gly
    1160            1165                1170

Ile Pro Gly Pro Ala Gly Gln Lys Gly Glu Pro Gly Gln Pro Gly
    1175            1180                1185

Phe Gly Asn Pro Gly Pro Pro Gly Leu Pro Gly Leu Ser Gly Gln
    1190            1195                1200

Lys Gly Asp Gly Gly Leu Pro Gly Ile Pro Gly Asn Pro Gly Leu
    1205            1210                1215

Pro Gly Pro Lys Gly Glu Pro Gly Phe His Gly Phe Pro Gly Val
    1220            1225                1230

Gln Gly Pro Pro Gly Pro Pro Gly Ser Pro Gly Pro Ala Leu Glu
    1235            1240                1245

Gly Pro Lys Gly Asn Pro Gly Pro Gln Gly Pro Pro Gly Arg Pro
    1250            1255                1260

Gly Leu Pro Gly Pro Glu Gly Pro Pro Gly Leu Pro Gly Asn Gly
    1265            1270                1275

Gly Ile Lys Gly Glu Lys Gly Asn Pro Gly Gln Pro Gly Leu Pro
    1280            1285                1290

Gly Leu Pro Gly Leu Lys Gly Asp Gln Gly Pro Pro Gly Leu Gln
    1295            1300                1305

Gly Asn Pro Gly Arg Pro Gly Leu Asn Gly Met Lys Gly Asp Pro
    1310            1315                1320

Gly Leu Pro Gly Val Pro Gly Phe Pro Gly Met Lys Gly Pro Ser
    1325            1330                1335

Gly Val Pro Gly Ser Ala Gly Pro Glu Gly Glu Pro Gly Leu Ile
    1340            1345                1350

Gly Pro Pro Gly Pro Pro Gly Leu Pro Gly Pro Ser Gly Gln Ser
    1355            1360                1365

Ile Ile Ile Lys Gly Asp Ala Gly Pro Pro Gly Ile Pro Gly Gln
    1370            1375                1380

Pro Gly Leu Lys Gly Leu Pro Gly Pro Gln Gly Pro Gln Gly Leu
    1385            1390                1395
```

Pro Gly Pro Thr Gly Pro Pro Gly Asp Pro Gly Arg Asn Gly Leu
    1400                1405                1410

Pro Gly Phe Asp Gly Ala Gly Gly Arg Lys Gly Asp Pro Gly Leu
    1415                1420                1425

Pro Gly Gln Pro Gly Thr Arg Gly Leu Asp Gly Pro Pro Gly Pro
    1430                1435                1440

Asp Gly Leu Gln Gly Pro Pro Gly Pro Pro Gly Thr Ser Ser Val
    1445                1450                1455

Ala His Gly Phe Leu Ile Thr Arg His Ser Gln Thr Thr Asp Ala
    1460                1465                1470

Pro Gln Cys Pro Gln Gly Thr Leu Gln Val Tyr Glu Gly Phe Ser
    1475                1480                1485

Leu Leu Tyr Val Gln Gly Asn Lys Arg Ala His Gly Gln Asp Leu
    1490                1495                1500

Gly Thr Ala Gly Ser Cys Leu Arg Arg Phe Ser Thr Met Pro Phe
    1505                1510                1515

Met Phe Cys Asn Ile Asn Asn Val Cys Asn Phe Ala Ser Arg Asn
    1520                1525                1530

Asp Tyr Ser Tyr Trp Leu Ser Thr Pro Glu Pro Met Pro Met Ser
    1535                1540                1545

Met Gln Pro Leu Lys Gly Gln Ser Ile Gln Pro Phe Ile Ser Arg
    1550                1555                1560

Cys Ala Val Cys Glu Ala Pro Ala Val Val Ile Ala Val His Ser
    1565                1570                1575

Gln Thr Ile Gln Ile Pro His Cys Pro Gln Gly Trp Asp Ser Leu
    1580                1585                1590

Trp Ile Gly Tyr Ser Phe Met Met His Thr Ser Ala Gly Ala Glu
    1595                1600                1605

Gly Ser Gly Gln Ala Leu Ala Ser Pro Gly Ser Cys Leu Glu Glu
    1610                1615                1620

Phe Arg Ser Ala Pro Phe Ile Glu Cys His Gly Arg Gly Thr Cys
    1625                1630                1635

Asn Tyr Tyr Ala Asn Ser Tyr Ser Phe Trp Leu Ala Thr Val Asp
    1640                1645                1650

Val Ser Asp Met Phe Ser Lys Pro Gln Ser Glu Thr Leu Lys Ala
    1655                1660                1665

Gly Asp Leu Arg Thr Arg Ile Ser Arg Cys Gln Val Cys Met Lys
    1670                1675                1680

Arg Thr
    1685

<210> SEQ ID NO 8
<211> LENGTH: 561
<212> TYPE: PRT
<213> ORGANISM: Homo sapiens

<400> SEQUENCE: 8

Met Ala Phe Pro Leu Glu Glu Ala Gly Arg Ile Lys Asp Cys Trp
1               5                   10                  15

Asp Asn Gln Glu Ala Pro Ala Leu Ser Thr Cys Ser Asn Ala Asn Ile
                20                  25                  30

Phe Arg Arg Ile Asn Ala Ile Leu Asp Asn Ser Leu Asp Phe Ser Arg
        35                  40                  45

Val Cys Thr Thr Pro Ile Asn Arg Gly Ile His Asp His Leu Pro Asp
    50                  55                  60

```
Phe Gln Asp Ser Glu Glu Thr Val Thr Ser Arg Met Leu Phe Pro Thr
 65                  70                  75                  80

Ser Ala Gln Glu Ser Ser Arg Gly Leu Pro Asp Ala Asn Asp Leu Cys
                 85                  90                  95

Leu Gly Leu Gln Ser Leu Ser Leu Thr Gly Trp Asp Arg Pro Trp Ser
            100                 105                 110

Thr Gln Asp Ser Asp Ser Ser Ala Gln Ser Ser Thr His Ser Val Leu
            115                 120                 125

Ser Met Leu His Asn Pro Leu Gly Asn Val Leu Gly Lys Pro Pro Leu
            130                 135                 140

Ser Phe Leu Pro Leu Asp Pro Leu Gly Ser Asp Leu Val Asp Lys Phe
145                 150                 155                 160

Pro Ala Pro Ser Val Arg Gly Ser Arg Leu Asp Thr Arg Pro Ile Leu
                165                 170                 175

Asp Ser Arg Ser Ser Ser Pro Ser Asp Ser Asp Thr Ser Gly Phe Ser
            180                 185                 190

Ser Gly Ser Asp His Leu Ser Asp Leu Ile Ser Ser Leu Arg Ile Ser
            195                 200                 205

Pro Pro Leu Pro Phe Leu Ser Leu Ser Gly Gly Pro Arg Asp Pro
210                 215                 220

Leu Lys Met Gly Val Gly Ser Arg Met Asp Gln Glu Gln Ala Ala Leu
225                 230                 235                 240

Ala Ala Val Thr Pro Ser Pro Thr Ser Ala Ser Lys Arg Trp Pro Gly
                245                 250                 255

Ala Ser Val Trp Pro Ser Trp Asp Leu Leu Glu Ala Pro Lys Asp Pro
                260                 265                 270

Phe Ser Ile Glu Arg Glu Ala Arg Leu His Arg Gln Ala Ala Ala Val
            275                 280                 285

Asn Glu Ala Thr Cys Thr Trp Ser Gly Gln Leu Pro Pro Arg Asn Tyr
            290                 295                 300

Lys Asn Pro Ile Tyr Ser Cys Lys Val Phe Leu Gly Val Pro Trp
305                 310                 315                 320

Asp Ile Thr Glu Ala Gly Leu Val Asn Thr Phe Arg Val Phe Gly Ser
                325                 330                 335

Leu Ser Val Glu Trp Pro Gly Lys Asp Gly Lys His Pro Arg Cys Pro
            340                 345                 350

Pro Lys Gly Tyr Val Tyr Leu Val Phe Glu Leu Glu Lys Ser Val Arg
            355                 360                 365

Ser Leu Leu Gln Ala Cys Ser His Asp Pro Leu Ser Pro Asp Gly Leu
            370                 375                 380

Ser Glu Tyr Tyr Phe Lys Met Ser Ser Arg Arg Met Arg Cys Lys Glu
385                 390                 395                 400

Val Gln Val Ile Pro Trp Val Leu Ala Asp Ser Asn Phe Val Arg Ser
                405                 410                 415

Pro Ser Gln Arg Leu Asp Pro Ser Arg Thr Val Phe Val Gly Ala Leu
            420                 425                 430

His Gly Met Leu Asn Ala Glu Ala Leu Ala Ala Ile Leu Asn Asp Leu
            435                 440                 445

Phe Gly Gly Val Val Tyr Ala Gly Ile Asp Thr Asp Lys His Lys Tyr
            450                 455                 460

Pro Ile Gly Ser Gly Arg Val Thr Phe Asn Asn Gln Arg Ser Tyr Leu
465                 470                 475                 480
```

-continued

```
Lys Ala Val Ser Ala Ala Phe Val Glu Ile Lys Thr Thr Lys Phe Thr
                485                 490                 495
Lys Lys Val Gln Ile Asp Pro Tyr Leu Glu Asp Ser Leu Cys His Ile
            500                 505                 510
Cys Ser Ser Gln Pro Gly Pro Phe Phe Cys Arg Asp Gln Val Cys Phe
            515                 520                 525
Lys Tyr Phe Cys Arg Ser Cys Trp His Trp Arg His Ser Met Glu Gly
            530                 535                 540
Leu Arg His His Ser Pro Leu Met Arg Asn Gln Lys Asn Arg Asp Ser
545                 550                 555                 560
Ser

<210> SEQ ID NO 9
<211> LENGTH: 1255
<212> TYPE: PRT
<213> ORGANISM: Homo sapiens

<400> SEQUENCE: 9

Met Glu Leu Ala Ala Leu Cys Arg Trp Gly Leu Leu Leu Ala Leu Leu
1               5                   10                  15
Pro Pro Gly Ala Ala Ser Thr Gln Val Cys Thr Gly Thr Asp Met Lys
            20                  25                  30
Leu Arg Leu Pro Ala Ser Pro Glu Thr His Leu Asp Met Leu Arg His
        35                  40                  45
Leu Tyr Gln Gly Cys Gln Val Val Gln Gly Asn Leu Glu Leu Thr Tyr
    50                  55                  60
Leu Pro Thr Asn Ala Ser Leu Ser Phe Leu Gln Asp Ile Gln Glu Val
65                  70                  75                  80
Gln Gly Tyr Val Leu Ile Ala His Asn Gln Val Arg Gln Val Pro Leu
                85                  90                  95
Gln Arg Leu Arg Ile Val Arg Gly Thr Gln Leu Phe Glu Asp Asn Tyr
            100                 105                 110
Ala Leu Ala Val Leu Asp Asn Gly Asp Pro Leu Asn Asn Thr Thr Pro
        115                 120                 125
Val Thr Gly Ala Ser Pro Gly Gly Leu Arg Glu Leu Gln Leu Arg Ser
    130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
        195                 200                 205
Ser Glu Asp Cys Gln Ser Leu Thr Arg Thr Val Cys Ala Gly Gly Cys
    210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
        275                 280                 285
```

```
Tyr Thr Phe Gly Ala Ser Cys Val Thr Ala Cys Pro Tyr Asn Tyr Leu
290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
        355                 360                 365
Lys Ile Phe Gly Ser Leu Ala Phe Leu Pro Glu Ser Phe Asp Gly Asp
370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
        675                 680                 685
Arg Leu Leu Gln Glu Thr Glu Leu Val Glu Pro Leu Thr Pro Ser Gly
690                 695                 700
Ala Met Pro Asn Gln Ala Gln Met Arg Ile Leu Lys Glu Thr Glu Leu
```

```
            705                 710                 715                 720
        Arg Lys Val Lys Val Leu Gly Ser Gly Ala Phe Gly Thr Val Tyr Lys
                        725                 730                 735
        Gly Ile Trp Ile Pro Asp Gly Glu Asn Val Lys Ile Pro Val Ala Ile
                        740                 745                 750
        Lys Val Leu Arg Glu Asn Thr Ser Pro Lys Ala Asn Lys Glu Ile Leu
                        755                 760                 765
        Asp Glu Ala Tyr Val Met Ala Gly Val Gly Ser Pro Tyr Val Ser Arg
                        770                 775                 780
        Leu Leu Gly Ile Cys Leu Thr Ser Thr Val Gln Leu Val Thr Gln Leu
        785                 790                 795                 800
        Met Pro Tyr Gly Cys Leu Leu Asp His Val Arg Glu Asn Arg Gly Arg
                        805                 810                 815
        Leu Gly Ser Gln Asp Leu Leu Asn Trp Cys Met Gln Ile Ala Lys Gly
                        820                 825                 830
        Met Ser Tyr Leu Glu Asp Val Arg Leu Val His Arg Asp Leu Ala Ala
                        835                 840                 845
        Arg Asn Val Leu Val Lys Ser Pro Asn His Val Lys Ile Thr Asp Phe
        850                 855                 860
        Gly Leu Ala Arg Leu Leu Asp Ile Asp Glu Thr Glu Tyr His Ala Asp
        865                 870                 875                 880
        Gly Gly Lys Val Pro Ile Lys Trp Met Ala Leu Glu Ser Ile Leu Arg
                        885                 890                 895
        Arg Arg Phe Thr His Gln Ser Asp Val Trp Ser Tyr Gly Val Thr Val
                        900                 905                 910
        Trp Glu Leu Met Thr Phe Gly Ala Lys Pro Tyr Asp Gly Ile Pro Ala
                        915                 920                 925
        Arg Glu Ile Pro Asp Leu Leu Glu Lys Gly Glu Arg Leu Pro Gln Pro
                        930                 935                 940
        Pro Ile Cys Thr Ile Asp Val Tyr Met Ile Met Val Lys Cys Trp Met
        945                 950                 955                 960
        Ile Asp Ser Glu Cys Arg Pro Arg Phe Arg Glu Leu Val Ser Glu Phe
                        965                 970                 975
        Ser Arg Met Ala Arg Asp Pro Gln Arg Phe Val Val Ile Gln Asn Glu
                        980                 985                 990
        Asp Leu Gly Pro Ala Ser Pro Leu  Asp Ser Thr Phe Tyr  Arg Ser Leu
                        995                1000               1005
        Leu Glu Asp Asp Asp Met Gly  Asp Leu Val Asp Ala   Glu Glu Tyr
        1010                1015               1020
        Leu Val  Pro Gln Gln Gly  Phe  Phe Cys Pro Asp   Ala Pro Gly
        1025                1030               1035
        Ala Gly  Gly Met Val His  His  Arg His Arg Ser  Ser Thr Arg
            1040                1045               1050
        Ser Gly  Gly Gly Asp Leu  Thr  Leu Gly Leu Glu Pro  Ser Glu Glu
                 1055                1060               1065
        Glu Ala  Pro Arg Ser Pro  Leu  Ala Pro Ser Glu Gly  Ala Gly Ser
                 1070                1075               1080
        Asp Val  Phe Asp Gly Asp  Leu  Gly Met Gly Ala Ala  Lys Gly Leu
                 1085                1090               1095
        Gln Ser  Leu Pro Thr His  Asp  Pro Ser Pro Leu Gln  Arg Tyr Ser
                 1100                1105               1110
        Glu Asp  Pro Thr Val Pro  Leu  Pro Ser Glu Thr Asp  Gly Tyr Val
                 1115                1120               1125
```

```
Ala Pro Leu Thr Cys Ser Pro Gln Pro Glu Tyr Val Asn Gln Pro
    1130                1135                1140

Asp Val Arg Pro Gln Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 10
<211> LENGTH: 854
<212> TYPE: PRT
<213> ORGANISM: Homo sapiens

<400> SEQUENCE: 10

Met Pro Pro Cys Ser Gly Gly Asp Gly Ser Thr Pro Pro Gly Pro Ser
1               5                   10                  15

Leu Arg Asp Arg Asp Cys Pro Ala Gln Ser Ala Glu Tyr Pro Arg Asp
                20                  25                  30

Arg Leu Asp Pro Arg Pro Gly Ser Pro Ser Glu Ala Ser Ser Pro Pro
            35                  40                  45

Phe Leu Arg Ser Arg Ala Pro Val Asn Trp Tyr Gln Glu Lys Ala Gln
    50                  55                  60

Val Phe Leu Trp His Leu Met Val Ser Gly Ser Thr Thr Leu Leu Cys
65                  70                  75                  80

Leu Trp Lys Gln Pro Phe His Val Ser Ala Phe Pro Val Thr Ala Ser
                85                  90                  95

Leu Ala Phe Arg Gln Ser Gln Gly Ala Gly Gln His Leu Tyr Lys Asp
                100                 105                 110

Leu Gln Pro Phe Ile Leu Leu Arg Leu Leu Met Pro Glu Glu Thr Gln
            115                 120                 125

Thr Gln Asp Gln Pro Met Glu Glu Glu Val Glu Thr Phe Ala Phe
    130                 135                 140

Gln Ala Glu Ile Ala Gln Leu Met Ser Leu Ile Ile Asn Thr Phe Tyr
145                 150                 155                 160

Ser Asn Lys Glu Ile Phe Leu Arg Glu Leu Ile Ser Asn Ser Ser Asp
                165                 170                 175

Ala Leu Asp Lys Ile Arg Tyr Glu Ser Leu Thr Asp Pro Ser Lys Leu
                180                 185                 190

Asp Ser Gly Lys Glu Leu His Ile Asn Leu Ile Pro Asn Lys Gln Asp
            195                 200                 205

Arg Thr Leu Thr Ile Val Asp Thr Gly Ile Gly Met Thr Lys Ala Asp
    210                 215                 220

Leu Ile Asn Asn Leu Gly Thr Ile Ala Lys Ser Gly Thr Lys Ala Phe
```

```
            225                 230                 235                 240
        Met Glu Ala Leu Gln Ala Gly Ala Asp Ile Ser Met Ile Gly Gln Phe
                        245                 250                 255
        Gly Val Gly Phe Tyr Ser Ala Tyr Leu Val Ala Glu Lys Val Thr Val
                        260                 265                 270
        Ile Thr Lys His Asn Asp Asp Glu Gln Tyr Ala Trp Glu Ser Ser Ala
                        275                 280                 285
        Gly Gly Ser Phe Thr Val Arg Thr Asp Thr Gly Glu Pro Met Gly Arg
                        290                 295                 300
        Gly Thr Lys Val Ile Leu His Leu Lys Glu Asp Gln Thr Glu Tyr Leu
        305                 310                 315                 320
        Glu Glu Arg Arg Ile Lys Glu Ile Val Lys Lys His Ser Gln Phe Ile
                        325                 330                 335
        Gly Tyr Pro Ile Thr Leu Phe Val Glu Lys Glu Arg Asp Lys Glu Val
                        340                 345                 350
        Ser Asp Asp Glu Ala Glu Glu Lys Glu Asp Lys Glu Glu Glu Lys Glu
                        355                 360                 365
        Lys Glu Glu Lys Glu Ser Glu Asp Lys Pro Glu Ile Glu Asp Val Gly
                        370                 375                 380
        Ser Asp Glu Glu Glu Glu Lys Lys Asp Gly Asp Lys Lys Lys Lys Lys
        385                 390                 395                 400
        Lys Ile Lys Glu Lys Tyr Ile Asp Gln Glu Glu Leu Asn Lys Thr Lys
                        405                 410                 415
        Pro Ile Trp Thr Arg Asn Pro Asp Asp Ile Thr Asn Glu Glu Tyr Gly
                        420                 425                 430
        Glu Phe Tyr Lys Ser Leu Thr Asn Asp Trp Glu Asp His Leu Ala Val
                        435                 440                 445
        Lys His Phe Ser Val Glu Gly Gln Leu Glu Phe Arg Ala Leu Leu Phe
                        450                 455                 460
        Val Pro Arg Arg Ala Pro Phe Asp Leu Phe Glu Asn Arg Lys Lys Lys
        465                 470                 475                 480
        Asn Asn Ile Lys Leu Tyr Val Arg Arg Val Phe Ile Met Asp Asn Cys
                        485                 490                 495
        Glu Glu Leu Ile Pro Glu Tyr Leu Asn Phe Ile Arg Gly Val Val Asp
                        500                 505                 510
        Ser Glu Asp Leu Pro Leu Asn Ile Ser Arg Glu Met Leu Gln Gln Ser
                        515                 520                 525
        Lys Ile Leu Lys Val Ile Arg Lys Asn Leu Val Lys Lys Cys Leu Glu
                        530                 535                 540
        Leu Phe Thr Glu Leu Ala Glu Asp Lys Glu Asn Tyr Lys Lys Phe Tyr
        545                 550                 555                 560
        Glu Gln Phe Ser Lys Asn Ile Lys Leu Gly Ile His Glu Asp Ser Gln
                        565                 570                 575
        Asn Arg Lys Lys Leu Ser Glu Leu Leu Arg Tyr Tyr Thr Ser Ala Ser
                        580                 585                 590
        Gly Asp Glu Met Val Ser Leu Lys Asp Tyr Cys Thr Arg Met Lys Glu
                        595                 600                 605
        Asn Gln Lys His Ile Tyr Tyr Ile Thr Gly Glu Thr Lys Asp Gln Val
                        610                 615                 620
        Ala Asn Ser Ala Phe Val Glu Arg Leu Arg Lys His Gly Leu Glu Val
        625                 630                 635                 640
        Ile Tyr Met Ile Glu Pro Ile Asp Glu Tyr Cys Val Gln Gln Leu Lys
                        645                 650                 655
```

-continued

```
Glu Phe Glu Gly Lys Thr Leu Val Ser Val Thr Lys Glu Gly Leu Glu
            660                 665                 670

Leu Pro Glu Asp Glu Glu Lys Lys Gln Glu Lys Lys Thr
            675                 680                 685

Lys Phe Glu Asn Leu Cys Lys Ile Met Lys Asp Ile Leu Glu Lys Lys
            690                 695                 700

Val Glu Lys Val Val Ser Asn Arg Leu Val Thr Ser Pro Cys Cys
705                 710                 715                 720

Ile Val Thr Ser Thr Tyr Gly Trp Thr Ala Asn Met Glu Arg Ile Met
                725                 730                 735

Lys Ala Gln Ala Leu Arg Asp Asn Ser Thr Met Gly Tyr Met Ala Ala
            740                 745                 750

Lys Lys His Leu Glu Ile Asn Pro Asp His Ser Ile Ile Glu Thr Leu
            755                 760                 765

Arg Gln Lys Ala Glu Ala Asp Lys Asn Asp Lys Ser Val Lys Asp Leu
            770                 775                 780

Val Ile Leu Leu Tyr Glu Thr Ala Leu Leu Ser Ser Gly Phe Ser Leu
785                 790                 795                 800

Glu Asp Pro Gln Thr His Ala Asn Arg Ile Tyr Arg Met Ile Lys Leu
            805                 810                 815

Gly Leu Gly Ile Asp Glu Asp Pro Thr Ala Asp Asp Thr Ser Ala
            820                 825                 830

Ala Val Thr Glu Glu Met Pro Pro Leu Glu Gly Asp Asp Asp Thr Ser
            835                 840                 845

Arg Met Glu Glu Val Asp
    850

<210> SEQ ID NO 11
<211> LENGTH: 712
<212> TYPE: PRT
<213> ORGANISM: Homo sapiens

<400> SEQUENCE: 11

Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
                20                  25                  30

Val Met Asp Ala Leu Glu Pro Ala Asp Trp Cys Gln Phe Ala Ala Leu
            35                  40                  45

Ile Val Arg Asp Gln Thr Glu Leu Arg Leu Cys Glu Arg Ser Gly Gln
        50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Ala Pro Leu Ser Pro Gly
            100                 105                 110

Thr Thr Ala Pro Arg Pro Ser Ser Ile Pro Ala Pro Ala Glu Ala Glu
            115                 120                 125

Ala Trp Ser Pro Arg Lys Leu Pro Ser Ala Ser Thr Phe Leu Ser
        130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
```

```
                165                 170                 175
Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
            195                 200                 205

Thr His Asn Phe Ser Glu Glu Leu Lys Ile Gly Gly Gly Phe Gly
            210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
                260                 265                 270

Asp Phe Ala Gly Tyr Cys Ala Gln Asn Gly Phe Tyr Cys Leu Val Tyr
            275                 280                 285

Gly Phe Leu Pro Asn Gly Ser Leu Glu Asp Arg Leu His Cys Gln Thr
            290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
                325                 330                 335

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
            355                 360                 365

Gly Ser Ser Pro Ser Gln Ser Ser Met Val Ala Arg Thr Gln Thr Val
            370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Val Leu Glu
                405                 410                 415

Thr Leu Ala Gly Gln Arg Ala Val Lys Thr His Gly Ala Arg Thr Lys
            420                 425                 430

Tyr Leu Lys Asp Leu Val Glu Glu Ala Glu Ala Gly Val Ala
            435                 440                 445

Leu Arg Ser Thr Gln Ser Thr Leu Gln Ala Gly Leu Ala Ala Asp Ala
            450                 455                 460

Trp Ala Ala Pro Ile Ala Met Gln Ile Tyr Lys Lys His Leu Asp Pro
465                 470                 475                 480

Arg Pro Gly Pro Cys Pro Pro Glu Leu Gly Leu Gly Leu Gly Gln Leu
            485                 490                 495

Ala Cys Cys Cys Leu His Arg Arg Ala Lys Arg Pro Pro Met Thr
            500                 505                 510

Gln Val Tyr Glu Arg Leu Glu Lys Leu Gln Ala Val Val Ala Gly Val
            515                 520                 525

Pro Gly His Ser Glu Ala Ala Ser Cys Ile Pro Pro Ser Pro Gln Glu
            530                 535                 540

Asn Ser Tyr Val Ser Ser Thr Gly Arg Ala His Ser Gly Ala Ala Pro
545                 550                 555                 560

Trp Gln Pro Leu Ala Ala Pro Ser Gly Ala Ser Ala Gln Ala Ala Glu
                565                 570                 575

Gln Leu Gln Arg Gly Pro Asn Gln Pro Val Glu Ser Asp Glu Ser Leu
            580                 585                 590
```

```
Gly Gly Leu Ser Ala Ala Leu Arg Ser Trp His Leu Thr Pro Ser Cys
            595                 600                 605

Pro Leu Asp Pro Ala Pro Leu Arg Glu Ala Gly Cys Pro Gln Gly Asp
    610                 615                 620

Thr Ala Gly Glu Ser Ser Trp Gly Ser Gly Pro Gly Ser Arg Pro Thr
625                 630                 635                 640

Ala Val Glu Gly Leu Ala Leu Gly Ser Ser Ala Ser Ser Ser Ser Glu
                645                 650                 655

Pro Pro Gln Ile Ile Ile Asn Pro Ala Arg Gln Lys Met Val Gln Lys
            660                 665                 670

Leu Ala Leu Tyr Glu Asp Gly Ala Leu Asp Ser Leu Gln Leu Leu Ser
            675                 680                 685

Ser Ser Ser Leu Pro Gly Leu Gly Leu Glu Gln Asp Arg Gln Gly Pro
            690                 695                 700

Glu Glu Ser Asp Glu Phe Gln Ser
705                 710

<210> SEQ ID NO 12
<211> LENGTH: 1560
<212> TYPE: PRT
<213> ORGANISM: Homo sapiens

<400> SEQUENCE: 12

Met Glu Pro Gly Ser Asp Asp Phe Leu Pro Pro Glu Cys Pro Val
1               5                   10                  15

Phe Glu Pro Ser Trp Ala Glu Phe Arg Asp Pro Leu Gly Tyr Ile Ala
                20                  25                  30

Lys Ile Arg Pro Ile Ala Glu Lys Ser Gly Ile Cys Lys Ile Arg Pro
            35                  40                  45

Pro Ala Asp Trp Gln Pro Pro Phe Ala Val Glu Val Asp Asn Phe Arg
    50                  55                  60

Phe Thr Pro Arg Ile Gln Arg Leu Asn Glu Leu Glu Ala Gln Thr Arg
65                  70                  75                  80

Val Lys Leu Asn Tyr Leu Asp Gln Ile Ala Lys Phe Trp Glu Ile Gln
                85                  90                  95

Gly Ser Ser Leu Lys Ile Pro Asn Val Glu Arg Arg Ile Leu Asp Leu
            100                 105                 110

Tyr Ser Leu Ser Lys Ile Val Val Glu Glu Gly Gly Tyr Glu Ala Ile
            115                 120                 125

Cys Lys Asp Arg Arg Trp Ala Arg Val Ala Gln Arg Leu Asn Tyr Pro
    130                 135                 140

Pro Gly Lys Asn Ile Gly Ser Leu Leu Arg Ser His Tyr Glu Arg Ile
145                 150                 155                 160

Val Tyr Pro Tyr Glu Met Tyr Gln Ser Gly Ala Asn Leu Val Gln Cys
                165                 170                 175

Asn Thr Arg Pro Phe Asp Asn Glu Glu Lys Asp Lys Glu Tyr Lys Pro
            180                 185                 190

His Ser Ile Pro Leu Arg Gln Ser Val Gln Pro Ser Lys Phe Asn Ser
    195                 200                 205

Tyr Gly Arg Arg Ala Lys Arg Leu Gln Pro Asp Pro Glu Pro Thr Glu
    210                 215                 220

Glu Asp Ile Glu Lys Asn Pro Glu Leu Lys Lys Leu Gln Ile Tyr Gly
225                 230                 235                 240

Ala Gly Pro Lys Met Met Gly Leu Gly Leu Met Ala Lys Asp Lys Thr
```

```
                     245                 250                 255
Leu Arg Lys Lys Asp Lys Glu Gly Pro Glu Cys Pro Thr Val Val
            260                 265                 270

Val Lys Glu Glu Leu Gly Gly Asp Val Lys Val Glu Ser Thr Ser Pro
            275                 280                 285

Lys Thr Phe Leu Glu Ser Lys Glu Glu Leu Ser His Ser Pro Glu Pro
            290                 295                 300

Cys Thr Lys Met Thr Met Arg Leu Arg Arg Asn His Ser Asn Ala Gln
305                 310                 315                 320

Phe Ile Glu Ser Tyr Val Cys Arg Met Cys Ser Arg Gly Asp Glu Asp
                    325                 330                 335

Asp Lys Leu Leu Leu Cys Asp Gly Cys Asp Asp Asn Tyr His Ile Phe
            340                 345                 350

Cys Leu Leu Pro Pro Leu Pro Glu Ile Pro Lys Gly Val Trp Arg Cys
            355                 360                 365

Pro Lys Cys Val Met Ala Glu Cys Lys Arg Pro Pro Glu Ala Phe Gly
            370                 375                 380

Phe Glu Gln Ala Thr Arg Glu Tyr Thr Leu Gln Ser Phe Gly Glu Met
385                 390                 395                 400

Ala Asp Ser Phe Lys Ala Asp Tyr Phe Asn Met Pro Val His Met Val
                    405                 410                 415

Pro Thr Glu Leu Val Glu Lys Glu Phe Trp Arg Leu Val Asn Ser Ile
            420                 425                 430

Glu Glu Asp Val Thr Val Glu Tyr Gly Ala Asp Ile His Ser Lys Glu
            435                 440                 445

Phe Gly Ser Gly Phe Pro Val Ser Asp Ser Lys Arg His Leu Thr Pro
450                 455                 460

Glu Glu Glu Glu Tyr Ala Thr Ser Gly Trp Asn Leu Asn Val Met Pro
465                 470                 475                 480

Val Leu Glu Gln Ser Val Leu Cys His Ile Asn Ala Asp Ile Ser Gly
                    485                 490                 495

Met Lys Val Pro Trp Leu Tyr Val Gly Met Val Phe Ser Ala Phe Cys
            500                 505                 510

Trp His Ile Glu Asp His Trp Ser Tyr Ser Ile Asn Tyr Leu His Trp
            515                 520                 525

Gly Glu Pro Lys Thr Trp Tyr Gly Val Pro Ser Leu Ala Ala Glu His
            530                 535                 540

Leu Glu Glu Val Met Lys Lys Leu Thr Pro Glu Leu Phe Asp Ser Gln
545                 550                 555                 560

Pro Asp Leu Leu His Gln Leu Val Thr Leu Met Asn Pro Asn Thr Leu
                    565                 570                 575

Met Ser His Gly Val Pro Val Val Arg Thr Asn Gln Cys Ala Gly Glu
            580                 585                 590

Phe Val Ile Thr Phe Pro Arg Ala Tyr His Ser Gly Phe Asn Gln Gly
            595                 600                 605

Tyr Asn Phe Ala Glu Ala Val Asn Phe Cys Thr Ala Asp Trp Leu Pro
            610                 615                 620

Ala Gly Arg Gln Cys Ile Glu His Tyr Arg Arg Leu Arg Arg Tyr Cys
625                 630                 635                 640

Val Phe Ser His Glu Glu Leu Ile Cys Lys Met Ala Ala Cys Pro Glu
                    645                 650                 655

Lys Leu Asp Leu Asn Leu Ala Ala Ala Val His Lys Glu Met Phe Ile
            660                 665                 670
```

```
Met Val Gln Glu Glu Arg Arg Leu Arg Lys Ala Leu Leu Glu Lys Gly
        675                 680                 685

Ile Thr Glu Ala Glu Arg Glu Ala Phe Glu Leu Leu Pro Asp Asp Glu
        690                 695                 700

Arg Gln Cys Ile Lys Cys Lys Thr Thr Cys Phe Leu Ser Ala Leu Ala
705                 710                 715                 720

Cys Tyr Asp Cys Pro Asp Gly Leu Val Cys Leu Ser His Ile Asn Asp
                725                 730                 735

Leu Cys Lys Cys Ser Ser Arg Gln Tyr Leu Arg Tyr Arg Tyr Thr
                740                 745                 750

Leu Asp Glu Leu Pro Ala Met Leu His Lys Leu Lys Val Arg Ala Glu
        755                 760                 765

Ser Phe Asp Thr Trp Ala Asn Lys Val Arg Val Ala Leu Glu Val Glu
770                 775                 780

Asp Gly Arg Lys Arg Ser Leu Glu Glu Leu Arg Ala Leu Glu Ser Glu
785                 790                 795                 800

Ala Arg Glu Arg Arg Phe Pro Asn Ser Glu Leu Leu Gln Gln Leu Lys
                805                 810                 815

Asn Cys Leu Ser Glu Ala Glu Ala Cys Val Ser Arg Ala Leu Gly Leu
                820                 825                 830

Val Ser Gly Gln Glu Ala Gly Pro His Arg Val Ala Gly Leu Gln Met
        835                 840                 845

Thr Leu Thr Glu Leu Arg Ala Phe Leu Asp Gln Met Asn Asn Leu Pro
850                 855                 860

Cys Ala Met His Gln Ile Gly Asp Val Lys Gly Val Leu Glu Gln Val
865                 870                 875                 880

Glu Ala Tyr Gln Ala Glu Ala Arg Glu Ala Leu Ala Ser Leu Pro Ser
                885                 890                 895

Ser Pro Gly Leu Leu Gln Ser Leu Leu Glu Arg Gly Arg Gln Leu Gly
                900                 905                 910

Val Glu Val Pro Glu Ala Gln Gln Leu Gln Arg Gln Val Glu Gln Ala
        915                 920                 925

Arg Trp Leu Asp Glu Val Lys Arg Thr Leu Ala Pro Ser Ala Arg Arg
        930                 935                 940

Gly Thr Leu Ala Val Met Arg Gly Leu Leu Val Ala Gly Ala Ser Val
945                 950                 955                 960

Ala Pro Ser Pro Ala Val Asp Lys Ala Gln Ala Glu Leu Gln Glu Leu
                965                 970                 975

Leu Thr Ile Ala Glu Arg Trp Glu Glu Lys Ala His Leu Cys Leu Glu
                980                 985                 990

Ala Arg Gln Lys His Pro Pro Ala Thr Leu Glu Ala Ile Ile Arg Glu
                995                 1000                1005

Ala Glu Asn Ile Pro Val His Leu Pro Asn Ile Gln Ala Leu Lys
        1010                1015                1020

Glu Ala Leu Ala Lys Ala Arg Ala Trp Ile Ala Asp Val Asp Glu
        1025                1030                1035

Ile Gln Asn Gly Asp His Tyr Pro Cys Leu Asp Asp Leu Glu Gly
        1040                1045                1050

Leu Val Ala Val Gly Arg Asp Leu Pro Val Gly Leu Glu Glu Leu
        1055                1060                1065

Arg Gln Leu Glu Leu Gln Val Leu Thr Ala His Ser Trp Arg Glu
        1070                1075                1080
```

```
Lys Ala Ser Lys Thr Phe Leu Lys Lys Asn Ser Cys Tyr Thr Leu
    1085                1090                1095

Leu Glu Val Leu Cys Pro Cys Ala Asp Ala Gly Ser Asp Ser Thr
    1100                1105                1110

Lys Arg Ser Arg Trp Met Glu Lys Glu Leu Gly Leu Tyr Lys Ser
    1115                1120                1125

Asp Thr Glu Leu Leu Gly Leu Ser Ala Gln Asp Leu Arg Asp Pro
    1130                1135                1140

Gly Ser Val Ile Val Ala Phe Lys Glu Gly Glu Gln Lys Glu Lys
    1145                1150                1155

Glu Gly Ile Leu Gln Leu Arg Arg Thr Asn Ser Ala Lys Pro Ser
    1160                1165                1170

Pro Leu Ala Ser Ser Thr Ala Ser Ser Thr Thr Ser Ile Cys
    1175                1180                1185

Val Cys Gly Gln Val Leu Ala Gly Ala Gly Ala Leu Gln Cys Asp
    1190                1195                1200

Leu Cys Gln Asp Trp Phe His Gly Arg Cys Val Ser Val Pro Arg
    1205                1210                1215

Leu Leu Ser Ser Pro Arg Pro Asn Pro Thr Ser Ser Pro Leu Leu
    1220                1225                1230

Ala Trp Trp Glu Trp Asp Thr Lys Phe Leu Cys Pro Leu Cys Met
    1235                1240                1245

Arg Ser Arg Arg Pro Arg Leu Glu Thr Ile Leu Ala Leu Leu Val
    1250                1255                1260

Ala Leu Gln Arg Leu Pro Val Arg Leu Pro Glu Gly Glu Ala Leu
    1265                1270                1275

Gln Cys Leu Thr Glu Arg Ala Ile Ser Trp Gln Gly Arg Ala Arg
    1280                1285                1290

Gln Ala Leu Ala Ser Glu Asp Val Thr Ala Leu Leu Gly Arg Leu
    1295                1300                1305

Ala Glu Leu Arg Gln Arg Leu Gln Ala Glu Pro Arg Pro Glu Glu
    1310                1315                1320

Pro Pro Asn Tyr Pro Ala Ala Pro Ala Ser Asp Pro Leu Arg Glu
    1325                1330                1335

Gly Ser Gly Lys Asp Met Pro Lys Val Gln Gly Leu Leu Glu Asn
    1340                1345                1350

Gly Asp Ser Val Thr Ser Pro Glu Lys Val Ala Pro Glu Glu Gly
    1355                1360                1365

Ser Gly Lys Arg Asp Leu Glu Leu Leu Ser Ser Leu Leu Pro Gln
    1370                1375                1380

Leu Thr Gly Pro Val Leu Glu Leu Pro Glu Ala Thr Arg Ala Pro
    1385                1390                1395

Leu Glu Glu Leu Met Met Glu Gly Asp Leu Leu Glu Val Thr Leu
    1400                1405                1410

Asp Glu Asn His Ser Ile Trp Gln Leu Leu Gln Ala Gly Gln Pro
    1415                1420                1425

Pro Asp Leu Glu Arg Ile Arg Thr Leu Leu Glu Leu Glu Lys Ala
    1430                1435                1440

Glu Arg His Gly Ser Arg Ala Arg Gly Arg Ala Leu Glu Arg Arg
    1445                1450                1455

Arg Arg Arg Lys Val Asp Arg Gly Gly Glu Gly Asp Asp Pro Ala
    1460                1465                1470

Arg Glu Glu Leu Glu Pro Lys Arg Val Arg Ser Ser Gly Pro Glu
```

```
                1475                1480                1485

Ala Glu Glu Val Gln Glu Glu Glu Leu Glu Glu Thr Gly
        1490                1495                1500

Gly Glu Gly Pro Pro Ala Pro Ile Pro Thr Thr Gly Ser Pro Ser
            1505                1510                1515

Thr Gln Glu Asn Gln Asn Gly Leu Glu Pro Ala Glu Gly Thr Thr
        1520                1525                1530

Ser Gly Pro Ser Ala Pro Phe Ser Thr Leu Thr Pro Arg Leu His
    1535                1540                1545

Leu Pro Cys Pro Gln Gln Pro Pro Gln Gln Gln Leu
    1550                1555                1560

<210> SEQ ID NO 13
<211> LENGTH: 1401
<212> TYPE: PRT
<213> ORGANISM: Homo sapiens

<400> SEQUENCE: 13

Met Lys Ser Cys Gly Val Ser Leu Ala Thr Ala Ala Ala Ala Ala
1               5                   10                  15

Ala Phe Gly Asp Glu Lys Lys Met Ala Ala Gly Lys Ala Ser Gly
            20                  25                  30

Glu Ser Glu Glu Ala Ser Pro Ser Leu Thr Ala Glu Glu Arg Glu Ala
        35                  40                  45

Leu Gly Gly Leu Asp Ser Arg Leu Phe Gly Phe Val Arg Phe His Glu
    50                  55                  60

Asp Gly Ala Arg Thr Lys Ala Leu Leu Gly Lys Ala Val Arg Cys Tyr
65                  70                  75                  80

Glu Ser Leu Ile Leu Lys Ala Glu Gly Lys Val Glu Ser Asp Phe Phe
                85                  90                  95

Cys Gln Leu Gly His Phe Asn Leu Leu Leu Glu Asp Tyr Pro Lys Ala
            100                 105                 110

Leu Ser Ala Tyr Gln Arg Tyr Tyr Ser Leu Gln Ser Asp Tyr Trp Lys
        115                 120                 125

Asn Ala Ala Phe Leu Tyr Gly Leu Gly Leu Val Tyr Phe His Tyr Asn
    130                 135                 140

Ala Phe Gln Trp Ala Ile Lys Ala Phe Gln Glu Val Leu Tyr Val Asp
145                 150                 155                 160

Pro Ser Phe Cys Arg Ala Lys Glu Ile His Leu Arg Leu Gly Leu Met
                165                 170                 175

Phe Lys Val Asn Thr Asp Tyr Glu Ser Ser Leu Lys His Phe Gln Leu
            180                 185                 190

Ala Leu Val Asp Cys Asn Pro Cys Thr Leu Ser Asn Ala Glu Ile Gln
        195                 200                 205

Phe His Ile Ala His Leu Tyr Glu Thr Gln Arg Lys Tyr His Ser Ala
    210                 215                 220

Lys Glu Ala Tyr Glu Gln Leu Leu Gln Thr Glu Asn Leu Ser Ala Gln
225                 230                 235                 240

Val Lys Ala Thr Val Leu Gln Gln Leu Gly Trp Met His His Thr Val
                245                 250                 255

Asp Leu Leu Gly Asp Lys Ala Thr Lys Glu Ser Tyr Ala Ile Gln Tyr
            260                 265                 270

Leu Gln Lys Ser Leu Glu Ala Asp Pro Asn Ser Gly Gln Ser Trp Tyr
        275                 280                 285
```

-continued

```
Phe Leu Gly Arg Cys Tyr Ser Ser Ile Gly Lys Val Gln Asp Ala Phe
    290                 295                 300

Ile Ser Tyr Arg Gln Ser Ile Asp Lys Ser Glu Ala Ser Ala Asp Thr
305                 310                 315                 320

Trp Cys Ser Ile Gly Val Leu Tyr Gln Gln Asn Gln Pro Met Asp
                325                 330                 335

Ala Leu Gln Ala Tyr Ile Cys Ala Val Gln Leu Asp His Gly His Ala
                340                 345                 350

Ala Ala Trp Met Asp Leu Gly Thr Leu Tyr Glu Ser Cys Asn Gln Pro
            355                 360                 365

Gln Asp Ala Ile Lys Cys Tyr Leu Asn Ala Thr Arg Ser Lys Ser Cys
    370                 375                 380

Ser Asn Thr Ser Ala Leu Ala Ala Arg Ile Lys Tyr Leu Gln Ala Gln
385                 390                 395                 400

Leu Cys Asn Leu Pro Gln Gly Ser Leu Gln Asn Lys Thr Lys Leu Leu
                405                 410                 415

Pro Ser Ile Glu Glu Ala Trp Ser Leu Pro Ile Pro Ala Glu Leu Thr
                420                 425                 430

Ser Arg Gln Gly Ala Met Asn Thr Ala Gln Gln Asn Thr Ser Asp Asn
            435                 440                 445

Trp Ser Gly Gly His Ala Val Ser His Pro Val Gln Gln Gln Ala
    450                 455                 460

His Ser Trp Cys Leu Thr Pro Gln Lys Leu Gln His Leu Glu Gln Leu
465                 470                 475                 480

Arg Ala Asn Arg Asn Asn Leu Asn Pro Ala Gln Lys Leu Met Leu Glu
                485                 490                 495

Gln Leu Glu Ser Gln Phe Val Leu Met Gln Gln His Gln Met Arg Pro
            500                 505                 510

Thr Gly Val Ala Gln Val Arg Ser Thr Gly Ile Pro Asn Gly Pro Thr
    515                 520                 525

Ala Asp Ser Ser Leu Pro Thr Asn Ser Val Ser Gly Gln Gln Pro Gln
530                 535                 540

Leu Ala Leu Thr Arg Val Pro Ser Val Ser Gln Pro Gly Val Arg Pro
545                 550                 555                 560

Ala Cys Pro Gly Gln Pro Leu Ala Asn Gly Pro Phe Ser Ala Gly His
                565                 570                 575

Val Pro Cys Ser Thr Ser Arg Thr Leu Gly Ser Thr Asp Thr Ile Leu
                580                 585                 590

Ile Gly Asn Asn His Ile Thr Gly Ser Gly Ser Asn Gly Asn Val Pro
            595                 600                 605

Tyr Leu Gln Arg Asn Ala Leu Thr Leu Pro His Asn Arg Thr Asn Leu
    610                 615                 620

Thr Ser Ser Ala Glu Glu Pro Trp Lys Asn Gln Leu Ser Asn Ser Thr
625                 630                 635                 640

Gln Gly Leu His Lys Gly Gln Ser Ser His Ser Ala Gly Pro Asn Gly
                645                 650                 655

Glu Arg Pro Leu Ser Ser Thr Gly Pro Ser Gln His Leu Gln Ala Ala
                660                 665                 670

Gly Ser Gly Ile Gln Asn Gln Asn Gly His Pro Thr Leu Pro Ser Asn
            675                 680                 685

Ser Val Thr Gln Gly Ala Ala Leu Asn His Leu Ser Ser His Thr Ala
    690                 695                 700

Thr Ser Gly Gly Gln Gln Gly Ile Thr Leu Thr Lys Glu Ser Lys Pro
```

```
            705                 710                 715                 720
Ser Gly Asn Ile Leu Thr Val Pro Glu Thr Ser Arg His Thr Gly Glu
                725                 730                 735

Thr Pro Asn Ser Thr Ala Ser Val Glu Gly Leu Pro Asn His Val His
                740                 745                 750

Gln Met Thr Ala Asp Ala Val Cys Ser Pro Ser His Gly Asp Ser Lys
                755                 760                 765

Ser Pro Gly Leu Leu Ser Ser Asp Asn Pro Gln Leu Ser Ala Leu Leu
                770                 775                 780

Met Gly Lys Ala Asn Asn Asn Val Gly Thr Gly Thr Cys Asp Lys Val
785                 790                 795                 800

Asn Asn Ile His Pro Ala Val His Thr Lys Thr Asp Asn Ser Val Ala
                805                 810                 815

Ser Ser Pro Ser Ser Ala Ile Ser Thr Ala Thr Pro Ser Pro Lys Ser
                820                 825                 830

Thr Glu Gln Thr Thr Thr Asn Ser Val Thr Ser Leu Asn Ser Pro His
                835                 840                 845

Ser Gly Leu His Thr Ile Asn Gly Glu Gly Met Glu Glu Ser Gln Ser
                850                 855                 860

Pro Met Lys Thr Asp Leu Leu Leu Val Asn His Lys Pro Ser Pro Gln
865                 870                 875                 880

Ile Ile Pro Ser Met Ser Val Ser Ile Tyr Pro Ser Ser Ala Glu Val
                885                 890                 895

Leu Lys Ala Cys Arg Asn Leu Gly Lys Asn Gly Leu Ser Asn Ser Ser
                900                 905                 910

Ile Leu Leu Asp Lys Cys Pro Pro Arg Pro Pro Ser Ser Pro Tyr
                915                 920                 925

Pro Pro Leu Pro Lys Asp Lys Leu Asn Pro Pro Thr Pro Ser Ile Tyr
                930                 935                 940

Leu Glu Asn Lys Arg Asp Ala Phe Phe Pro Pro Leu His Gln Phe Cys
945                 950                 955                 960

Thr Asn Pro Asn Asn Pro Val Thr Val Ile Arg Gly Leu Ala Gly Ala
                965                 970                 975

Leu Lys Leu Asp Leu Gly Leu Phe Ser Thr Lys Thr Leu Val Glu Ala
                980                 985                 990

Asn Asn Glu His Met Val Glu Val Arg Thr Gln Leu Leu Gln Pro Ala
                995                1000                1005

Asp Glu Asn Trp Asp Pro Thr Gly Thr Lys Lys Ile Trp His Cys
                1010                1015                1020

Glu Ser Asn Arg Ser His Thr Thr Ile Ala Lys Tyr Ala Gln Tyr
                1025                1030                1035

Gln Ala Ser Ser Phe Gln Glu Ser Leu Arg Glu Glu Asn Glu Lys
                1040                1045                1050

Arg Ser His His Lys Asp His Ser Asp Ser Glu Ser Thr Ser Ser
                1055                1060                1065

Asp Asn Ser Gly Arg Arg Arg Lys Gly Pro Phe Lys Thr Ile Lys
                1070                1075                1080

Phe Gly Thr Asn Ile Asp Leu Ser Asp Asp Lys Lys Trp Lys Leu
                1085                1090                1095

Gln Leu His Glu Leu Thr Lys Leu Pro Ala Phe Val Arg Val Val
                1100                1105                1110

Ser Ala Gly Asn Leu Leu Ser His Val Gly His Thr Ile Leu Gly
                1115                1120                1125
```

Met Asn Thr Val Gln Leu Tyr Met Lys Val Pro Gly Ser Arg Thr
1130                1135                1140

Pro Gly His Gln Glu Asn Asn Phe Cys Ser Val Asn Ile Asn
    1145                1150                1155

Ile Gly Pro Gly Asp Cys Glu Trp Phe Val Pro Glu Gly Tyr
1160                1165                1170

Trp Gly Val Leu Asn Asp Phe Cys Glu Lys Asn Leu Asn Phe
1175                1180                1185

Leu Met Gly Ser Trp Trp Pro Asn Leu Glu Asp Leu Tyr Glu Ala
1190                1195                1200

Asn Val Pro Val Tyr Arg Phe Ile Gln Arg Pro Gly Asp Leu Val
1205                1210                1215

Trp Ile Asn Ala Gly Thr Val His Trp Val Gln Ala Ile Gly Trp
1220                1225                1230

Cys Asn Asn Ile Ala Trp Asn Val Gly Pro Leu Thr Ala Cys Gln
1235                1240                1245

Tyr Lys Leu Ala Val Glu Arg Tyr Glu Trp Asn Lys Leu Gln Ser
1250                1255                1260

Val Lys Ser Ile Val Pro Met Val His Leu Ser Trp Asn Met Ala
1265                1270                1275

Arg Asn Ile Lys Val Ser Asp Pro Lys Leu Phe Glu Met Ile Lys
1280                1285                1290

Tyr Cys Leu Leu Arg Thr Leu Lys Gln Cys Gln Thr Leu Arg Glu
1295                1300                1305

Ala Leu Ile Ala Ala Gly Lys Glu Ile Ile Trp His Gly Arg Thr
1310                1315                1320

Lys Glu Glu Pro Ala His Tyr Cys Ser Ile Cys Glu Val Glu Val
1325                1330                1335

Phe Asp Leu Leu Phe Val Thr Asn Glu Ser Asn Ser Arg Lys Thr
1340                1345                1350

Tyr Ile Val His Cys Gln Asp Cys Ala Arg Lys Thr Ser Gly Asn
1355                1360                1365

Leu Glu Asn Phe Val Val Leu Glu Gln Tyr Lys Met Glu Asp Leu
1370                1375                1380

Met Gln Val Tyr Asp Gln Phe Thr Leu Ala Pro Pro Leu Pro Ser
1385                1390                1395

Ala Ser Ser
1400

<210> SEQ ID NO 14
<211> LENGTH: 859
<212> TYPE: PRT
<213> ORGANISM: Homo sapiens

<400> SEQUENCE: 14

Met Ala Cys Arg Trp Ser Thr Lys Glu Ser Pro Arg Trp Arg Ser Ala
1               5                   10                  15

Leu Leu Leu Leu Phe Leu Ala Gly Val Tyr Gly Asn Gly Ala Leu Ala
                20                  25                  30

Glu His Ser Glu Asn Val His Ile Ser Gly Val Ser Thr Ala Cys Gly
                35                  40                  45

Glu Thr Pro Glu Gln Ile Arg Ala Pro Ser Gly Ile Ile Thr Ser Pro
            50                  55                  60

Gly Trp Pro Ser Glu Tyr Pro Ala Lys Ile Asn Cys Ser Trp Phe Ile

```
                65                  70                  75                  80
Arg Ala Asn Pro Gly Glu Ile Ile Thr Ile Ser Phe Gln Asp Phe Asp
                    85                  90                  95
Ile Gln Gly Ser Arg Arg Cys Asn Leu Asp Trp Leu Thr Ile Glu Thr
                    100                 105                 110
Tyr Lys Asn Ile Glu Ser Tyr Arg Ala Cys Gly Ser Thr Ile Pro Pro
                    115                 120                 125
Pro Tyr Ile Ser Ser Gln Asp His Ile Trp Ile Arg Phe His Ser Asp
                    130                 135                 140
Asp Asn Ile Ser Arg Lys Gly Phe Arg Leu Ala Tyr Phe Ser Gly Lys
145                 150                 155                 160
Ser Glu Glu Pro Asn Cys Ala Cys Asp Gln Phe Arg Cys Gly Asn Gly
                    165                 170                 175
Lys Cys Ile Pro Glu Ala Trp Lys Cys Asn Asn Met Asp Glu Cys Gly
                    180                 185                 190
Asp Ser Ser Asp Glu Glu Ile Cys Ala Lys Glu Ala Asn Pro Pro Thr
                    195                 200                 205
Ala Ala Ala Phe Gln Pro Cys Ala Tyr Asn Gln Phe Gln Cys Leu Ser
                    210                 215                 220
Arg Phe Thr Lys Val Tyr Thr Cys Leu Pro Glu Ser Leu Lys Cys Asp
225                 230                 235                 240
Gly Asn Ile Asp Cys Leu Asp Leu Gly Asp Glu Ile Asp Cys Asp Val
                    245                 250                 255
Pro Thr Cys Gly Gln Trp Leu Lys Tyr Phe Tyr Gly Thr Phe Asn Ser
                    260                 265                 270
Pro Asn Tyr Pro Asp Phe Tyr Pro Pro Gly Ser Asn Cys Thr Trp Leu
                    275                 280                 285
Ile Asp Thr Gly Asp His Arg Lys Val Ile Leu Arg Phe Thr Asp Phe
                    290                 295                 300
Lys Leu Asp Gly Thr Gly Tyr Gly Asp Tyr Val Lys Ile Tyr Asp Gly
305                 310                 315                 320
Leu Glu Glu Asn Pro His Lys Leu Leu Arg Val Leu Thr Ala Phe Asp
                    325                 330                 335
Ser His Ala Pro Leu Thr Val Val Ser Ser Gly Gln Ile Arg Val
                    340                 345                 350
His Phe Cys Ala Asp Lys Val Asn Ala Ala Arg Gly Phe Asn Ala Thr
                    355                 360                 365
Tyr Gln Val Asp Gly Phe Cys Leu Pro Trp Glu Ile Pro Cys Gly Gly
                    370                 375                 380
Asn Trp Gly Cys Tyr Thr Glu Gln Gln Arg Cys Asp Gly Tyr Trp His
385                 390                 395                 400
Cys Pro Asn Gly Arg Asp Glu Thr Asn Cys Thr Met Cys Gln Lys Glu
                    405                 410                 415
Glu Phe Pro Cys Ser Arg Asn Gly Val Cys Tyr Pro Arg Ser Asp Arg
                    420                 425                 430
Cys Asn Tyr Gln Asn His Cys Pro Asn Gly Ser Asp Glu Lys Asn Cys
                    435                 440                 445
Phe Phe Cys Gln Pro Gly Asn Phe His Cys Lys Asn Asn Arg Cys Val
                    450                 455                 460
Phe Glu Ser Trp Val Cys Asp Ser Gln Asp Cys Gly Asp Gly Ser
465                 470                 475                 480
Asp Glu Glu Asn Cys Pro Val Ile Val Pro Thr Arg Val Ile Thr Ala
                    485                 490                 495
```

```
Ala Val Ile Gly Ser Leu Ile Cys Gly Leu Leu Val Ile Ala Leu
            500                 505                 510

Gly Cys Thr Cys Lys Leu Tyr Ser Leu Arg Met Phe Glu Arg Ser
            515                 520                 525

Phe Glu Thr Gln Leu Ser Arg Val Glu Ala Glu Leu Leu Arg Arg Glu
530                 535                 540

Ala Pro Pro Ser Tyr Gly Gln Leu Ile Ala Gln Gly Leu Ile Pro Pro
545                 550                 555                 560

Val Glu Asp Phe Pro Val Cys Ser Pro Asn Gln Ala Ser Val Leu Glu
                565                 570                 575

Asn Leu Arg Leu Ala Val Arg Ser Gln Leu Gly Phe Thr Ser Val Arg
            580                 585                 590

Leu Pro Met Ala Gly Arg Ser Ser Asn Ile Trp Asn Arg Ile Phe Asn
            595                 600                 605

Phe Ala Arg Ser Arg His Ser Gly Ser Leu Ala Leu Val Ser Ala Asp
            610                 615                 620

Gly Asp Glu Val Val Pro Ser Gln Ser Thr Ser Arg Glu Pro Glu Arg
625                 630                 635                 640

Asn His Thr His Arg Ser Leu Phe Ser Val Glu Ser Asp Asp Thr Asp
                645                 650                 655

Thr Glu Asn Glu Arg Arg Asp Met Ala Gly Ala Ser Gly Gly Val Ala
            660                 665                 670

Ala Pro Leu Pro Gln Lys Val Pro Pro Thr Thr Ala Val Glu Ala Thr
            675                 680                 685

Val Gly Ala Cys Ala Ser Ser Ser Thr Gln Ser Thr Arg Gly Gly His
            690                 695                 700

Ala Asp Asn Gly Arg Asp Val Thr Ser Val Glu Pro Pro Ser Val Ser
705                 710                 715                 720

Pro Ala Arg His Gln Leu Thr Ser Ala Leu Ser Arg Met Thr Gln Gly
                725                 730                 735

Leu Arg Trp Val Arg Phe Thr Leu Gly Arg Ser Ser Ser Leu Ser Gln
            740                 745                 750

Asn Gln Ser Pro Leu Arg Gln Leu Asp Asn Gly Val Ser Gly Arg Glu
            755                 760                 765

Asp Asp Asp Asp Val Glu Met Leu Ile Pro Ile Ser Asp Gly Ser Ser
770                 775                 780

Asp Phe Asp Val Asn Asp Cys Ser Arg Pro Leu Leu Asp Leu Ala Ser
785                 790                 795                 800

Asp Gln Gly Gln Gly Leu Arg Gln Pro Tyr Asn Ala Thr Asn Pro Gly
                805                 810                 815

Val Arg Pro Ser Asn Arg Asp Gly Pro Cys Glu Arg Cys Gly Ile Val
            820                 825                 830

His Thr Ala Gln Ile Pro Asp Thr Cys Leu Glu Val Thr Leu Lys Asn
            835                 840                 845

Glu Thr Ser Asp Asp Glu Ala Leu Leu Leu Cys
850                 855
```

<210> SEQ ID NO 15
<211> LENGTH: 1070
<212> TYPE: PRT
<213> ORGANISM: Homo sapiens

<400> SEQUENCE: 15

Met Val Leu Asp Asp Leu Pro Asn Leu Glu Asp Ile Tyr Thr Ser Leu

```
1               5                   10                  15
Cys Ser Ser Thr Met Glu Asp Ser Glu Met Asp Phe Asp Ser Gly Leu
                20                  25                  30
Glu Asp Asp Thr Lys Ser Asp Ser Ile Leu Glu Asp Ser Thr Ile
                35                  40                  45
Phe Val Ala Phe Lys Gly Asn Ile Asp Asp Lys Asp Phe Lys Trp Lys
    50                  55                  60
Leu Asp Ala Ile Leu Lys Asn Val Pro Asn Leu Leu His Met Glu Ser
65                  70                  75                  80
Ser Lys Leu Lys Val Gln Lys Val Glu Pro Trp Asn Ser Val Arg Val
                85                  90                  95
Thr Phe Asn Ile Pro Arg Glu Ala Ala Glu Arg Leu Arg Ile Leu Ala
                100                 105                 110
Gln Ser Asn Asn Gln Leu Arg Asp Leu Gly Ile Leu Ser Val Gln
                115                 120                 125
Ile Glu Gly Glu Gly Ala Ile Asn Leu Ala Leu Ala Gln Asn Arg Ser
            130                 135                 140
Gln Asp Val Arg Met Asn Gly Pro Met Gly Ala Gly Asn Ser Val Arg
145                 150                 155                 160
Met Glu Ala Gly Phe Pro Met Ala Ser Gly Pro Gly Ile Ile Arg Met
                165                 170                 175
Asn Asn Pro Ala Thr Val Met Ile Pro Pro Gly Gly Asn Val Ser Ser
                180                 185                 190
Ser Met Met Ala Pro Gly Pro Asn Pro Glu Leu Gln Pro Arg Thr Pro
            195                 200                 205
Arg Pro Ala Ser Gln Ser Asp Ala Met Asp Pro Leu Leu Ser Gly Leu
    210                 215                 220
His Ile Gln Gln Gln Ser His Pro Ser Gly Ser Leu Ala Pro Pro His
225                 230                 235                 240
His Pro Met Gln Pro Val Ser Val Asn Arg Gln Met Asn Pro Ala Asn
                245                 250                 255
Phe Pro Gln Leu Gln Gln Gln Gln Gln Gln Gln Gln Gln Gln Gln Gln
                260                 265                 270
Gln Gln Gln Gln Gln Gln Gln Gln Gln Gln Gln Gln Leu Gln Ala
    275                 280                 285
Arg Pro Pro Gln Gln His Gln Gln Gln Pro Gln Gly Ile Arg Pro
290                 295                 300
Gln Phe Thr Ala Pro Thr Gln Val Pro Val Pro Pro Gly Trp Asn Gln
305                 310                 315                 320
Leu Pro Ser Gly Ala Leu Gln Pro Pro Ala Gln Gly Ser Leu Gly
                325                 330                 335
Thr Met Thr Ala Asn Gln Gly Trp Lys Lys Ala Pro Leu Pro Gly Pro
                340                 345                 350
Met Gln Gln Gln Leu Gln Ala Arg Pro Ser Leu Ala Thr Val Gln Thr
            355                 360                 365
Pro Ser His Pro Pro Pro Pro Tyr Pro Phe Gly Ser Gln Gln Ala Ser
    370                 375                 380
Gln Ala His Thr Asn Phe Pro Gln Met Ser Asn Pro Gly Gln Phe Thr
385                 390                 395                 400
Ala Pro Gln Met Lys Ser Leu Gln Gly Gly Pro Ser Arg Val Pro Thr
                405                 410                 415
Pro Leu Gln Gln Pro His Leu Thr Asn Lys Ser Pro Ala Ser Ser Pro
                420                 425                 430
```

```
Ser Ser Phe Gln Gln Gly Ser Pro Ala Ser Ser Pro Thr Val Asn Gln
        435                 440                 445

Thr Gln Gln Gln Met Gly Pro Arg Pro Pro Gln Asn Asn Pro Leu Pro
450                 455                 460

Gln Gly Phe Gln Gln Pro Val Ser Ser Pro Gly Arg Asn Pro Met Val
465                 470                 475                 480

Gln Gln Gly Asn Val Pro Pro Asn Phe Met Val Met Gln Gln Gln Pro
                485                 490                 495

Pro Asn Gln Gly Pro Gln Ser Leu His Pro Gly Leu Gly Gly Met Pro
                500                 505                 510

Lys Arg Leu Pro Pro Gly Phe Ser Ala Gly Gln Ala Asn Pro Asn Phe
            515                 520                 525

Met Gln Gly Gln Val Pro Ser Thr Thr Ala Thr Thr Pro Gly Asn Ser
            530                 535                 540

Gly Ala Pro Gln Leu Gln Ala Asn Gln Asn Val Gln His Ala Gly Gly
545                 550                 555                 560

Gln Gly Ala Gly Pro Pro Gln Asn Gln Met Gln Val Ser His Gly Pro
                565                 570                 575

Pro Asn Met Met Gln Pro Ser Leu Met Gly Ile His Gly Asn Met Asn
                580                 585                 590

Asn Gln Gln Ala Gly Thr Ser Gly Val Pro Gln Val Asn Leu Ser Asn
            595                 600                 605

Met Gln Gly Gln Pro Gln Gln Gly Pro Pro Ser Gln Leu Met Gly Met
            610                 615                 620

His Gln Gln Ile Val Pro Ser Gly Gln Met Val Gln Gln Gln Gly
625                 630                 635                 640

Thr Leu Asn Pro Gln Asn Pro Met Ile Leu Ser Arg Ala Gln Leu Met
                645                 650                 655

Pro Gln Gly Gln Met Met Val Asn Pro Pro Ser Gln Asn Leu Gly Pro
            660                 665                 670

Ser Pro Gln Arg Met Thr Pro Pro Lys Gln Met Leu Ser Gln Gln Gly
        675                 680                 685

Pro Gln Met Met Ala Pro His Asn Gln Met Met Gly Pro Gln Gly Gln
        690                 695                 700

Val Leu Leu Gln Gln Asn Pro Met Ile Glu Gln Ile Met Thr Asn Gln
705                 710                 715                 720

Met Gln Gly Asn Lys Gln Gln Phe Asn Thr Gln Asn Gln Ser Asn Val
                725                 730                 735

Met Pro Gly Pro Ala Gln Ile Met Arg Gly Pro Thr Pro Asn Met Gln
                740                 745                 750

Gly Asn Met Val Gln Phe Thr Gly Gln Met Ser Gly Gln Met Leu Pro
            755                 760                 765

Gln Gln Gly Pro Val Asn Asn Ser Pro Ser Gln Val Met Gly Ile Gln
        770                 775                 780

Gly Gln Val Leu Arg Pro Pro Gly Pro Ser Pro His Met Ala Gln Gln
785                 790                 795                 800

His Gly Asp Pro Ala Thr Thr Ala Asn Asn Asp Val Ser Leu Ser Gln
                805                 810                 815

Met Met Pro Asp Val Ser Ile Gln Gln Thr Asn Met Val Pro Pro His
                820                 825                 830

Val Gln Ala Met Gln Gly Asn Ser Ala Ser Gly Asn His Phe Ser Gly
            835                 840                 845
```

```
His Gly Met Ser Phe Asn Ala Pro Phe Ser Gly Ala Pro Asn Gly Asn
    850                 855                 860

Gln Met Ser Cys Gly Gln Asn Pro Gly Phe Pro Val Asn Lys Asp Val
865                 870                 875                 880

Thr Leu Thr Ser Pro Leu Leu Val Asn Leu Leu Gln Ser Asp Ile Ser
                885                 890                 895

Ala Gly His Phe Gly Val Asn Asn Lys Gln Asn Asn Thr Asn Ala Asn
            900                 905                 910

Lys Pro Lys Lys Lys Pro Pro Arg Lys Lys Lys Asn Ser Gln Gln
        915                 920                 925

Asp Leu Asn Thr Pro Asp Thr Arg Pro Ala Gly Leu Glu Glu Ala Asp
    930                 935                 940

Gln Pro Pro Leu Pro Gly Glu Gln Gly Ile Asn Leu Asp Asn Ser Gly
945                 950                 955                 960

Pro Lys Leu Pro Glu Phe Ser Asn Arg Pro Pro Ala Pro Ser Gln Asn
                965                 970                 975

Leu Val Ser Lys Glu Thr Ser Thr Thr Ala Leu Gln Ala Ser Val Ala
            980                 985                 990

Arg Pro Glu Leu Glu Val Asn Ala Ala Ile Val Ser Gly Gln Ser Ser
    995                 1000                1005

Glu Pro Lys Glu Ile Val Glu Lys Ser Lys Ile Pro Gly Arg Arg
    1010                1015                1020

Asn Ser Arg Thr Glu Glu Pro Thr Val Ala Ser Glu Ser Val Glu
    1025                1030                1035

Asn Gly His Arg Lys Arg Ser Ser Arg Pro Ala Ser Ala Ser Ser
    1040                1045                1050

Ser Thr Lys Asp Ile Thr Ser Ala Val Gln Ser Lys Arg Arg Lys
    1055                1060                1065

Ser Lys
    1070

<210> SEQ ID NO 16
<211> LENGTH: 1630
<212> TYPE: PRT
<213> ORGANISM: Homo sapiens

<400> SEQUENCE: 16

Met Pro Phe Ala Lys Arg Ile Val Glu Pro Gln Trp Leu Cys Arg Gln
1               5                   10                  15

Arg Arg Pro Ala Pro Gly Pro Ala Val Asp Ala Ser Gly Gly Ser Ala
            20                  25                  30

Glu Pro Pro Pro Leu Gln Pro Gly Arg Arg Asp Leu Asp Glu
        35                  40                  45

Val Glu Ala Pro Gly Pro Glu Pro Ala Arg Ala Val Pro Ala Pro
    50                  55                  60

Ser Gly Leu Pro Pro Pro Pro Pro Leu Pro Ala Pro Ala Asp Gln
65                  70                  75                  80

Thr Gln Pro Pro His Gly Glu Ala Ser Val Ala Gly Glu Glu Ser Thr
                85                  90                  95

Ala Gly Ile Pro Glu Ala Ala Pro Ala Ala Gly Glu Ala Ser Ser Ala
            100                 105                 110

Ala Ala Ala Ala Val Leu Leu Met Leu Asp Leu Cys Ala Val Ser
        115                 120                 125

Asn Ala Ala Leu Ala Arg Val Leu Arg Gln Leu Ser Asp Val Ala Arg
    130                 135                 140
```

```
His Ala Cys Ser Leu Phe Gln Glu Leu Glu Ser Asp Ile Gln Leu Thr
145                 150                 155                 160

His Arg Arg Val Trp Ala Leu Gln Gly Lys Leu Gly Gly Val Gln Arg
                165                 170                 175

Val Leu Ser Thr Leu Asp Pro Lys Gln Glu Ala Val Pro Val Ser Asn
            180                 185                 190

Leu Asp Ile Glu Ser Lys Leu Ser Val Tyr Tyr Arg Ala Pro Trp His
                195                 200                 205

Gln Gln Arg Asn Ile Phe Leu Pro Ala Thr Arg Pro Pro Cys Val Glu
            210                 215                 220

Glu Leu His Arg His Ala Arg Gln Ser Leu Gln Ala Leu Arg Arg Glu
225                 230                 235                 240

His Arg Ser Arg Ser Asp Arg Arg Glu Gln Arg Ala Ala Ala Pro Leu
                245                 250                 255

Ser Ile Ala Ala Pro Pro Leu Pro Ala Tyr Pro Pro Ala His Ser Gln
            260                 265                 270

Arg Arg Arg Glu Phe Lys Asp Arg His Phe Leu Thr Ser His Pro Pro
                275                 280                 285

Glu Asp Glu Asp Thr Asp Val Met Leu Gly Arg Pro Lys Asn Pro
290                 295                 300

Ile His Asn Ile Pro Ser Thr Leu Asp Lys Gln Thr Asn Trp Ser Lys
305                 310                 315                 320

Ala Leu Pro Leu Pro Thr Pro Glu Glu Lys Met Lys Gln Asp Ala Gln
                325                 330                 335

Val Ile Ser Ser Cys Ile Ile Pro Ile Asn Val Thr Gly Val Gly Phe
            340                 345                 350

Asp Arg Glu Ala Ser Ile Arg Cys Ser Leu Val His Ser Gln Ser Val
                355                 360                 365

Leu Gln Arg Arg Arg Lys Leu Arg Arg Lys Thr Ile Ser Gly Ile
    370                 375                 380

Pro Arg Arg Val Gln Gln Glu Ile Asp Ser Asp Glu Ser Pro Val Ala
385                 390                 395                 400

Arg Glu Arg Asn Val Ile Val His Thr Asn Pro Asp Pro Ser Asn Thr
                405                 410                 415

Val Asn Arg Ile Ser Gly Thr Arg Asp Ser Glu Cys Gln Thr Glu Asp
            420                 425                 430

Ile Leu Ile Ala Ala Pro Ser Arg Arg Ile Arg Ala Gln Arg Gly
                435                 440                 445

Gln Ser Ile Ala Ala Ser Leu Ser His Ser Ala Gly Asn Ile Ser Ala
    450                 455                 460

Leu Ala Asp Lys Gly Asp Thr Met Phe Thr Pro Ala Val Ser Ser Arg
465                 470                 475                 480

Thr Arg Ser Arg Ser Leu Pro Arg Glu Gly Asn Arg Gly Gly Asp Ala
                485                 490                 495

Glu Pro Lys Val Gly Ala Lys Pro Ser Ala Tyr Glu Glu Gly Glu Ser
            500                 505                 510

Phe Val Gly Asp His Glu Arg Thr Pro Asn Asp Phe Ser Glu Ala Pro
                515                 520                 525

Ser Ser Pro Ser Ala Gln Asp His Gln Pro Thr Leu Gly Leu Ala Cys
    530                 535                 540

Ser Gln His Leu His Ser Pro Gln His Lys Leu Ser Glu Arg Gly Arg
545                 550                 555                 560
```

-continued

| | | | | | | | | | | | |
|---|---|---|---|---|---|---|---|---|---|---|---|
|Ser|Arg|Leu|Ser|Arg 565|Met|Ala|Ala|Asp 570|Ser|Gly|Ser|Cys|Asp|Ile 575|Ser|

Ser Arg Leu Ser Arg Met Ala Ala Asp Ser Gly Ser Cys Asp Ile Ser
565                 570                 575

Ser Asn Ser Asp Thr Phe Gly Ser Pro Ile His Cys Ile Ser Thr Ala
    580                 585                 590

Gly Val Leu Leu Ser Ser His Met Asp Gln Lys Asp Asp His Gln Ser
        595                 600             605

Ser Ser Gly Asn Trp Ser Gly Ser Ser Ser Thr Cys Pro Ser Gln Thr
    610                 615             620

Ser Glu Thr Ile Pro Pro Ala Ala Ser Pro Pro Leu Thr Gly Ser Ser
625                 630                 635                 640

His Cys Asp Ser Glu Leu Ser Leu Asn Thr Ala Pro His Ala Asn Glu
                645                 650                 655

Asp Ala Ser Val Phe Val Thr Glu Gln Tyr Asn Asp His Leu Asp Lys
            660                 665                 670

Val Arg Gly His Arg Ala Asn Ser Phe Thr Ser Thr Val Ala Asp Leu
        675                 680                 685

Leu Asp Asp Pro Asn Asn Ser Asn Thr Ser Asp Ser Glu Trp Asn Tyr
    690                 695                 700

Leu His His His Asp Ala Ser Cys Arg Gln Asp Phe Ser Pro Glu
705                 710                 715                 720

Arg Pro Lys Ala Asp Ser Leu Gly Cys Pro Ser Phe Thr Ser Met Ala
                725                 730                 735

Thr Tyr Asp Ser Phe Leu Glu Lys Ser Pro Ser Asp Lys Ala Asp Thr
            740                 745                 750

Ser Ser His Phe Ser Val Asp Thr Glu Gly Tyr Tyr Thr Ser Met His
        755                 760                 765

Phe Asp Cys Gly Leu Lys Gly Asn Lys Ser Tyr Val Cys His Tyr Ala
    770                 775                 780

Ala Leu Gly Pro Glu Asn Gly Gln Gly Val Gly Ala Ser Pro Gly Leu
785                 790                 795                 800

Pro Asp Cys Ala Trp Gln Asp Tyr Leu Asp His Lys Arg Gln Gly Arg
                805                 810                 815

Pro Ser Ile Ser Phe Arg Lys Pro Lys Ala Lys Pro Thr Pro Pro Lys
            820                 825                 830

Arg Ser Ser Leu Arg Lys Ser Asp Gly Asn Ala Asp Ile Ser Glu
    835                 840                 845

Lys Lys Glu Pro Lys Ile Ser Ser Gly Gln His Leu Pro His Ser Ser
850                 855                 860

Arg Glu Met Lys Leu Pro Leu Asp Phe Ala Asn Thr Pro Ser Arg Met
865                 870                 875                 880

Glu Asn Ala Asn Leu Pro Thr Lys Gln Glu Pro Ser Trp Ile Asn Gln
                885                 890                 895

Ser Glu Gln Gly Ile Lys Glu Pro Gln Leu Asp Ala Ser Asp Ile Pro
            900                 905                 910

Pro Phe Lys Asp Glu Val Ala Glu Ser Thr His Tyr Ala Asp Leu Trp
        915                 920                 925

Leu Leu Asn Asp Leu Lys Thr Asn Asp Pro Tyr Arg Ser Leu Ser Asn
    930                 935                 940

Ser Ser Thr Ala Thr Gly Thr Thr Val Ile Glu Cys Ile Lys Ser Pro
945                 950                 955                 960

Glu Ser Ser Glu Ser Gln Thr Ser Gln Ser Glu Ser Arg Ala Thr Thr
                965                 970                 975

Pro Ser Leu Pro Ser Val Asp Asn Glu Phe Lys Leu Ala Ser Pro Glu

-continued

```
                980                 985                 990
Lys Leu Ala Gly Leu Ala Ser Pro Ser Ser Gly Tyr Ser Ser Gln Ser
            995                1000               1005
Glu Thr Pro Thr Ser Ser Phe Pro Thr Ala Phe Phe Ser Gly Pro
   1010               1015                1020
Leu Ser Pro Gly Gly Ser Lys Arg Lys Pro Lys Val Pro Glu Arg
   1025               1030                1035
Lys Ser Ser Leu Gln Gln Pro Ser Leu Lys Asp Gly Thr Ile Ser
   1040               1045                1050
Leu Ser Lys Asp Leu Glu Leu Pro Ile Ile Pro Pro Thr His Leu
   1055               1060                1065
Asp Leu Ser Ala Leu His Asn Val Leu Asn Lys Pro Phe His His
   1070               1075                1080
Arg His Pro Leu His Val Phe Thr His Asn Lys Gln Asn Thr Val
   1085               1090                1095
Gly Glu Thr Leu Arg Ser Asn Pro Pro Pro Ser Leu Ala Ile Thr
   1100               1105                1110
Pro Thr Ile Leu Lys Ser Val Asn Leu Arg Ser Ile Asn Lys Ser
   1115               1120                1125
Glu Glu Val Lys Gln Lys Glu Glu Asn Asn Thr Asp Leu Pro Tyr
   1130               1135                1140
Leu Glu Glu Ser Thr Leu Thr Thr Ala Ala Leu Ser Pro Ser Lys
   1145               1150                1155
Ile Arg Pro His Thr Ala Asn Lys Ser Val Ser Arg Gln Tyr Ser
   1160               1165                1170
Thr Glu Asp Thr Ile Leu Ser Phe Leu Asp Ser Ser Ala Val Glu
   1175               1180                1185
Met Gly Pro Asp Lys Leu His Leu Glu Lys Asn Ser Thr Phe Asp
   1190               1195                1200
Val Lys Asn Arg Cys Asp Pro Glu Thr Ile Thr Ser Ala Gly Ser
   1205               1210                1215
Ser Leu Leu Asp Ser Asn Val Thr Lys Asp Gln Val Arg Thr Glu
   1220               1225                1230
Thr Glu Pro Ile Pro Glu Asn Thr Pro Thr Lys Asn Cys Ala Phe
   1235               1240                1245
Pro Thr Glu Gly Phe Gln Arg Val Ser Ala Ala Arg Pro Asn Asp
   1250               1255                1260
Leu Asp Gly Lys Ile Ile Gln Tyr Gly Pro Gly Pro Asp Glu Thr
   1265               1270                1275
Leu Glu Gln Val Gln Lys Ala Pro Ser Ala Gly Leu Glu Glu Val
   1280               1285                1290
Ala Gln Pro Glu Ser Val Asp Val Ile Thr Ser Gln Ser Asp Ser
   1295               1300                1305
Pro Thr Arg Ala Thr Asp Val Ser Asn Gln Phe Lys His Gln Phe
   1310               1315                1320
Val Met Ser Arg His His Asp Lys Val Pro Gly Thr Ile Ser Tyr
   1325               1330                1335
Glu Ser Glu Ile Thr Ser Val Asn Ser Phe Pro Glu Lys Cys Ser
   1340               1345                1350
Lys Gln Glu Asn Ile Ala Ser Gly Ile Ser Ala Lys Ser Ala Ser
   1355               1360                1365
Asp Asn Ser Lys Ala Glu Glu Thr Gln Gly Asn Val Asp Glu Ala
   1370               1375                1380
```

Ser Leu Lys Glu Ser Ser Pro Ser Asp Asp Ser Ile Ile Ser Pro
    1385                1390                1395

Leu Ser Glu Asp Ser Gln Ala Glu Ala Glu Gly Val Phe Val Ser
    1400                1405                1410

Pro Asn Lys Pro Arg Thr Thr Glu Asp Leu Phe Ala Val Ile His
    1415                1420                1425

Arg Ser Lys Arg Lys Val Leu Gly Arg Lys Asp Ser Gly Asp Met
    1430                1435                1440

Ser Val Arg Ser Lys Ser Arg Ala Pro Leu Ser Ser Ser Ser Ser
    1445                1450                1455

Ser Ala Ser Ser Ile Thr Ser Pro Ser Ser Asn Val Thr Thr Pro
    1460                1465                1470

Asn Ser Gln Arg Ser Pro Gly Leu Ile Tyr Arg Asn Ala Lys Lys
    1475                1480                1485

Ser Asn Thr Ser Asn Glu Glu Phe Lys Leu Leu Leu Leu Lys Lys
    1490                1495                1500

Gly Ser Arg Ser Asp Ser Ser Tyr Arg Met Ser Ala Thr Glu Ile
    1505                1510                1515

Leu Lys Ser Pro Ile Leu Pro Lys Pro Pro Gly Glu Leu Thr Ala
    1520                1525                1530

Glu Ser Pro Gln Ser Thr Asp Asp Ala His Gln Gly Ser Gln Gly
    1535                1540                1545

Ala Glu Ala Leu Ser Pro Leu Ser Pro Cys Ser Pro Arg Val Asn
    1550                1555                1560

Ala Glu Gly Phe Ser Ser Lys Ser Phe Ala Thr Ser Ala Ser Ala
    1565                1570                1575

Arg Val Gly Arg Ser Arg Ala Pro Pro Ala Ala Ser Ser Ser Arg
    1580                1585                1590

Tyr Ser Val Arg Cys Arg Leu Tyr Asn Thr Pro Met Gln Ala Ile
    1595                1600                1605

Ser Glu Gly Glu Thr Glu Asn Ser Asp Gly Ser Pro His Asp Asp
    1610                1615                1620

Arg Ser Ser Gln Ser Ser Thr
    1625                1630

<210> SEQ ID NO 17
<211> LENGTH: 1388
<212> TYPE: PRT
<213> ORGANISM: Homo sapiens

<400> SEQUENCE: 17

Met Ser Ile Pro Leu His Ser Leu Arg Phe Asn Asn Thr Met Arg Glu
1               5                   10                  15

Glu Asn Val Glu Pro Gln Asn Lys Gln Met Ala Phe Cys Arg Pro Met
                20                  25                  30

Thr Glu Thr Arg Ala Asp Val Gln Ile Leu His Ser His Val Gln Leu
            35                  40                  45

Pro Ile Val Ser Thr Ser Ala Ser Asp Pro Gly Gly Thr Ser Thr Gln
        50                  55                  60

Leu Met Thr Ser Pro Val Phe Asp Thr Met Ser Ala Pro Leu Met Gly
65                  70                  75                  80

Val Pro Asn Ser Gly Ala Leu Ser Pro Pro Leu Met Pro Ala Ser Asp
                85                  90                  95

Ser Gly Ala Leu Ser Pro Leu Leu Met Pro Ala Ser Asp Ser Gly Ala

```
                    100                 105                 110
Leu Ser Pro Leu Leu Met Pro Ala Leu Asp Ser Gly Thr Leu Ser Pro
            115                 120                 125
Leu Leu Ser Thr Ser Glu Tyr Gly Val Met Ser Pro Gly Met Met Thr
            130                 135                 140
Ile Pro Asp Phe Gly Thr Met Ser Ala Thr Leu Met Val Ala Pro Asp
145                 150                 155                 160
Ser Ala Glu Ile Ser Pro Leu Ala Met Pro Ala Pro Ser Ser Gly Val
                165                 170                 175
Val Cys Thr Pro Ile Met Ser Thr Ser Ser Glu Ala Met Ser Thr
            180                 185                 190
Pro Leu Met Leu Ala Pro Asp Ser Gly Glu Leu Ser Pro Ile Leu Met
            195                 200                 205
Gln Asp Met Asn Pro Gly Val Met Ser Thr Gln Pro Val Pro Ala Pro
            210                 215                 220
Ser Ser Glu Ala Met Ser Pro Leu Gln Ile Thr Asp Glu Asp Thr Glu
225                 230                 235                 240
Ala Met Ser Lys Val Leu Met Thr Ala Leu Ala Ser Gly Glu Ile Ser
                245                 250                 255
Ser Leu Leu Met Ser Gly Thr Asp Ser Glu Ala Ile Ser Ser Leu Ile
            260                 265                 270
Met Ser Ala Val Ala Ser Gly Gly Thr Ser Pro Gln Pro Thr Ser Thr
            275                 280                 285
Gln Asn Ser Gly Gly Ile Pro Thr Pro Leu Met Ser Asp Leu Asp Ser
            290                 295                 300
Gly Ile Met Ser Ser Leu Leu Met Ser Ser Pro Gly Ser Glu Val Met
305                 310                 315                 320
Ser Thr Pro Leu Leu Ser Val Pro Asp Ala Gly Glu Met Ser Thr Leu
                325                 330                 335
Pro Lys Pro Ala Pro Asp Ala Glu Ala Met Ser Pro Ala Leu Met Thr
            340                 345                 350
Ala Leu Pro Ser Gly Val Met Pro Thr Gln Thr Met Pro Ala Pro Gly
            355                 360                 365
Ser Gly Ala Met Ser Pro Trp Ser Thr Gln Asn Val Asp Ser Glu Met
            370                 375                 380
Met Ser Asn Pro Pro Val Arg Ala Thr Ala Ser Gly Val Met Ser Ala
385                 390                 395                 400
Pro Pro Val Arg Ala Leu Asp Ser Gly Ala Met Ser Thr Pro Leu Met
                405                 410                 415
Gly Ala Pro Ala Ser Gly Asn Met Ser Thr Leu Gln Lys Thr Val Pro
            420                 425                 430
Ala Ser Gly Ala Met Thr Thr Ser Leu Met Thr Val Pro Ser Ser Gly
            435                 440                 445
Val Met Ser Thr Glu Gln Met Ser Ala Thr Ala Ser Arg Val Met Ser
            450                 455                 460
Ala Gln Leu Thr Met Ala Lys Thr Ser Gly Ala Met Pro Thr Gly Ser
465                 470                 475                 480
Met Lys Ala Val Ala Lys Gln Tyr Lys Arg Ala Thr Ala Ser Gly Lys
                485                 490                 495
Met Ser Thr Pro Leu Arg Arg Ala Pro Thr Ser Gly Ala Met Ser Thr
            500                 505                 510
Gln Pro Val Thr Ala Thr Ala Ser Glu Thr Met Ser Met Pro Gln Leu
            515                 520                 525
```

```
Thr Val Pro Ala Ser Gly Ser Met Ser Met Leu Gln Met Arg Ala Pro
    530                 535                 540

Val Ser Glu Ala Met Ser Met Pro Gln Met Arg Thr Met Ala Ser Gly
545                 550                 555                 560

Leu Thr Ser Ala Ala Gln Met Lys Ala Met Thr Ser Gly Ala Met Ser
                565                 570                 575

Thr Pro Leu Met Thr Ala Gln Thr Ser Gly Ser Thr Ser Thr Leu Leu
                580                 585                 590

Met Arg Asp Thr Ala Ser Gly Val Met Ser Cys Pro Gln Met Arg Ser
            595                 600                 605

Leu Ala Ser Gly Ala Leu Ser Lys Pro Leu Met Thr Pro Lys Ala Ser
            610                 615                 620

Gly Thr Met Phe Thr Glu Lys Met Thr Thr Thr Ala Ser Glu Ala Met
625                 630                 635                 640

Pro Thr Leu Leu Met Arg Asp Thr Val Ser Gly Ala Leu Ser Met Pro
                645                 650                 655

Gln Met Thr Asp Thr Ala Ser Gly Gly Leu Ser Ala Ser Leu Met Arg
                660                 665                 670

Asp Thr Ala Ser Gly Ala Met Ser Thr Ser Gln Met Thr Ala Thr Val
            675                 680                 685

Ser Gly Gly Met Ser Met Pro Leu Met Arg Ala Gln Asp Pro Gly Val
    690                 695                 700

Met Pro Ala Ser Leu Met Arg Ala Lys Val Ser Gly Lys Met Leu Ser
705                 710                 715                 720

Gln Pro Met Ser Thr Gln Asp Pro Gly Gly Met Ser Met Ser Pro Met
                725                 730                 735

Lys Ser Met Thr Ala Gly Gly Met Gln Met Asn Ser Pro Thr Ser Asp
                740                 745                 750

Val Met Ser Thr Pro Thr Val Arg Ala Trp Thr Ser Glu Thr Met Ser
            755                 760                 765

Thr Pro Leu Met Arg Thr Ser Asp Pro Gly Glu Arg Pro Ser Leu Leu
    770                 775                 780

Thr Arg Ala Ser Ser Ser Gly Glu Met Ser Leu Pro Leu Met Arg Ala
785                 790                 795                 800

Pro Ala Ser Gly Glu Ile Ala Thr Pro Leu Arg Ser Pro Ala Tyr Gly
                805                 810                 815

Ala Met Ser Ala Pro Gln Met Thr Ala Thr Ala Ser Gly Met Met Ser
                820                 825                 830

Ser Met Pro Gln Val Lys Ala Pro Ile Ser Gly Ala Met Ser Met Pro
            835                 840                 845

Leu Thr Arg Ser Thr Ala Ser Gly Gly Met Ser Met Pro Leu Met Arg
    850                 855                 860

Ala Pro Asp Ser Arg Val Thr Ser Thr Ser Gln Met Met Pro Thr Ala
865                 870                 875                 880

Ser Gly Asp Met Cys Thr Leu Pro Val Arg Ala Pro Ala Ser Gly Gly
                885                 890                 895

Val Ser Ser Pro Leu Val Arg Ala Pro Ala Ser Gly Thr Met Ser Thr
                900                 905                 910

Pro Leu Arg Arg Pro Ser Ala Cys Glu Thr Val Ser Thr Glu Leu Met
            915                 920                 925

Arg Ala Ser Ala Ser Gly His Met Ser Thr Ala Gln Thr Thr Ala Met
            930                 935                 940
```

Val Ser Gly Gly Met Ser Lys Pro Leu Met Arg Ala Pro Ala Ser Gly
945                 950                 955                 960

Thr Met Pro Met Pro Leu Met Ser Ala Met Ala Ser Gly Glu Met Ser
            965                 970                 975

Met Pro Leu Met Glu Thr Met Ala Ser Gly Ala Thr Ser Thr Leu Gln
            980                 985                 990

Thr Ser Val Ala Asn Ser Arg Ser Met Ser Leu Ser Gln Thr Thr Tyr
        995                 1000                1005

Thr Val Ser Gly Arg Met Ala Thr Ala Pro Ile Arg Ala Ser Ala
    1010                1015                1020

Ser Gly Ala Arg Ser Thr Ser Phe Met Arg Ala Ser Val Ser Gly
    1025                1030                1035

Ser Met Pro Met Pro Leu Pro Arg Ala Thr Ala Ser Gly Cys Gly
    1040                1045                1050

Met Gly Met Ser Met Pro Gln Met Thr Ala Thr Asp Ser Arg Gly
    1055                1060                1065

Met Ser Thr Pro Leu Met Arg Ala Ser Gly Pro Gly Thr Met Ser
    1070                1075                1080

Thr Pro Gln Thr Ala Phe Gly Val Met Ser Thr Pro Glu Ile Lys
    1085                1090                1095

Ala Thr Asp Ser Gly Glu Ala Ser Thr Ser His Ile Asn Ile Thr
    1100                1105                1110

Ala Ser Gly Ser Lys Pro Thr Ser His Met Thr Ala Thr Thr Pro
    1115                1120                1125

Glu Thr Ala Lys Pro Pro Pro Lys Glu Val Pro Ser Phe Gly Met
    1130                1135                1140

Leu Thr Pro Ala Leu Cys Tyr Leu Leu Glu Glu Gln Glu Ala Ala
    1145                1150                1155

Arg Gly Ser Cys Ser Val Glu Glu Met Glu Ile Asp Glu Glu
    1160                1165                1170

Lys Gln Met Lys Gly Phe Leu Asp Asp Ser Glu Arg Met Ala Phe
    1175                1180                1185

Leu Val Ser Leu His Leu Gly Ala Ala Glu Arg Trp Phe Ile Leu
    1190                1195                1200

Gln Met Glu Val Gly Glu Pro Leu Ser His Glu Asn Lys Ser Phe
    1205                1210                1215

Leu Arg Arg Ser Gln Gly Ile Tyr Asp Ser Leu Ser Glu Ile Asp
    1220                1225                1230

Ile Leu Ser Ala Val Leu Cys His Pro Lys Gln Gly Gln Lys Ser
    1235                1240                1245

Val Arg Gln Tyr Ala Thr Asp Phe Leu Leu Leu Ala Arg His Leu
    1250                1255                1260

Ser Trp Ser Asp Ala Ile Leu Arg Thr Arg Phe Leu Glu Gly Leu
    1265                1270                1275

Ser Glu Ala Val Thr Thr Lys Met Gly Arg Ile Phe Leu Lys Val
    1280                1285                1290

Ala Gly Ser Leu Lys Glu Leu Ile Asp Arg Ser Leu Tyr Thr Glu
    1295                1300                1305

Cys Gln Leu Ala Glu Glu Lys Asp Ser Pro Gly Asn Ser Ser Gln
    1310                1315                1320

Val Leu Pro Thr Ala Cys Lys Arg Asn Asn Glu Glu Ala Met Gly
    1325                1330                1335

Asn Glu Leu Ser Ser Gln Gln Gln Thr Glu Glu His Gln His Val

-continued

```
            1340                1345                1350
Ser Lys Arg Cys Tyr Tyr Leu Lys Glu His Gly Asp Pro Gln Glu
    1355                1360                1365
Gly Leu His Asp His Leu Gly Gln Ser Thr Gly His His Gln Lys
    1370                1375                1380
Ala His Thr Asn Lys
    1385

<210> SEQ ID NO 18
<211> LENGTH: 1312
<212> TYPE: PRT
<213> ORGANISM: Homo sapiens

<400> SEQUENCE: 18

Met Glu Glu Asp Glu Ser Arg Gly Lys Thr Glu Ser Gly Glu
1               5                   10                  15
Asp Arg Gly Asp Gly Pro Pro Asp Arg Asp Pro Thr Leu Ser Pro Ser
                20                  25                  30
Ala Phe Ile Leu Arg Ala Ile Gln Gln Ala Val Gly Ser Ser Leu Gln
            35                  40                  45
Gly Asp Leu Pro Asn Asp Lys Asp Gly Ser Arg Cys His Gly Leu Arg
        50                  55                  60
Trp Arg Arg Cys Arg Ser Pro Arg Ser Glu Pro Arg Ser Gln Glu Ser
65                  70                  75                  80
Gly Gly Thr Asp Thr Ala Thr Val Leu Asp Met Ala Thr Asp Ser Phe
                85                  90                  95
Leu Ala Gly Leu Val Ser Val Leu Asp Pro Pro Asp Thr Trp Val Pro
            100                 105                 110
Ser Arg Leu Asp Leu Arg Pro Gly Glu Ser Glu Asp Met Leu Glu Leu
        115                 120                 125
Val Ala Glu Val Arg Ile Gly Asp Arg Asp Pro Ile Pro Leu Pro Val
    130                 135                 140
Pro Ser Leu Leu Pro Arg Leu Arg Ala Trp Arg Thr Gly Lys Thr Val
145                 150                 155                 160
Ser Pro Gln Ser Asn Ser Ser Arg Pro Thr Cys Ala Arg His Leu Thr
                165                 170                 175
Leu Gly Thr Gly Asp Gly Gly Pro Ala Pro Pro Ala Pro Ser Ser
            180                 185                 190
Ala Ser Ser Ser Pro Ser Pro Ser Pro Ser Ser Ser Pro Ser Pro
        195                 200                 205
Pro Pro Pro Pro Pro Ala Pro Pro Ala Pro Pro Ala Pro Arg
    210                 215                 220
Phe Asp Ile Tyr Asp Pro Phe His Pro Thr Asp Glu Ala Tyr Ser Pro
225                 230                 235                 240
Pro Pro Ala Pro Glu Gln Lys Tyr Asp Pro Phe Glu Pro Thr Gly Ser
                245                 250                 255
Asn Pro Ser Ser Ser Ala Gly Thr Pro Ser Pro Glu Glu Glu Glu
            260                 265                 270
Glu Glu Glu Glu Glu Glu Glu Glu Glu Asp Glu Glu Glu Glu
        275                 280                 285
Gly Leu Ser Gln Ser Ile Ser Arg Ile Ser Glu Thr Leu Ala Gly Ile
    290                 295                 300
Tyr Asp Asp Asn Ser Leu Ser Gln Asp Phe Pro Gly Asp Glu Ser Pro
305                 310                 315                 320
```

-continued

```
Arg Pro Asp Ala Gln Pro Thr Gln Pro Thr Pro Ala Pro Gly Thr Pro
                325                 330                 335

Pro Gln Val Asp Ser Thr Arg Ala Asp Gly Ala Met Arg Arg Arg Val
            340                 345                 350

Phe Val Val Gly Thr Glu Ala Glu Ala Cys Arg Glu Gly Lys Val Ser
            355                 360                 365

Val Glu Val Val Thr Ala Gly Gly Ala Ala Leu Pro Pro Pro Leu Leu
370                 375                 380

Pro Pro Gly Asp Ser Glu Ile Glu Glu Gly Glu Ile Val Gln Pro Glu
385                 390                 395                 400

Glu Glu Pro Arg Leu Ala Leu Ser Leu Phe Arg Pro Gly Gly Arg Ala
                405                 410                 415

Ala Arg Pro Thr Pro Ala Ala Ser Ala Thr Pro Thr Ala Gln Pro Leu
            420                 425                 430

Pro Gln Pro Pro Ala Pro Arg Ala Pro Glu Gly Asp Asp Phe Leu Ser
        435                 440                 445

Leu His Ala Glu Ser Asp Gly Glu Gly Ala Leu Gln Val Asp Leu Gly
    450                 455                 460

Glu Pro Ala Pro Ala Pro Pro Ala Ala Asp Ser Arg Trp Gly Gly Leu
465                 470                 475                 480

Asp Leu Arg Arg Lys Ile Leu Thr Gln Arg Arg Glu Arg Tyr Arg Gln
                485                 490                 495

Arg Ser Pro Ser Pro Ala Pro Ala Pro Ala Pro Ala Ala Ala Ala Gly
            500                 505                 510

Pro Pro Thr Arg Lys Lys Ser Arg Arg Glu Arg Lys Arg Ser Gly Glu
            515                 520                 525

Ala Lys Glu Ala Ala Ser Ser Ser Gly Thr Gln Pro Ala Pro Pro
    530                 535                 540

Ala Pro Ala Ser Pro Trp Asp Ser Lys Lys His Arg Ser Arg Asp Arg
545                 550                 555                 560

Lys Pro Gly Ser His Ala Ser Ser Ala Arg Arg Ser Arg Ser
                565                 570                 575

Arg Ser Arg Ser Arg Ser Thr Arg Arg Arg Ser Arg Ser Thr Asp Arg
            580                 585                 590

Arg Arg Gly Gly Ser Arg Arg Ser Arg Ser Arg Glu Lys Arg Arg Arg
            595                 600                 605

Arg Arg Arg Ser Ala Ser Pro Pro Ala Thr Ser Ser Ser Ser Ser
    610                 615                 620

Ser Arg Arg Glu Arg His Arg Gly Lys His Arg Asp Gly Gly Ser
625                 630                 635                 640

Lys Lys Lys Lys Lys Arg Ser Arg Ser Arg Gly Glu Lys Arg Ser Gly
                645                 650                 655

Asp Gly Ser Glu Lys Ala Pro Ala Pro Ala Pro Pro Ser Gly Ser
            660                 665                 670

Thr Ser Cys Gly Asp Arg Asp Ser Arg Arg Arg Gly Ala Val Pro Pro
            675                 680                 685

Ser Ile Gln Asp Leu Thr Asp His Asp Leu Phe Ala Ile Lys Arg Thr
        690                 695                 700

Ile Thr Val Gly Arg Leu Asp Lys Ser Asp Pro Arg Gly Pro Ser Pro
705                 710                 715                 720

Ala Pro Ala Ser Ser Pro Lys Arg Glu Val Leu Tyr Asp Ser Glu Gly
                725                 730                 735

Leu Ser Gly Glu Glu Arg Gly Gly Lys Ser Ser Gln Lys Asp Arg Arg
```

```
                    740                 745                 750
Arg Ser Gly Ala Ala Ser Ser Ser Ser Ser Arg Glu Lys Gly Ser
                755                 760                 765
Arg Arg Lys Ala Leu Asp Gly Gly Asp Arg Arg Asp Arg Asp Arg
                770                 775                 780
Asp Arg Asp Arg Asp Arg Ser Ser Lys Lys Ala Arg Pro Pro Lys Glu
785                 790                 795                 800
Ser Ala Pro Ser Ser Gly Pro Pro Lys Pro Pro Val Ser Ser Gly
                805                 810                 815
Ser Gly Ser Ser Ser Ser Ser Ser Cys Ser Ser Arg Lys Val Lys
                820                 825                 830
Leu Gln Ser Lys Val Ala Val Leu Ile Arg Glu Gly Val Ser Ser Thr
                835                 840                 845
Thr Pro Ala Lys Asp Ala Ala Ser Ala Gly Leu Gly Ser Ile Gly Val
    850                 855                 860
Lys Phe Ser Arg Asp Arg Glu Ser Arg Ser Pro Phe Leu Lys Pro Asp
865                 870                 875                 880
Glu Arg Ala Pro Thr Glu Met Ala Lys Ala Ala Pro Gly Ser Thr Lys
                885                 890                 895
Pro Lys Lys Thr Lys Val Lys Ala Lys Ala Gly Ala Lys Lys Thr Lys
                900                 905                 910
Gly Thr Lys Gly Lys Thr Lys Pro Ser Lys Thr Arg Lys Lys Val Arg
                915                 920                 925
Ser Gly Gly Gly Ser Gly Gly Ser Gly Gly Gln Val Ser Leu Lys Lys
                930                 935                 940
Ser Lys Ala Asp Ser Cys Ser Gln Ala Ala Gly Thr Lys Gly Ala Glu
945                 950                 955                 960
Glu Thr Ser Trp Ser Gly Glu Glu Arg Ala Ala Lys Val Pro Ser Thr
                965                 970                 975
Pro Pro Pro Lys Ala Ala Pro Pro Pro Ala Leu Thr Pro Asp Ser
                980                 985                 990
Gln Thr Val Asp Ser Ser Cys Lys Thr Pro Glu Val Ser Phe Leu Pro
                995                 1000                1005
Glu Glu Ala Thr Glu Glu Ala Gly Val Arg Gly Gly Ala Glu Glu
    1010                1015                1020
Glu Glu Glu Glu Glu Glu Glu Glu Glu Glu Glu Glu Glu Glu Glu
    1025                1030                1035
Glu Gln Gln Pro Ala Thr Thr Thr Ala Thr Ser Thr Ala Ala Ala
    1040                1045                1050
Ala Pro Ser Thr Ala Pro Ser Ala Gly Ser Thr Ala Gly Asp Ser
    1055                1060                1065
Gly Ala Glu Asp Gly Pro Ala Ser Arg Val Ser Gln Leu Pro Thr
    1070                1075                1080
Leu Pro Pro Pro Met Pro Trp Asn Leu Pro Ala Gly Val Asp Cys
    1085                1090                1095
Thr Thr Ser Gly Val Leu Ala Leu Thr Ala Leu Leu Phe Lys Met
    1100                1105                1110
Glu Glu Ala Asn Leu Ala Ser Arg Ala Lys Ala Gln Glu Leu Ile
    1115                1120                1125
Gln Ala Thr Asn Gln Ile Leu Ser His Arg Lys Pro Pro Ser Ser
    1130                1135                1140
Leu Gly Met Thr Pro Ala Pro Val Pro Thr Ser Leu Gly Leu Pro
    1145                1150                1155
```

-continued

```
Pro Gly Pro Ser Ser Tyr Leu Leu Pro Gly Ser Leu Pro Leu Gly
    1160                1165                1170

Gly Cys Gly Ser Thr Pro Pro Thr Pro Thr Gly Leu Ala Ala Thr
    1175                1180                1185

Ser Asp Lys Arg Glu Gly Ser Ser Ser Glu Gly Arg Gly Asp
    1190                1195                1200

Thr Asp Lys Tyr Leu Lys Lys Leu His Thr Gln Glu Arg Ala Val
    1205                1210                1215

Glu Glu Val Lys Leu Ala Ile Lys Pro Tyr Tyr Gln Lys Lys Asp
    1220                1225                1230

Ile Thr Lys Glu Glu Tyr Lys Asp Ile Leu Arg Lys Ala Val His
    1235                1240                1245

Lys Ile Cys His Ser Lys Ser Gly Glu Ile Asn Pro Val Lys Val
    1250                1255                1260

Ser Asn Leu Val Arg Ala Tyr Val Gln Arg Tyr Arg Tyr Phe Arg
    1265                1270                1275

Lys His Gly Arg Lys Pro Gly Asp Pro Gly Pro Pro Arg Pro
    1280                1285                1290

Pro Lys Glu Pro Gly Pro Pro Asp Lys Gly Gly Pro Gly Leu Pro
    1295                1300                1305

Leu Pro Pro Leu
    1310

<210> SEQ ID NO 19
<211> LENGTH: 1336
<212> TYPE: PRT
<213> ORGANISM: Homo sapiens

<400> SEQUENCE: 19

Met Glu Asn Leu Pro Ala Val Thr Thr Glu Glu Pro Thr Pro Met Gly
1               5                   10                  15

Arg Gly Pro Val Gly Pro Ser Gly Gly Gly Ser Thr Arg Asp Gln Val
                20                  25                  30

Arg Thr Val Val Met Arg Pro Ser Val Ser Trp Glu Lys Ala Gly Pro
            35                  40                  45

Glu Glu Ala Lys Ala Pro Val Arg Gly Asp Glu Ala Pro Pro Ala Arg
        50                  55                  60

Val Ala Gly Pro Ala Ala Gly Thr Pro Pro Cys Gln Met Gly Val Tyr
65                  70                  75                  80

Pro Thr Asp Leu Thr Leu Gln Leu Leu Ala Val Arg Arg Lys Ser Arg
                85                  90                  95

Leu Arg Asp Pro Gly Leu Gln Gln Thr Leu Arg Gly Gln Leu Arg Leu
                100                 105                 110

Leu Glu Asn Asp Ser Arg Glu Met Ala Arg Val Leu Gly Glu Leu Ser
            115                 120                 125

Ala Arg Leu Leu Ser Ile His Ser Asp Gln Asp Arg Ile Val Val Thr
        130                 135                 140

Phe Lys Thr Phe Glu Glu Ile Trp Lys Phe Ser Thr Tyr His Ala Leu
145                 150                 155                 160

Gly Phe Thr His His Cys Leu Ala Asn Leu Leu Met Asp Gln Ala Phe
                165                 170                 175

Trp Leu Leu Leu Pro Ser Glu Glu Glu Thr Ala Ile Gln Val His
                180                 185                 190

Val Asp Glu Asn Ala Leu Arg Leu Thr His Glu Ser Leu Leu Ile Gln
```

```
            195                 200                 205
Glu Gly Pro Phe Phe Val Leu Cys Pro Asp His His Val Arg Val Met
210                 215                 220

Thr Gly Pro Arg Asp Ala Gly Asn Gly Pro Gln Ala Leu Arg Gln Ala
225                 230                 235                 240

Ser Gly Ala Pro Gln Gly Glu Ala Ala Pro Glu Thr Asp Ser Ser Pro
                245                 250                 255

Pro Ser Pro Ser Val Ser Ser Glu Glu Val Ala Val Ala Ala Ala Pro
                260                 265                 270

Glu Pro Leu Ile Pro Phe His Gln Trp Ala Leu Arg Ile Pro Gln Asp
            275                 280                 285

Pro Ile Asp Asp Ala Met Gly Gly Pro Val Met Pro Gly Asn Pro Leu
        290                 295                 300

Met Ala Val Gly Leu Ala Ser Ala Leu Ala Asp Phe Gln Gly Ser Gly
305                 310                 315                 320

Pro Glu Glu Met Thr Phe Arg Gly Gly Asp Leu Ile Glu Ile Leu Gly
                325                 330                 335

Ala Gln Val Pro Ser Leu Pro Trp Cys Val Gly Arg His Ala Ala Ser
                340                 345                 350

Gly Arg Val Gly Phe Val Arg Ser Ser Leu Ile Ser Met Gln Gly Pro
            355                 360                 365

Val Ser Glu Leu Glu Ser Ala Ile Phe Leu Asn Glu Glu Glu Lys Ser
        370                 375                 380

Phe Phe Ser Glu Gly Cys Phe Ser Glu Glu Asp Ala Arg Gln Leu Leu
385                 390                 395                 400

Arg Arg Met Ser Gly Thr Asp Val Cys Ser Val Tyr Ser Leu Asp Ser
                405                 410                 415

Val Glu Glu Ala Glu Thr Glu Gln Pro Gln Glu Lys Glu Ile Pro Pro
                420                 425                 430

Pro Cys Leu Ser Pro Glu Pro Gln Glu Thr Leu Gln Lys Val Lys Asn
            435                 440                 445

Val Leu Glu Gln Cys Lys Thr Cys Pro Gly Cys Pro Gln Glu Pro Ala
        450                 455                 460

Ser Trp Gly Leu Cys Ala Ala Ser Ser Asp Val Ser Leu Gln Asp Pro
465                 470                 475                 480

Glu Glu Pro Ser Phe Cys Leu Glu Ala Glu Asp Asp Trp Glu Asp Pro
                485                 490                 495

Glu Ala Leu Ser Ser Leu Leu Leu Phe Leu Asn Ala Pro Gly Tyr Lys
                500                 505                 510

Ala Ser Phe Arg Gly Leu Tyr Asp Val Ala Leu Pro Trp Leu Ser Ser
            515                 520                 525

Val Phe Arg Ser Phe Ser Asp Glu Glu Glu Leu Thr Gly Arg Leu Ala
        530                 535                 540

Gln Ala Arg Gly Ala Ala Lys Lys Ala Gly Leu Leu Met Ala Leu Ala
545                 550                 555                 560

Arg Leu Cys Phe Leu Leu Gly Arg Leu Cys Ser Arg Arg Leu Lys Leu
                565                 570                 575

Ser Gln Ala Arg Val Tyr Phe Glu Glu Ala Leu Gly Ala Leu Glu Gly
                580                 585                 590

Ser Phe Gly Asp Leu Phe Leu Val Val Ala Val Tyr Ala Asn Leu Ala
            595                 600                 605

Ser Ile Tyr Arg Lys Gln Lys Asn Arg Glu Lys Cys Ala Gln Val Val
        610                 615                 620
```

```
Pro Lys Ala Met Ala Leu Leu Leu Gly Thr Pro Asp His Ile Cys Ser
625                 630                 635                 640

Thr Glu Ala Glu Gly Glu Leu Leu Gln Leu Ala Leu Arg Arg Ala Val
            645                 650                 655

Gly Gly Gln Ser Leu Gln Ala Glu Ala Arg Ala Cys Phe Leu Leu Ala
                660                 665                 670

Arg His His Val His Leu Lys Gln Pro Glu Glu Ala Leu Pro Phe Leu
        675                 680                 685

Glu Arg Leu Leu Leu Leu His Arg Asp Ser Gly Ala Pro Glu Ala Ala
690                 695                 700

Trp Leu Ser Asp Cys Tyr Leu Leu Ala Asp Ile Tyr Ser Arg Lys
705                 710                 715                 720

Cys Leu Pro His Leu Val Leu Ser Cys Val Lys Val Ala Ser Leu Arg
                725                 730                 735

Thr Arg Gly Ser Leu Ala Gly Ser Leu Arg Ser Val Asn Leu Val Leu
                740                 745                 750

Gln Asn Ala Pro Gln Pro His Ser Leu Pro Ala Gln Thr Ser His Tyr
            755                 760                 765

Leu Arg Gln Ala Leu Ala Ser Leu Thr Pro Gly Thr Gly Gln Ala Leu
770                 775                 780

Arg Gly Pro Leu Tyr Thr Ser Leu Ala Gln Leu Tyr Ser His His Gly
785                 790                 795                 800

Cys His Gly Pro Ala Ile Thr Phe Met Thr Gln Ala Val Glu Ala Ser
                805                 810                 815

Ala Ile Ala Gly Val Arg Ala Ile Val Asp His Leu Val Ala Leu Ala
                820                 825                 830

Trp Leu His Val Leu His Gly Gln Ser Pro Val Ala Leu Asp Ile Leu
                835                 840                 845

Gln Ser Val Arg Asp Ala Val Val Ala Ser Glu Asp Gln Glu Gly Val
850                 855                 860

Ile Ala Asn Met Val Ala Val Ala Leu Lys Arg Thr Gly Arg Thr Arg
865                 870                 875                 880

Gln Ala Ala Glu Ser Tyr Tyr Arg Ala Leu Arg Val Ala Arg Asp Leu
                885                 890                 895

Gly Gln Gln Arg Asn Gln Ala Val Gly Leu Ala Asn Phe Gly Ala Leu
                900                 905                 910

Cys Leu His Ala Gly Ala Ser Arg Leu Ala Gln His Tyr Leu Leu Glu
            915                 920                 925

Ala Val Arg Leu Phe Ser Arg Leu Pro Leu Gly Glu Cys Gly Arg Asp
930                 935                 940

Phe Thr His Val Leu Leu Gln Leu Gly His Leu Cys Thr Arg Gln Gly
945                 950                 955                 960

Pro Ala Gln Gln Gly Lys Gly Tyr Tyr Glu Trp Ala Leu Leu Val Ala
                965                 970                 975

Val Glu Met Gly His Val Glu Ser Gln Leu Arg Ala Val Gln Arg Leu
            980                 985                 990

Cys His Phe Tyr Ser Ala Val Met Pro Ser Glu Ala Gln Cys Val Ile
            995                 1000                1005

Tyr His Glu Leu Gln Leu Ser Leu Ala Cys Lys Val Ala Asp Lys
    1010                1015                1020

Val Leu Glu Gly Gln Leu Leu Glu Thr Ile Ser Gln Leu Tyr Leu
    1025                1030                1035
```

Ser Leu Gly Thr Glu Arg Ala Tyr Lys Ser Ala Leu Asp Tyr Thr
1040                1045                1050

Lys Arg Ser Leu Gly Ile Phe Ile Asp Leu Gln Lys Lys Glu Lys
1055                1060                1065

Glu Ala His Ala Trp Leu Gln Ala Gly Lys Ile Tyr Tyr Ile Leu
1070                1075                1080

Arg Gln Ser Glu Leu Val Asp Leu Tyr Ile Gln Val Ala Gln Asn
1085                1090                1095

Val Ala Leu Tyr Thr Gly Asp Pro Asn Leu Gly Leu Glu Leu Phe
1100                1105                1110

Glu Ala Ala Gly Asp Ile Phe Phe Asp Gly Ala Trp Glu Arg Glu
1115                1120                1125

Lys Ala Val Ser Phe Tyr Arg Asp Arg Ala Leu Pro Leu Ala Val
1130                1135                1140

Thr Thr Gly Asn Arg Lys Ala Glu Leu Arg Leu Cys Asn Lys Leu
1145                1150                1155

Val Ala Leu Leu Ala Thr Leu Glu Glu Pro Gln Glu Gly Leu Glu
1160                1165                1170

Phe Ala His Met Ala Leu Ala Leu Ser Ile Thr Leu Gly Asp Arg
1175                1180                1185

Leu Asn Glu Arg Val Ala Tyr His Arg Leu Ala Ala Leu Gln His
1190                1195                1200

Arg Leu Gly His Gly Glu Leu Ala Glu His Phe Tyr Leu Lys Ala
1205                1210                1215

Leu Ser Leu Cys Asn Ser Pro Leu Glu Phe Asp Glu Glu Thr Leu
1220                1225                1230

Tyr Tyr Val Lys Val Tyr Leu Val Leu Gly Asp Ile Ile Phe Tyr
1235                1240                1245

Asp Leu Lys Asp Pro Phe Asp Ala Ala Gly Tyr Tyr Gln Leu Ala
1250                1255                1260

Leu Ala Ala Ala Val Asp Leu Gly Asn Lys Lys Ala Gln Leu Lys
1265                1270                1275

Ile Tyr Thr Arg Leu Ala Thr Ile Tyr His Asn Phe Leu Leu Asp
1280                1285                1290

Arg Glu Lys Ser Leu Phe Phe Tyr Gln Lys Ala Arg Thr Phe Ala
1295                1300                1305

Thr Glu Leu Asn Val Arg Arg Val Asn Leu Pro Pro Leu Pro Leu
1310                1315                1320

Cys Gly Trp Ala Pro Trp Leu Ala Pro Ser His Pro Arg
1325                1330                1335

<210> SEQ ID NO 20
<211> LENGTH: 1120
<212> TYPE: PRT
<213> ORGANISM: Homo sapiens

<400> SEQUENCE: 20

Met Trp Leu Lys Pro Glu Glu Val Leu Leu Lys Asn Ala Leu Lys Leu
1               5                   10                  15

Trp Leu Met Glu Arg Ser Asn Asp Tyr Phe Val Leu Gln Arg Arg
                20                  25                  30

Gly Tyr Gly Glu Glu Gly Gly Gly Leu Thr Gly Leu Leu Val Gly
            35                  40                  45

Thr Leu Asp Ser Val Leu Asp Ser Thr Ala Lys Val Ala Pro Phe Arg
50                  55                  60

```
Ile Leu His Gln Thr Pro Asp Ser Gln Val Tyr Leu Ser Ile Ala Cys
 65              70                  75                  80

Gly Ala Asn Arg Glu Ile Thr Lys His Trp Asp Trp Leu Glu Gln
                 85                  90                  95

Asn Ile Met Lys Thr Leu Ser Val Phe Asp Ser Asn Glu Asp Ile Thr
            100                 105                 110

Asn Phe Val Gln Gly Lys Ile Arg Gly Leu Ile Ala Glu Gly Lys
                115                 120                 125

His Cys Phe Ala Lys Glu Asp Pro Glu Lys Phe Arg Glu Ala Leu
    130                 135                 140

Leu Lys Phe Glu Lys Cys Phe Gly Leu Pro Glu Lys Glu Lys Leu Val
145                 150                 155                 160

Thr Tyr Tyr Ser Cys Ser Tyr Trp Lys Gly Arg Val Pro Cys Gln Gly
                165                 170                 175

Trp Leu Tyr Leu Ser Thr Asn Phe Leu Ser Phe Tyr Ser Phe Leu Leu
                180                 185                 190

Gly Ser Glu Ile Lys Leu Ile Ile Ser Trp Asp Glu Val Ser Lys Leu
                195                 200                 205

Glu Lys Thr Ser Asn Val Ile Leu Thr Glu Ser Ile His Val Cys Ser
    210                 215                 220

Gln Gly Glu Asn His Tyr Phe Ser Met Phe Leu His Ile Asn Gln Thr
225                 230                 235                 240

Tyr Leu Leu Met Glu Gln Leu Ala Asn Tyr Ala Ile Arg Arg Leu Phe
                245                 250                 255

Asp Lys Glu Thr Phe Asp Asn Asp Pro Val Leu Tyr Asn Pro Leu Gln
                260                 265                 270

Ile Thr Lys Arg Gly Leu Glu Asn Arg Ala His Ser Glu Gln Phe Asn
                275                 280                 285

Ala Phe Phe Arg Leu Pro Lys Gly Glu Ser Leu Lys Glu Val His Glu
                290                 295                 300

Cys Phe Leu Trp Val Pro Phe Ser His Phe Asn Thr His Gly Lys Met
305                 310                 315                 320

Cys Ile Ser Glu Asn Tyr Ile Cys Phe Ala Ser Gln Asp Gly Asn Gln
                325                 330                 335

Cys Ser Val Ile Ile Pro Leu Arg Glu Val Leu Ala Ile Asp Lys Thr
                340                 345                 350

Asn Asp Ser Ser Lys Ser Val Ile Ile Ser Ile Lys Gly Lys Thr Ala
                355                 360                 365

Phe Arg Phe His Glu Val Lys Asp Phe Glu Gln Leu Val Ala Lys Leu
                370                 375                 380

Arg Leu Arg Cys Gly Ala Ala Ser Thr Gln Tyr His Asp Ile Ser Thr
385                 390                 395                 400

Glu Leu Ala Ile Ser Ser Glu Ser Thr Glu Pro Ser Asp Asn Phe Glu
                405                 410                 415

Val Gln Ser Leu Thr Ser Gln Arg Glu Cys Ser Lys Thr Val Asn Thr
                420                 425                 430

Glu Ala Leu Met Thr Val Phe His Pro Gln Asn Leu Glu Thr Leu Asn
                435                 440                 445

Ser Lys Met Leu Lys Glu Lys Met Lys Glu Gln Ser Trp Lys Ile Leu
    450                 455                 460

Phe Ala Glu Cys Gly Arg Gly Val Ser Met Phe Arg Thr Lys Lys Thr
465                 470                 475                 480
```

```
Arg Asp Leu Val Val Arg Gly Ile Pro Glu Thr Leu Arg Gly Glu Leu
            485             490             495

Trp Met Leu Phe Ser Gly Ala Val Asn Asp Met Ala Thr Asn Pro Asp
            500             505             510

Tyr Tyr Thr Glu Val Val Glu Gln Ser Leu Gly Thr Cys Asn Leu Ala
            515             520             525

Thr Glu Glu Ile Glu Arg Asp Leu Arg Arg Ser Leu Pro Glu His Pro
            530             535             540

Ala Phe Gln Ser Asp Thr Gly Ile Ser Ala Leu Arg Arg Val Leu Thr
545             550             555             560

Ala Tyr Ala Tyr Arg Asn Pro Lys Ile Gly Tyr Cys Gln Ala Met Asn
            565             570             575

Ile Leu Thr Ser Val Leu Leu Leu Tyr Ala Lys Glu Glu Ala Phe
            580             585             590

Trp Leu Leu Val Ala Val Cys Glu Arg Met Leu Pro Asp Tyr Phe Asn
            595             600             605

Arg Arg Ile Ile Gly Ala Leu Val Asp Gln Ala Val Phe Glu Glu Leu
            610             615             620

Ile Arg Asp His Leu Pro Gln Leu Thr Glu His Met Thr Asp Met Thr
625             630             635             640

Phe Phe Ser Ser Val Ser Leu Ser Trp Phe Leu Thr Leu Phe Ile Ser
            645             650             655

Val Leu Pro Ile Glu Ser Ala Val Asn Val Val Asp Cys Phe Phe Tyr
            660             665             670

Asp Gly Ile Lys Ala Ile Leu Gln Leu Gly Leu Ala Ile Leu Asp Tyr
            675             680             685

Asn Leu Asp Lys Leu Leu Thr Cys Lys Asp Asp Ala Glu Ala Val Thr
            690             695             700

Ala Leu Asn Arg Phe Phe Asp Asn Val Thr Asn Lys Asp Ser Pro Leu
705             710             715             720

Pro Ser Asn Val Gln Gln Gly Ser Asn Val Ser Asp Glu Lys Thr Ser
            725             730             735

His Thr Arg Val Asp Ile Thr Asp Leu Ile Arg Glu Ser Asn Glu Lys
            740             745             750

Tyr Gly Asn Ile Arg Tyr Glu Asp Ile His Ser Met Arg Cys Arg Asn
            755             760             765

Arg Leu Tyr Val Ile Gln Thr Leu Glu Glu Thr Thr Lys Gln Asn Val
            770             775             780

Leu Arg Val Val Ser Gln Asp Val Lys Leu Ser Leu Gln Glu Leu Asp
785             790             795             800

Glu Leu Tyr Val Ile Phe Lys Lys Glu Leu Phe Leu Ser Cys Tyr Trp
            805             810             815

Cys Leu Gly Cys Pro Val Leu Lys His His Asp Pro Ser Leu Pro Tyr
            820             825             830

Leu Glu Gln Tyr Gln Ile Asp Cys Gln Gln Phe Arg Ala Leu Tyr His
            835             840             845

Leu Leu Ser Pro Trp Ala His Ser Ala Asn Lys Asp Ser Leu Ala Leu
850             855             860

Trp Thr Phe Arg Leu Leu Asp Glu Asn Ser Asp Cys Leu Ile Asn Phe
865             870             875             880

Lys Glu Phe Ser Ser Ala Ile Asp Ile Met Tyr Asn Gly Ser Phe Thr
            885             890             895

Glu Lys Leu Lys Leu Leu Phe Lys Leu His Ile Pro Pro Ala Tyr Thr
```

```
                    900             905             910
Glu Val Lys Ser Lys Asp Ala Ser Lys Gly Asp Glu Leu Ser Lys Glu
                915             920             925

Glu Leu Leu Tyr Phe Ser Gln Leu His Val Ser Lys Pro Ala Asn Glu
            930             935             940

Lys Glu Ala Glu Ser Ala Lys His Ser Pro Glu Lys Gly Lys Gly Lys
945             950             955             960

Ile Asp Ile Gln Ala Tyr Leu Ser Gln Trp Gln Asp Glu Leu Phe Lys
                965             970             975

Lys Glu Glu Asn Ile Lys Asp Leu Pro Arg Met Asn Gln Ser Gln Phe
            980             985             990

Ile Gln Phe Ser Lys Thr Leu Tyr  Asn Leu Phe His Glu  Asp Pro Glu
            995             1000            1005

Glu Glu  Ser Leu Tyr Gln Ala  Ile Ala Val Val Thr  Ser Leu Leu
    1010            1015            1020

Leu Arg Met Glu Glu Val Gly  Arg Lys Leu His Ser  Pro Thr Ser
    1025            1030            1035

Ser Ala Lys Gly Phe Ser Gly  Thr Val Cys Gly Ser  Gly Gly Pro
    1040            1045            1050

Ser Glu  Glu Lys Thr Gly Ser  His Leu Glu Lys Asp  Pro Cys Ser
    1055            1060            1065

Phe Arg  Glu Glu Pro Gln Trp  Ser Phe Ala Phe Glu  Gln Ile Leu
    1070            1075            1080

Ala Ser  Leu Leu Asn Glu Pro  Ala Leu Val Arg Phe  Phe Glu Lys
    1085            1090            1095

Pro Ile  Asp Val Lys Ala Lys  Leu Glu Asn Ala Arg  Ile Ser Gln
    1100            1105            1110

Leu Arg  Ser Arg Thr Lys Met
    1115            1120

<210> SEQ ID NO 21
<211> LENGTH: 2002
<212> TYPE: PRT
<213> ORGANISM: Homo sapiens

<400> SEQUENCE: 21

Met Glu Gln Asp Arg Thr Asn His Val Glu Gly Asn Arg Leu Ser Pro
1               5               10              15

Phe Leu Ile Pro Ser Pro Pro Ile Cys Gln Thr Glu Pro Leu Ala Thr
                20              25              30

Lys Leu Gln Asn Gly Ser Pro Leu Pro Glu Arg Ala His Pro Glu Val
            35              40              45

Asn Gly Asp Thr Lys Trp His Ser Phe Lys Ser Tyr Tyr Gly Ile Pro
    50              55              60

Cys Met Lys Gly Ser Gln Asn Ser Arg Val Ser Pro Asp Phe Thr Gln
65              70              75              80

Glu Ser Arg Gly Tyr Ser Lys Cys Leu Gln Asn Gly Gly Ile Lys Arg
                85              90              95

Thr Val Ser Glu Pro Ser Leu Ser Gly Leu Leu Gln Ile Lys Lys Leu
            100             105             110

Lys Gln Asp Gln Lys Ala Asn Gly Glu Arg Arg Asn Phe Gly Val Ser
        115             120             125

Gln Glu Arg Asn Pro Gly Glu Ser Ser Gln Pro Asn Val Ser Asp Leu
    130             135             140
```

```
Ser Asp Lys Lys Glu Ser Val Ser Val Ala Gln Glu Asn Ala Val
145                 150                 155                 160

Lys Asp Phe Thr Ser Phe Ser Thr His Asn Cys Ser Gly Pro Glu Asn
                165                 170                 175

Pro Glu Leu Gln Ile Leu Asn Glu Gln Glu Gly Lys Ser Ala Asn Tyr
            180                 185                 190

His Asp Lys Asn Ile Val Leu Leu Lys Asn Lys Ala Val Leu Met Pro
        195                 200                 205

Asn Gly Ala Thr Val Ser Ala Ser Ser Val Glu His Thr His Gly Glu
    210                 215                 220

Leu Leu Glu Lys Thr Leu Ser Gln Tyr Tyr Pro Asp Cys Val Ser Ile
225                 230                 235                 240

Ala Val Gln Lys Thr Thr Ser His Ile Asn Ala Ile Asn Ser Gln Ala
                245                 250                 255

Thr Asn Glu Leu Ser Cys Glu Ile Thr His Pro Ser His Thr Ser Gly
            260                 265                 270

Gln Ile Asn Ser Ala Gln Thr Ser Asn Ser Glu Leu Pro Pro Lys Pro
        275                 280                 285

Ala Ala Val Val Ser Glu Ala Cys Asp Ala Asp Asp Ala Asp Asn Ala
    290                 295                 300

Ser Lys Leu Ala Ala Met Leu Asn Thr Cys Ser Phe Gln Lys Pro Glu
305                 310                 315                 320

Gln Leu Gln Gln Gln Lys Ser Val Phe Glu Ile Cys Pro Ser Pro Ala
                325                 330                 335

Glu Asn Asn Ile Gln Gly Thr Thr Lys Leu Ala Ser Gly Glu Glu Phe
            340                 345                 350

Cys Ser Gly Ser Ser Ser Asn Leu Gln Ala Pro Gly Gly Ser Ser Glu
        355                 360                 365

Arg Tyr Leu Lys Gln Asn Glu Met Asn Gly Ala Tyr Phe Lys Gln Ser
    370                 375                 380

Ser Val Phe Thr Lys Asp Ser Phe Ser Ala Thr Thr Thr Pro Pro Pro
385                 390                 395                 400

Pro Ser Gln Leu Leu Leu Ser Pro Pro Pro Leu Pro Gln Val Pro
                405                 410                 415

Gln Leu Pro Ser Glu Gly Lys Ser Thr Leu Asn Gly Gly Val Leu Glu
            420                 425                 430

Glu His His His Tyr Pro Asn Gln Ser Asn Thr Thr Leu Leu Arg Glu
        435                 440                 445

Val Lys Ile Glu Gly Lys Pro Glu Ala Pro Pro Ser Gln Ser Pro Asn
    450                 455                 460

Pro Ser Thr His Val Cys Ser Pro Ser Pro Met Leu Ser Glu Arg Pro
465                 470                 475                 480

Gln Asn Asn Cys Val Asn Arg Asn Asp Ile Gln Thr Ala Gly Thr Met
                485                 490                 495

Thr Val Pro Leu Cys Ser Glu Lys Thr Arg Pro Met Ser Glu His Leu
            500                 505                 510

Lys His Asn Pro Pro Ile Phe Gly Ser Ser Gly Glu Leu Gln Asp Asn
        515                 520                 525

Cys Gln Gln Leu Met Arg Asn Lys Glu Gln Glu Ile Leu Lys Gly Arg
    530                 535                 540

Asp Lys Glu Gln Thr Arg Asp Leu Val Pro Pro Thr Gln His Tyr Leu
545                 550                 555                 560

Lys Pro Gly Trp Ile Glu Leu Lys Ala Pro Arg Phe His Gln Ala Glu
```

-continued

```
            565                 570                 575
Ser His Leu Lys Arg Asn Glu Ala Ser Leu Pro Ser Ile Leu Gln Tyr
            580                 585                 590

Gln Pro Asn Leu Ser Asn Gln Met Thr Ser Lys Gln Tyr Thr Gly Asn
            595                 600                 605

Ser Asn Met Pro Gly Gly Leu Pro Arg Gln Ala Tyr Thr Gln Lys Thr
            610                 615                 620

Thr Gln Leu Glu His Lys Ser Gln Met Tyr Gln Val Glu Met Asn Gln
625                 630                 635                 640

Gly Gln Ser Gln Gly Thr Val Asp Gln His Leu Gln Phe Gln Lys Pro
                    645                 650                 655

Ser His Gln Val His Phe Ser Lys Thr Asp His Leu Pro Lys Ala His
                    660                 665                 670

Val Gln Ser Leu Cys Gly Thr Arg Phe His Phe Gln Gln Arg Ala Asp
                    675                 680                 685

Ser Gln Thr Glu Lys Leu Met Ser Pro Val Leu Lys Gln His Leu Asn
            690                 695                 700

Gln Gln Ala Ser Glu Thr Glu Pro Phe Ser Asn Ser His Leu Leu Gln
705                 710                 715                 720

His Lys Pro His Lys Gln Ala Ala Gln Thr Gln Pro Ser Gln Ser Ser
                    725                 730                 735

His Leu Pro Gln Asn Gln Gln Gln Gln Lys Leu Gln Ile Lys Asn
                    740                 745                 750

Lys Glu Glu Ile Leu Gln Thr Phe Pro His Pro Gln Ser Asn Asn Asp
            755                 760                 765

Gln Gln Arg Glu Gly Ser Phe Phe Gly Gln Thr Lys Val Glu Glu Cys
            770                 775                 780

Phe His Gly Glu Asn Gln Tyr Ser Lys Ser Glu Phe Glu Thr His
785                 790                 795                 800

Asn Val Gln Met Gly Leu Glu Glu Val Gln Asn Ile Asn Arg Arg Asn
                    805                 810                 815

Ser Pro Tyr Ser Gln Thr Met Lys Ser Ser Ala Cys Lys Ile Gln Val
            820                 825                 830

Ser Cys Ser Asn Asn Thr His Leu Val Ser Glu Asn Lys Glu Gln Thr
            835                 840                 845

Thr His Pro Glu Leu Phe Ala Gly Asn Lys Thr Gln Asn Leu His His
            850                 855                 860

Met Gln Tyr Phe Pro Asn Asn Val Ile Pro Lys Gln Asp Leu Leu His
865                 870                 875                 880

Arg Cys Phe Gln Glu Gln Glu Gln Lys Ser Gln Gln Ala Ser Val Leu
                    885                 890                 895

Gln Gly Tyr Lys Asn Arg Asn Gln Asp Met Ser Gly Gln Gln Ala Ala
                    900                 905                 910

Gln Leu Ala Gln Gln Arg Tyr Leu Ile His Asn His Ala Asn Val Phe
            915                 920                 925

Pro Val Pro Asp Gln Gly Gly Ser His Thr Gln Thr Pro Pro Gln Lys
            930                 935                 940

Asp Thr Gln Lys His Ala Ala Leu Arg Trp His Leu Leu Gln Lys Gln
945                 950                 955                 960

Glu Gln Gln Gln Thr Gln Gln Pro Gln Thr Glu Ser Cys His Ser Gln
                    965                 970                 975

Met His Arg Pro Ile Lys Val Glu Pro Gly Cys Lys Pro His Ala Cys
            980                 985                 990
```

-continued

```
Met His Thr Ala Pro Pro Glu Asn Lys Thr Trp Lys Lys Val Thr Lys
            995                 1000                1005

Gln Glu Asn Pro Pro Ala Ser Cys Asp Asn Val Gln Gln Lys Ser
    1010                1015                1020

Ile Ile Glu Thr Met Glu Gln His Leu Lys Gln Phe His Ala Lys
    1025                1030                1035

Ser Leu Phe Asp His Lys Ala Leu Thr Leu Lys Ser Gln Lys Gln
    1040                1045                1050

Val Lys Val Glu Met Ser Gly Pro Val Thr Val Leu Thr Arg Gln
    1055                1060                1065

Thr Thr Ala Ala Glu Leu Asp Ser His Thr Pro Ala Leu Glu Gln
    1070                1075                1080

Gln Thr Thr Ser Ser Glu Lys Thr Pro Thr Lys Arg Thr Ala Ala
    1085                1090                1095

Ser Val Leu Asn Asn Phe Ile Glu Ser Pro Ser Lys Leu Leu Asp
    1100                1105                1110

Thr Pro Ile Lys Asn Leu Leu Asp Thr Pro Val Lys Thr Gln Tyr
    1115                1120                1125

Asp Phe Pro Ser Cys Arg Cys Val Glu Gln Ile Ile Glu Lys Asp
    1130                1135                1140

Glu Gly Pro Phe Tyr Thr His Leu Gly Ala Gly Pro Asn Val Ala
    1145                1150                1155

Ala Ile Arg Glu Ile Met Glu Glu Arg Phe Gly Gln Lys Gly Lys
    1160                1165                1170

Ala Ile Arg Ile Glu Arg Val Ile Tyr Thr Gly Lys Glu Gly Lys
    1175                1180                1185

Ser Ser Gln Gly Cys Pro Ile Ala Lys Trp Val Val Arg Arg Ser
    1190                1195                1200

Ser Ser Glu Glu Lys Leu Leu Cys Leu Val Arg Glu Arg Ala Gly
    1205                1210                1215

His Thr Cys Glu Ala Ala Val Ile Val Ile Leu Ile Leu Val Trp
    1220                1225                1230

Glu Gly Ile Pro Leu Ser Leu Ala Asp Lys Leu Tyr Ser Glu Leu
    1235                1240                1245

Thr Glu Thr Leu Arg Lys Tyr Gly Thr Leu Thr Asn Arg Arg Cys
    1250                1255                1260

Ala Leu Asn Glu Glu Arg Thr Cys Ala Cys Gln Gly Leu Asp Pro
    1265                1270                1275

Glu Thr Cys Gly Ala Ser Phe Ser Phe Gly Cys Ser Trp Ser Met
    1280                1285                1290

Tyr Tyr Asn Gly Cys Lys Phe Ala Arg Ser Lys Ile Pro Arg Lys
    1295                1300                1305

Phe Lys Leu Leu Gly Asp Asp Pro Lys Glu Glu Lys Leu Glu
    1310                1315                1320

Ser His Leu Gln Asn Leu Ser Thr Leu Met Ala Pro Thr Tyr Lys
    1325                1330                1335

Lys Leu Ala Pro Asp Ala Tyr Asn Asn Gln Ile Glu Tyr Glu His
    1340                1345                1350

Arg Ala Pro Glu Cys Arg Leu Gly Leu Lys Glu Gly Arg Pro Phe
    1355                1360                1365

Ser Gly Val Thr Ala Cys Leu Asp Phe Cys Ala His Ala His Arg
    1370                1375                1380
```

-continued

```
Asp Leu His Asn Met Gln Asn Gly Ser Thr Leu Val Cys Thr Leu
    1385                1390                1395

Thr Arg Glu Asp Asn Arg Glu Phe Gly Gly Lys Pro Glu Asp Glu
    1400                1405                1410

Gln Leu His Val Leu Pro Leu Tyr Lys Val Ser Asp Val Asp Glu
    1415                1420                1425

Phe Gly Ser Val Glu Ala Gln Glu Lys Lys Arg Ser Gly Ala
    1430                1435                1440

Ile Gln Val Leu Ser Ser Phe Arg Arg Lys Val Arg Met Leu Ala
    1445                1450                1455

Glu Pro Val Lys Thr Cys Arg Gln Arg Lys Leu Glu Ala Lys Lys
    1460                1465                1470

Ala Ala Ala Glu Lys Leu Ser Ser Leu Glu Asn Ser Ser Asn Lys
    1475                1480                1485

Asn Glu Lys Glu Lys Ser Ala Pro Ser Arg Thr Lys Gln Thr Glu
    1490                1495                1500

Asn Ala Ser Gln Ala Lys Gln Leu Ala Glu Leu Leu Arg Leu Ser
    1505                1510                1515

Gly Pro Val Met Gln Gln Ser Gln Gln Pro Gln Pro Leu Gln Lys
    1520                1525                1530

Gln Pro Pro Gln Pro Gln Gln Gln Arg Pro Gln Gln Gln
    1535                1540                1545

Pro His His Pro Gln Thr Glu Ser Val Asn Ser Tyr Ser Ala Ser
    1550                1555                1560

Gly Ser Thr Asn Pro Tyr Met Arg Arg Pro Asn Pro Val Ser Pro
    1565                1570                1575

Tyr Pro Asn Ser Ser His Thr Ser Asp Ile Tyr Gly Ser Thr Ser
    1580                1585                1590

Pro Met Asn Phe Tyr Ser Thr Ser Ser Gln Ala Ala Gly Ser Tyr
    1595                1600                1605

Leu Asn Ser Ser Asn Pro Met Asn Pro Tyr Pro Gly Leu Leu Asn
    1610                1615                1620

Gln Asn Thr Gln Tyr Pro Ser Tyr Gln Cys Asn Gly Asn Leu Ser
    1625                1630                1635

Val Asp Asn Cys Ser Pro Tyr Leu Gly Ser Tyr Ser Pro Gln Ser
    1640                1645                1650

Gln Pro Met Asp Leu Tyr Arg Tyr Pro Ser Gln Asp Pro Leu Ser
    1655                1660                1665

Lys Leu Ser Leu Pro Pro Ile His Thr Leu Tyr Gln Pro Arg Phe
    1670                1675                1680

Gly Asn Ser Gln Ser Phe Thr Ser Lys Tyr Leu Gly Tyr Gly Asn
    1685                1690                1695

Gln Asn Met Gln Gly Asp Gly Phe Ser Ser Cys Thr Ile Arg Pro
    1700                1705                1710

Asn Val His His Val Gly Lys Leu Pro Pro Tyr Pro Thr His Glu
    1715                1720                1725

Met Asp Gly His Phe Met Gly Ala Thr Ser Arg Leu Pro Pro Asn
    1730                1735                1740

Leu Ser Asn Pro Asn Met Asp Tyr Lys Asn Gly Glu His His Ser
    1745                1750                1755

Pro Ser His Ile Ile His Asn Tyr Ser Ala Ala Pro Gly Met Phe
    1760                1765                1770

Asn Ser Ser Leu His Ala Leu His Leu Gln Asn Lys Glu Asn Asp
```

-continued

```
               1775                1780                1785

Met Leu Ser His Thr Ala Asn Gly Leu Ser Lys Met Leu Pro Ala
        1790                1795                1800

Leu Asn His Asp Arg Thr Ala Cys Val Gln Gly Gly Leu His Lys
    1805                1810                1815

Leu Ser Asp Ala Asn Gly Gln Glu Lys Gln Pro Leu Ala Leu Val
    1820                1825                1830

Gln Gly Val Ala Ser Gly Ala Glu Asp Asn Asp Glu Val Trp Ser
    1835                1840                1845

Asp Ser Glu Gln Ser Phe Leu Asp Pro Asp Ile Gly Gly Val Ala
    1850                1855                1860

Val Ala Pro Thr His Gly Ser Ile Leu Ile Glu Cys Ala Lys Arg
    1865                1870                1875

Glu Leu His Ala Thr Thr Pro Leu Lys Asn Pro Asn Arg Asn His
    1880                1885                1890

Pro Thr Arg Ile Ser Leu Val Phe Tyr Gln His Lys Ser Met Asn
    1895                1900                1905

Glu Pro Lys His Gly Leu Ala Leu Trp Glu Ala Lys Met Ala Glu
    1910                1915                1920

Lys Ala Arg Glu Lys Glu Glu Cys Glu Lys Tyr Gly Pro Asp
    1925                1930                1935

Tyr Val Pro Gln Lys Ser His Gly Lys Lys Val Lys Arg Glu Pro
    1940                1945                1950

Ala Glu Pro His Glu Thr Ser Glu Pro Thr Tyr Leu Arg Phe Ile
    1955                1960                1965

Lys Ser Leu Ala Glu Arg Thr Met Ser Val Thr Thr Asp Ser Thr
    1970                1975                1980

Val Thr Thr Ser Pro Tyr Ala Phe Thr Arg Val Thr Gly Pro Tyr
    1985                1990                1995

Asn Arg Tyr Ile
    2000

<210> SEQ ID NO 22
<211> LENGTH: 409
<212> TYPE: PRT
<213> ORGANISM: Homo sapiens

<400> SEQUENCE: 22

Met Ala Leu Arg Pro Glu Asp Pro Ser Ser Gly Phe Arg His Ser Asn
1               5                   10                  15

Val Val Ala Phe Ile Asn Glu Lys Met Ala Arg His Thr Lys Gly Pro
            20                  25                  30

Glu Phe Tyr Leu Glu Asn Ile Ser Leu Ser Trp Glu Lys Val Glu Asp
        35                  40                  45

Lys Leu Arg Ala Ile Leu Glu Asp Ser Glu Val Pro Ser Glu Val Lys
    50                  55                  60

Glu Ala Cys Thr Trp Gly Ser Leu Ala Leu Gly Val Arg Phe Ala His
65                  70                  75                  80

Arg Gln Ala Gln Leu Gln Arg His Arg Val Arg Trp Leu His Gly Phe
                85                  90                  95

Ala Lys Leu His Lys Ser Ala Ala Gln Ala Leu Ala Ser Asp Leu Lys
            100                 105                 110

Lys Leu Arg Glu Gln Gln Glu Thr Glu Arg Lys Glu Ala Ala Ser Arg
        115                 120                 125
```

Leu Arg Met Ala Gln Thr Ser Leu Val Glu Val Gln Lys Glu Arg Asp
130                 135                 140

Lys Glu Leu Val Ser Pro His Glu Trp Glu Gln Gly Ala Gly Trp Pro
145                 150                 155                 160

Gly Leu Ala Thr Ala Gly Gly Val Cys Thr Glu Gly Ala Ala Glu Glu
                165                 170                 175

Glu Glu Glu Ala Ala Val Ala Ala Ala Gly Ala Ala Gly Gly Lys Gly
            180                 185                 190

Ala Glu Glu Gln Arg Asp Val Val Ala Ala Pro Val Glu
            195                 200                 205

Ala Met Ala Pro Pro Val Glu Ala Gly Ala Ala Pro Met Glu Thr Gln
210                 215                 220

Phe Pro His Val Glu Ala Arg Ala Ala Ser Met Glu Thr Thr Glu Lys
225                 230                 235                 240

Leu Glu Arg Ile Leu Leu Gln Leu Leu Gly Asp Ala Asp Gln Glu Lys
                245                 250                 255

Tyr Thr Tyr Trp Gly Gln Lys Glu Gly Asp Leu Arg Ser Val Glu Thr
            260                 265                 270

Ala Thr Ser Tyr Phe Ser Gly Thr Thr Asn Pro Trp Ser Arg Ala Ser
        275                 280                 285

Ser Glu Pro Leu Pro Val Gln Leu Pro Ala Ser Tyr Ser Tyr Ser Tyr
290                 295                 300

Ser Ser Pro Phe Ser Ser Phe Ser Asp Ile Pro Thr Ile Ser Pro Pro
305                 310                 315                 320

Gln Ala Thr Val Thr Ala Pro Val Pro Pro Gln Leu Pro Ser Asp Trp
                325                 330                 335

Glu Ala Phe Asp Thr Ser Leu Trp Ser Asp Gly Pro His Arg Ile
            340                 345                 350

Asp His Gln Glu His Pro Arg Asp Arg Arg Tyr Ser Glu Pro His Gln
        355                 360                 365

Gln Arg Pro Pro Val Tyr Arg Arg Pro Gly Asp Trp Asp Cys Pro Trp
370                 375                 380

Cys Asn Ala Val Asn Phe Ser Arg Arg Asp Thr Cys Phe Asp Cys Gly
385                 390                 395                 400

Lys Gly Ile Trp Leu Gln Lys Pro His
                405

<210> SEQ ID NO 23
<211> LENGTH: 472
<212> TYPE: PRT
<213> ORGANISM: Homo sapiens

<400> SEQUENCE: 23

Met Ala Gly Pro Gly Trp Gly Pro Pro Arg Leu Asp Gly Phe Ile Leu
1               5                   10                  15

Thr Glu Arg Leu Gly Ser Gly Thr Tyr Ala Thr Val Tyr Lys Ala Tyr
                20                  25                  30

Ala Lys Lys Asp Thr Arg Glu Val Val Ala Ile Lys Cys Val Ala Lys
            35                  40                  45

Lys Ser Leu Asn Lys Ala Ser Val Glu Asn Leu Leu Thr Glu Ile Glu
        50                  55                  60

Ile Leu Lys Gly Ile Arg His Pro His Ile Val Gln Leu Lys Asp Phe
65                  70                  75                  80

Gln Trp Asp Ser Asp Asn Ile Tyr Leu Ile Met Glu Phe Cys Ala Gly
                85                  90                  95

```
Gly Asp Leu Ser Arg Phe Ile His Thr Arg Ile Leu Pro Glu Lys
            100                 105                 110

Val Ala Arg Val Phe Met Gln Gln Leu Ala Ser Ala Leu Gln Phe Leu
    115                 120                 125

His Glu Arg Asn Ile Ser His Leu Asp Leu Lys Pro Gln Asn Ile Leu
130                 135                 140

Leu Ser Ser Leu Glu Lys Pro His Leu Lys Leu Ala Asp Phe Gly Phe
145                 150                 155                 160

Ala Gln His Met Ser Pro Trp Asp Glu Lys His Val Leu Arg Gly Ser
                165                 170                 175

Pro Leu Tyr Met Ala Pro Glu Met Val Cys Gln Arg Gln Tyr Asp Ala
            180                 185                 190

Arg Val Asp Leu Trp Ser Met Gly Val Ile Leu Tyr Glu Ala Leu Phe
        195                 200                 205

Gly Gln Pro Pro Phe Ala Ser Arg Ser Phe Ser Glu Leu Glu Glu Lys
    210                 215                 220

Ile Arg Ser Asn Arg Val Ile Glu Leu Pro Leu Arg Pro Leu Leu Ser
225                 230                 235                 240

Arg Asp Cys Arg Asp Leu Leu Gln Arg Leu Leu Glu Arg Asp Pro Ser
                245                 250                 255

Arg Arg Ile Ser Phe Gln Asp Phe Phe Ala His Pro Trp Val Asp Leu
            260                 265                 270

Glu His Met Pro Ser Gly Glu Ser Leu Gly Arg Ala Thr Ala Leu Val
        275                 280                 285

Val Gln Ala Val Lys Lys Asp Gln Glu Gly Asp Ser Ala Ala Ala Leu
    290                 295                 300

Ser Leu Tyr Cys Lys Ala Leu Asp Phe Phe Val Pro Ala Leu His Tyr
305                 310                 315                 320

Glu Val Asp Ala Gln Arg Lys Glu Ala Ile Lys Ala Lys Val Gly Gln
                325                 330                 335

Tyr Val Ser Arg Ala Glu Glu Leu Lys Ala Ile Val Ser Ser Ser Asn
            340                 345                 350

Gln Ala Leu Leu Arg Gln Gly Thr Ser Ala Arg Asp Leu Leu Arg Glu
        355                 360                 365

Met Ala Arg Asp Lys Pro Arg Leu Leu Ala Ala Leu Glu Val Ala Ser
    370                 375                 380

Ala Ala Met Ala Lys Glu Glu Ala Gly Gly Glu Gln Asp Ala Leu
385                 390                 395                 400

Asp Leu Tyr Gln His Ser Leu Gly Glu Leu Leu Leu Leu Leu Ala Ala
                405                 410                 415

Glu Pro Pro Gly Arg Arg Glu Leu Leu His Thr Glu Val Gln Asn
            420                 425                 430

Leu Met Ala Arg Ala Glu Tyr Leu Lys Glu Gln Val Lys Met Arg Glu
    435                 440                 445

Ser Arg Trp Glu Ala Asp Thr Leu Asp Lys Glu Gly Leu Ser Glu Ser
    450                 455                 460

Val Arg Ser Ser Cys Thr Leu Gln
465                 470

<210> SEQ ID NO 24
<211> LENGTH: 1743
<212> TYPE: PRT
<213> ORGANISM: Homo sapiens
```

```
<400> SEQUENCE: 24

Met Ala Thr Asp Ser Gly Asp Pro Ala Ser Thr Glu Asp Ser Glu Lys
1               5                   10                  15

Pro Asp Gly Ile Ser Phe Glu Asn Arg Val Pro Gln Val Ala Ala Thr
            20                  25                  30

Leu Thr Val Glu Ala Arg Leu Lys Glu Lys Asn Ser Thr Phe Ser Ala
        35                  40                  45

Ser Gly Glu Thr Val Glu Arg Lys Arg Phe Arg Lys Ser Val Glu
    50                  55                  60

Met Thr Glu Asp Asp Lys Val Ala Glu Ser Ser Pro Lys Asp Glu Arg
65                  70                  75                  80

Ile Lys Ala Ala Met Asn Ile Pro Arg Val Asp Lys Leu Pro Ser Asn
                85                  90                  95

Val Leu Arg Gly Gly Gln Glu Val Lys Tyr Glu Gln Cys Ser Lys Ser
            100                 105                 110

Thr Ser Glu Ile Ser Lys Asp Cys Phe Lys Lys Asn Glu Lys Glu
        115                 120                 125

Met Glu Glu Glu Ala Glu Met Lys Ala Val Ala Thr Ser Pro Ser Gly
    130                 135                 140

Arg Phe Leu Lys Phe Asp Ile Glu Leu Gly Arg Gly Ala Phe Lys Thr
145                 150                 155                 160

Val Tyr Lys Gly Leu Asp Thr Glu Thr Trp Val Glu Val Ala Trp Cys
                165                 170                 175

Glu Leu Gln Asp Arg Lys Leu Thr Lys Ala Glu Gln Gln Arg Phe Lys
            180                 185                 190

Glu Glu Ala Glu Met Leu Lys Gly Leu Gln His Pro Asn Ile Val Arg
        195                 200                 205

Phe Tyr Asp Ser Trp Glu Ser Ile Leu Lys Gly Lys Lys Cys Ile Val
210                 215                 220

Leu Val Thr Glu Leu Met Thr Ser Gly Thr Leu Lys Thr Tyr Leu Lys
225                 230                 235                 240

Arg Phe Lys Val Met Lys Pro Lys Val Leu Arg Ser Trp Cys Arg Gln
                245                 250                 255

Ile Leu Lys Gly Leu Gln Phe Leu His Thr Arg Thr Pro Ile Ile
            260                 265                 270

His Arg Asp Leu Lys Cys Asp Asn Ile Phe Ile Thr Gly Pro Thr Gly
        275                 280                 285

Ser Val Lys Ile Gly Asp Leu Gly Leu Ala Thr Leu Met Arg Thr Ser
    290                 295                 300

Phe Ala Lys Ser Val Ile Gly Thr Pro Glu Phe Met Ala Pro Glu Met
305                 310                 315                 320

Tyr Glu Glu His Tyr Asp Glu Ser Val Asp Val Tyr Ala Phe Gly Met
                325                 330                 335

Cys Met Leu Glu Met Ala Thr Ser Glu Tyr Pro Tyr Ser Glu Cys Gln
            340                 345                 350

Asn Ala Ala Gln Ile Tyr Arg Lys Val Thr Ser Gly Ile Lys Pro Ala
        355                 360                 365

Ser Phe Asn Lys Val Thr Asp Pro Glu Val Lys Glu Ile Ile Glu Gly
    370                 375                 380

Cys Ile Arg Gln Asn Lys Ser Glu Arg Leu Ser Ile Arg Asp Leu Leu
385                 390                 395                 400

Asn His Ala Phe Phe Ala Glu Asp Thr Gly Leu Arg Val Glu Leu Ala
                405                 410                 415
```

-continued

```
Glu Glu Asp Asp Cys Ser Asn Ser Ser Leu Ala Leu Arg Leu Trp Val
            420                 425                 430

Glu Asp Pro Lys Lys Leu Lys Gly Lys His Lys Asp Asn Glu Ala Ile
            435                 440                 445

Glu Phe Ser Phe Asn Leu Glu Thr Asp Thr Pro Glu Glu Val Ala Tyr
            450                 455                 460

Glu Met Val Lys Ser Gly Phe Phe His Glu Ser Asp Ser Lys Ala Val
465                 470                 475                 480

Ala Lys Ser Ile Arg Asp Arg Val Thr Pro Ile Lys Lys Thr Arg Glu
                485                 490                 495

Lys Lys Pro Ala Gly Cys Leu Glu Glu Arg Arg Asp Ser Gln Cys Lys
            500                 505                 510

Ser Met Gly Asn Val Phe Pro Gln Pro Gln Asn Thr Thr Leu Pro Leu
            515                 520                 525

Ala Pro Ala Gln Gln Thr Gly Ala Glu Cys Glu Glu Thr Glu Val Asp
            530                 535                 540

Gln His Val Arg Gln Gln Leu Leu Gln Arg Lys Pro Gln Gln His Cys
545                 550                 555                 560

Ser Ser Val Thr Gly Asp Asn Leu Ser Glu Ala Gly Ala Ala Ser Val
                565                 570                 575

Ile His Ser Asp Thr Ser Ser Gln Pro Ser Val Ala Tyr Ser Ser Asn
            580                 585                 590

Gln Thr Met Gly Ser Gln Met Val Ser Asn Ile Pro Gln Ala Glu Val
            595                 600                 605

Asn Val Pro Gly Gln Ile Tyr Ser Ser Gln Gln Leu Val Gly His Tyr
            610                 615                 620

Gln Gln Val Ser Gly Leu Gln Lys His Ser Lys Leu Thr Gln Pro Gln
625                 630                 635                 640

Ile Leu Pro Leu Val Gln Gly Gln Ser Thr Val Leu Pro Val His Val
                645                 650                 655

Leu Gly Pro Thr Val Val Ser Gln Pro Gln Val Ser Pro Leu Thr Val
            660                 665                 670

Gln Lys Val Pro Gln Ile Lys Pro Val Ser Gln Pro Val Gly Ala Glu
            675                 680                 685

Gln Gln Ala Ala Leu Leu Lys Pro Asp Leu Val Arg Ser Leu Asn Gln
            690                 695                 700

Asp Val Ala Thr Thr Lys Glu Asn Val Ser Ser Pro Asp Asn Pro Ser
705                 710                 715                 720

Gly Asn Gly Lys Gln Asp Arg Ile Lys Gln Arg Arg Ala Ser Cys Pro
                725                 730                 735

Arg Pro Glu Lys Gly Thr Lys Phe Gln Leu Thr Val Leu Gln Val Ser
            740                 745                 750

Thr Ser Gly Asp Asn Met Val Glu Cys Gln Leu Glu Thr His Asn Asn
            755                 760                 765

Lys Met Val Thr Phe Lys Phe Asp Val Asp Gly Asp Ala Pro Glu Asp
            770                 775                 780

Ile Ala Asp Tyr Met Val Glu Asp Asn Phe Val Leu Glu Ser Glu Lys
785                 790                 795                 800

Glu Lys Phe Val Glu Glu Leu Arg Ala Ile Val Gly Gln Ala Gln Glu
                805                 810                 815

Ile Leu His Val His Phe Ala Thr Glu Arg Ala Thr Gly Val Asp Ser
            820                 825                 830
```

```
Ile Thr Val Asp Ser Asn Ser Gln Thr Gly Ser Ser Glu Gln Val
            835                 840                 845

Gln Ile Asn Ser Thr Ser Thr Gln Thr Ser Asn Glu Ser Ala Pro Gln
    850                 855                 860

Ser Ser Pro Val Gly Arg Trp Arg Phe Cys Ile Asn Gln Thr Ile Arg
865                 870                 875                 880

Asn Arg Glu Thr Gln Ser Pro Pro Ser Leu Gln His Ser Met Ser Ala
                885                 890                 895

Val Pro Gly Arg His Pro Leu Pro Ser Pro Lys Asn Thr Ser Asn Lys
                900                 905                 910

Glu Ile Ser Arg Asp Thr Leu Leu Thr Ile Glu Asn Asn Pro Cys His
            915                 920                 925

Arg Ala Leu Phe Thr Ser Lys Ser Glu His Lys Asp Val Val Asp Gly
            930                 935                 940

Lys Ile Ser Glu Cys Ala Ser Val Glu Thr Lys Gln Pro Ala Ile Leu
945                 950                 955                 960

Tyr Gln Val Glu Asp Asn Arg Gln Ile Met Ala Pro Val Thr Asn Ser
                965                 970                 975

Ser Ser Tyr Ser Thr Thr Ser Val Arg Ala Val Pro Ala Glu Cys Glu
            980                 985                 990

Gly Leu Thr Lys Gln Ala Ser Ile Phe Ile Pro Val Tyr Pro Cys His
            995                 1000                1005

Gln Thr Ala Ser Gln Ala Asp Ala Leu Met Ser His Pro Gly Glu
    1010                1015                1020

Ser Thr Gln Thr Ser Gly Asn Ser Leu Thr Thr Leu Ala Phe Asp
    1025                1030                1035

Gln Lys Pro Gln Thr Leu Ser Val Gln Gln Pro Ala Met Asp Ala
    1040                1045                1050

Glu Phe Ile Ser Gln Glu Gly Glu Thr Thr Val Asn Thr Glu Ala
    1055                1060                1065

Ser Ser Pro Lys Thr Val Ile Pro Thr Gln Thr Pro Gly Leu Glu
    1070                1075                1080

Pro Thr Thr Leu Gln Pro Thr Thr Val Leu Glu Ser Asp Gly Glu
    1085                1090                1095

Arg Pro Pro Lys Leu Glu Phe Ala Asp Asn Arg Ile Lys Thr Leu
    1100                1105                1110

Asp Glu Lys Leu Arg Asn Leu Leu Tyr Gln Glu His Ser Ile Ser
    1115                1120                1125

Ser Ile Tyr Pro Glu Ser Gln Lys Asp Thr Gln Ser Ile Asp Ser
    1130                1135                1140

Pro Phe Ser Ser Ser Ala Glu Asp Thr Leu Ser Cys Pro Val Thr
    1145                1150                1155

Glu Val Ile Ala Ile Ser His Cys Gly Ile Lys Asp Ser Pro Val
    1160                1165                1170

Gln Ser Pro Asn Phe Gln Gln Thr Gly Ser Lys Leu Leu Ser Asn
    1175                1180                1185

Val Ala Ala Ser Gln Pro Ala Asn Ile Ser Val Phe Lys Arg Asp
    1190                1195                1200

Leu Asn Val Ile Thr Ser Val Pro Ser Glu Leu Cys Leu His Glu
    1205                1210                1215

Met Ser Ser Asp Ala Ser Leu Pro Gly Asp Pro Glu Ala Tyr Pro
    1220                1225                1230

Ala Ala Val Ser Ser Gly Gly Ala Ile His Leu Gln Thr Gly Val
```

|   |   |   | 1235 |   |   |   | 1240 |   |   |   | 1245 |   |   |
|---|---|---|------|---|---|---|------|---|---|---|------|---|---|

Glu Thr Glu Glu Met Arg Ser Ala Ile Ala Pro Asp Pro Ile Pro
    1250                     1255                 1260

Leu Thr Arg Glu Ser Thr Ala Asp Thr Arg Ala Leu Asn Arg Cys
    1265                     1270                 1275

Lys Ala Met Ser Gly Ser Phe Gln Arg Gly Arg Phe Gln Val Ile
    1280                     1285                 1290

Thr Ile Pro Gln Gln Gln Ser Ala Lys Met Thr Ser Phe Gly Ile
    1295                     1300                 1305

Glu His Ile Ser Val Phe Ser Glu Thr Asn His Ser Ser Glu Glu
    1310                     1315                 1320

Ala Phe Ile Lys Thr Ala Lys Ser Gln Leu Val Glu Ile Glu Pro
    1325                     1330                 1335

Ala Thr Gln Asn Pro Lys Thr Ser Phe Ser Tyr Glu Lys Leu Gln
    1340                     1345                 1350

Ala Leu Gln Glu Thr Cys Lys Glu Asn Lys Gly Val Pro Lys Gln
    1355                     1360                 1365

Gly Asp Asn Phe Leu Ser Phe Ser Ala Ala Cys Glu Thr Asp Val
    1370                     1375                 1380

Ser Ser Val Thr Pro Glu Lys Glu Phe Glu Glu Thr Ser Ala Thr
    1385                     1390                 1395

Gly Ser Ser Met Gln Ser Gly Ser Glu Leu Leu Leu Lys Glu Arg
    1400                     1405                 1410

Glu Ile Leu Thr Ala Gly Lys Gln Pro Ser Ser Asp Ser Glu Phe
    1415                     1420                 1425

Ser Ala Ser Leu Ala Gly Ser Gly Lys Ser Val Ala Lys Thr Gly
    1430                     1435                 1440

Pro Glu Ser Asn Gln Cys Leu Pro His His Glu Glu Gln Ala Tyr
    1445                     1450                 1455

Ala Gln Thr Gln Ser Ser Leu Phe Tyr Ser Pro Ser Ser Pro Met
    1460                     1465                 1470

Ser Ser Asp Asp Glu Ser Glu Ile Glu Asp Glu Asp Leu Lys Val
    1475                     1480                 1485

Glu Leu Gln Arg Leu Arg Glu Lys His Ile Gln Glu Val Val Asn
    1490                     1495                 1500

Leu Gln Thr Gln Gln Asn Lys Glu Leu Gln Glu Leu Tyr Glu Arg
    1505                     1510                 1515

Leu Arg Ser Ile Lys Asp Ser Lys Thr Gln Ser Thr Glu Ile Pro
    1520                     1525                 1530

Leu Pro Pro Ala Ser Pro Arg Arg Pro Arg Ser Phe Lys Ser Lys
    1535                     1540                 1545

Leu Arg Ser Arg Pro Gln Ser Leu Thr His Val Asp Asn Gly Ile
    1550                     1555                 1560

Val Ala Thr Asp Pro Leu Cys Val Glu Ser Asn Ala Ala Ser Cys
    1565                     1570                 1575

Gln Gln Ser Pro Ala Ser Lys Lys Gly Met Phe Thr Asp Asp Leu
    1580                     1585                 1590

His Lys Leu Val Asp Asp Trp Thr Lys Glu Ala Val Gly Asn Ser
    1595                     1600                 1605

Leu Ile Lys Pro Ser Leu Asn Gln Leu Lys Gln Ser Gln His Lys
    1610                     1615                 1620

Leu Glu Thr Glu Asn Trp Asn Lys Val Ser Glu Asn Thr Pro Ser
    1625                     1630                 1635

-continued

```
Thr Met Gly Tyr Thr Ser Thr Trp Ile Ser Ser Leu Ser Gln Ile
    1640                1645                1650

Arg Gly Ala Val Pro Thr Ser Leu Pro Gln Gly Leu Ser Leu Pro
    1655                1660                1665

Ser Phe Pro Gly Pro Leu Ser Ser Tyr Gly Met Pro His Val Cys
    1670                1675                1680

Gln Tyr Asn Ala Val Ala Gly Ala Gly Tyr Pro Val Gln Trp Val
    1685                1690                1695

Gly Ile Ser Gly Thr Thr Gln Gln Ser Val Val Ile Pro Ala Gln
    1700                1705                1710

Ser Gly Gly Pro Phe Gln Pro Gly Met Asn Met Gln Ala Phe Pro
    1715                1720                1725

Thr Ser Ser Val Gln Asn Pro Ala Thr Ile Pro Pro Gly Pro Lys
    1730                1735                1740

<210> SEQ ID NO 25
<211> LENGTH: 590
<212> TYPE: PRT
<213> ORGANISM: Homo sapiens

<400> SEQUENCE: 25

Met Arg Pro Arg Pro Leu Val Phe Met Ser Leu Val Cys Ala Leu
1               5                   10                  15

Leu Asn Thr Cys Gln Ala His Arg Val His Asp Asp Lys Pro Asn Ile
                20                  25                  30

Val Leu Ile Met Val Asp Asp Leu Gly Ile Gly Asp Leu Gly Cys Tyr
                35                  40                  45

Gly Asn Asp Thr Met Arg Thr Pro His Ile Asp Arg Leu Ala Arg Glu
        50                  55                  60

Gly Val Arg Leu Thr Gln His Ile Ser Ala Ala Ser Leu Cys Ser Pro
65                  70                  75                  80

Ser Arg Ser Ala Phe Leu Thr Gly Arg Tyr Pro Ile Arg Ser Gly Met
                85                  90                  95

Val Ser Ser Gly Asn Arg Arg Val Ile Gln Asn Leu Ala Val Pro Ala
                100                 105                 110

Gly Leu Pro Leu Asn Glu Thr Thr Leu Ala Ala Leu Leu Lys Lys Gln
            115                 120                 125

Gly Tyr Ser Thr Gly Leu Ile Gly Lys Trp His Gln Gly Leu Asn Cys
        130                 135                 140

Asp Ser Arg Ser Asp Gln Cys His His Pro Tyr Asn Tyr Gly Phe Asp
145                 150                 155                 160

Tyr Tyr Tyr Gly Met Pro Phe Thr Leu Val Asp Ser Cys Trp Pro Asp
                165                 170                 175

Pro Ser Arg Asn Thr Glu Leu Ala Phe Glu Ser Gln Leu Trp Leu Cys
                180                 185                 190

Val Gln Leu Val Ala Ile Ala Ile Leu Thr Leu Thr Phe Gly Lys Leu
            195                 200                 205

Ser Gly Trp Val Ser Val Pro Trp Leu Leu Ile Phe Ser Met Ile Leu
        210                 215                 220

Phe Ile Phe Leu Leu Gly Tyr Ala Trp Phe Ser Ser His Thr Ser Pro
225                 230                 235                 240

Leu Tyr Trp Asp Cys Leu Leu Met Arg Gly His Glu Ile Thr Glu Gln
                245                 250                 255

Pro Met Lys Ala Glu Arg Ala Gly Ser Ile Met Val Lys Glu Ala Ile
```

```
            260                 265                 270
Ser Phe Leu Glu Arg His Ser Lys Glu Thr Phe Leu Phe Phe Ser
            275                 280                 285

Phe Leu His Val His Thr Pro Leu Pro Thr Thr Asp Asp Phe Thr Gly
            290                 295                 300

Thr Ser Lys His Gly Leu Tyr Gly Asp Asn Val Glu Glu Met Asp Ser
305                 310                 315                 320

Met Val Gly Lys Ile Leu Asp Ala Ile Asp Asp Phe Gly Leu Arg Asn
                325                 330                 335

Asn Thr Leu Val Tyr Phe Thr Ser Asp His Gly Gly His Leu Glu Ala
                340                 345                 350

Arg Arg Gly His Ala Gln Leu Gly Gly Trp Asn Gly Ile Tyr Lys Gly
                355                 360                 365

Gly Lys Gly Met Gly Gly Trp Glu Gly Gly Ile Arg Val Pro Gly Ile
            370                 375                 380

Val Arg Trp Pro Gly Lys Val Pro Ala Gly Arg Leu Ile Lys Glu Pro
385                 390                 395                 400

Thr Ser Leu Met Asp Ile Leu Pro Thr Val Ala Ser Val Ser Gly Gly
                405                 410                 415

Ser Leu Pro Gln Asp Arg Val Ile Asp Gly Arg Asp Leu Met Pro Leu
                420                 425                 430

Leu Gln Gly Asn Val Arg His Ser Glu His Glu Phe Leu Phe His Tyr
                435                 440                 445

Cys Gly Ser Tyr Leu His Ala Val Arg Trp Ile Pro Lys Asp Asp Ser
            450                 455                 460

Gly Ser Val Trp Lys Ala His Tyr Val Thr Pro Val Phe Gln Pro Pro
465                 470                 475                 480

Ala Ser Gly Gly Cys Tyr Val Thr Ser Leu Cys Arg Cys Phe Gly Glu
                485                 490                 495

Gln Val Thr Tyr His Asn Pro Pro Leu Leu Phe Asp Leu Ser Arg Asp
            500                 505                 510

Pro Ser Glu Ser Thr Pro Leu Thr Pro Ala Thr Glu Pro Leu His Asp
            515                 520                 525

Phe Val Ile Lys Lys Val Ala Asn Ala Leu Lys Glu His Gln Glu Thr
            530                 535                 540

Ile Val Pro Val Thr Tyr Gln Leu Ser Glu Leu Asn Gln Gly Arg Thr
545                 550                 555                 560

Trp Leu Lys Pro Cys Cys Gly Val Phe Pro Phe Cys Leu Cys Asp Lys
                565                 570                 575

Glu Glu Glu Val Ser Gln Pro Arg Gly Pro Asn Glu Lys Arg
            580                 585                 590

<210> SEQ ID NO 26
<211> LENGTH: 469
<212> TYPE: PRT
<213> ORGANISM: Homo sapiens

<400> SEQUENCE: 26

Met Ile Thr Glu Gly Ala Gln Ala Pro Arg Leu Leu Leu Pro Pro Leu
1               5                   10                  15

Leu Leu Leu Leu Thr Leu Pro Ala Thr Gly Ser Asp Pro Val Leu Cys
                20                  25                  30

Phe Thr Gln Tyr Glu Glu Ser Ser Gly Lys Cys Lys Gly Leu Leu Gly
            35                  40                  45
```

```
Gly Gly Val Ser Val Glu Asp Cys Cys Leu Asn Thr Ala Phe Ala Tyr
 50                  55                  60
Gln Lys Arg Ser Gly Gly Leu Cys Gln Pro Cys Arg Ser Pro Arg Trp
 65                  70                  75                  80
Ser Leu Trp Ser Thr Trp Ala Pro Cys Ser Val Thr Cys Ser Glu Gly
                 85                  90                  95
Ser Gln Leu Arg Tyr Arg Arg Cys Val Gly Trp Asn Gly Gln Cys Ser
            100                 105                 110
Gly Lys Val Ala Pro Gly Thr Leu Glu Trp Gln Leu Gln Ala Cys Glu
            115                 120                 125
Asp Gln Gln Cys Cys Pro Glu Met Gly Gly Trp Ser Gly Trp Gly Pro
130                 135                 140
Trp Glu Pro Cys Ser Val Thr Cys Ser Lys Gly Thr Arg Thr Arg Arg
145                 150                 155                 160
Arg Ala Cys Asn His Pro Ala Pro Lys Cys Gly Gly His Cys Pro Gly
                165                 170                 175
Gln Ala Gln Glu Ser Glu Ala Cys Asp Thr Gln Val Cys Pro Thr
            180                 185                 190
His Gly Ala Trp Ala Thr Trp Gly Pro Trp Thr Pro Cys Ser Ala Ser
            195                 200                 205
Cys His Gly Gly Pro His Glu Pro Lys Glu Thr Arg Ser Arg Lys Cys
210                 215                 220
Ser Ala Pro Glu Pro Ser Gln Lys Pro Gly Lys Pro Cys Pro Gly
225                 230                 235                 240
Leu Ala Tyr Glu Gln Arg Arg Cys Thr Gly Leu Pro Pro Cys Pro Val
            245                 250                 255
Ala Gly Gly Trp Gly Pro Trp Gly Pro Val Ser Pro Cys Pro Val Thr
            260                 265                 270
Cys Gly Leu Gly Gln Thr Met Glu Gln Arg Thr Cys Asn His Pro Val
            275                 280                 285
Pro Gln His Gly Gly Pro Phe Cys Ala Gly Asp Ala Thr Arg Thr His
            290                 295                 300
Ile Cys Asn Thr Ala Val Pro Cys Pro Val Asp Gly Glu Trp Asp Ser
305                 310                 315                 320
Trp Gly Glu Trp Ser Pro Cys Ile Arg Arg Asn Met Lys Ser Ile Ser
                325                 330                 335
Cys Gln Glu Ile Pro Gly Gln Gln Ser Arg Gly Arg Thr Cys Arg Gly
            340                 345                 350
Arg Lys Phe Asp Gly His Arg Cys Ala Gly Gln Gln Gln Asp Ile Arg
            355                 360                 365
His Cys Tyr Ser Ile Gln His Cys Pro Leu Lys Gly Ser Trp Ser Glu
            370                 375                 380
Trp Ser Thr Trp Gly Leu Cys Met Pro Pro Cys Gly Pro Asn Pro Thr
385                 390                 395                 400
Arg Ala Arg Gln Arg Leu Cys Thr Pro Leu Leu Pro Lys Tyr Pro Pro
                405                 410                 415
Thr Val Ser Met Val Glu Gly Gln Gly Glu Lys Asn Val Thr Phe Trp
            420                 425                 430
Gly Arg Pro Leu Pro Arg Cys Glu Glu Leu Gln Gly Gln Lys Leu Val
            435                 440                 445
Val Glu Glu Lys Arg Pro Cys Leu His Val Pro Ala Cys Lys Asp Pro
450                 455                 460
Glu Glu Glu Glu Leu
```

<210> SEQ ID NO 27
<211> LENGTH: 791
<212> TYPE: PRT
<213> ORGANISM: Homo sapiens

<400> SEQUENCE: 27

Met Gly Asp Gln Arg Leu Gln Asp Trp Leu Arg Ser Pro Gly Met Asp
1               5                   10                  15

Ser Lys Pro Trp Tyr Cys Asn Lys Arg Pro Ser Lys Cys Phe Ala Lys
            20                  25                  30

Cys Lys His Arg Arg Leu Arg Phe Pro Pro Met Asp Thr Gln Asn Trp
        35                  40                  45

Val Phe Val Lys Glu Gly Met Asp Asp Phe Arg Tyr Gly Cys Pro Ser
    50                  55                  60

Pro Glu Asp Thr Leu Val Cys Arg Arg Asp Glu Phe Leu Leu Pro Lys
65                  70                  75                  80

Ile Ser Leu Arg Gly Pro Gln Ala Asp Pro Lys Ser Gly Gln Lys Lys
                85                  90                  95

Leu Leu Lys Lys Ala Ala Leu Phe Ser Lys Leu Ser Pro Ala Gln Leu
            100                 105                 110

Ala Arg Lys Ala Phe Val Glu Gln Val Glu Ala Gln Leu Met Ala Lys
        115                 120                 125

His Pro Leu Ala Met Tyr Pro Asn Leu Gly Glu Asp Met Pro Pro Asp
    130                 135                 140

Leu Leu Leu Gln Val Leu Lys His Leu Asp Pro Glu Arg Glu Leu Glu
145                 150                 155                 160

Asp Ala Trp Ala Cys Cys Glu Thr Gln Glu Lys Thr Thr Glu Val Pro
                165                 170                 175

Thr Glu Pro Gly Lys His Pro Cys Gly Glu Phe Cys Leu Lys Pro Pro
            180                 185                 190

Glu Thr Pro Val Ser His Leu Leu Pro Glu Pro Pro Glu Thr Gly Val
        195                 200                 205

Ser His Leu Ser Pro Glu Pro Pro Lys Thr Pro Val Ser Ser Leu Arg
    210                 215                 220

Pro Glu Pro Pro Glu Thr Gly Val Ser His Leu Arg Pro Glu Pro Pro
225                 230                 235                 240

Glu Thr Gly Val Ser His Ile Arg Pro Gly Pro Pro Ile Thr Arg Arg
                245                 250                 255

Arg Ser Ser Leu Leu Arg Gln Leu Leu Lys Leu Asp Ser Glu Arg Lys
            260                 265                 270

Leu Glu Asp Ala Arg Ala Pro Cys Glu Gly Arg Glu Lys Thr Thr Asp
        275                 280                 285

Glu Pro Thr Glu Pro Gly Lys Tyr Pro Cys Gly Lys Phe Cys Pro Arg
    290                 295                 300

Pro Phe Glu Thr Pro Leu Ser His Leu Arg Gln Glu Pro Pro Lys Thr
305                 310                 315                 320

Pro Val Ser Ser Leu Arg Pro Glu Pro Pro Glu Thr Gly Glu Ser His
                325                 330                 335

Leu Arg Leu Glu His Ser Lys Thr Arg Arg Gly Ser Ser Leu Arg Ser
            340                 345                 350

Glu Pro Ser Glu Thr Gly Val Ser Arg Leu Arg Leu Ala Pro Pro Lys
        355                 360                 365

```
Thr Arg Arg Gly Ser Ser Leu His Ala Glu Pro Ser Lys Thr Gly Val
    370                 375                 380

Ser His Leu Ser Pro Glu Pro Lys Thr Glu Val Ser His Leu His
385                 390                 395                 400

Pro Val Pro Pro Lys Thr Gly Val Cys His Leu Arg Leu Glu Pro Pro
                    405                 410                 415

Asp Thr Ser Gln Val Ser Asn Leu Leu Leu Tyr Ile Leu Lys Val Leu
                420                 425                 430

Asp Ser Gly Arg Thr Leu Lys Asp Val Trp Asp Arg Cys Glu Ala Arg
            435                 440                 445

Val Lys Lys Thr Lys Glu Pro Thr Glu Pro His Lys Ser Pro Cys Gly
        450                 455                 460

Glu Pro Cys Leu Gln Pro Pro Glu Thr Gln Val Ser His Pro His Pro
465                 470                 475                 480

Glu His Pro Lys Thr Arg Arg Ser Ser Leu His Ser Gln Pro Pro
                    485                 490                 495

Lys Thr Arg Arg Thr Ser Ser Leu Arg Ser Glu Pro Pro Lys Thr Arg
                500                 505                 510

Arg Thr Ser Ser Leu Arg Ser Glu Pro Pro Lys Thr Arg Arg Thr Ser
        515                 520                 525

Ser Leu Gly Pro Glu Pro Pro Lys Thr Arg Arg Val Ser Ser Leu Arg
    530                 535                 540

Pro Glu Leu Pro Lys Ser Arg Arg Val Ser Ser Leu His Pro Glu Pro
545                 550                 555                 560

Pro Lys Ala Pro Glu Ser His Gln Phe Ser Glu Pro Pro Lys Ile Arg
                565                 570                 575

Ala Ser Tyr Ile Lys Glu Leu Leu Gln Glu Asp Thr Pro Ser Thr Lys
            580                 585                 590

Glu Cys Val Ser Asp Ser Leu Gln Tyr Arg Tyr Thr Ser Glu Lys Leu
        595                 600                 605

Arg Glu Phe Phe Lys Trp Ala Gly Asp Leu Gly Ala Asp Glu Glu Ser
    610                 615                 620

Ile Arg Asn Leu Phe Asp Phe Thr Pro Lys Tyr Arg Ala Thr His Glu
625                 630                 635                 640

Asp Gln Lys Phe Lys Lys Val Lys Glu Cys Ser Ser Glu Leu Lys Tyr
                645                 650                 655

Ser Met Glu Leu Asp Glu Lys Asp Glu Asp Lys Phe Phe Ser Gln Glu
            660                 665                 670

Lys Tyr Trp Gly Arg Lys Phe His Thr Pro Ser Asn Ser Tyr Thr Ala
        675                 680                 685

Gln Arg Val Lys Met Lys Tyr Gly Ala Trp Tyr Leu Lys Pro Lys Leu
    690                 695                 700

Trp Lys Lys Leu Arg Ser Asp Glu Pro Leu Ile Asp Pro Lys Leu Leu
705                 710                 715                 720

Leu Lys Lys Pro Asp Glu Pro Asp Val Leu Asp Leu Tyr Gly Pro
                725                 730                 735

Ile Ala Phe Lys Asp Phe Ile Leu Ser Lys Gly Tyr Glu Met Pro Gly
            740                 745                 750

Ile Ile Gln Arg Leu Phe Ala Arg Arg Gly Trp Thr Tyr Asp Ser Val
        755                 760                 765

Lys Thr Pro Ile Gln Arg Ala Met Ile Phe Tyr Lys Tyr Lys Glu Ile
    770                 775                 780

Val Glu Ala Ser Glu Glu Asp
```

<210> SEQ ID NO 28
<211> LENGTH: 823
<212> TYPE: PRT
<213> ORGANISM: Homo sapiens

<400> SEQUENCE: 28

Met Lys Arg His Arg Pro Val Ser Ser Asp Ser Ser Asp Glu Ser
1               5                   10                  15

Pro Ser Thr Ser Phe Thr Ser Gly Ser Met Tyr Arg Ile Lys Ser Lys
            20                  25                  30

Ile Pro Asn Glu His Lys Lys Pro Ala Glu Val Phe Arg Lys Asp Leu
        35                  40                  45

Ile Ser Ala Met Lys Leu Pro Asp Ser His His Ile Asn Pro Asp Ser
50                  55                  60

Tyr Tyr Leu Phe Ala Asp Thr Trp Lys Glu Glu Trp Glu Lys Gly Val
65                  70                  75                  80

Gln Val Pro Ala Ser Pro Asp Thr Val Pro Gln Pro Ser Leu Arg Ile
                85                  90                  95

Ile Ala Glu Lys Val Lys Asp Val Leu Phe Ile Arg Pro Arg Lys Tyr
            100                 105                 110

Ile His Cys Ser Ser Pro Asp Thr Thr Glu Pro Gly Tyr Ile Asn Ile
        115                 120                 125

Met Glu Leu Ala Ala Ser Val Cys Arg Tyr Asp Leu Asp Asp Met Asp
130                 135                 140

Ile Phe Trp Leu Gln Glu Leu Asn Glu Asp Leu Ala Glu Met Gly Cys
145                 150                 155                 160

Gly Pro Val Asp Glu Asn Leu Met Glu Lys Thr Val Glu Val Leu Glu
                165                 170                 175

Arg His Cys His Glu Asn Met Asn His Ala Ile Glu Thr Glu Glu Gly
            180                 185                 190

Leu Gly Ile Glu Tyr Asp Glu Asp Val Ile Cys Asp Val Cys Arg Ser
        195                 200                 205

Pro Asp Ser Glu Glu Gly Asn Asp Met Val Phe Cys Asp Lys Cys Asn
    210                 215                 220

Val Cys Val His Gln Ala Cys Tyr Gly Ile Leu Lys Val Pro Glu Gly
225                 230                 235                 240

Ser Trp Leu Cys Arg Ser Cys Val Leu Gly Ile Tyr Pro Gln Cys Val
                245                 250                 255

Leu Cys Pro Lys Lys Gly Gly Ala Leu Lys Thr Thr Lys Thr Gly Thr
            260                 265                 270

Lys Trp Ala His Val Ser Cys Ala Leu Trp Ile Pro Glu Val Ser Ile
        275                 280                 285

Ala Cys Pro Glu Arg Met Glu Pro Ile Thr Lys Ile Ser His Ile Pro
    290                 295                 300

Pro Ser Arg Trp Ala Leu Val Cys Asn Leu Cys Lys Leu Lys Thr Gly
305                 310                 315                 320

Ala Cys Ile Gln Cys Ser Ile Lys Ser Cys Ile Thr Ala Phe His Val
                325                 330                 335

Thr Cys Ala Phe Glu His Gly Leu Glu Met Lys Thr Ile Leu Asp Glu
            340                 345                 350

Gly Asp Glu Val Lys Phe Lys Ser Tyr Cys Leu Lys His Ser Gln Asn
        355                 360                 365

```
Arg Gln Lys Leu Gly Glu Ala Glu Tyr Pro His His Arg Ala Lys Glu
    370                 375                 380
Gln Ser Gln Ala Lys Ser Glu Lys Thr Ser Leu Arg Ala Gln Lys Leu
385                 390                 395                 400
Arg Glu Leu Glu Glu Glu Phe Tyr Ser Leu Val Arg Val Glu Asp Val
                405                 410                 415
Ala Ala Glu Leu Gly Met Pro Thr Leu Ala Val Asp Phe Ile Tyr Asn
            420                 425                 430
Tyr Trp Lys Leu Lys Arg Lys Ser Asn Phe Asn Lys Pro Leu Phe Pro
        435                 440                 445
Pro Lys Glu Asp Glu Glu Asn Gly Leu Val Gln Pro Lys Glu Glu Ser
    450                 455                 460
Ile His Thr Arg Met Arg Met Phe Met His Leu Arg Gln Asp Leu Glu
465                 470                 475                 480
Arg Val Arg Asn Leu Cys Tyr Met Ile Ser Arg Glu Lys Leu Lys
                485                 490                 495
Leu Ser His Asn Lys Ile Gln Glu Gln Ile Phe Gly Leu Gln Val Gln
                500                 505                 510
Leu Leu Asn Gln Glu Ile Asp Ala Gly Leu Pro Leu Thr Asn Ala Leu
            515                 520                 525
Glu Asn Ser Leu Phe Tyr Pro Pro Arg Ile Thr Leu Lys Leu Lys
    530                 535                 540
Met Pro Lys Ser Thr Pro Glu Asp His Arg Asn Ser Ser Thr Glu Thr
545                 550                 555                 560
Asp Gln Gln Pro His Ser Pro Asp Ser Ser Ser Val His Ser Ile
                565                 570                 575
Arg Asn Met Gln Val Pro Gln Glu Ser Leu Glu Met Arg Thr Lys Ser
            580                 585                 590
Tyr Pro Arg Tyr Pro Leu Glu Ser Lys Asn Asn Arg Leu Leu Ala Ser
        595                 600                 605
Leu Ser His Ser Arg Ser Glu Ala Lys Glu Ser Ser Pro Ala Trp Arg
    610                 615                 620
Thr Pro Ser Ser Glu Cys Tyr His Gly Gln Ser Leu Gly Lys Pro Leu
625                 630                 635                 640
Val Leu Gln Ala Ala Leu His Gly Gln Ser Ser Ile Gly Asn Gly Lys
                645                 650                 655
Ser Gln Pro Asn Ser Lys Phe Ala Lys Ser Asn Gly Leu Glu Gly Ser
            660                 665                 670
Trp Ser Gly Asn Val Thr Gln Lys Asp Ser Ser Ser Glu Met Phe Cys
        675                 680                 685
Asp Gln Glu Pro Val Phe Ser Pro His Leu Val Ser Gln Gly Ser Phe
    690                 695                 700
Arg Lys Ser Thr Val Glu His Phe Ser Arg Ser Phe Lys Glu Thr Thr
705                 710                 715                 720
Asn Arg Trp Val Lys Asn Thr Glu Asp Leu Gln Cys Tyr Val Lys Pro
                725                 730                 735
Thr Lys Asn Met Ser Pro Lys Glu Gln Phe Trp Gly Arg Gln Val Leu
            740                 745                 750
Arg Arg Ser Ala Gly Arg Ala Pro Tyr Gln Glu Asn Asp Gly Tyr Cys
        755                 760                 765
Pro Asp Leu Glu Leu Ser Asp Ser Glu Ala Glu Ser Asp Gly Asn Lys
    770                 775                 780
Glu Lys Val Arg Val Arg Lys Asp Ser Ser Asp Arg Glu Asn Pro Pro
```

His Asp Ser Arg Arg Asp Cys His Gly Lys Ser Lys Thr His Pro Leu
785                 790                 795                 800

Ser His Ser Ser Met Gln Arg
            805                 810                 815

<210> SEQ ID NO 29
<211> LENGTH: 518
<212> TYPE: PRT
<213> ORGANISM: Homo sapiens

<400> SEQUENCE: 29

Met Ala Val Ala Leu Gly Cys Ala Ile Gln Ala Ser Leu Asn Gln Gly
1               5                   10                  15

Ser Val Phe Gln Glu Tyr Asp Thr Asp Cys Glu Val Phe Arg Gln Arg
            20                  25                  30

Phe Arg Gln Phe Gln Tyr Arg Glu Ala Ala Gly Pro His Glu Ala Phe
        35                  40                  45

Asn Lys Leu Trp Glu Leu Cys Cys Gln Trp Leu Lys Pro Lys Met Arg
    50                  55                  60

Ser Lys Glu Gln Ile Leu Glu Leu Val Leu Glu Gln Phe Leu Thr
65                  70                  75                  80

Ile Leu Pro Thr Glu Ile Glu Thr Trp Val Arg Glu His Cys Pro Glu
                85                  90                  95

Asn Arg Glu Arg Val Val Ser Leu Ile Glu Asp Leu Gln Arg Glu Leu
            100                 105                 110

Glu Ile Pro Glu Gln Gln Val Asp Met His Asp Met Leu Leu Glu Glu
        115                 120                 125

Leu Ala Pro Val Gly Thr Ala His Ile Pro Pro Thr Met His Leu Glu
    130                 135                 140

Ser Pro Ala Leu Gln Val Met Gly Pro Ala Gln Glu Ala Pro Val Ala
145                 150                 155                 160

Glu Ala Trp Ile Pro Gln Ala Gly Pro Pro Glu Leu Asn Tyr Gly Ala
                165                 170                 175

Thr Gly Glu Cys Gln Asn Phe Leu Asp Pro Gly Tyr Pro Leu Pro Lys
            180                 185                 190

Leu Asp Met Asn Phe Ser Leu Glu Asn Arg Glu Glu Pro Trp Val Lys
        195                 200                 205

Glu Leu Gln Asp Ser Lys Glu Met Lys Gln Leu Leu Asp Ser Lys Ile
    210                 215                 220

Gly Phe Glu Ile Gly Ile Glu Asn Glu Asp Thr Ser Lys Gln Lys
225                 230                 235                 240

Lys Met Glu Thr Met Tyr Pro Phe Ile Val Thr Leu Glu Gly Asn Ala
                245                 250                 255

Leu Gln Gly Pro Ile Leu Gln Lys Asp Tyr Val Gln Leu Glu Asn Gln
            260                 265                 270

Trp Glu Thr Pro Pro Glu Asp Leu Gln Thr Asp Leu Ala Lys Leu Val
        275                 280                 285

Asp Gln Gln Asn Pro Thr Leu Gly Glu Thr Pro Glu Asn Ser Asn Leu
    290                 295                 300

Glu Glu Pro Leu Asn Pro Lys Pro His Lys Lys Ser Pro Gly Glu
305                 310                 315                 320

Lys Pro His Arg Cys Pro Gln Cys Gly Lys Cys Phe Ala Arg Lys Ser
                325                 330                 335

-continued

Gln Leu Thr Gly His Gln Arg Ile His Ser Gly Glu Glu Pro His Lys
              340                 345                 350

Cys Pro Glu Cys Gly Lys Arg Phe Leu Arg Ser Ser Asp Leu Tyr Arg
            355                 360                 365

His Gln Arg Leu His Thr Gly Glu Arg Pro Tyr Glu Cys Thr Val Cys
    370                 375                 380

Lys Lys Arg Phe Thr Arg Arg Ser His Leu Ile Gly His Gln Arg Thr
385                 390                 395                 400

His Ser Glu Glu Thr Tyr Lys Cys Leu Cys Gly Lys Ser Phe
                405                 410                 415

Cys His Gly Ser Ser Leu Lys Arg His Leu Lys Thr His Thr Gly Glu
            420                 425                 430

Lys Pro His Arg Cys His Asn Cys Gly Lys Ser Phe Ser Arg Leu Thr
            435                 440                 445

Ala Leu Thr Leu His Gln Arg Thr His Thr Glu Glu Arg Pro Phe Lys
            450                 455                 460

Cys Asn Tyr Cys Gly Lys Ser Phe Arg Gln Arg Pro Ser Leu Val Ile
465                 470                 475                 480

His Leu Arg Ile His Thr Gly Glu Lys Pro Tyr Lys Cys Thr His Cys
                485                 490                 495

Ser Lys Ser Phe Arg Gln Arg Ala Gly Leu Ile Met His Gln Val Thr
            500                 505                 510

His Phe Arg Gly Leu Ile
            515

<210> SEQ ID NO 30
<211> LENGTH: 434
<212> TYPE: PRT
<213> ORGANISM: Homo sapiens

<400> SEQUENCE: 30

Met Val Gln Asp Gly Thr Phe Lys Thr Arg Asp Ser Thr Trp Thr Cys
1               5                   10                  15

Glu Ser Thr Arg Met Ala Ala Pro Pro Ser Tyr Cys Phe Val Ala
                20                  25                  30

Phe Pro Pro Arg Ala Lys Asp Gly Leu Val Val Phe Gly Lys Asn Ser
            35                  40                  45

Ala Arg Pro Arg Asp Glu Val Gln Glu Val Val Tyr Phe Ser Ala Ala
        50                  55                  60

Asp His Glu Pro Glu Ser Lys Val Glu Cys Thr Tyr Ile Ser Ile Asp
65                  70                  75                  80

Gln Val Pro Arg Thr Tyr Ala Ile Met Ile Ser Arg Pro Ala Trp Leu
                85                  90                  95

Trp Gly Ala Glu Met Gly Ala Asn Glu His Gly Val Cys Ile Ala Asn
            100                 105                 110

Glu Ala Ile Asn Thr Arg Glu Pro Ala Ala Glu Ile Glu Ala Leu Leu
        115                 120                 125

Gly Met Asp Leu Val Arg Leu Gly Leu Glu Arg Gly Glu Thr Ala Lys
    130                 135                 140

Glu Ala Leu Asp Val Ile Val Ser Leu Leu Glu Glu His Gly Gln Gly
145                 150                 155                 160

Gly Asn Tyr Phe Glu Asp Ala Asn Ser Cys His Ser Phe Gln Ser Ala
                165                 170                 175

Tyr Leu Ile Val Asp Arg Asp Glu Ala Trp Val Leu Glu Thr Ile Gly
            180                 185                 190

```
Lys Tyr Trp Ala Ala Glu Lys Val Thr Glu Gly Val Arg Cys Ile Cys
            195                 200                 205
Ser Gln Leu Ser Leu Thr Thr Lys Met Asp Ala Glu His Pro Glu Leu
        210                 215                 220
Arg Ser Tyr Ala Gln Ser Gln Gly Trp Trp Thr Gly Glu Gly Glu Phe
225                 230                 235                 240
Asn Phe Ser Glu Val Phe Ser Pro Val Glu Asp His Leu Asp Cys Gly
                245                 250                 255
Ala Gly Lys Asp Ser Leu Glu Lys Gln Glu Glu Ser Ile Thr Val Gln
            260                 265                 270
Thr Met Met Asn Thr Leu Arg Asp Lys Ala Ser Gly Val Cys Ile Asp
        275                 280                 285
Ser Glu Phe Phe Leu Thr Thr Ala Ser Gly Val Ser Val Leu Pro Gln
290                 295                 300
Asn Arg Ser Ser Pro Cys Ile His Tyr Phe Thr Gly Thr Pro Asp Pro
305                 310                 315                 320
Ser Arg Ser Ile Phe Lys Pro Phe Ile Phe Val Asp Asp Val Lys Leu
                325                 330                 335
Val Pro Lys Thr Gln Ser Pro Cys Phe Gly Asp Asp Pro Ala Lys
            340                 345                 350
Lys Glu Pro Arg Phe Gln Glu Lys Pro Asp Arg Arg His Glu Leu Tyr
        355                 360                 365
Lys Ala His Glu Trp Ala Arg Ala Ile Ile Glu Ser Asp Gln Glu Gln
        370                 375                 380
Gly Arg Lys Leu Arg Ser Thr Met Leu Glu Leu Glu Lys Gln Gly Leu
385                 390                 395                 400
Glu Ala Met Glu Glu Ile Leu Thr Ser Ser Glu Pro Leu Asp Pro Ala
                405                 410                 415
Glu Val Gly Asp Leu Phe Tyr Asp Cys Val Asp Thr Glu Ile Lys Phe
            420                 425                 430
Phe Lys

<210> SEQ ID NO 31
<211> LENGTH: 29
<212> TYPE: DNA
<213> ORGANISM: Artificial Sequence
<220> FEATURE:
<223> OTHER INFORMATION: ACSS3

<400> SEQUENCE: 31
gggataagat tgctatcatc tatgacagt                                29

<210> SEQ ID NO 32
<211> LENGTH: 29
<212> TYPE: DNA
<213> ORGANISM: Artificial Sequence
<220> FEATURE:
<223> OTHER INFORMATION: ACSS3

<400> SEQUENCE: 32
gaaggctcta caatgagaat gtatgctat                                29

<210> SEQ ID NO 33
<211> LENGTH: 30
<212> TYPE: DNA
<213> ORGANISM: Artificial Sequence
<220> FEATURE:
<223> OTHER INFORMATION: ACSS3
```

<400> SEQUENCE: 33
ttcagtcaga tgctcagact taaatagatt                                          30

<210> SEQ ID NO 34
<211> LENGTH: 22
<212> TYPE: DNA
<213> ORGANISM: Artificial Sequence
<220> FEATURE:
<223> OTHER INFORMATION: ACSS3

<400> SEQUENCE: 34
acagtcatgt gactgggctt tt                                                  22

<210> SEQ ID NO 35
<211> LENGTH: 29
<212> TYPE: DNA
<213> ORGANISM: Artificial Sequence
<220> FEATURE:
<223> OTHER INFORMATION: ACSS3

<400> SEQUENCE: 35
ctctagatat aaatgcaaca gaggagcaa                                           29

<210> SEQ ID NO 36
<211> LENGTH: 25
<212> TYPE: DNA
<213> ORGANISM: Artificial Sequence
<220> FEATURE:
<223> OTHER INFORMATION: ACSS3

<400> SEQUENCE: 36
ccattgacaa tggcagataa agctg                                               25

<210> SEQ ID NO 37
<211> LENGTH: 28
<212> TYPE: DNA
<213> ORGANISM: Artificial Sequence
<220> FEATURE:
<223> OTHER INFORMATION: ADAM21

<400> SEQUENCE: 37
gggctttcga ggagtattaa aaataagt                                            28

<210> SEQ ID NO 38
<211> LENGTH: 24
<212> TYPE: DNA
<213> ORGANISM: Artificial Sequence
<220> FEATURE:
<223> OTHER INFORMATION: ADAM21

<400> SEQUENCE: 38
tgctacttcc ttctctgtta agcc                                                24

<210> SEQ ID NO 39
<211> LENGTH: 30
<212> TYPE: DNA
<213> ORGANISM: Artificial Sequence
<220> FEATURE:
<223> OTHER INFORMATION: ADAM21

<400> SEQUENCE: 39
gtatttcttg ttgtcaacat agtggattcc                                          30

<210> SEQ ID NO 40

```
<211> LENGTH: 22
<212> TYPE: DNA
<213> ORGANISM: Artificial Sequence
<220> FEATURE:
<223> OTHER INFORMATION: ADAM21

<400> SEQUENCE: 40
atgctgtagc tgggaaagac tg                                            22

<210> SEQ ID NO 41
<211> LENGTH: 25
<212> TYPE: DNA
<213> ORGANISM: Artificial Sequence
<220> FEATURE:
<223> OTHER INFORMATION: ADAM21

<400> SEQUENCE: 41
cttaaaccag ggatcatgtc tgcat                                         25

<210> SEQ ID NO 42
<211> LENGTH: 22
<212> TYPE: DNA
<213> ORGANISM: Artificial Sequence
<220> FEATURE:
<223> OTHER INFORMATION: ADAM21

<400> SEQUENCE: 42
gtcttgttca cactgctgta cg                                            22

<210> SEQ ID NO 43
<211> LENGTH: 26
<212> TYPE: DNA
<213> ORGANISM: Artificial Sequence
<220> FEATURE:
<223> OTHER INFORMATION: ADAM21

<400> SEQUENCE: 43
gatgtctttt gtgggagagt tcaatg                                        26

<210> SEQ ID NO 44
<211> LENGTH: 22
<212> TYPE: DNA
<213> ORGANISM: Artificial Sequence
<220> FEATURE:
<223> OTHER INFORMATION: ADAM21

<400> SEQUENCE: 44
ggccacacac agtaccatct tt                                            22

<210> SEQ ID NO 45
<211> LENGTH: 25
<212> TYPE: DNA
<213> ORGANISM: Artificial Sequence
<220> FEATURE:
<223> OTHER INFORMATION: AFF2

<400> SEQUENCE: 45
tcaccaggat aatacccatc cttca                                         25

<210> SEQ ID NO 46
<211> LENGTH: 22
<212> TYPE: DNA
<213> ORGANISM: Artificial Sequence
<220> FEATURE:
<223> OTHER INFORMATION: AFF2

<400> SEQUENCE: 46
```

<210> SEQ ID NO 47
<211> LENGTH: 19
<212> TYPE: DNA
<213> ORGANISM: Artificial Sequence
<220> FEATURE:
<223> OTHER INFORMATION: AFF2

<400> SEQUENCE: 47
tcggagagca gctctgagt					19

<210> SEQ ID NO 48
<211> LENGTH: 20
<212> TYPE: DNA
<213> ORGANISM: Artificial Sequence
<220> FEATURE:
<223> OTHER INFORMATION: AFF2

<400> SEQUENCE: 48
ctgtgggaca ggcagatcat					20

<210> SEQ ID NO 49
<211> LENGTH: 25
<212> TYPE: DNA
<213> ORGANISM: Artificial Sequence
<220> FEATURE:
<223> OTHER INFORMATION: AFF2

<400> SEQUENCE: 49
ggctttgaag cataagttgt caaca					25

<210> SEQ ID NO 50
<211> LENGTH: 22
<212> TYPE: DNA
<213> ORGANISM: Artificial Sequence
<220> FEATURE:
<223> OTHER INFORMATION: AFF2

<400> SEQUENCE: 50
gggtcatgaa gctccacact tt					22

<210> SEQ ID NO 51
<211> LENGTH: 24
<212> TYPE: DNA
<213> ORGANISM: Artificial Sequence
<220> FEATURE:
<223> OTHER INFORMATION: AFF2

<400> SEQUENCE: 51
gccaaatcca aggaaatctg tggt					24

<210> SEQ ID NO 52
<211> LENGTH: 27
<212> TYPE: DNA
<213> ORGANISM: Artificial Sequence
<220> FEATURE:
<223> OTHER INFORMATION: AFF2

<400> SEQUENCE: 52
agaggttttt caggttctca tgatctc					27

<210> SEQ ID NO 53
<211> LENGTH: 22
<212> TYPE: DNA agtctgcatc ttgtttggct ga					22

```
<213> ORGANISM: Artificial Sequence
<220> FEATURE:
<223> OTHER INFORMATION: ALG13

<400> SEQUENCE: 53
tccggatacc tgcataagca ag                                              22

<210> SEQ ID NO 54
<211> LENGTH: 26
<212> TYPE: DNA
<213> ORGANISM: Artificial Sequence
<220> FEATURE:
<223> OTHER INFORMATION: ALG13

<400> SEQUENCE: 54
catccattga tgcctcattc aaagac                                          26

<210> SEQ ID NO 55
<211> LENGTH: 28
<212> TYPE: DNA
<213> ORGANISM: Artificial Sequence
<220> FEATURE:
<223> OTHER INFORMATION: ALG13

<400> SEQUENCE: 55
gaagactaag gattgtgagt ttgtagca                                        28

<210> SEQ ID NO 56
<211> LENGTH: 30
<212> TYPE: DNA
<213> ORGANISM: Artificial Sequence
<220> FEATURE:
<223> OTHER INFORMATION: ALG13

<400> SEQUENCE: 56
tcctgttgat atttctttac cttttctgct                                      30

<210> SEQ ID NO 57
<211> LENGTH: 25
<212> TYPE: DNA
<213> ORGANISM: Artificial Sequence
<220> FEATURE:
<223> OTHER INFORMATION: ALG13

<400> SEQUENCE: 57
tctttgttag tgattgcctc accat                                           25

<210> SEQ ID NO 58
<211> LENGTH: 22
<212> TYPE: DNA
<213> ORGANISM: Artificial Sequence
<220> FEATURE:
<223> OTHER INFORMATION: ALG13

<400> SEQUENCE: 58
agtctctccc acatcaagag ca                                              22

<210> SEQ ID NO 59
<211> LENGTH: 27
<212> TYPE: DNA
<213> ORGANISM: Artificial Sequence
<220> FEATURE:
<223> OTHER INFORMATION: BAP1

<400> SEQUENCE: 59
gtaggagaga agaagactga gagcact                                         27
```

<210> SEQ ID NO 60
<211> LENGTH: 23
<212> TYPE: DNA
<213> ORGANISM: Artificial Sequence
<220> FEATURE:
<223> OTHER INFORMATION: BAP1

<400> SEQUENCE: 60
gtggaggctg agattgcaaa cta                                           23

<210> SEQ ID NO 61
<211> LENGTH: 23
<212> TYPE: DNA
<213> ORGANISM: Artificial Sequence
<220> FEATURE:
<223> OTHER INFORMATION: BAP1

<400> SEQUENCE: 61
ttccaatcaa gaacttggca cct                                           23

<210> SEQ ID NO 62
<211> LENGTH: 19
<212> TYPE: DNA
<213> ORGANISM: Artificial Sequence
<220> FEATURE:
<223> OTHER INFORMATION: BAP1

<400> SEQUENCE: 62
gtcgtggaag ccacggaca                                                19

<210> SEQ ID NO 63
<211> LENGTH: 22
<212> TYPE: DNA
<213> ORGANISM: Artificial Sequence
<220> FEATURE:
<223> OTHER INFORMATION: BAP1

<400> SEQUENCE: 63
gccgtgtctg tactctcatt gc                                            22

<210> SEQ ID NO 64
<211> LENGTH: 22
<212> TYPE: DNA
<213> ORGANISM: Artificial Sequence
<220> FEATURE:
<223> OTHER INFORMATION: BAP1

<400> SEQUENCE: 64
ccatcaacgt cttggctgag aa                                            22

<210> SEQ ID NO 65
<211> LENGTH: 23
<212> TYPE: DNA
<213> ORGANISM: Artificial Sequence
<220> FEATURE:
<223> OTHER INFORMATION: BAP1

<400> SEQUENCE: 65
aacctggtag ccttagaaag ctg                                           23

<210> SEQ ID NO 66
<211> LENGTH: 23
<212> TYPE: DNA
<213> ORGANISM: Artificial Sequence
<220> FEATURE:

<223> OTHER INFORMATION: BAP1

<400> SEQUENCE: 66
ttgtcccagg aggaagaaga cct                                    23

<210> SEQ ID NO 67
<211> LENGTH: 24
<212> TYPE: DNA
<213> ORGANISM: Artificial Sequence
<220> FEATURE:
<223> OTHER INFORMATION: BAP1

<400> SEQUENCE: 67
gggacttggc ataattgtga ttgt                                   24

<210> SEQ ID NO 68
<211> LENGTH: 22
<212> TYPE: DNA
<213> ORGANISM: Artificial Sequence
<220> FEATURE:
<223> OTHER INFORMATION: BAP1

<400> SEQUENCE: 68
atcccacagc cctcccaaca aa                                     22

<210> SEQ ID NO 69
<211> LENGTH: 22
<212> TYPE: DNA
<213> ORGANISM: Artificial Sequence
<220> FEATURE:
<223> OTHER INFORMATION: BAP1

<400> SEQUENCE: 69
gcttcaccac tagcttgggt tt                                     22

<210> SEQ ID NO 70
<211> LENGTH: 23
<212> TYPE: DNA
<213> ORGANISM: Artificial Sequence
<220> FEATURE:
<223> OTHER INFORMATION: BAP1

<400> SEQUENCE: 70
gggagactgt gagcttttct tgg                                    23

<210> SEQ ID NO 71
<211> LENGTH: 21
<212> TYPE: DNA
<213> ORGANISM: Artificial Sequence
<220> FEATURE:
<223> OTHER INFORMATION: BAP1

<400> SEQUENCE: 71
ggacttgttg ctggctgact t                                      21

<210> SEQ ID NO 72
<211> LENGTH: 22
<212> TYPE: DNA
<213> ORGANISM: Artificial Sequence
<220> FEATURE:
<223> OTHER INFORMATION: BAP1

<400> SEQUENCE: 72
gggtctaccc tttctcctct ga                                     22

```
<210> SEQ ID NO 73
<211> LENGTH: 27
<212> TYPE: DNA
<213> ORGANISM: Artificial Sequence
<220> FEATURE:
<223> OTHER INFORMATION: BAP1

<400> SEQUENCE: 73
gtatgttcac gaatcagaga caaatgc                                       27

<210> SEQ ID NO 74
<211> LENGTH: 22
<212> TYPE: DNA
<213> ORGANISM: Artificial Sequence
<220> FEATURE:
<223> OTHER INFORMATION: BAP1

<400> SEQUENCE: 74
cgaccgcagg atcaagtatg ag                                            22

<210> SEQ ID NO 75
<211> LENGTH: 22
<212> TYPE: DNA
<213> ORGANISM: Artificial Sequence
<220> FEATURE:
<223> OTHER INFORMATION: BAP1

<400> SEQUENCE: 75
cagcctggcc tcatacttga tc                                            22

<210> SEQ ID NO 76
<211> LENGTH: 24
<212> TYPE: DNA
<213> ORGANISM: Artificial Sequence
<220> FEATURE:
<223> OTHER INFORMATION: BAP1

<400> SEQUENCE: 76
caggatatct gcctcaacct gatg                                          24

<210> SEQ ID NO 77
<211> LENGTH: 22
<212> TYPE: DNA
<213> ORGANISM: Artificial Sequence
<220> FEATURE:
<223> OTHER INFORMATION: BAP1

<400> SEQUENCE: 77
catggtgcct accatggtca at                                            22

<210> SEQ ID NO 78
<211> LENGTH: 22
<212> TYPE: DNA
<213> ORGANISM: Artificial Sequence
<220> FEATURE:
<223> OTHER INFORMATION: BAP1

<400> SEQUENCE: 78
cctgagaagc agaatggcct ta                                            22

<210> SEQ ID NO 79
<211> LENGTH: 20
<212> TYPE: DNA
<213> ORGANISM: Artificial Sequence
<220> FEATURE:
<223> OTHER INFORMATION: BAP1
```

<400> SEQUENCE: 79
cgcactgcac taaggccatt                                              20

<210> SEQ ID NO 80
<211> LENGTH: 22
<212> TYPE: DNA
<213> ORGANISM: Artificial Sequence
<220> FEATURE:
<223> OTHER INFORMATION: BAP1

<400> SEQUENCE: 80
gccaaggccc ataatagcca tg                                           22

<210> SEQ ID NO 81
<211> LENGTH: 22
<212> TYPE: DNA
<213> ORGANISM: Artificial Sequence
<220> FEATURE:
<223> OTHER INFORMATION: BAP1

<400> SEQUENCE: 81
cacacacctg gcatggctat ta                                           22

<210> SEQ ID NO 82
<211> LENGTH: 24
<212> TYPE: DNA
<213> ORGANISM: Artificial Sequence
<220> FEATURE:
<223> OTHER INFORMATION: BAP1

<400> SEQUENCE: 82
cccatagtcc tacctgagga gaaa                                         24

<210> SEQ ID NO 83
<211> LENGTH: 22
<212> TYPE: DNA
<213> ORGANISM: Artificial Sequence
<220> FEATURE:
<223> OTHER INFORMATION: BAP1

<400> SEQUENCE: 83
ctgaaaccct tggtgaagtc ct                                           22

<210> SEQ ID NO 84
<211> LENGTH: 23
<212> TYPE: DNA
<213> ORGANISM: Artificial Sequence
<220> FEATURE:
<223> OTHER INFORMATION: BAP1

<400> SEQUENCE: 84
ttggtttcac agctgatacc caa                                          23

<210> SEQ ID NO 85
<211> LENGTH: 22
<212> TYPE: DNA
<213> ORGANISM: Artificial Sequence
<220> FEATURE:
<223> OTHER INFORMATION: BAP1

<400> SEQUENCE: 85
atcccaccct ccaaacaaag ca                                           22

<210> SEQ ID NO 86
<211> LENGTH: 26

```
<212> TYPE: DNA
<213> ORGANISM: Artificial Sequence
<220> FEATURE:
<223> OTHER INFORMATION: BAP1

<400> SEQUENCE: 86
cccagccctg tatatggatt tatctt                                          26

<210> SEQ ID NO 87
<211> LENGTH: 23
<212> TYPE: DNA
<213> ORGANISM: Artificial Sequence
<220> FEATURE:
<223> OTHER INFORMATION: BAP1

<400> SEQUENCE: 87
gctgctgctt tctgtgagat ttt                                             23

<210> SEQ ID NO 88
<211> LENGTH: 22
<212> TYPE: DNA
<213> ORGANISM: Artificial Sequence
<220> FEATURE:
<223> OTHER INFORMATION: BAP1

<400> SEQUENCE: 88
gggtgcaagt ggaggagatc ta                                              22

<210> SEQ ID NO 89
<211> LENGTH: 22
<212> TYPE: DNA
<213> ORGANISM: Artificial Sequence
<220> FEATURE:
<223> OTHER INFORMATION: BAP1

<400> SEQUENCE: 89
ccctgacatt tgctctgaag gt                                              22

<210> SEQ ID NO 90
<211> LENGTH: 22
<212> TYPE: DNA
<213> ORGANISM: Artificial Sequence
<220> FEATURE:
<223> OTHER INFORMATION: BAP1

<400> SEQUENCE: 90
tcggtaagag cctttctcc ct                                               22

<210> SEQ ID NO 91
<211> LENGTH: 23
<212> TYPE: DNA
<213> ORGANISM: Artificial Sequence
<220> FEATURE:
<223> OTHER INFORMATION: BAP1

<400> SEQUENCE: 91
tcttaccgaa atcttccacg agc                                             23

<210> SEQ ID NO 92
<211> LENGTH: 22
<212> TYPE: DNA
<213> ORGANISM: Artificial Sequence
<220> FEATURE:
<223> OTHER INFORMATION: BAP1

<400> SEQUENCE: 92
```
aagatgaata agggctggct gg                              22

<210> SEQ ID NO 93
<211> LENGTH: 28
<212> TYPE: DNA
<213> ORGANISM: Artificial Sequence
<220> FEATURE:
<223> OTHER INFORMATION: BAP1

<400> SEQUENCE: 93
cttactgaac actgtaacac tggaaaga                        28

<210> SEQ ID NO 94
<211> LENGTH: 28
<212> TYPE: DNA
<213> ORGANISM: Artificial Sequence
<220> FEATURE:
<223> OTHER INFORMATION: BAP1

<400> SEQUENCE: 94
gtgggaacag agctaatatt ctcaagag                        28

<210> SEQ ID NO 95
<211> LENGTH: 22
<212> TYPE: DNA
<213> ORGANISM: Artificial Sequence
<220> FEATURE:
<223> OTHER INFORMATION: BRWD3

<400> SEQUENCE: 95
agaggatcct cagtggacac aa                              22

<210> SEQ ID NO 96
<211> LENGTH: 24
<212> TYPE: DNA
<213> ORGANISM: Artificial Sequence
<220> FEATURE:
<223> OTHER INFORMATION: BRWD3

<400> SEQUENCE: 96
ctagaggagc taccagagcc aaac                            24

<210> SEQ ID NO 97
<211> LENGTH: 26
<212> TYPE: DNA
<213> ORGANISM: Artificial Sequence
<220> FEATURE:
<223> OTHER INFORMATION: BRWD3

<400> SEQUENCE: 97
attgttttta catgccattg ccagaa                          26

<210> SEQ ID NO 98
<211> LENGTH: 30
<212> TYPE: DNA
<213> ORGANISM: Artificial Sequence
<220> FEATURE:
<223> OTHER INFORMATION: BRWD3

<400> SEQUENCE: 98
ttgatgttag gctgaacatg aaaactttt                       30

<210> SEQ ID NO 99
<211> LENGTH: 30
<212> TYPE: DNA
<213> ORGANISM: Artificial Sequence

```
<220> FEATURE:
<223> OTHER INFORMATION: COL4A5

<400> SEQUENCE: 99
attaaattct ctgtggcaaa caataaggac                                        30

<210> SEQ ID NO 100
<211> LENGTH: 22
<212> TYPE: DNA
<213> ORGANISM: Artificial Sequence
<220> FEATURE:
<223> OTHER INFORMATION: COL4A5

<400> SEQUENCE: 100
tgggaaacca cgatcacctt tt                                                22

<210> SEQ ID NO 101
<211> LENGTH: 20
<212> TYPE: DNA
<213> ORGANISM: Artificial Sequence
<220> FEATURE:
<223> OTHER INFORMATION: COL4A5

<400> SEQUENCE: 101
cagctggaca gaagggtgaa                                                   20

<210> SEQ ID NO 102
<211> LENGTH: 29
<212> TYPE: DNA
<213> ORGANISM: Artificial Sequence
<220> FEATURE:
<223> OTHER INFORMATION: COL4A5

<400> SEQUENCE: 102
gtgtgtggta gcttagtaag aaagaagat                                         29

<210> SEQ ID NO 103
<211> LENGTH: 26
<212> TYPE: DNA
<213> ORGANISM: Artificial Sequence
<220> FEATURE:
<223> OTHER INFORMATION: COL4A5

<400> SEQUENCE: 103
caaaaactgg tttctctcac accaat                                            26

<210> SEQ ID NO 104
<211> LENGTH: 22
<212> TYPE: DNA
<213> ORGANISM: Artificial Sequence
<220> FEATURE:
<223> OTHER INFORMATION: COL4A5

<400> SEQUENCE: 104
tggaggacca gcatctcctt ta                                                22

<210> SEQ ID NO 105
<211> LENGTH: 25
<212> TYPE: DNA
<213> ORGANISM: Artificial Sequence
<220> FEATURE:
<223> OTHER INFORMATION: COL4A5

<400> SEQUENCE: 105
cctcattctt ttcctgtagg tccaa                                             25
```

```
<210> SEQ ID NO 106
<211> LENGTH: 25
<212> TYPE: DNA
<213> ORGANISM: Artificial Sequence
<220> FEATURE:
<223> OTHER INFORMATION: COL4A5

<400> SEQUENCE: 106
tctctcagac tcaaagactt tccct                                          25

<210> SEQ ID NO 107
<211> LENGTH: 24
<212> TYPE: DNA
<213> ORGANISM: Artificial Sequence
<220> FEATURE:
<223> OTHER INFORMATION: COL4A5

<400> SEQUENCE: 107
ccttgaaagg ctgtttgcta ttgt                                           24

<210> SEQ ID NO 108
<211> LENGTH: 29
<212> TYPE: DNA
<213> ORGANISM: Artificial Sequence
<220> FEATURE:
<223> OTHER INFORMATION: COL4A5

<400> SEQUENCE: 108
tcttgaagca aagttgcaaa cattattga                                      29

<210> SEQ ID NO 109
<211> LENGTH: 23
<212> TYPE: DNA
<213> ORGANISM: Artificial Sequence
<220> FEATURE:
<223> OTHER INFORMATION: COL4A5

<400> SEQUENCE: 109
ctgcttggaa gagtttcgtt cag                                            23

<210> SEQ ID NO 110
<211> LENGTH: 23
<212> TYPE: DNA
<213> ORGANISM: Artificial Sequence
<220> FEATURE:
<223> OTHER INFORMATION: COL4A5

<400> SEQUENCE: 110
ccctagcatc tctgaaggaa gct                                            23

<210> SEQ ID NO 111
<211> LENGTH: 22
<212> TYPE: DNA
<213> ORGANISM: Artificial Sequence
<220> FEATURE:
<223> OTHER INFORMATION: CPEB1

<400> SEQUENCE: 111
cccacctgat ctcgacagaa ga                                             22

<210> SEQ ID NO 112
<211> LENGTH: 22
<212> TYPE: DNA
<213> ORGANISM: Artificial Sequence
<220> FEATURE:
<223> OTHER INFORMATION: CPEB1
```

```
<400> SEQUENCE: 112
tggccaataa tgtgcccttc tt                                            22

<210> SEQ ID NO 113
<211> LENGTH: 23
<212> TYPE: DNA
<213> ORGANISM: Artificial Sequence
<220> FEATURE:
<223> OTHER INFORMATION: CPEB1

<400> SEQUENCE: 113
cacaagaaaa tccagtgcct caa                                           23

<210> SEQ ID NO 114
<211> LENGTH: 22
<212> TYPE: DNA
<213> ORGANISM: Artificial Sequence
<220> FEATURE:
<223> OTHER INFORMATION: CPEB1

<400> SEQUENCE: 114
aagtctgtcc gatccttgct tc                                            22

<210> SEQ ID NO 115
<211> LENGTH: 22
<212> TYPE: DNA
<213> ORGANISM: Artificial Sequence
<220> FEATURE:
<223> OTHER INFORMATION: CPEB1

<400> SEQUENCE: 115
ctaactgagg gtgctggaaa ct                                            22

<210> SEQ ID NO 116
<211> LENGTH: 23
<212> TYPE: DNA
<213> ORGANISM: Artificial Sequence
<220> FEATURE:
<223> OTHER INFORMATION: CPEB1

<400> SEQUENCE: 116
gctgttggct gcaaagaaaa cta                                           23

<210> SEQ ID NO 117
<211> LENGTH: 23
<212> TYPE: DNA
<213> ORGANISM: Artificial Sequence
<220> FEATURE:
<223> OTHER INFORMATION: ERBB2

<400> SEQUENCE: 117
gtttgagtga aggcattcat ggt                                           23

<210> SEQ ID NO 118
<211> LENGTH: 26
<212> TYPE: DNA
<213> ORGANISM: Artificial Sequence
<220> FEATURE:
<223> OTHER INFORMATION: ERBB2

<400> SEQUENCE: 118
gatctcttcc agagtctcaa acactt                                        26

<210> SEQ ID NO 119
```

```
<211> LENGTH: 22
<212> TYPE: DNA
<213> ORGANISM: Artificial Sequence
<220> FEATURE:
<223> OTHER INFORMATION: ERBB2

<400> SEQUENCE: 119
caagagggtg gttcccagaa tt                                              22

<210> SEQ ID NO 120
<211> LENGTH: 22
<212> TYPE: DNA
<213> ORGANISM: Artificial Sequence
<220> FEATURE:
<223> OTHER INFORMATION: ERBB2

<400> SEQUENCE: 120
gagtgaaggg caatgaaggg ta                                              22

<210> SEQ ID NO 121
<211> LENGTH: 22
<212> TYPE: DNA
<213> ORGANISM: Artificial Sequence
<220> FEATURE:
<223> OTHER INFORMATION: ERBB2

<400> SEQUENCE: 121
ggctggctcc gatgtatttg at                                              22

<210> SEQ ID NO 122
<211> LENGTH: 22
<212> TYPE: DNA
<213> ORGANISM: Artificial Sequence
<220> FEATURE:
<223> OTHER INFORMATION: ERBB2

<400> SEQUENCE: 122
caacgtagcc atcagtctca ga                                              22

<210> SEQ ID NO 123
<211> LENGTH: 29
<212> TYPE: DNA
<213> ORGANISM: Artificial Sequence
<220> FEATURE:
<223> OTHER INFORMATION: HSP90AA1

<400> SEQUENCE: 123
attacatagt ataaggctta cccagacca                                       29

<210> SEQ ID NO 124
<211> LENGTH: 23
<212> TYPE: DNA
<213> ORGANISM: Artificial Sequence
<220> FEATURE:
<223> OTHER INFORMATION: HSP90AA1

<400> SEQUENCE: 124
cgacaagtct gtgaaggatc tgg                                             23

<210> SEQ ID NO 125
<211> LENGTH: 31
<212> TYPE: DNA
<213> ORGANISM: Artificial Sequence
<220> FEATURE:
<223> OTHER INFORMATION: HSP90AA1

<400> SEQUENCE: 125
```

```
cctgataact ttcaaaattt tgctttgttg c                              31

<210> SEQ ID NO 126
<211> LENGTH: 23
<212> TYPE: DNA
<213> ORGANISM: Artificial Sequence
<220> FEATURE:
<223> OTHER INFORMATION: HSP90AA1

<400> SEQUENCE: 126
gtccttggaa tgactcagtg cat                                      23

<210> SEQ ID NO 127
<211> LENGTH: 32
<212> TYPE: DNA
<213> ORGANISM: Artificial Sequence
<220> FEATURE:
<223> OTHER INFORMATION: HSP90AA1

<400> SEQUENCE: 127
cagacagaaa ttcactctgc aattacataa aa                            32

<210> SEQ ID NO 128
<211> LENGTH: 20
<212> TYPE: DNA
<213> ORGANISM: Artificial Sequence
<220> FEATURE:
<223> OTHER INFORMATION: HSP90AA1

<400> SEQUENCE: 128
caggtgaacc tatgggtcgt                                          20

<210> SEQ ID NO 129
<211> LENGTH: 23
<212> TYPE: DNA
<213> ORGANISM: Artificial Sequence
<220> FEATURE:
<223> OTHER INFORMATION: HSP90AA1

<400> SEQUENCE: 129
cccaagaagt tcacactgaa acc                                      23

<210> SEQ ID NO 130
<211> LENGTH: 20
<212> TYPE: DNA
<213> ORGANISM: Artificial Sequence
<220> FEATURE:
<223> OTHER INFORMATION: HSP90AA1

<400> SEQUENCE: 130
tgagacgttc gcctttcagg                                          20

<210> SEQ ID NO 131
<211> LENGTH: 19
<212> TYPE: DNA
<213> ORGANISM: Artificial Sequence
<220> FEATURE:
<223> OTHER INFORMATION: IRAK1

<400> SEQUENCE: 131
cgcctaggct ctcgtcact                                           19

<210> SEQ ID NO 132
<211> LENGTH: 19
<212> TYPE: DNA
```

```
<213> ORGANISM: Artificial Sequence
<220> FEATURE:
<223> OTHER INFORMATION: IRAK1

<400> SEQUENCE: 132
cccgcaggag aactcctac                                                19

<210> SEQ ID NO 133
<211> LENGTH: 20
<212> TYPE: DNA
<213> ORGANISM: Artificial Sequence
<220> FEATURE:
<223> OTHER INFORMATION: IRAK1

<400> SEQUENCE: 133
ccaggtgtca ggagtgcttt                                               20

<210> SEQ ID NO 134
<211> LENGTH: 21
<212> TYPE: DNA
<213> ORGANISM: Artificial Sequence
<220> FEATURE:
<223> OTHER INFORMATION: IRAK1

<400> SEQUENCE: 134
acaggtttcg tcacccaaac a                                             21

<210> SEQ ID NO 135
<211> LENGTH: 22
<212> TYPE: DNA
<213> ORGANISM: Artificial Sequence
<220> FEATURE:
<223> OTHER INFORMATION: KDM5C

<400> SEQUENCE: 135
tccgtaccct ctttggctct ag                                            22

<210> SEQ ID NO 136
<211> LENGTH: 25
<212> TYPE: DNA
<213> ORGANISM: Artificial Sequence
<220> FEATURE:
<223> OTHER INFORMATION: KDM5C

<400> SEQUENCE: 136
tgtctttctg cctgtctgta atcac                                         25

<210> SEQ ID NO 137
<211> LENGTH: 20
<212> TYPE: DNA
<213> ORGANISM: Artificial Sequence
<220> FEATURE:
<223> OTHER INFORMATION: KDM5C

<400> SEQUENCE: 137
ccagaagtgt gcggatcctc                                               20

<210> SEQ ID NO 138
<211> LENGTH: 20
<212> TYPE: DNA
<213> ORGANISM: Artificial Sequence
<220> FEATURE:
<223> OTHER INFORMATION: KDM5C

<400> SEQUENCE: 138
agttgactgg ccctgtgttg                                               20
```

<210> SEQ ID NO 139
<211> LENGTH: 23
<212> TYPE: DNA
<213> ORGANISM: Artificial Sequence
<220> FEATURE:
<223> OTHER INFORMATION: KDM5C

<400> SEQUENCE: 139
cccacacaca cagatagagg ttg					23

<210> SEQ ID NO 140
<211> LENGTH: 21
<212> TYPE: DNA
<213> ORGANISM: Artificial Sequence
<220> FEATURE:
<223> OTHER INFORMATION: KDM5C

<400> SEQUENCE: 140
ctgtcctggg tatggcagat c					21

<210> SEQ ID NO 141
<211> LENGTH: 21
<212> TYPE: DNA
<213> ORGANISM: Artificial Sequence
<220> FEATURE:
<223> OTHER INFORMATION: KDM5C

<400> SEQUENCE: 141
ccatctgtgt cgaagctcct t					21

<210> SEQ ID NO 142
<211> LENGTH: 21
<212> TYPE: DNA
<213> ORGANISM: Artificial Sequence
<220> FEATURE:
<223> OTHER INFORMATION: KDM5C

<400> SEQUENCE: 142
gttctctgcc catgtgcaga t					21

<210> SEQ ID NO 143
<211> LENGTH: 22
<212> TYPE: DNA
<213> ORGANISM: Artificial Sequence
<220> FEATURE:
<223> OTHER INFORMATION: KDM5C

<400> SEQUENCE: 143
ctcttctggg tctccactca ac					22

<210> SEQ ID NO 144
<211> LENGTH: 22
<212> TYPE: DNA
<213> ORGANISM: Artificial Sequence
<220> FEATURE:
<223> OTHER INFORMATION: KDM5C

<400> SEQUENCE: 144
cctagccctg ctgtggataa ag					22

<210> SEQ ID NO 145
<211> LENGTH: 23
<212> TYPE: DNA
<213> ORGANISM: Artificial Sequence
<220> FEATURE:

<223> OTHER INFORMATION: KDM5C

<400> SEQUENCE: 145
caggttgttc atctggtcca gaa                                          23

<210> SEQ ID NO 146
<211> LENGTH: 25
<212> TYPE: DNA
<213> ORGANISM: Artificial Sequence
<220> FEATURE:
<223> OTHER INFORMATION: KDM5C

<400> SEQUENCE: 146
agtcttagca tagacatgga gggaa                                        25

<210> SEQ ID NO 147
<211> LENGTH: 22
<212> TYPE: DNA
<213> ORGANISM: Artificial Sequence
<220> FEATURE:
<223> OTHER INFORMATION: KDM5C

<400> SEQUENCE: 147
gcctcactca ggcagttctt ta                                           22

<210> SEQ ID NO 148
<211> LENGTH: 26
<212> TYPE: DNA
<213> ORGANISM: Artificial Sequence
<220> FEATURE:
<223> OTHER INFORMATION: KDM5C

<400> SEQUENCE: 148
cctctgcctc tattcaatac tgccta                                       26

<210> SEQ ID NO 149
<211> LENGTH: 22
<212> TYPE: DNA
<213> ORGANISM: Artificial Sequence
<220> FEATURE:
<223> OTHER INFORMATION: KDM5C

<400> SEQUENCE: 149
ctactggagc acttgcagag at                                           22

<210> SEQ ID NO 150
<211> LENGTH: 22
<212> TYPE: DNA
<213> ORGANISM: Artificial Sequence
<220> FEATURE:
<223> OTHER INFORMATION: KDM5C

<400> SEQUENCE: 150
gatgatgagc gccagtgtat ca                                           22

<210> SEQ ID NO 151
<211> LENGTH: 22
<212> TYPE: DNA
<213> ORGANISM: Artificial Sequence
<220> FEATURE:
<223> OTHER INFORMATION: KDM5C

<400> SEQUENCE: 151
cccgaacttc caccagaata gg                                           22

```
<210> SEQ ID NO 152
<211> LENGTH: 23
<212> TYPE: DNA
<213> ORGANISM: Artificial Sequence
<220> FEATURE:
<223> OTHER INFORMATION: KDM5C

<400> SEQUENCE: 152
ccagagaagc tagacctgaa cct                                              23

<210> SEQ ID NO 153
<211> LENGTH: 23
<212> TYPE: DNA
<213> ORGANISM: Artificial Sequence
<220> FEATURE:
<223> OTHER INFORMATION: KDM5C

<400> SEQUENCE: 153
ccatcttgca gataagctcc tca                                              23

<210> SEQ ID NO 154
<211> LENGTH: 23
<212> TYPE: DNA
<213> ORGANISM: Artificial Sequence
<220> FEATURE:
<223> OTHER INFORMATION: KDM5C

<400> SEQUENCE: 154
gaagcaggag ggttgtagag aag                                              23

<210> SEQ ID NO 155
<211> LENGTH: 22
<212> TYPE: DNA
<213> ORGANISM: Artificial Sequence
<220> FEATURE:
<223> OTHER INFORMATION: KDM5C

<400> SEQUENCE: 155
gcaaagttgt agccttggtt ga                                               22

<210> SEQ ID NO 156
<211> LENGTH: 27
<212> TYPE: DNA
<213> ORGANISM: Artificial Sequence
<220> FEATURE:
<223> OTHER INFORMATION: KDM5C

<400> SEQUENCE: 156
caggaaaatc tctatctcaa cagccat                                          27

<210> SEQ ID NO 157
<211> LENGTH: 22
<212> TYPE: DNA
<213> ORGANISM: Artificial Sequence
<220> FEATURE:
<223> OTHER INFORMATION: KDM5C

<400> SEQUENCE: 157
gaggtcaggc tggctatcaa at                                               22

<210> SEQ ID NO 158
<211> LENGTH: 22
<212> TYPE: DNA
<213> ORGANISM: Artificial Sequence
<220> FEATURE:
<223> OTHER INFORMATION: KDM5C
```

```
<400> SEQUENCE: 158
cctgcatgac caaggtgtga tt                                               22

<210> SEQ ID NO 159
<211> LENGTH: 22
<212> TYPE: DNA
<213> ORGANISM: Artificial Sequence
<220> FEATURE:
<223> OTHER INFORMATION: KDM5C

<400> SEQUENCE: 159
ggagcccaca ctgacttgat tc                                               22

<210> SEQ ID NO 160
<211> LENGTH: 22
<212> TYPE: DNA
<213> ORGANISM: Artificial Sequence
<220> FEATURE:
<223> OTHER INFORMATION: KDM5C

<400> SEQUENCE: 160
gtactgtgcc acatcaatgc ag                                               22

<210> SEQ ID NO 161
<211> LENGTH: 25
<212> TYPE: DNA
<213> ORGANISM: Artificial Sequence
<220> FEATURE:
<223> OTHER INFORMATION: KDM5C

<400> SEQUENCE: 161
atgccagaga tatctgcatt gatgt                                            25

<210> SEQ ID NO 162
<211> LENGTH: 30
<212> TYPE: DNA
<213> ORGANISM: Artificial Sequence
<220> FEATURE:
<223> OTHER INFORMATION: KDM5C

<400> SEQUENCE: 162
gttccctagg ctaaagaaaa tgacttaaga                                       30

<210> SEQ ID NO 163
<211> LENGTH: 29
<212> TYPE: DNA
<213> ORGANISM: Artificial Sequence
<220> FEATURE:
<223> OTHER INFORMATION: KDM5C

<400> SEQUENCE: 163
agatactaaa tgatttgcct aagctcaca                                        29

<210> SEQ ID NO 164
<211> LENGTH: 26
<212> TYPE: DNA
<213> ORGANISM: Artificial Sequence
<220> FEATURE:
<223> OTHER INFORMATION: KDM5C

<400> SEQUENCE: 164
tagcattgag gaagatgtga ctgttg                                           26

<210> SEQ ID NO 165
<211> LENGTH: 25
```

```
<212> TYPE: DNA
<213> ORGANISM: Artificial Sequence
<220> FEATURE:
<223> OTHER INFORMATION: KDM5C

<400> SEQUENCE: 165
gggaatgctt attgaaggga caaga                                           25

<210> SEQ ID NO 166
<211> LENGTH: 23
<212> TYPE: DNA
<213> ORGANISM: Artificial Sequence
<220> FEATURE:
<223> OTHER INFORMATION: KDM5C

<400> SEQUENCE: 166
cctaagacct tcctggagag caa                                             23

<210> SEQ ID NO 167
<211> LENGTH: 22
<212> TYPE: DNA
<213> ORGANISM: Artificial Sequence
<220> FEATURE:
<223> OTHER INFORMATION: KDM5C

<400> SEQUENCE: 167
gtagcctcat ggtcatcttg gt                                              22

<210> SEQ ID NO 168
<211> LENGTH: 26
<212> TYPE: DNA
<213> ORGANISM: Artificial Sequence
<220> FEATURE:
<223> OTHER INFORMATION: KDM5C

<400> SEQUENCE: 168 ccattttct ctctcccaga taagga                                           26

<210> SEQ ID NO 169
<211> LENGTH: 22
<212> TYPE: DNA
<213> ORGANISM: Artificial Sequence
<220> FEATURE:
<223> OTHER INFORMATION: KDM5C

<400> SEQUENCE: 169
tccctccacc tcaaagctct aa                                              22

<210> SEQ ID NO 170
<211> LENGTH: 30
<212> TYPE: DNA
<213> ORGANISM: Artificial Sequence
<220> FEATURE:
<223> OTHER INFORMATION: KDM5C

<400> SEQUENCE: 170
taatgaggag aaggacaagg aatacaaacc                                      30

<210> SEQ ID NO 171
<211> LENGTH: 23
<212> TYPE: DNA
<213> ORGANISM: Artificial Sequence
<220> FEATURE:
<223> OTHER INFORMATION: KDM5C

<400> SEQUENCE: 171
```

```
gcaaggagcc aatattttig cct                                           23

<210> SEQ ID NO 172
<211> LENGTH: 23
<212> TYPE: DNA
<213> ORGANISM: Artificial Sequence
<220> FEATURE:
<223> OTHER INFORMATION: KDM5C

<400> SEQUENCE: 172
ctacaggcct actccctcac ata                                           23

<210> SEQ ID NO 173
<211> LENGTH: 22
<212> TYPE: DNA
<213> ORGANISM: Artificial Sequence
<220> FEATURE:
<223> OTHER INFORMATION: KDM5C

<400> SEQUENCE: 173
accaccagct cctagtcttc tc                                            22

<210> SEQ ID NO 174
<211> LENGTH: 24
<212> TYPE: DNA
<213> ORGANISM: Artificial Sequence
<220> FEATURE:
<223> OTHER INFORMATION: KDM5C

<400> SEQUENCE: 174
cttttggtga cttccggtct taca                                          24

<210> SEQ ID NO 175
<211> LENGTH: 19
<212> TYPE: DNA
<213> ORGANISM: Artificial Sequence
<220> FEATURE:
<223> OTHER INFORMATION: KDM5C

<400> SEQUENCE: 175
cgatgggcct gattttcgc                                                19

<210> SEQ ID NO 176
<211> LENGTH: 19
<212> TYPE: DNA
<213> ORGANISM: Artificial Sequence
<220> FEATURE:
<223> OTHER INFORMATION: KDM5C

<400> SEQUENCE: 176
gcgccatgag tccttaagg                                                19

<210> SEQ ID NO 177
<211> LENGTH: 22
<212> TYPE: DNA
<213> ORGANISM: Artificial Sequence
<220> FEATURE:
<223> OTHER INFORMATION: KDM6A

<400> SEQUENCE: 177
ccaagcaaga attcatgcac gt                                            22

<210> SEQ ID NO 178
<211> LENGTH: 28
<212> TYPE: DNA
<213> ORGANISM: Artificial Sequence
```

```
<220> FEATURE:
<223> OTHER INFORMATION: KDM6A

<400> SEQUENCE: 178
agactcatag tctgtgttca ctttgaac                                          28

<210> SEQ ID NO 179
<211> LENGTH: 23
<212> TYPE: DNA
<213> ORGANISM: Artificial Sequence
<220> FEATURE:
<223> OTHER INFORMATION: KDM6A

<400> SEQUENCE: 179
cactgttcat tgggttcagg cta                                               23

<210> SEQ ID NO 180
<211> LENGTH: 30
<212> TYPE: DNA
<213> ORGANISM: Artificial Sequence
<220> FEATURE:
<223> OTHER INFORMATION: KDM6A

<400> SEQUENCE: 180
aaaaaggaac agtcctattg gatataatcc                                        30

<210> SEQ ID NO 181
<211> LENGTH: 22
<212> TYPE: DNA
<213> ORGANISM: Artificial Sequence
<220> FEATURE:
<223> OTHER INFORMATION: LRP12

<400> SEQUENCE: 181
acctcgggta ctctgagttg ag                                                22

<210> SEQ ID NO 182
<211> LENGTH: 24
<212> TYPE: DNA
<213> ORGANISM: Artificial Sequence
<220> FEATURE:
<223> OTHER INFORMATION: LRP12

<400> SEQUENCE: 182
aagtttgttt tccgtggagt ctga                                              24

<210> SEQ ID NO 183
<211> LENGTH: 24
<212> TYPE: DNA
<213> ORGANISM: Artificial Sequence
<220> FEATURE:
<223> OTHER INFORMATION: LRP12

<400> SEQUENCE: 183
tccacggaaa acaaacttct gtga                                              24

<210> SEQ ID NO 184
<211> LENGTH: 22
<212> TYPE: DNA
<213> ORGANISM: Artificial Sequence
<220> FEATURE:
<223> OTHER INFORMATION: LRP12

<400> SEQUENCE: 184
ttcctatggc aggcagatca ag                                                22
```

<210> SEQ ID NO 185
<211> LENGTH: 24
<212> TYPE: DNA
<213> ORGANISM: Artificial Sequence
<220> FEATURE:
<223> OTHER INFORMATION: NCOA6

<400> SEQUENCE: 185
ctgggaagtt tgttaggatc cgaa                                          24

<210> SEQ ID NO 186
<211> LENGTH: 22
<212> TYPE: DNA
<213> ORGANISM: Artificial Sequence
<220> FEATURE:
<223> OTHER INFORMATION: NCOA6

<400> SEQUENCE: 186
caaggagagc ttgaatgtgc ct                                            22

<210> SEQ ID NO 187
<211> LENGTH: 22
<212> TYPE: DNA
<213> ORGANISM: Artificial Sequence
<220> FEATURE:
<223> OTHER INFORMATION: NCOA6

<400> SEQUENCE: 187
cccaaaatgg cctgcagata tg                                            22

<210> SEQ ID NO 188
<211> LENGTH: 22
<212> TYPE: DNA
<213> ORGANISM: Artificial Sequence
<220> FEATURE:
<223> OTHER INFORMATION: NCOA6

<400> SEQUENCE: 188
ggccatggga tgtctttcaa tg                                            22

<210> SEQ ID NO 189
<211> LENGTH: 23
<212> TYPE: DNA
<213> ORGANISM: Artificial Sequence
<220> FEATURE:
<223> OTHER INFORMATION: NCOA6

<400> SEQUENCE: 189
ctccactgaa aggtgcattg aaa                                           23

<210> SEQ ID NO 190
<211> LENGTH: 26
<212> TYPE: DNA
<213> ORGANISM: Artificial Sequence
<220> FEATURE:
<223> OTHER INFORMATION: NCOA6

<400> SEQUENCE: 190
ggtgatcctg ctactacagc aaataa                                        26

<210> SEQ ID NO 191
<211> LENGTH: 25
<212> TYPE: DNA
<213> ORGANISM: Artificial Sequence
<220> FEATURE:
<223> OTHER INFORMATION: NCOA6

```
<400> SEQUENCE: 191
gcagggctca aatgatcaaa taagc                                    25

<210> SEQ ID NO 192
<211> LENGTH: 23
<212> TYPE: DNA
<213> ORGANISM: Artificial Sequence
<220> FEATURE:
<223> OTHER INFORMATION: NCOA6

<400> SEQUENCE: 192
ttggctcaga accgaagcca aga                                      23

<210> SEQ ID NO 193
<211> LENGTH: 30
<212> TYPE: DNA
<213> ORGANISM: Artificial Sequence
<220> FEATURE:
<223> OTHER INFORMATION: NHS

<400> SEQUENCE: 193
tccaagtaaa tgaaatttg tttgccattt                                30

<210> SEQ ID NO 194
<211> LENGTH: 22
<212> TYPE: DNA
<213> ORGANISM: Artificial Sequence
<220> FEATURE:
<223> OTHER INFORMATION: NHS

<400> SEQUENCE: 194
gggatacccg agatggtttt cc                                       22

<210> SEQ ID NO 195
<211> LENGTH: 26
<212> TYPE: DNA
<213> ORGANISM: Artificial Sequence
<220> FEATURE:
<223> OTHER INFORMATION: NHS

<400> SEQUENCE: 195
acagcaaccc tctttaaaag atggaa                                   26

<210> SEQ ID NO 196
<211> LENGTH: 30
<212> TYPE: DNA
<213> ORGANISM: Artificial Sequence
<220> FEATURE:
<223> OTHER INFORMATION: NHS

<400> SEQUENCE: 196
tctcctactg tgttctgctt attatgagta                               30

<210> SEQ ID NO 197
<211> LENGTH: 22
<212> TYPE: DNA
<213> ORGANISM: Artificial Sequence
<220> FEATURE:
<223> OTHER INFORMATION: NHS

<400> SEQUENCE: 197
accgtcatcc actgcatgtt tt                                       22

<210> SEQ ID NO 198
```

```
<211> LENGTH: 28
<212> TYPE: DNA
<213> ORGANISM: Artificial Sequence
<220> FEATURE:
<223> OTHER INFORMATION: NHS

<400> SEQUENCE: 198
cttaacttct tcagacttgt tgatggac                                          28

<210> SEQ ID NO 199
<211> LENGTH: 23
<212> TYPE: DNA
<213> ORGANISM: Artificial Sequence
<220> FEATURE:
<223> OTHER INFORMATION: RGAG1

<400> SEQUENCE: 199
gaatgatgtc atccatgcca caa                                               23

<210> SEQ ID NO 200
<211> LENGTH: 22
<212> TYPE: DNA
<213> ORGANISM: Artificial Sequence
<220> FEATURE:
<223> OTHER INFORMATION: RGAG1

<400> SEQUENCE: 200
agtgtgcaca tgtctccaga ag                                                22

<210> SEQ ID NO 201
<211> LENGTH: 22
<212> TYPE: DNA
<213> ORGANISM: Artificial Sequence
<220> FEATURE:
<223> OTHER INFORMATION: RGAG1

<400> SEQUENCE: 201
gtccacattg caaaccagtg tt                                                22

<210> SEQ ID NO 202
<211> LENGTH: 22
<212> TYPE: DNA
<213> ORGANISM: Artificial Sequence
<220> FEATURE:
<223> OTHER INFORMATION: RGAG1

<400> SEQUENCE: 202
catgggcatc gatccagaaa ct                                                22

<210> SEQ ID NO 203
<211> LENGTH: 26
<212> TYPE: DNA
<213> ORGANISM: Artificial Sequence
<220> FEATURE:
<223> OTHER INFORMATION: RGAG1

<400> SEQUENCE: 203
ccacatcatt tatgagagcc tcagtt                                            26

<210> SEQ ID NO 204
<211> LENGTH: 22
<212> TYPE: DNA
<213> ORGANISM: Artificial Sequence
<220> FEATURE:
<223> OTHER INFORMATION: RGAG1

<400> SEQUENCE: 204
```

```
tgtggtgtgg acattgttcc ag                                              22

<210> SEQ ID NO 205
<211> LENGTH: 21
<212> TYPE: DNA
<213> ORGANISM: Artificial Sequence
<220> FEATURE:
<223> OTHER INFORMATION: SCAF1

<400> SEQUENCE: 205
ccatgtgtcc cattggcttc t                                               21

<210> SEQ ID NO 206
<211> LENGTH: 20
<212> TYPE: DNA
<213> ORGANISM: Artificial Sequence
<220> FEATURE:
<223> OTHER INFORMATION: SCAF1

<400> SEQUENCE: 206
gggttcgtga gcaaaggagg                                                 20

<210> SEQ ID NO 207
<211> LENGTH: 19
<212> TYPE: DNA
<213> ORGANISM: Artificial Sequence
<220> FEATURE:
<223> OTHER INFORMATION: SCAF1

<400> SEQUENCE: 207
cgctttagct ccgcctctc                                                  19

<210> SEQ ID NO 208
<211> LENGTH: 19
<212> TYPE: DNA
<213> ORGANISM: Artificial Sequence
<220> FEATURE:
<223> OTHER INFORMATION: SCAF1

<400> SEQUENCE: 208
actagcgacc caactccgc                                                  19

<210> SEQ ID NO 209
<211> LENGTH: 21
<212> TYPE: DNA
<213> ORGANISM: Artificial Sequence
<220> FEATURE:
<223> OTHER INFORMATION: SCAF1

<400> SEQUENCE: 209
gggacctcca ctccaaactc t                                               21

<210> SEQ ID NO 210
<211> LENGTH: 24
<212> TYPE: DNA
<213> ORGANISM: Artificial Sequence
<220> FEATURE:
<223> OTHER INFORMATION: SCAF1

<400> SEQUENCE: 210
ctcaccagga taaaggcaga agga                                            24

<210> SEQ ID NO 211
<211> LENGTH: 19
<212> TYPE: DNA
```

```
<213> ORGANISM: Artificial Sequence
<220> FEATURE:
<223> OTHER INFORMATION: SCAF1

<400> SEQUENCE: 211
atggtccgcc agacagaga                                                    19

<210> SEQ ID NO 212
<211> LENGTH: 22
<212> TYPE: DNA
<213> ORGANISM: Artificial Sequence
<220> FEATURE:
<223> OTHER INFORMATION: SCAF1

<400> SEQUENCE: 212
gtgcttcaag ggagccaaga gt                                                22

<210> SEQ ID NO 213
<211> LENGTH: 21
<212> TYPE: DNA
<213> ORGANISM: Artificial Sequence
<220> FEATURE:
<223> OTHER INFORMATION: SCAF1

<400> SEQUENCE: 213
gcacttgagt ctagctgtca g                                                 21

<210> SEQ ID NO 214
<211> LENGTH: 22
<212> TYPE: DNA
<213> ORGANISM: Artificial Sequence
<220> FEATURE:
<223> OTHER INFORMATION: SCAF1

<400> SEQUENCE: 214
ccgccatacc tttatcattg gg                                                22

<210> SEQ ID NO 215
<211> LENGTH: 22
<212> TYPE: DNA
<213> ORGANISM: Artificial Sequence
<220> FEATURE:
<223> OTHER INFORMATION: SH3TC1

<400> SEQUENCE: 215
ccacaggctt cactcatcac tg                                                22

<210> SEQ ID NO 216
<211> LENGTH: 22
<212> TYPE: DNA
<213> ORGANISM: Artificial Sequence
<220> FEATURE:
<223> OTHER INFORMATION: SH3TC1

<400> SEQUENCE: 216
caacgctcac cttcttggat ga                                                22

<210> SEQ ID NO 217
<211> LENGTH: 22
<212> TYPE: DNA
<213> ORGANISM: Artificial Sequence
<220> FEATURE:
<223> OTHER INFORMATION: SH3TC1

<400> SEQUENCE: 217
cagtgaccac ctccatcctt tt                                                22
```

<210> SEQ ID NO 218
<211> LENGTH: 21
<212> TYPE: DNA
<213> ORGANISM: Artificial Sequence
<220> FEATURE:
<223> OTHER INFORMATION: SH3TC1

<400> SEQUENCE: 218
ggcggtgaag agtctgtttc c                                              21

<210> SEQ ID NO 219
<211> LENGTH: 27
<212> TYPE: DNA
<213> ORGANISM: Artificial Sequence
<220> FEATURE:
<223> OTHER INFORMATION: SH3TC1

<400> SEQUENCE: 219
tctgtctgtc aaatcaagga atggaaa                                        27

<210> SEQ ID NO 220
<211> LENGTH: 22
<212> TYPE: DNA
<213> ORGANISM: Artificial Sequence
<220> FEATURE:
<223> OTHER INFORMATION: SH3TC1

<400> SEQUENCE: 220
cctggcatcc tcctcagaaa ag                                             22

<210> SEQ ID NO 221
<211> LENGTH: 30
<212> TYPE: DNA
<213> ORGANISM: Artificial Sequence
<220> FEATURE:
<223> OTHER INFORMATION: TBC1D8B

<400> SEQUENCE: 221
atgagataca tcagcatgct aatagaagtg                                     30

<210> SEQ ID NO 222
<211> LENGTH: 26
<212> TYPE: DNA
<213> ORGANISM: Artificial Sequence
<220> FEATURE:
<223> OTHER INFORMATION: TBC1D8B

<400> SEQUENCE: 222
catatcagtc atgtgttctg tcagct                                         26

<210> SEQ ID NO 223
<211> LENGTH: 29
<212> TYPE: DNA
<213> ORGANISM: Artificial Sequence
<220> FEATURE:
<223> OTHER INFORMATION: TBC1D8B

<400> SEQUENCE: 223
agcagacatg gtttttaaaa tcttccaaa                                      29

<210> SEQ ID NO 224
<211> LENGTH: 29
<212> TYPE: DNA
<213> ORGANISM: Artificial Sequence
<220> FEATURE:

<223> OTHER INFORMATION: TBC1D8B

<400> SEQUENCE: 224
cagtcaatct gatactgttc caaatatgg                                    29

<210> SEQ ID NO 225
<211> LENGTH: 29
<212> TYPE: DNA
<213> ORGANISM: Artificial Sequence
<220> FEATURE:
<223> OTHER INFORMATION: TBC1D8B

<400> SEQUENCE: 225
ccatatttgg aacagtatca gattgactg                                    29

<210> SEQ ID NO 226
<211> LENGTH: 28
<212> TYPE: DNA
<213> ORGANISM: Artificial Sequence
<220> FEATURE:
<223> OTHER INFORMATION: TBC1D8B

<400> SEQUENCE: 226
taccaattgc agaggagaat tctttgaa                                     28

<210> SEQ ID NO 227
<211> LENGTH: 25
<212> TYPE: DNA
<213> ORGANISM: Artificial Sequence
<220> FEATURE:
<223> OTHER INFORMATION: TBC1D8B

<400> SEQUENCE: 227
tggaaggaaa ctacatagcc ctaca                                        25

<210> SEQ ID NO 228
<211> LENGTH: 23
<212> TYPE: DNA
<213> ORGANISM: Artificial Sequence
<220> FEATURE:
<223> OTHER INFORMATION: TBC1D8B

<400> SEQUENCE: 228
caacagcgat gcaagaatct gtt                                          23

<210> SEQ ID NO 229
<211> LENGTH: 22
<212> TYPE: DNA
<213> ORGANISM: Artificial Sequence
<220> FEATURE:
<223> OTHER INFORMATION: TET2

<400> SEQUENCE: 229
taactgcagt gggcctgaaa at                                           22

<210> SEQ ID NO 230
<211> LENGTH: 22
<212> TYPE: DNA
<213> ORGANISM: Artificial Sequence
<220> FEATURE:
<223> OTHER INFORMATION: TET2

<400> SEQUENCE: 230
agttcaccat gtgtgtgttc ca                                           22

```
<210> SEQ ID NO 231
<211> LENGTH: 24
<212> TYPE: DNA
<213> ORGANISM: Artificial Sequence
<220> FEATURE:
<223> OTHER INFORMATION: TET2

<400> SEQUENCE: 231
cctgtgatgc tgatgatgct gata                                          24

<210> SEQ ID NO 232
<211> LENGTH: 23
<212> TYPE: DNA
<213> ORGANISM: Artificial Sequence
<220> FEATURE:
<223> OTHER INFORMATION: TET2

<400> SEQUENCE: 232
aattcttcac cagacgctag ctt                                           23

<210> SEQ ID NO 233
<211> LENGTH: 24
<212> TYPE: DNA
<213> ORGANISM: Artificial Sequence
<220> FEATURE:
<223> OTHER INFORMATION: TET2

<400> SEQUENCE: 233
ggaaaaagca ctctgaatgg tgga                                          24

<210> SEQ ID NO 234
<211> LENGTH: 23
<212> TYPE: DNA
<213> ORGANISM: Artificial Sequence
<220> FEATURE:
<223> OTHER INFORMATION: TET2

<400> SEQUENCE: 234
gcctttcaga aagcatcgga gaa                                           23

<210> SEQ ID NO 235
<211> LENGTH: 22
<212> TYPE: DNA
<213> ORGANISM: Artificial Sequence
<220> FEATURE:
<223> OTHER INFORMATION: TET2

<400> SEQUENCE: 235
aactgccagc agttgatgag aa                                            22

<210> SEQ ID NO 236
<211> LENGTH: 25
<212> TYPE: DNA
<213> ORGANISM: Artificial Sequence
<220> FEATURE:
<223> OTHER INFORMATION: TET2

<400> SEQUENCE: 236
ttacgtttta gatgggattc cgctt                                         25

<210> SEQ ID NO 237
<211> LENGTH: 22
<212> TYPE: DNA
<213> ORGANISM: Artificial Sequence
<220> FEATURE:
<223> OTHER INFORMATION: TET2
```

<400> SEQUENCE: 237
caccaagcgg aatcccatct aa                                                22

<210> SEQ ID NO 238
<211> LENGTH: 23
<212> TYPE: DNA
<213> ORGANISM: Artificial Sequence
<220> FEATURE:
<223> OTHER INFORMATION: TET2

<400> SEQUENCE: 238
agctgtgttg ttttctgggt gta                                               23

<210> SEQ ID NO 239
<211> LENGTH: 23
<212> TYPE: DNA
<213> ORGANISM: Artificial Sequence
<220> FEATURE:
<223> OTHER INFORMATION: TET2

<400> SEQUENCE: 239
aaacacaacc atcccagagt tca                                               23

<210> SEQ ID NO 240
<211> LENGTH: 29
<212> TYPE: DNA
<213> ORGANISM: Artificial Sequence
<220> FEATURE:
<223> OTHER INFORMATION: TET2

<400> SEQUENCE: 240
ccatgaaaac attcttccac tttagtctg                                         29

<210> SEQ ID NO 241
<211> LENGTH: 22
<212> TYPE: DNA
<213> ORGANISM: Artificial Sequence
<220> FEATURE:
<223> OTHER INFORMATION: TET2

<400> SEQUENCE: 241
gggtcactgc atgtttggac tt                                                22

<210> SEQ ID NO 242
<211> LENGTH: 24
<212> TYPE: DNA
<213> ORGANISM: Artificial Sequence
<220> FEATURE:
<223> OTHER INFORMATION: TET2

<400> SEQUENCE: 242
gcagtgtgag aacagactca acag                                              24

<210> SEQ ID NO 243
<211> LENGTH: 24
<212> TYPE: DNA
<213> ORGANISM: Artificial Sequence
<220> FEATURE:
<223> OTHER INFORMATION: TET2

<400> SEQUENCE: 243
aagtctctga cgtggatgag tttg                                              24

<210> SEQ ID NO 244
<211> LENGTH: 22

<212> TYPE: DNA
<213> ORGANISM: Artificial Sequence
<220> FEATURE:
<223> OTHER INFORMATION: TET2

<400> SEQUENCE: 244
gaaagctttt cagctgcagc tt                                    22

<210> SEQ ID NO 245
<211> LENGTH: 27
<212> TYPE: DNA
<213> ORGANISM: Artificial Sequence
<220> FEATURE:
<223> OTHER INFORMATION: TET2

<400> SEQUENCE: 245
aggtttggaa atagccagag ttttaca                               27

<210> SEQ ID NO 246
<211> LENGTH: 22
<212> TYPE: DNA
<213> ORGANISM: Artificial Sequence
<220> FEATURE:
<223> OTHER INFORMATION: TET2

<400> SEQUENCE: 246
atctagaggt ggctcccatg aa                                    22

<210> SEQ ID NO 247
<211> LENGTH: 30
<212> TYPE: DNA
<213> ORGANISM: Artificial Sequence
<220> FEATURE:
<223> OTHER INFORMATION: TEX13A

<400> SEQUENCE: 247
tcgagatata catgcttcgg ttctattttg                            30

<210> SEQ ID NO 248
<211> LENGTH: 23
<212> TYPE: DNA
<213> ORGANISM: Artificial Sequence
<220> FEATURE:
<223> OTHER INFORMATION: TEX13A

<400> SEQUENCE: 248
ctcatcagca aagacctcca gta                                   23

<210> SEQ ID NO 249
<211> LENGTH: 22
<212> TYPE: DNA
<213> ORGANISM: Artificial Sequence
<220> FEATURE:
<223> OTHER INFORMATION: TEX13A

<400> SEQUENCE: 249
gggttcgtgg ttccagagaa at                                    22

<210> SEQ ID NO 250
<211> LENGTH: 22
<212> TYPE: DNA
<213> ORGANISM: Artificial Sequence
<220> FEATURE:
<223> OTHER INFORMATION: TEX13A

<400> SEQUENCE: 250

-continued

```
cctccatgga gaccacagag aa                                          22

<210> SEQ ID NO 251
<211> LENGTH: 21
<212> TYPE: DNA
<213> ORGANISM: Artificial Sequence
<220> FEATURE:
<223> OTHER INFORMATION: TEX13A

<400> SEQUENCE: 251
tctctccagc ttctctgtgg t                                           21

<210> SEQ ID NO 252
<211> LENGTH: 22
<212> TYPE: DNA
<213> ORGANISM: Artificial Sequence
<220> FEATURE:
<223> OTHER INFORMATION: TEX13A

<400> SEQUENCE: 252
ctgctggagg aaaaggagca ga                                          22

<210> SEQ ID NO 253
<211> LENGTH: 22
<212> TYPE: DNA
<213> ORGANISM: Artificial Sequence
<220> FEATURE:
<223> OTHER INFORMATION: ULK3

<400> SEQUENCE: 253
gcctgaagag agtgtccctt ct                                          22

<210> SEQ ID NO 254
<211> LENGTH: 24
<212> TYPE: DNA
<213> ORGANISM: Artificial Sequence
<220> FEATURE:
<223> OTHER INFORMATION: ULK3

<400> SEQUENCE: 254
ccaagaaaag tctgaacaag gcat                                        24

<210> SEQ ID NO 255
<211> LENGTH: 23
<212> TYPE: DNA
<213> ORGANISM: Artificial Sequence
<220> FEATURE:
<223> OTHER INFORMATION: WNK3

<400> SEQUENCE: 255
gctgaagaga aggaggagac tga                                         23

<210> SEQ ID NO 256
<211> LENGTH: 30
<212> TYPE: DNA
<213> ORGANISM: Artificial Sequence
<220> FEATURE:
<223> OTHER INFORMATION: WNK3

<400> SEQUENCE: 256
cctggcttct tcagtcaata aggtaaataa                                  30

<210> SEQ ID NO 257
<211> LENGTH: 27
<212> TYPE: DNA
<213> ORGANISM: Artificial Sequence
```

```
<220> FEATURE:
<223> OTHER INFORMATION: WNK3

<400> SEQUENCE: 257
gaaacttgct ggtaatgtcc tactagt                                    27

<210> SEQ ID NO 258
<211> LENGTH: 22
<212> TYPE: DNA
<213> ORGANISM: Artificial Sequence
<220> FEATURE:
<223> OTHER INFORMATION: WNK3

<400> SEQUENCE: 258
ggcaggagct gcatcagtta ta                                         22

<210> SEQ ID NO 259
<211> LENGTH: 23
<212> TYPE: DNA
<213> ORGANISM: Artificial Sequence
<220> FEATURE:
<223> OTHER INFORMATION: WNK3

<400> SEQUENCE: 259
gtgctgctgt ggttttcttt gta                                        23

<210> SEQ ID NO 260
<211> LENGTH: 24
<212> TYPE: DNA
<213> ORGANISM: Artificial Sequence
<220> FEATURE:
<223> OTHER INFORMATION: WNK3

<400> SEQUENCE: 260
gggattctca gtgcaagtct atgg                                       24

<210> SEQ ID NO 261
<211> LENGTH: 25
<212> TYPE: DNA
<213> ORGANISM: Artificial Sequence
<220> FEATURE:
<223> OTHER INFORMATION: ARSF

<400> SEQUENCE: 261
gtgcatgacg acaagcctaa tattg                                      25

<210> SEQ ID NO 262
<211> LENGTH: 22
<212> TYPE: DNA
<213> ORGANISM: Artificial Sequence
<220> FEATURE:
<223> OTHER INFORMATION: ARSF

<400> SEQUENCE: 262
acgactgacg aacgtatgac tg                                         22

<210> SEQ ID NO 263
<211> LENGTH: 20
<212> TYPE: DNA
<213> ORGANISM: Artificial Sequence
<220> FEATURE:
<223> OTHER INFORMATION: CFP

<400> SEQUENCE: 263
gctgtagcag tgccggatat                                            20
```

```
<210> SEQ ID NO 264
<211> LENGTH: 24
<212> TYPE: DNA
<213> ORGANISM: Artificial Sequence
<220> FEATURE:
<223> OTHER INFORMATION: CFP

<400> SEQUENCE: 264
acatgaagtc catcagctgt caag                                          24

<210> SEQ ID NO 265
<211> LENGTH: 22
<212> TYPE: DNA
<213> ORGANISM: Artificial Sequence
<220> FEATURE:
<223> OTHER INFORMATION: CFP

<400> SEQUENCE: 265
ccgggatttc ttgacagctg at                                            22

<210> SEQ ID NO 266
<211> LENGTH: 23
<212> TYPE: DNA
<213> ORGANISM: Artificial Sequence
<220> FEATURE:
<223> OTHER INFORMATION: CFP

<400> SEQUENCE: 266
tgattccctg ctttggtcca atc                                           23

<210> SEQ ID NO 267
<211> LENGTH: 21
<212> TYPE: DNA
<213> ORGANISM: Artificial Sequence
<220> FEATURE:
<223> OTHER INFORMATION: CFP

<400> SEQUENCE: 267
cccactctga ggacctctgt a                                             21

<210> SEQ ID NO 268
<211> LENGTH: 20
<212> TYPE: DNA
<213> ORGANISM: Artificial Sequence
<220> FEATURE:
<223> OTHER INFORMATION: CFP

<400> SEQUENCE: 268
gaatgggcag tgctctggaa                                               20

<210> SEQ ID NO 269
<211> LENGTH: 20
<212> TYPE: DNA
<213> ORGANISM: Artificial Sequence
<220> FEATURE:
<223> OTHER INFORMATION: CFP

<400> SEQUENCE: 269
ggcaaaggca gtgttgagac                                               20

<210> SEQ ID NO 270
<211> LENGTH: 19
<212> TYPE: DNA
<213> ORGANISM: Artificial Sequence
<220> FEATURE:
<223> OTHER INFORMATION: CFP
```

<400> SEQUENCE: 270
gtgtccaggc ccaccacat                                              19

<210> SEQ ID NO 271
<211> LENGTH: 21
<212> TYPE: DNA
<213> ORGANISM: Artificial Sequence
<220> FEATURE:
<223> OTHER INFORMATION: FAM47A

<400> SEQUENCE: 271
actggatctc cgacgagtga t                                           21

<210> SEQ ID NO 272
<211> LENGTH: 23
<212> TYPE: DNA
<213> ORGANISM: Artificial Sequence
<220> FEATURE:
<223> OTHER INFORMATION: FAM47A

<400> SEQUENCE: 272
gagactggag tgtcccatct aag                                         23

<210> SEQ ID NO 273
<211> LENGTH: 25
<212> TYPE: DNA
<213> ORGANISM: Artificial Sequence
<220> FEATURE:
<223> OTHER INFORMATION: PHF16(JADE3)

<400> SEQUENCE: 273
acgccattgc catgaaaata tgaac                                       25

<210> SEQ ID NO 274
<211> LENGTH: 23
<212> TYPE: DNA
<213> ORGANISM: Artificial Sequence
<220> FEATURE:
<223> OTHER INFORMATION: PHF16(JADE3)

<400> SEQUENCE: 274
tccactctca ctaacctgat gca                                         23

<210> SEQ ID NO 275
<211> LENGTH: 24
<212> TYPE: DNA
<213> ORGANISM: Artificial Sequence
<220> FEATURE:
<223> OTHER INFORMATION: PHF16(JADE3)

<400> SEQUENCE: 275
ccattctagg agtgaagcaa agga                                        24

<210> SEQ ID NO 276
<211> LENGTH: 22
<212> TYPE: DNA
<213> ORGANISM: Artificial Sequence
<220> FEATURE:
<223> OTHER INFORMATION: PHF16(JADE3)

<400> SEQUENCE: 276
gccattggat ttggcaaact tg                                          22

<210> SEQ ID NO 277

```
<211> LENGTH: 22
<212> TYPE: DNA
<213> ORGANISM: Artificial Sequence
<220> FEATURE:
<223> OTHER INFORMATION: ZNF449

<400> SEQUENCE: 277
ggagctgaac tatggtgcta ct                                            22

<210> SEQ ID NO 278
<211> LENGTH: 29
<212> TYPE: DNA
<213> ORGANISM: Artificial Sequence
<220> FEATURE:
<223> OTHER INFORMATION: ZNF449

<400> SEQUENCE: 278
cattgagtaa ttggtgtttc taacccaac                                     29

<210> SEQ ID NO 279
<211> LENGTH: 28
<212> TYPE: DNA
<213> ORGANISM: Artificial Sequence
<220> FEATURE:
<223> OTHER INFORMATION: SCRN1

<400> SEQUENCE: 279
ttttgctggt aatttagtaa ggtgggaa                                      28

<210> SEQ ID NO 280
<211> LENGTH: 23
<212> TYPE: DNA
<213> ORGANISM: Artificial Sequence
<220> FEATURE:
<223> OTHER INFORMATION: SCRN1

<400> SEQUENCE: 280
cctggaagcc atggaagaaa tcc                                           23

<210> SEQ ID NO 281
<211> LENGTH: 24
<212> TYPE: DNA
<213> ORGANISM: Artificial Sequence
<220> FEATURE:
<223> OTHER INFORMATION: SCRN1

<400> SEQUENCE: 281
agggtatgag aaggagaatc gtga                                          24

<210> SEQ ID NO 282
<211> LENGTH: 22
<212> TYPE: DNA
<213> ORGANISM: Artificial Sequence
<220> FEATURE:
<223> OTHER INFORMATION: SCRN1

<400> SEQUENCE: 282
gaactcagga gttacgctca ga                                            22
```

GENDER-SPECIFIC MARKERS FOR DIAGNOSING PROGNOSIS AND DETERMINING TREATMENT STRATEGY FOR RENAL CANCER PATIENTS

SEQUENCE LISTING

The Sequence Listing submitted in text format (.txt) filed on May 25, 2018, named "SequenceListing.txt", created on Apr. 25, 2018 (310 KB), is incorporated herein by reference.

TECHNICAL FIELD

The present invention relates to a marker for diagnosing prognosis of a patient with kidney cancer, a kit for diagnosing prognosis of a patient with kidney cancer including the same, and a method of providing information required to diagnose the prognosis of kidney cancer and determine a therapeutic strategy for kidney cancer using the kit for diagnosing prognosis of a patient with kidney cancer.

BACKGROUND ART

The kidney is an important urinary organ that serves to excrete waste materials from the body by filtering blood to generate urine. Also, the kidney is an important endocrine organ that produces hormones such as angiotensin that controls the blood pressure, erythropoietin as a haemopoietic factor, and the like.

Tumors occurring in the kidney include renal cell carcinoma arising from the adults, Wilms' tumor arising from the children, sarcoma as a rare tumor, and the like. Later on, the renal cell carcinoma as a malignant tumor having the highest incidence rate is referred to as kidney cancer. In Japan, the kidney cancer develops at an incidence frequency of approximately 2.5 per every 100,000 persons. In this case, the kidney cancer tends to occur at a higher frequency for men, that is, the proportion of men and women is 2 to 3:1. Among the urological malignant tumors, the kidney cancer is the most common tumor following prostate cancer and bladder cancer. The kidney cancer refers to renal cell carcinoma that develops mostly in the parenchyma (including medulla and cortex in which cells producing urine in the kidney are held together) of the kidney.

A genetic factor is known to be one of risk factors for kidney cancer, but such risk factors generally include smoking, excessive fat intake, and the like. Also, it has been know that the incidence rate of tumor is high in patients receiving dialysis for a long time.

In the case of kidney cancer, patients rarely have any observable symptoms when a tumor has the maximum diameter of 5 cm or less. Generally, the kidney cancer is often found when patients take a medical examination through a CT scan, and the like. Hematuria, celioncus, pain, and the like appear as the symptoms of large tumors. Also, pyrexy, weight loss, anaemia, and the like are often caused as the systemic symptoms, and erythrocytosis, hypertension, hypercalcemia, and the like are rarely caused by endocrine factors. Meanwhile, development of phlebismus or varicocele in the abdominal wall often occurs by tremors in the inferior vena cava of the kidney. Approximately 20% of the kidney cancers are found from the metastasis to the lungs or bone. Because tumor has a strong tendency to spread into the vein in the case of kidney cancer, the kidney cancer easily metastasizes into other organs.

Kidney cancer has few symptoms when it has a small tumor size, but has symptoms only when the tumor grows to push organs. Therefore, because the diagnosis of the kidney cancer is often delayed, the metastasis of kidney cancer into other organs is found in approximately 30% of patients, compared to when the kidney cancer is diagnosed at an early stage. The most common symptom is hematuria, but is found only in 60% of the patients. On the contrary, because patients have symptoms such as dyspnoea, cough, headaches, and the like depending on the metastasized sites, the patients who are diagnosed with kidney cancer due to such metastatic symptoms also account for 30% of the entire patients. Because hypertension, hypercalcemia, hepatic dysfunction, and the like may be caused by certain hormones especially produced by cancer cells, tumors may be often found while checking these other symptoms in kidney cancer. However, there are many current cases in which tumors are found by chance in imaging tests while patients receive medical checkups without any symptoms. In this case, because the tumors are generally found at early stages, the results of tumor treatment have been relatively successful. Therefore, it has been known that it is very important to diagnose such kidney cancer.

In U.S., patients with kidney cancer account for approximately 3% of adult cancer patients, and approximately 32,000 cancer patients are newly reported every year. Also, approximately 12,000 cases are assumed to die from kidney cancer, with an increasing incidence frequency worldwide every year. In Korea, the incidence frequency of kidney cancer is reported to be lower than that in U.S. Therefore, the National Cancer Registry data (2012) reported that 1,578 new cases of cancer patients are registered so that it accounts for 1.6% of the total number of cancer occurrences. Kidney cancer occurs commonly in people between 40 to 60 years old, and the current state of cancer incidence by gender (National Cancer Registry data on 2012) reports that kidney cancer occurs most commonly in people in their 60s (479 cases, 30.2%), followed by 50s (412 cases, 26.0%), and 40s (268 cases, 16.9%) in the corresponding order thereof. When patients with kidney cancer undergo surgery to remove the tumor after the onset of kidney cancer, the patients have a high survival rate. However, because the patients have no clear symptoms at an early stage, it is difficult to diagnose kidney cancer at this stage. For these reasons, there is a need for development of a marker capable of diagnosing kidney cancer at an early stage and checking the patients' remaining lives after the onset of cancer.

Transglutaminase 2 (Registered Korean Patent No. 1267580) is disclosed as a marker used to detect or diagnose kidney cancer in humans. Although markers for diagnosing cancers including kidney cancer have been developed, there is no research on markers capable of determining the prognosis of patients with kidney cancer, particularly the relationship between the gender of patients with kidney cancer and the mutation of a certain gene.

To develop a therapeutic agent for diagnosing kidney cancer or healing patients with kidney cancer so as to determine a therapeutic strategy, the present inventors have conducted research on the relationship between the gene mutation and the gender of the patients found in the patients with kidney cancer on the basis of the need for development of the markers capable of diagnosing the prognosis of the patients with kidney cancer.

DISCLOSURE

Technical Problem

To apply a suitable therapeutic strategy to patients with kidney cancer, a development of markers which aid in predicting the prognosis of patients with kidney cancer and determining a therapeutic strategy thereof is needed. Therefore, it is an object of the present invention to provide a marker which aids in predicting the prognosis of patients with kidney cancer and determining a therapeutic strategy thereof based on the gender of the patients with kidney cancer.

Technical Solution

To solve the above problems, according to an aspect of the present invention, there is provided a kit for providing information required to predict a therapeutic effect against kidney cancer or diagnose prognosis of a patient with kidney cancer according to the gender of the patient with kidney cancer, wherein the kit is able to detect a gender-specific marker that is a mutation of a gene coding for at least one selected from the group consisting of ACSS3, ADAM21, AFF2, ALG13, BAP1, BRWD3, COL4A5, CPEB1, ERBB2, HSP90AA1, IRAK1, KDM5C, KDM6A, LRP12, NCOA6, NHS, RGAG1, SCAF1, SH3TC1, TBC1D8B, TET2, TEX13A, ULK3, WNK3, ARSF, CFP, FAM47A, PHF16, ZNF449, and SCRN1.

According to another aspect of the present invention, there is provided a method of providing information required to verify a difference in therapeutic effect against kidney cancer according to the gender of patients with kidney cancer. In this case, the method includes preparing a DNA test sample from a sample of a patient with kidney cancer whose gender is identified; amplifying the DNA test sample using the kit; determining whether or not there is a gender-specific marker specific to a gender group of target patients from the results of amplification; treating the patient with kidney cancer, in which the gender-specific marker is identified, with any candidate material for treating kidney cancer or healing the patient with kidney cancer using any method; and choosing any candidate material for treating kidney cancer or any method of treating kidney cancer as a therapeutic candidate material or a therapeutic method, which is suitable for the gender group of patients with kidney cancer in which the gender-specific marker is identified, when the any candidate material or the any method is used to treat kidney cancer.

According to still another aspect of the present invention, there is provided a method of providing information required to diagnose prognosis of kidney cancer according to the gender of a patient with kidney cancer. In this case, the method includes preparing a DNA test sample from a sample of a patient with kidney cancer; amplifying the DNA test sample using the kit; and determining whether or not there is a gender-specific marker from the results of amplification.

Advantageous Effects

Because there is a relationship between the gender of a patient with kidney cancer and a mutation of a gene selected from a gene group consisting of ACSS3, ADAM21, AFF2, ALG13, BAP1, BRWD3, COL4A5, CPEB1, ERBB2, HSP90AA1, IRAK1, KDM5C, KDM6A, LRP12, NCOA6, NHS, RGAG1, SCAF1, SH3TC1, TBC1D8B, TET2, TEX13A, ULK3, WNK3, ARSF, CFP, FAM47A, PHF16, ZNF449, and SCRN1, all genes of which are found in the present invention, the presence of the mutation of the gene can be checked to predict a difference in therapeutic effect against kidney cancer and a difference in survival rate of the patient with kidney cancer according to the gender of the patient with kidney cancer.

In addition, because there is a relationship between a survival rate of the patient with kidney cancer who has a certain gender and a mutation of one gene selected from a gene group consisting of ACSS3, ALG13, ARSF, CFP, FAM47A, KDM6A, PHF16, ZNF449, and SCRN1, all genes of which are found in the present invention, or a relationship between the mutation of the gene and a relapse rate of kidney cancer, mutations of the genes according to the present invention can be used as the marker to predict the prognosis of the patient with kidney cancer.

However, the effects of the present invention are not limited to the effects as described above, and other effects not disclosed herein will be clearly understood from the following detailed description by those skilled in the art.

DESCRIPTION OF DRAWINGS

FIG. 1 is a diagram showing gender-specific mutant genes specifically shown from candidate genes when patients with kidney cancer who are classified according to the gender thereof are compared with each other. Each of numerical values represents the number of the patients with kidney cancer in which mutated genes are identified.

FIGS. 2 to 10 are graphs plotted for an overall survival rate or a disease-free survival rate of patients with kidney cancer (red) who have mutations in respective ACSS3, ALG13, ARSF, CFP, FAM47A, KDM6A, PHF16, ZNF449, and SCRN1 genes and patients with kidney cancer (blue) who have no mutations in the corresponding genes.

BEST MODE

Unless defined otherwise in this specification, all the technical and scientific terms used herein have the same meanings as what are generally understood by a person skilled in the related art to which the present invention belongs. In general, the nomenclatures used in this specification and the experimental methods described below are widely known and generally used in the related art.

Hereinafter, the present invention will be described in detail.

1. Gender-Specific Mutant Genes in Patient with Kidney Cancer and Primer Sets Capable of Detecting the Mutant Genes One aspect of the present invention provides a kit for providing information required to predict a difference in therapeutic effect against kidney cancer or diagnose prognosis of a patient with kidney cancer according to the gender of the patient with kidney cancer, wherein the kit may detect a gender-specific marker that is a mutation of at least one gene selected from a gene group consisting of ACSS3 (Gene Bank Accession Number: NM_024560.3), ADAM21 (Gene Bank Accession Number: NM_003813.3), AFF2 (Gene Bank Accession Number: NM_002025.3), ALG13 (Gene Bank Accession Number: NM_001099922.2), ARSF (Gene Bank Accession Number: NM_001201538.1), BAP1 (Gene Bank Accession Number: NM_004656.3), BRWD3 (Gene Bank Accession Number: NM_153252.4), CFP (Gene Bank Accession Number: NM_001145252.1), COL4A5 (Gene Bank Accession Number: NM_000495.4), CPEB1 (Gene Bank Accession Number: NM_030594.4), ERBB2 (Gene Bank Accession Number: NM_004448.3), FAM47A (Gene Bank Accession Number: NM_203408.3), HSP90AA1 (Gene Bank Accession Number: NM_001017963.2), IRAK1 (Gene Bank Accession Number: NM_001569.3), KDM5C (Gene Bank Accession Number: NM_004187.3), KDM6A (Gene Bank Accession Number: NM_021140.3), LRP12 (Gene Bank Accession Number: NM_013437.4), NCOA6 (Gene Bank Accession Number: NM_001242539.2), NHS (Gene Bank Accession Number: NM_198270.3), PHF16(JADE3) (Gene Bank Accession Number: NM_001077445.2), RGAG1 (Gene Bank Accession Number: NM_020769.2), SCAF1 (Gene Bank Accession Number: NM_021228.2), SCRN1 (Gene Bank Accession Number: NM_001145514.1), SH3TC1 (Gene Bank Accession Number: NM_018986.4), TBC1D8B (Gene Bank Accession Number: NM_017752.2), TET2 (Gene Bank Accession Number: NM_001127208.2), TEX13A (Gene Bank Accession Number: NM_001291277.1), ULK3 (Gene Bank Accession Number: NM_001099436.3), WNK3 (Gene Bank Accession Number: NM_001002838.3), and ZNF449 (Gene Bank Accession Number: NM_152695.5).

The full names of abbreviations for the genes may be ACSS3 (Homo sapiens acyl-CoA synthetase short chain family member 3), ADAM21 (Homo sapiens ADAM metallopeptidase domain 21), AFF2 (Homo sapiens AF4/FMR2 family member 2), ALG13 (UDP-N-acetylglucosaminyl-transferase subunit), BAP1 (BRCA1-associated protein 1), BRWD3 (bromodomain and WD repeat domain containing 3), COL4A5 (collagen type IV alpha 5 chain), CPEB1 (cytoplasmic polyadenylation element binding protein 1), ERBB2 (erb-b2 receptor tyrosine kinase 2), HSP90AA1 (heat shock protein 90 alpha family class A member 1), IRAK1 (interleukin 1 receptor associated kinase 1), KDM5C (lysine demethylase 5C), KDM6A (lysine demethylase 6A), LRP12 (LDL receptor related protein 12), NCOA6 (nuclear receptor coactivator 6), NHS (NHS actin remodeling regulator), RGAG1 (retrotransposon Gag like 9), SCAF1 (SR-related CTD associated factor 1), SH3TC1 (SH3 domain and tetratricopeptide repeats 1), TBC1D8B (TBC1 domain family member 8B), TET2 (tet methylcytosine dioxygenase 2), TEX13A (testis-expressed 13A), ULK3 (unc-51 like kinase 3), WNK3 (WINK lysine-deficient protein kinase 3), ARSF (arylsulfatase F), CFP (complement factor properdin), FAM47A (family with sequence similarity 47 member A), PHF16 (jade family PHD finger 3), ZNF449 (zinc finger protein 449), and SCRN1 (secernin 1).

According to one exemplary embodiment of the present invention, there is provided a kit for providing information required to predict a difference in therapeutic effect against kidney cancer or diagnose prognosis of a patient with kidney cancer according to the gender of the patient with kidney cancer, wherein the kit may detect a mutation of at least one gene selected from the following genes: a mutation of a gene coding for at least one selected from the group consisting of ACSS3, ADAM21, AFF2, ALG13, BAP1, BRWD3, COL4A5, CPEB1, ERBB2, HSP90AA1, IRAK1, KDM5C, KDM6A, LRP12, NCOA6, NHS, RGAG1, SCAF1, SH3TC1, TBC1D8B, TET2, TEX13A, ULK3, WNK3, ARSF, CFP, FAM47A, PHF16, ZNF449, and SCRN1.

In the present invention, the term 'diagnosis' refers to a process in which the presence or nature of a pathologic status is determined, that is, a process in which a difference in therapeutic effect against cancer according to the gender of a cancer patient is verified for the objects of the present invention and a process in which the relapse and metastasis of cancer, drug response and resistance, and the like in the corresponding subject after cancer treatment are judged. Preferably, when the mutations of the genes of the present invention are used, it is also possible to predict a difference in survival rate by checking whether there are mutations in a test sample of a patient with kidney cancer. In this case, a difference in therapeutic effect against kidney cancer and the prognosis of the corresponding patient in the future according to the gender of the corresponding patient with kidney cancer may be determined from the difference in survival rate.

In the present invention, the term 'prognosis' refers to the prediction of the progress and cure of a disease having a probability of cancer-attributable death or progression, including, for example, the relapse and metastatic spread of a neoplastic disease such as cancer, and drug resistance. The prognosis may refer to a prediction of the prognosis of kidney cancer for the objects of the present invention. Preferably, the prognosis may refer to a prediction of a disease-free survival rate or survival rate of the patient with kidney cancer.

In the present invention, the term 'cancer' includes any members belonging to a class of diseases characterized by the uncontrolled growth of abnormal cells. The term includes all stages and grades of cancers, including all types of known cancers and neoplastic conditions, cancers before/after metastasis, regardless whether the cancer is characterized by any one malignant, benign, soft tissue, or solid cancer.

In the present invention, the term 'gene' and modified products thereof include DNA fragments associated with the synthesis of polypeptide chains; each of the DNA fragments includes regions upstream and downstream from a coding region, for example, a promoter and a 3'-untranslated region, respectively, and also includes intervening sequences (introns) between respective coding fragments (exons).

The mutation of the gene may include any one or more mutations, and may, for example, have at least one mutation selected from the group consisting of truncating mutation, missense mutation, nonsense mutation, frameshift mutation, in-frame mutation, splice mutation, and splice region mutation. The frameshift mutation may be at least one selected from a frameshift insertion (FS ins) mutation and a frameshift deletion (FS del) mutation. The in-frame mutation may be at least one selected from an in-frame insertion (IF ins) mutation and an in-frame deletion (IF del) mutation.

In conjunction with mutations in a polypeptide sequence, the term "X#Y" is obviously recognized in the related art. Here, the sign "#" represents a mutation position with respect to the amino acid number of a polypeptide, "X" represents an amino acid found at the position of a wild-type amino acid sequence, and "Y" represents a mutant amino acid found at the same position. For example, the sign "G1717V" with respect to a BAZ2B polypeptide means that there is a glycine residue at amino acid number 1,717 of a wild-type BAZ2B sequence, and the glycine residue is replaced with valine in a mutant BAZ2B sequence.

The mutations of the genes are as follows:

The mutation of the gene coding for ACSS3 is a nonsense mutation 'R634*', a splice mutation 'X152_splice' (where T is substituted with C at position 81503485 on the chromosome), or a missense mutation 'G268D', wherein the sign in a notation of the nonsense mutation means that the synthesis of amino acids is terminated at the corresponding amino acid position (a description thereof is omitted hereinafter), in an amino acid sequence set forth in SEQ ID NO: 1; the mutation of the gene coding for ADAM21 is at least one mutation selected from the group consisting of N265Y, R408C, T589S, and I161V in an amino acid sequence set forth in SEQ ID NO: 2; the mutation of the gene coding for AFF2 is at least one missense mutation selected from the group consisting of S770F, P513H, T640N, and I149K in an amino acid sequence set forth in SEQ ID NO: 3; the mutation of the gene coding for ALG13 is at least one missense mutation selected from P925T and V456E, or a frameshift deletion (FS del) mutation 'L195Pfs*23', where a notation of the frameshift mutation is based on the amino acid type (an amino acid position) and the amino acid type fs* (the number of nucleotides downstream from the amino acid position to a stop codon) (both the FS ins mutation and FS del mutation are denoted by the same notation, and a description thereof is omitted hereinafter), in an amino acid sequence set forth in SEQ ID NO: 4; the mutation of the gene coding for BAP1 is a nonstart mutation 'M1?' (where T is substituted with C at position 52443894 and C is substituted with T at position 52443892 on the chromosome), at least one nonsense mutation selected from the group consisting of G128*, E402*, Q253*, Q267*, S460*, Y627*, S279*, R60*, Q40*, Q156*, and K626*, at least one FS del mutation selected from the group consisting of E283Gfs*52, V335Efs*56, K711Sfs*25, R700Gfs*36, D74Efs*4, and D407Vfs*23, at least one missense mutation selected from the group consisting of F170V, F170C, E31A, N78S, L49V, D75G, S10T, N229H, G109V, L17P, A145G, and A1061T, at least one splice mutation selected from the group consisting of X23_splice (where C is substituted with T at position 52443729 on the chromosome), X41_splice (where A is substituted with G at position 52443568 on the chromosome), X41_splice (where A is substituted with T at position 52443568 on the chromosome), X23_splice (where ACCTGCGATGAGGAAAGGAAAGCAG at positions 52443623 to 52443647 are deleted from the chromosome), and X311_splice (where C is substituted with A at position 52439311 on the chromosome), or an in-frame deletion (IF del) mutation 'K659del', where the sign 'del' in a notation of the IF del mutation represents a deletion of the corresponding amino acid at the corresponding amino acid position (a description thereof is omitted hereinafter), in an amino acid sequence set forth in SEQ ID NO: 5; the mutation of the gene coding for BRWD3 is at least one missense mutation selected from G287A and I1747N in an amino acid sequence set forth in SEQ ID NO: 6; the mutation of the gene coding for COL4A5 is at least one missense mutation selected from the group consisting of P1184L, P756S, P1365S, G1427V, and A1656T, or a splice mutation 'X1510_splice' (where G is substituted with T at position 107935977 on the chromosome) in an amino acid sequence set forth in SEQ ID NO: 7; the mutation of the gene coding for CPEB1 is at least one missense mutation selected from S393R and G136V, or a splice mutation 'X499_splice' (where C is substituted with A at position 83215272 on the chromosome) in an amino acid sequence set forth in SEQ ID NO: 8; the mutation of the gene coding for ERBB2 is at least one missense mutation selected from the group consisting of E1114G, S649T, and V219I, or an FS ins mutation 'N1388Qfs*14' in an amino acid sequence set forth in SEQ ID NO: 9; the mutation of the gene coding for HSP90AA1 is at least one missense mutation selected from the group consisting of D512N, H806R, I325T, and L167V in an amino acid sequence set forth in SEQ ID NO: 10; the mutation of the gene coding for IRAK1 is a nonsense mutation 'Q280*', or at least one missense mutation selected from V548M and Q584K in an amino acid sequence set forth in SEQ ID NO: 11; the mutation of the gene coding for KDM5C is at least one nonsense mutation selected from the group consisting of R681*, Q813*, E284*, E798*, Y639*, S1110*, K459*, and R215*, at least one missense mutation selected from the group consisting of E1152K, R1458W, G536W, C730R, E592V, C512W, C730F, and H733P, a splice mutation 'X321_splice' (where A is substituted with G at position 53244975 on the chromosome), or at least one FS del mutation selected from the group consisting of T471Vfs*5, Q1427Pfs*50, E122Vfs*14, E1131Sfs*16, H988Tfs*18, P27Lfs*46, F56Cfs*18, D1414Efs*54, and G845Rfs*2 in an amino acid sequence set forth in SEQ ID NO: 12; the mutation of the gene coding for KDM6A is a missense mutation 'A30V', an FS mutation 'A1246Pfs*19', or an IF del mutation 'V156del' in an amino acid sequence set forth in SEQ ID NO: 13; the mutation of the gene coding for LRP12 is at least one missense mutation selected from the group consisting of S622L, E639K, and V671I in an amino acid sequence set forth in SEQ ID NO: 14; the mutation of the gene coding for NCOA6 is at least one missense mutation selected from the group consisting of G164E, N877I, N864Y, and V1444A, or an FS ins mutation 'H832Sfs*47' in an amino acid sequence set forth in SEQ ID NO: 15; the mutation of the gene coding for NHS is at least one missense mutation selected from the group consisting of C360R, P1107A, and D1069H in an amino acid sequence set forth in SEQ ID NO: 16; the mutation of the gene coding for RGAG1 is at least one missense mutation selected from the group consisting of A1015G, M858V, and G1053R in an amino acid sequence set forth in SEQ ID NO: 17; the mutation of the gene coding for SCAF1 is at least one FS ins mutation selected from the group consisting of A219Sfs*11, P211Tfs*19, P211Tfs*19, and A216Pfs*94, or an FS del mutation 'A216Pfs*94' in an amino acid sequence set forth in SEQ ID NO: 18; the mutation of the gene coding for SH3TC1 is at least one missense mutation selected from A375V and L180F or an FS del mutation 'R238Sfs*38' in an amino acid sequence set forth in SEQ ID NO: 19; the mutation of the gene coding for TBC1D8B is at least one missense mutation selected from the group consisting of G1059V, A614T, and Y815F, or a nonsense mutation 'S861*' in an amino acid sequence set forth in SEQ ID NO: 20; the mutation of the gene coding for TET2 is at least one missense mutation selected from the group consisting of Q317K, L757V, V449E, N1714K, D194E, N1390H, R1451Q, M600I, and P554S, or a nonsense mutation 'K326*' in an amino acid sequence set forth in SEQ ID NO: 21; the mutation of the gene coding for TEX13A is at least one missense mutation selected from R393S and Y257D, or a splice mutation 'X199_splice' (where C at position 104464282 is deleted from the chromosome) in an amino acid sequence set forth in SEQ ID NO: 22; the mutation of the gene coding for ULK3 is an FS del mutation 'Q81Sfs*41' and at least one missense mutation selected from D79H and L77V in an amino acid sequence set forth in SEQ ID NO: 23; the mutation of the gene coding for WNK3 is at least one nonsense mutation selected from S865* and Y589* and a missense mutation 'E537G' in an amino acid sequence set forth in SEQ ID NO: 24; the mutation of the gene coding for ARSF is a missense mutation 'I42F' in an amino acid sequence set forth in SEQ ID NO: 25; the mutation of the gene coding for CFP is at least one missense mutation selected from the group consisting of S27L, R359Q, and E135K, or an FS ins mutation 'E323Gfs*34' in an amino acid sequence set forth in SEQ ID NO: 26; the mutation of the gene coding for FAM47A is at least one missense mutation selected from R505H and E507Q, or at least one IF del mutation selected from L235_H246del and L235_H246del in an amino acid sequence set forth in SEQ ID NO: 27; the mutation of the gene coding for PHF16 is at least one missense mutation selected from K656Q and R207W in an amino acid sequence set forth in SEQ ID NO: 28; the mutation of the gene coding for ZNF449 is a missense mutation 'F183I' in an amino acid sequence set forth in SEQ ID NO: 29; and the mutation of the gene coding for SCRN1 is a missense mutation 'D427Y' or an FS ins mutation 'A257Cfs*34' in an amino acid sequence set forth in SEQ ID NO: 30.

An analytical method for diagnosing the prognosis of kidney cancer using the mutation of the gene, a next-generation sequencing (NGS) method, RT-PCR, a direct nucleic acid sequencing method, a microarray, and the like may be used. In this case, any methods may be used without limitation as long as the methods can be used to determine the presence of mutations using the mutation of the gene according to the present invention. According to one exemplary embodiment, the presence of mutations is determined using an anti-antibody (a mutant antibody against each gene) or nucleic acid probe that hybridizes with a mutant polynucleotide of each of the gene under a stringent condition. According to another exemplary embodiment, the anti-antibody or nucleic acid probe is detectably labeled. According to still another exemplary embodiment, a label is selected from the group consisting of an immunofluorescent label, a chemiluminescent label, a phosphorescent label, an enzyme label, a radioactive label, avidin/biotin, colloidal gold particles, coloring particles, and magnetic particles. According to yet another exemplary embodiment, the presence of mutations is determined using an radioimmunoassay, a Western blot assay, an immunofluorescence assay, an enzyme immunoassay, an immunoprecipitation assay, a chemiluminescence assay, an immunohistochemical assay, a dot-blot assay, a slot-blot assay, or a flow cytometric assay. According to yet another exemplary embodiment, the presence of mutations is determined by RT-PCR. According to yet another exemplary embodiment, the presence of mutations is determined by nucleic acid sequencing.

In the present invention, the term 'polynucleotide' generally refers to any polyribonucleotide or polydeoxyribonucleotide that may be unmodified RNA or DNA or modified RNA or DNA. Therefore, non-limiting examples of the polynucleotide as defined herein include single- and double-stranded DNAs, DNAs including single- and double-stranded regions, single- and double-stranded RNAs, and RNAs including single- and double-stranded regions, and hybrid molecules including DNAs and RNAs that may be single-stranded or more typically double-stranded or may include single- and double-stranded regions. Therefore, the DNA or RNA having a modified backbone due to its stability or other reasons is a 'polynucleotide' as described in the terms intended herein. Also, the DNA or RNA containing unusual bases such as inosine or modified bases such as a tritiated base is encompassed in the term 'polynucleotide' as defined herein. Generally, the term 'polynucleotide' includes all chemically, enzymatically and/or metabolically modified forms of an unmodified polynucleotide. The polynucleotide may be prepared by various methods including an in vitro recombinant DNA-mediated technology, and prepared by expression of DNA in cells and organisms.

Primer sets capable of detecting the mutation of the gene, that is, primer sets for diagnosing prognosis of kidney cancer are as follows: at least one primer set selected from the group consisting of base sequence pairs set forth in SEQ ID NO: 31 and SEQ ID NO: 32, SEQ ID NO: 33 and SEQ ID NO: 34, and SEQ ID NO: 35 and SEQ ID NO: 36 to detect the mutation of ACSS3; at least one primer set selected from the group consisting of base sequence pairs set forth in SEQ ID NO: 37 and SEQ ID NO: 38, SEQ ID NO: 39 and SEQ ID NO: 40, SEQ ID NO: 41 and SEQ ID NO: 42, and SEQ ID NO: 43 and SEQ ID NO: 44 to detect the mutation of ADAM21; at least one primer set selected from the group consisting of base sequence pairs set forth in SEQ ID NO: 45 and SEQ ID NO: 46, SEQ ID NO: 47 and SEQ ID NO: 48, SEQ ID NO: 49 and SEQ ID NO: 50, and SEQ ID NO: 51 and SEQ ID NO: 52 to detect the mutation of AFF2; at least one primer set selected from the group consisting of base sequence pairs set forth in SEQ ID NO: 53 and SEQ ID NO: 54, SEQ ID NO: 55 and SEQ ID NO: 56, and SEQ ID NO: 57 and SEQ ID NO: 58 to detect the mutation of ALG13; at least one primer set selected from the group consisting of base sequence pairs set forth in SEQ ID NO: 59 and SEQ ID NO: 60, SEQ ID NO: 61 and SEQ ID NO: 62, SEQ ID NO: 63 and SEQ ID NO: 64, SEQ ID NO: 65 and SEQ ID NO: 66, SEQ ID NO: 67 and SEQ ID NO: 68, SEQ ID NO: 69 and SEQ ID NO: 70, SEQ ID NO: 71 and SEQ ID NO: 72, SEQ ID NO: 73 and SEQ ID NO: 74, SEQ ID NO: 75 and SEQ ID NO: 76, SEQ ID NO: 77 and SEQ ID NO: 78, SEQ ID NO: 79 and SEQ ID NO: 80, SEQ ID NO: 81 and SEQ ID NO: 82, SEQ ID NO: 83 and SEQ ID NO: 84, SEQ ID NO: 85 and SEQ ID NO: 86, SEQ ID NO: 87 and SEQ ID NO: 88, SEQ ID NO: 89 and SEQ ID NO: 90, SEQ ID NO: 91 and SEQ ID NO: 92, and SEQ ID NO: 93 and SEQ ID NO: 94 to detect the mutation of BAP1; at least one primer set selected from base sequence pairs set forth in SEQ ID NO: 95 and SEQ ID NO: 96, and SEQ ID NO: 97 and SEQ ID NO: 98 to detect the mutation of BRWD3; at least one primer set selected from the group consisting of base sequence pairs set forth in SEQ ID NO: 99 and SEQ ID NO: 100, SEQ ID NO: 101 and SEQ ID NO: 102, SEQ ID NO: 103 and SEQ ID NO: 104, SEQ ID NO: 105 and SEQ ID NO: 106, SEQ ID NO: 107 and SEQ ID NO: 108, and SEQ ID NO: 109 and SEQ ID NO: 110 to detect the mutation of COL4A5; at least one primer set selected from the group consisting of base sequence pairs set forth in SEQ ID NO: 111 and SEQ ID NO: 112, SEQ ID NO: 113 and SEQ ID NO: 114, and SEQ ID NO: 115 and SEQ ID NO: 116 to detect the mutation of CPEB1; at least one primer set selected from the group consisting of base sequence pairs set forth in SEQ ID NO: 117 and SEQ ID NO: 118, SEQ ID NO: 119 and SEQ ID NO: 120, and SEQ ID NO: 121 and SEQ ID NO: 122 to detect the mutation of ERBB2; at least one primer set selected from the group consisting of base sequence pairs set forth in SEQ ID NO: 123 and SEQ ID NO: 124, SEQ ID NO: 125 and SEQ ID NO: 126, SEQ ID NO: 127 and SEQ ID NO: 128, and SEQ ID NO: 129 and SEQ ID NO: 130 to detect the mutation of HSP90AA1; at least one primer set selected from base sequence pairs set forth in SEQ ID NO: 131 and SEQ ID NO: 132, and SEQ ID NO: 133 and SEQ ID NO: 134 to detect the mutation of IRAK1; at least one primer set selected from the group consisting of base sequence pairs set forth in SEQ ID NO: 135 and SEQ ID NO: 136, SEQ ID NO: 137 and SEQ ID NO: 138, SEQ ID NO: 139 and SEQ ID NO: 140, SEQ ID NO: 141 and SEQ ID NO: 142, SEQ ID NO: 143 and SEQ ID NO: 144, SEQ ID NO: 145 and SEQ ID NO: 146, SEQ ID NO: 147 and SEQ ID NO: 148, SEQ ID NO: 149 and SEQ ID NO: 150, SEQ ID NO: 151 and SEQ ID NO: 152, SEQ ID NO: 153 and SEQ ID NO: 154, SEQ ID NO: 155 and SEQ ID NO: 156, SEQ ID NO: 157 and SEQ ID NO: 158, SEQ ID NO: 159 and SEQ ID NO: 160, SEQ ID NO: 161 and SEQ ID NO: 162, SEQ ID NO: 163 and SEQ ID NO: 164, SEQ ID NO: 165 and SEQ ID NO: 166, SEQ ID NO: 167 and SEQ ID NO: 168, SEQ ID NO: 169 and SEQ ID NO: 170, SEQ ID NO: 171 and SEQ ID NO: 172, SEQ ID NO: 173 and SEQ ID NO: 174, and SEQ ID NO: 175 and SEQ ID NO: 176 to detect the mutation of KDM5C; at least one primer set selected from base sequence pairs set forth in SEQ ID NO: 177 and SEQ ID NO: 178, and SEQ ID NO: 179 and SEQ ID NO: 180 to detect the mutation of KDM6A; at least one primer set selected from base sequence pairs set forth in SEQ ID NO: 181 and SEQ ID NO: 182, and SEQ ID NO: 183 and SEQ ID NO: 184 to detect the mutation of LRP12; at least one primer set selected from the group consisting of base sequence pairs set forth in SEQ ID NO: 185 and SEQ ID NO: 186, SEQ ID NO: 187 and SEQ ID NO: 188, SEQ ID NO: 189 and SEQ ID NO: 190, and SEQ ID NO: 191 and SEQ ID NO: 192 to detect the mutation of NCOA6; at least one primer set selected from the group consisting of base sequence pairs set forth in SEQ ID NO: 193 and SEQ ID NO: 194, SEQ ID NO: 195 and SEQ ID NO: 196, and SEQ ID NO: 197 and SEQ ID NO: 198 to detect the mutation of NHS; at least one primer set selected from the group consisting of base sequence pairs set forth in SEQ ID NO: 199 and SEQ ID NO: 200, SEQ ID NO: 201 and SEQ ID NO: 202, and SEQ ID NO: 203 and SEQ ID NO: 204 to detect the mutation of RGAG1; at least one primer set selected from the group consisting of base sequence pairs set forth in SEQ ID NO: 205 and SEQ ID NO: 206, SEQ ID NO: 207 and SEQ ID NO: 208, SEQ ID NO: 209 and SEQ ID NO: 210, SEQ ID NO: 211 and SEQ ID NO: 212, and SEQ ID NO: 213 and SEQ ID NO: 214 to detect the mutation of SCAF1; at least one primer set selected from the group consisting of base sequence pairs set forth in SEQ ID NO: 215 and SEQ ID NO: 216, SEQ ID NO: 217 and SEQ ID NO: 218, and SEQ ID NO: 219 and SEQ ID NO: 220 to detect the mutation of SH3TC1; at least one primer set selected from the group consisting of base sequence pairs set forth in SEQ ID NO: 221 and SEQ ID NO: 222, SEQ ID NO: 223 and SEQ ID NO: 224, SEQ ID NO: 225 and SEQ ID NO: 226, and SEQ ID NO: 227 and SEQ ID NO: 228 to detect the mutation of TBC1D8B; at least one primer set selected from the group consisting of base sequence pairs set forth in SEQ ID NO: 229 and SEQ ID NO: 230, SEQ ID NO: 231 and SEQ ID NO: 232, SEQ ID NO: 233 and SEQ ID NO: 234, SEQ ID NO: 235 and SEQ ID NO: 236, SEQ ID NO: 237 and SEQ ID NO: 238, SEQ ID NO: 239 and SEQ ID NO: 240, SEQ ID NO: 241 and SEQ ID NO: 242, SEQ ID NO: 243 and SEQ ID NO: 244, and SEQ ID NO: 245 and SEQ ID NO: 246 to detect the mutation of TET2; at least one primer set selected from the group consisting of base sequence pairs set forth in SEQ ID NO: 247 and SEQ ID NO: 248, SEQ ID NO: 249 and SEQ ID NO: 250, and SEQ ID NO: 251 and SEQ ID NO: 252 to detect the mutation of TEX13A; a primer set consisting of base sequence pairs set forth in SEQ ID NO: 253 and SEQ ID NO: 254 to detect the mutation of ULK3; at least one primer set selected from the group consisting of base sequence pairs set forth in SEQ ID NO: 255 and SEQ ID NO: 256, SEQ ID NO: 257 and SEQ ID NO: 258, and SEQ ID NO: 259 and SEQ ID NO: 260 to detect the mutation of WNK3; a primer set consisting of base sequence pairs set forth in SEQ ID NO: 261 and SEQ ID NO: 262 to detect the mutation of ARSF; at least one primer set selected from the group consisting of base sequence pairs set forth in SEQ ID NO: 263 and SEQ ID NO: 264, SEQ ID NO: 265 and SEQ ID NO: 266, SEQ ID NO: 267 and SEQ ID NO: 268, and SEQ ID NO: 269 and SEQ ID NO: 270 to detect the mutation of CFP; a primer set consisting of base sequence pairs set forth in SEQ ID NO: 271 and SEQ ID NO: 272 to detect the mutation of FAM47A; at least one primer set selected from the group consisting of base sequence pairs set forth in SEQ ID NO: 273 and SEQ ID NO: 274, and SEQ ID NO: 275 and SEQ ID NO: 276 to detect the mutation of PHF16; a primer set consisting of base sequence pairs set forth in SEQ ID NO: 277 and SEQ ID NO: 278 to detect the mutation of ZNF449; and at least one primer set selected from base sequence pairs set forth in SEQ ID NO: 279 and SEQ ID NO: 280, and SEQ ID NO: 281 and SEQ ID NO: 282 to detect the mutation of SCRN1.

The kit of the present invention thus manufactured is very economical because a lot of time and cost may be save, compared to typical gene mutation search methods known in the art. Several days or Several months are averagely taken to search for one gene thoroughly using the conventional gene mutation search methods such as single strand conformational polymorphism (SSCP), a protein truncation test (PTT), cloning, direct sequencing, and the like. Also, the gene mutation may be rapidly and simply examined accurately using the next-generation sequencing (NGS) method. When the mutation is checked using conventional analytical methods such as SSCP, cloning, direct sequencing, restriction fragment length polymorphism (RFLP), and the like, approximately one month is taken to complete the check. On the other hand, when the kit of the present invention is used and a DNA test sample is prepared, results may be obtained within approximately 10 to 11 hours. Because a primer set capable of detecting the mutation of the gene is stacked in one chip, the time and cost may be saved compared to the conventional methods. Because less than half the reagents' cost per experiment is averagely consumed compared to the conventional methods, a higher cost saving effect may be expected in consideration of the researchers' labor costs.

2. Method of Providing Information Required to Diagnose Prognosis of Kidney Cancer Using Survival-Specific Mutant Gene According to another aspect of the present invention, there is provided a method of providing information required to verify a difference in therapeutic effect against kidney cancer according to the gender of a patient with kidney cancer. Here, the method includes preparing a DNA test sample from a sample of a patient with kidney cancer whose gender is identified; amplifying the DNA test sample using the kit; determining whether or not there is a gender-specific marker specific to a gender group of target patients from the results of amplification; treating the patient with kidney cancer, in which the gender-specific marker is identified, with any candidate material for treating kidney cancer or healing the patient with kidney cancer using any method; and choosing any candidate material for treating kidney cancer or any method of treating kidney cancer as a therapeutic candidate material or a therapeutic method, which is suitable for the gender group of patients with kidney cancer in which the gender-specific marker is identified, when the any candidate material or the any method is used to treat kidney cancer.

According to still another aspect of the present invention, there is provided a method of providing information required to diagnose prognosis of kidney cancer according to the gender of a patient with kidney cancer. Here, the method includes preparing a DNA test sample from a sample of a patient with kidney cancer; amplifying the DNA test sample using the kit; and determining whether or not there is a gender-specific marker from the results of amplification.

The 'kit for diagnosing prognosis of kidney cancer' is as described in '1. gender-specific mutant genes in patient with kidney cancer and primer sets capable of detecting the mutant genes', and thus a specific description thereof is omitted.

The any candidate material for treating kidney cancer may be a therapeutic agent generally used to treat kidney cancer, or a novel material whose therapeutic effect against kidney cancer is not known, but the present invention is not limited thereto. It may be determined whether or not the any therapeutic candidate material has a therapeutic effect on a certain group of patients by treating a patient with kidney cancer having a gender-specific marker with the therapeutic candidate material to check the therapeutic effect. When the therapeutic candidate material has a therapeutic effect against kidney cancer, it may be predicted that the therapeutic candidate material has a high therapeutic effect when the therapeutic candidate material is applied to a group of patients having the same gender-specific marker, thereby providing useful information to determine a therapeutic strategy. Also, when a therapeutic effect is not exerted by the use of the any therapeutic candidate material, the unnecessary treatment needs not to be performed by suspending the therapy on the group of patients having the same gender-specific marker. Therefore, a therapeutic strategy may be effectively designed.

Any method of treating kidney cancer may also be applied instead of the any therapeutic candidate material. After verifying a therapeutic effect in a group of patients having a certain gender-specific marker, it may be determined whether or not the method is applied to the group of patients having the same gender-specific marker. When the therapeutic effect is verified in the group of patients having the gender-specific marker, the any therapeutic candidate material and the any method of treating kidney cancer may be used together.

The term 'sample' used herein includes any biological specimen obtained from a patient. The sample includes whole blood, plasma, serum, red blood cells, white blood cells (for example, peripheral blood mononuclear cells), a ductal fluid, hydrops abdominis, a pleural efflux, a nipple aspirate, a lymph fluid (for example, disseminated tumor cells of lymph nodes), a bone marrow aspirate, saliva, urine, feces (that is, stool), phlegm, a bronchial lavage fluid, tear, a fine needle aspirate (for example, collected by random mammary fine needle aspiration), any other bodily fluids, a tissue sample (for example, a tumor tissue), for example, a tumor biopsy (for example, an aspiration biopsy) or a lymph node (for example, a sentinel lymph node biopsy), a tissue sample (for example, a tumor tissue), for example, a surgical resection of tumor, and cell extracts thereof. In some embodiments, the sample is whole blood or some components thereof, for example, plasma, serum or cell pellets. In another embodiment, the sample is obtained by isolating circulating cells of a solid tumor from the whole blood or cell fractions thereof using any techniques known in the related art. In still another embodiment, the sample is, for example, a formalin-fixed paraffin-embedded (FFPE) tumor tissue sample from a solid tumor such as colon cancer.

In certain embodiments, the sample is a tumor lysate or extract prepared from a frozen tissue obtained from a target having colon cancer.

The term 'patient' generally includes a human, and may also include other animals, for example, other primates, rodents, dogs, cats, horses, sheep, pigs, and the like.

The term 'subject' includes targets excluding a human, which are diagnosed with kidney cancer or suspected to have kidney cancer.

The method may be used to predict an overall survival rate or disease-free survival rate of the patient with kidney cancer.

In the present invention, the term 'overall survival rate' includes clinical endpoints recorded for patients who are diagnosed with a disease, for example, cancer or alive for a predetermined period after treatment of the disease, and refers to a survival probability of the patients regardless of the relapse of cancer.

In the present invention, the term 'disease-free survival rate (DFS)' includes a survival period of a patient without the relapse of cancer after treatment of a certain disease (for example, cancer).

According to the present invention, the presence of mutations of the gene of the present invention in a sample of a patient with kidney cancer may be analyzed to verify what the prognosis of a subject having a target test sample is for cancer. Also, such a method may be established by comparing overall survival rates or disease-free survival rates of control subjects who are known to have a good prognosis and have no mutations. In the present invention, the subject known to have a good prognosis refers to a subject who has no family histories such as metastasis, relapse, death, and the like after the onset of cancer.

The sample of the subject suspected to have cancer refers to a test sample of a subject or a tissue which already develops cancer or tumor or is expected to develop cancer or tumor, that is, a target test sample used to diagnose the prognosis of cancer or tumor.

The gender-specific marker may be a mutation of a gene coding for one selected from the group consisting of ACSS3, ADAM21, AFF2, ALG13, BAP1, BRWD3, COL4A5, CPEB1, ERBB2, HSP90AA1, IRAK1, KDM5C, KDM6A, LRP12, NCOA6, NHS, RGAG1, SCAF1, SH3TC1, TBC1D8B, TET2, TEX13A, ULK3, WNK3, ARSF, CFP, FAM47A, PHF16, ZNF449, and SCRN1. In females of the patients with kidney cancer, the gender-specific marker may be a mutation of a gene coding for one selected from the group consisting of ACSS3, ADAM21, AFF2, ALG13, BAP1, BRWD3, COL4A5, CPEB1, ERBB2, HSP90AA1, IRAK1, KDM5C, KDM6A, LRP12, NCOA6, NHS, RGAG1, SCAF1, SH3TC1, TBC1D8B, TEX13A, ULK3, WNK3, ARSF, CFP, FAM47A, PHF16, ZNF449, and SCRN1. In males of the patients with kidney cancer, the gender-specific marker may be a mutation of a gene coding for TET2.

The method of providing information required to diagnose the prognosis of kidney cancer according to the gender of the patient with kidney cancer may be used to predict the overall survival rate or disease-free survival rate of the patient with kidney cancer. For example, the method may further include judging that the survival rate of the patient with kidney cancer is not good or that a relapse rate of kidney cancer in the patient with kidney cancer is high when the mutation is identified in the gene coding for one selected from the group consisting of ACSS3, ALG13, ARSF, CFP, FAM47A, KDM6A, PHF16, ZNF449, and SCRN1, and the patient with kidney cancer is female.

The method of providing information required to diagnose the prognosis of kidney cancer according to the gender of the patient with kidney cancer may further include judging that the survival rate of the patient with kidney cancer is not good when the gender of the patient with kidney cancer is female and the mutation is identified in the gene coding for one selected from the group consisting of ACSS3, ALG13, ARSF, CFP, FAM47A, KDM6A, PHF16, and ZNF449, and the patient with kidney cancer is male.

The method of providing information required to diagnose the prognosis of kidney cancer according to the gender of the patient with kidney cancer may further include judging that the relapse rate of kidney cancer in the patient with kidney cancer is high when the gender of the patient with kidney cancer is female and the mutation is identified in the gene coding for one selected from the group consisting of ACSS3, ARSF, CFP, FAM47A, ZNF449, and SCRN1.

As described above, the mutation of at least one gene selected from a gene group consisting of ACSS3, ADAM21, AFF2, ALG13, BAP1, BRWD3, COL4A5, CPEB1, ERBB2, HSP90AA1, IRAK1, KDM5C, KDM6A, LRP12, NCOA6, NHS, RGAG1, SCAF1, SH3TC1, TBC1D8B, TET2, TEX13A, ULK3, WNK3, ARSF, CFP, FAM47A, PHF16, ZNF449, and SCRN1 is used as the mutation of the gene of the present invention to verify that there is a difference in gene mutations according to the gender of a patient who develops cancer, particularly kidney cancer, but this fact is still unknown. Also, the mutation of at least one gene selected from a gene group consisting of ACSS3, ALG13, ARSF, CFP, FAM47A, KDM6A, PHF16, ZNF449, and SCRN1 may be used to diagnose the prognosis of cancer, particularly kidney cancer, in a patient having a certain gender, but this fact is also still unknown. Further, there is no report on the fact that the overall survival rate or disease-free survival rate may be different in each of the genes. The present inventors have first found that the mutation of the genes may be used as a diagnostic marker capable of predicting a difference in therapeutic effect against kidney cancer or diagnosing the prognosis of the patient with kidney cancer according to the gender of the patient with kidney cancer.

The method for providing information required to predict a difference in therapeutic effect against kidney cancer according to the gender of the patient with kidney cancer according to the present invention may be used to diagnose a gene mutation in kidney cancer based on the gender, increase the survival rate of the patient with kidney cancer, or reduce the relapse rate of kidney cancer. Because the therapeutic effect against kidney cancer may be predicted and the survival rate of the patient with kidney cancer or the relapse rate of kidney cancer may be predicted using the information on the gene mutation which varies depending on the gender of the patient who develops kidney cancer, the method for diagnosing the prognosis of kidney cancer according to the present invention may be used to screen therapeutic agents suitable for each patient and select therapeutic methods so as to provide information, thereby effectively designing a therapeutic strategy for kidney cancer.

Mode for Invention

Hereinafter, the present invention will be described in further detail with reference to examples and experimental examples thereof.

However, it should be understood that the following examples are just preferred examples for the purpose of illustration only and is not intended to limit or define the scope of the invention.

<Example 1> Acquisition of Genetic Information and Clinical Information

To check whether the genes of (ACSS3, ADAM21, AFF2, ALG13, BAP1, BRWD3, COL4A5, CPEB1, ERBB2, HSP90AA1, IRAK1, KDM5C, KDM6A, LRP12, NCOA6, NHS, RGAG1, SCAF1, SH3TC1, TBC1D8B, TET2, TEX13A, ULK3, WNK3, ARSF, CFP, FAM47A, PHF16, ZNF449, and SCRN1) may be used as a kidney cancer marker according to the gender of a patient with kidney cancer, the data on the relapse, metastasis, death, and observation time of 417 patients with clear cell renal cell carcinoma whose genetic information and clinical information were all secured were obtained from The Cancer Genome Atlas (TCGA), and used for analyses. The following Table 1 lists the data on the relapse, metastasis, and death of the patients with clear cell renal cell carcinoma.

TABLE 1

|  |  | Gender | | Total | |
| --- | --- | --- | --- | --- | --- |
|  |  | Male | Female | Number of patients | Ratio (%) |
| Relapse | 0 | 148 (54.6%) | 81 (55.5%) | 229 | 55.2% |
|  | 1 | 77 (28.4%) | 32 (21.9%) | 109 | 26.1% |
|  | Not detected | 46 (17.0%) | 33 (22.6%) | 79 | 18.7% |
| Metastasis | 0 | 224 (82.7%) | 127 (87.0%) | 351 | 84.2% |
|  | 1 | 47 (17.3%) | 19 (13.0%) | 66 | 15.8% |
| Death | 0 | 181 (66.8%) | 89 (61.0%) | 270 | 65.0% |
|  | 1 | 90 (33.2%) | 57 (39.0%) | 147 | 35.0% |
| Total number of patients |  | 271 | 146 | 417 | |

<Example 2> Confirmation of Usability as Gender-Specific Marker 417 patients were divided into two groups based on the gender thereof to check a correlation between of the gender and the mutations of the candidate genes in Example 1 using three feature selection methods (Information Gain, Chi-Square, and MR). Mutation positions of the genes are listed in the following Tables 2 to 6.

TABLE 2

| Gene | Accession No. | AA change | Type | Copy # | COSMIC | Mutation Assessor | Chr | Start Pos | End Pos | Ref | Var |
| --- | --- | --- | --- | --- | --- | --- | --- | --- | --- | --- | --- |
| ACSS3 | NM_024560.3 | R634* | Nonsense | Diploid | 4 |  | chr12 | 81647354 | 81647354 | C | T |
|  |  | X152_splice | Splice | Gain |  |  | chr12 | 81503485 | 81503485 | T | C |
|  |  | G268D | Missense | Gain | 1 | Low | chr12 | 81536908 | 81536908 | G | A |
| ADAM21 | NM_003813.3 | N265Y | Missense | ShallowDel | 2 | Medium | chr14 | 70925009 | 70925009 | A | T |
|  |  | R408C | Missense | Diploid | 3 | Medium | chr14 | 70925438 | 70925438 | C | T |
|  |  | T589S | Missense | Diploid | 1 | Low | chr14 | 70925981 | 70925981 | A | T |
|  |  | I161V | Missense | Diploid | 3 | Low | chr14 | 70924697 | 70924697 | A | G |
| AFF2 | NM_002025.3 | S770F | Missense | DeepDel | 1 | Low | chr23 | 148037884 | 148037884 | C | T |
|  |  | P513H | Missense | Diploid | 1 | Medium | chr23 | 148035250 | 148035250 | C | A |
|  |  | T640N | Missense | Gain | 1 | Low | chr23 | 148037494 | 148037494 | C | A |
|  |  | I149K | Missense | Diploid | 1 | Neutral | chr23 | 147743694 | 147743694 | T | A |
|  |  | I149K | Missense | Diploid | 1 | Neutral | chr23 | 147743694 | 147743694 | T | A |
|  |  | I149K | Missense | Diploid | 1 | Neutral | chr23 | 147743694 | 147743694 | T | A |

TABLE 2-continued

| Gene | Accession No. | AA change | Type | Copy # | COSMIC | Mutation Assessor | Chr | Start Pos | End Pos | Ref | Var |
|---|---|---|---|---|---|---|---|---|---|---|---|
| ALG13 | NM_001099922.2 | P925T | Missense | Diploid | | Low | chr23 | 110987973 | 110987973 | C | A |
| | | L195Pfs*23 | FS del | Diploid | | | chr23 | 110951455 | 110951455 | T | — |
| | | V456E | Missense | Diploid | | Medium | chr23 | 110964871 | 110964871 | T | A |
| BAP1 | NM_004656.3 | M1? | Nonstart | ShallowDel | 6 | | chr3 | 52443894 | 52443894 | T | C |
| | | G128* | Nonsense | ShallowDel | 2 | | chr3 | 52441470 | 52441470 | C | A |
| | | E402* | Nonsense | ShallowDel | | | chr3 | 52438515 | 52438515 | C | A |
| | | E283Gfs*52 | FS del | ShallowDel | 1 | | chr3 | 52439864 | 52439864 | T | — |
| | | V335Efs*56 | FS del | ShallowDel | 1 | | chr3 | 52439219 | 52439238 | GCTGCCTGGAGGCTTCACCA | — |
| | | Q253* | Nonsense | ShallowDel | 2 | | chr3 | 52440295 | 52440295 | G | A |
| | | Q267* | Nonsense | ShallowDel | 1 | | chr3 | 52439913 | 52439913 | G | A |

TABLE 3

| Gene | Accession No. | AA change | Type | Copy # | COSMIC | Mutation Assessor | Chr | Start Pos | End Pos | Ref | Var |
|---|---|---|---|---|---|---|---|---|---|---|---|
| BAP1 | NM_004656.3 | S460* | Nonsense | ShallowDel | 3 | | chr3 | 52437782 | 52437782 | G | C |
| | | F170V | Missense | ShallowDel | 4 | High | chr3 | 52441262 | 52441262 | A | C |
| | | K711Sfs*25 | FS del | ShallowDel | 1 | | chr3 | 52436362 | 52436362 | T | — |
| | | Y627* | Nonsense | ShallowDel | 1 | | chr3 | 52437163 | 52437163 | G | C |
| | | R717Gfs*19 | FS del | ShallowDel | 1 | | chr3 | 52436345 | 52436345 | G | — |
| | | X23_splice | Splice | ShallowDel | | | chr3 | 52443729 | 52443729 | C | T |
| | | S279* | Nonsense | ShallowDel | 1 | | chr3 | 52439876 | 52439876 | G | T |
| BAP1 | NM_004656.3 | R60* | Nonsense | DeepDel | 4 | | chr3 | 52442567 | 52442567 | G | A |
| | | M1? | Nonstart | ShallowDel | 6 | | chr3 | 52443892 | 52443892 | C | T |
| | | M1? | Nonstart | ShallowDel | 6 | | chr3 | 52443892 | 52443892 | C | T |
| | | R700Gfs*36 | FS del | ShallowDel | 1 | | chr3 | 52436397 | 52436397 | C | — |
| | | X41_splice | Splice | ShallowDel | | | chr3 | 52443568 | 52443568 | A | G |
| | | Q40* | Nonsense | ShallowDel | 2 | | chr3 | 52443574 | 52443574 | G | A |
| | | Q156* | Nonsense | ShallowDel | 1 | | chr3 | 52441304 | 52441304 | G | A |
| | | K626* | Nonsense | ShallowDel | 1 | | chr3 | 52437168 | 52437168 | T | A |
| | | D74Efs*4 | FS del | ShallowDel | 1 | | chr3 | 52442523 | 52442523 | A | — |
| | | X41_splice | Splice | ShallowDel | | | chr3 | 52443568 | 52443568 | A | T |
| | | D407Vfs*23 | FS del | ShallowDel | 2 | | chr3 | 52438499 | 52438499 | T | — |
| | | F170C | Missense | ShallowDel | 4 | High | chr3 | 52441261 | 52441261 | A | C |
| | | X23_splice | Splice | ShallowDel | | | chr3 | 52443623 | 52443647 | ACCTGCGATGAGGAAAGGAAAGCAG | — |
| | | X311_splice | Splice | ShallowDel | | | chr3 | 52439311 | 52439311 | C | A |
| | | E31A | Missense | ShallowDel | 5 | High | chr3 | 52443600 | 52443600 | T | G |
| | | N785 | Missense | ShallowDel | 2 | Neutral | chr3 | 52442512 | 52442512 | T | C |
| | | N785 | Missense | ShallowDel | 2 | Neutral | chr3 | 52442512 | 52442512 | T | C |
| | | L49V | Missense | ShallowDel | 2 | High | chr3 | 52442600 | 52442600 | G | C |
| | | D75G | Missense | ShallowDel | 1 | Neutral | chr3 | 52442521 | 52442521 | T | C |
| | | S10T | Missense | ShallowDel | 4 | High | chr3 | 52443866 | 52443866 | C | G |
| | | N229H | Missense | ShallowDel | 1 | Medium | chr3 | 52440367 | 52440367 | T | G |
| | | G109V | Missense | ShallowDel | 1 | High | chr3 | 52442023 | 52442023 | C | A |
| | | L17P | Missense | ShallowDel | 1 | Medium | chr3 | 52443747 | 52443747 | A | G |
| | | A145G | Missense | ShallowDel | 1 | Medium | chr3 | 52441418 | 52441418 | G | C |
| | | K659del | IF del | DeepDel | | | chr3 | 52436801 | 52436803 | CTT | — |
| | | A1061T | Missense | Diploid | 2 | Medium | chr23 | 79948521 | 79948521 | C | T |

TABLE 4

| Gene | Accession No. | AA change | Type | Copy # | COSMIC | Mutation Assessor | Chr | Start Pos | End Pos | Ref | Var |
|---|---|---|---|---|---|---|---|---|---|---|---|
| BRWD3 | NM_153252.4 | G287A | Missense | Diploid | 1 | Neutral | chr23 | 79991541 | 79991541 | C | G |
| | | I1747N | Missense | Diploid | 1 | Neutral | chr23 | 79932277 | 79932277 | A | T |

TABLE 4-continued

| Gene | Accession No. | AA change | Type | Copy # | COSMIC | Mutation Assessor | Chr | Start Pos | End Pos | Ref | Var |
|---|---|---|---|---|---|---|---|---|---|---|---|
| COL4A5 | NM_000495.4 | P1184L | Missense | Diploid | 1 | Medium | chr23 | 107909822 | 107909822 | C | T |
| | | P756S | Missense | Diploid | 1 | Medium | chr23 | 107849993 | 107849993 | C | T |
| | | P1365S | Missense | Diploid | | Medium | chr23 | 107924995 | 107924995 | C | T |
| | | G1427V | Missense | Diploid | | High | chr23 | 107929324 | 107929324 | G | T |
| | | X1510_splice | Splice | Diploid | | | chr23 | 107935977 | 107935977 | G | T |
| | | A1656T | Missense | Diploid | | Neutral | chr23 | 107938641 | 107938641 | G | A |
| CPEB1 | NM_030594.4 | S393R | Missense | Diploid | | Medium | chr15 | 83221251 | 83221251 | G | C |
| | | G136V | Missense | Diploid | | Neutral | chr15 | 83226709 | 83226709 | C | A |
| | | X499_splice | Splice | Diploid | | | chr15 | 83215272 | 83215272 | C | A |
| ERBB2 | NM_004448.3 | E1114G | Missense | Diploid | 1 | Low | chr17 | 37883729 | 37883729 | A | G |
| | | S649T | Missense | Diploid | 1 | Low | chr17 | 37876087 | 37876087 | G | C |
| | | V219I | Missense | Diploid | 1 | Neutral | chr17 | 37866350 | 37866350 | G | A |
| | | N388Qfs*14 | FS ins | Diploid | | | chr17 | 37871549 | 37871550 | — | C |
| HSP90AA1 | NM_001017963.2 | D512N | Missense | ShallowDel | 2 | High | chr14 | 102550300 | 102550300 | C | T |
| | | H806R | Missense | Diploid | 1 | High | chr14 | 102548486 | 102548486 | T | C |
| | | I325T | Missense | ShallowDel | 1 | High | chr14 | 102551690 | 102551690 | A | G |
| | | L167V | Missense | ShallowDel | 1 | Medium | chr14 | 102552583 | 102552583 | G | C |

TABLE 5

| Gene | Accession No. | AA change | Type | Copy # | COSMIC | Mutation Assessor | Chr | Start Pos | End Pos | Ref | Var |
|---|---|---|---|---|---|---|---|---|---|---|---|
| IRAK1 | NM_001569.3 | Q280* | Nonsense | Diploid | 1 | | chr23 | 153283528 | 153283528 | G | A |
| | | V548M | Missense | Diploid | 1 | Neutral | chr23 | 153278782 | 153278782 | C | T |
| | | Q584K | Missense | Diploid | 1 | Low | chr23 | 153278674 | 153278674 | G | T |
| KDM5C | NM_004187.3 | R681* | Nonsense | Diploid | 3 | | chr23 | 53230752 | 53230752 | G | A |
| | | Q813* | Nonsense | Diploid | 2 | | chr23 | 53227751 | 53227751 | G | A |
| | | E1152K | Missense | Diploid | 1 | Medium | chr23 | 53223905 | 53223905 | C | T |
| | | X321_splice | Splice | Diploid | | | chr23 | 53244975 | 53244975 | A | G |
| | | T471Vfs*5 | FS del | Diploid | | | chr23 | 53240028 | 53240031 | GGTA | — |
| | | R1458W | Missense | Diploid | 1 | Low | chr23 | 53222460 | 53222460 | G | A |
| | | G536W | Missense | Diploid | 1 | High | chr23 | 53239736 | 53239736 | C | A |
| | | E284* | Nonsense | Diploid | 1 | | chr23 | 53245090 | 53245090 | C | A |
| | | Q1427Pfs*50 | FS del | Diploid | 1 | | chr23 | 53222653 | 53222656 | GGCT | — |
| | | C730R | Missense | Diploid | 2 | Medium | chr23 | 53228214 | 53228214 | A | G |
| | | E592V | Missense | Diploid | 1 | High | chr23 | 53231127 | 53231127 | T | A |
| | | E798* | Nonsense | Diploid | 1 | | chr23 | 53227796 | 53227796 | C | A |
| | | C512W | Missense | Diploid | 1 | High | chr23 | 53239905 | 53239905 | G | C |
| | | Y639* | Nonsense | Diploid | 1 | | chr23 | 53230876 | 53230877 | — | T |
| | | S1110* | Nonsense | Diploid | 1 | | chr23 | 53224222 | 53224222 | G | C |
| | | E122Vfs*14 | FS del | Diploid | 1 | | chr23 | 53247129 | 53247135 | CCACCT T | — |
| | | K459* | Nonsense | Diploid | 1 | | chr23 | 53240705 | 53240705 | T | A |
| | | E1131Sfs*16 | FS del | Diploid | 1 | | chr23 | 53224160 | 53224160 | C | — |
| | | C730F | Missense | Diploid | 2 | Medium | chr23 | 53228213 | 53228213 | C | A |
| | | H988Tfs*18 | FS del | Diploid | 1 | | chr23 | 53225887 | 53225887 | G | — |
| | | H733P | Missense | Diploid | 1 | Medium | chr23 | 53228204 | 53228204 | T | G |
| | | P27Lfs*46 | FS del | Diploid | 1 | | chr23 | 53253992 | 53253992 | G | — |
| | | F56Cfs*18 | FS del | Diploid | 1 | | chr23 | 53250081 | 53250082 | AA | — |
| | | D1414Efs*54 | FS del | Diploid | 1 | | chr23 | 53222684 | 53222694 | TGTGGTTCTCA | — |
| | | R215* | Nonsense | Diploid | 1 | | chr23 | 53246339 | 53246339 | T | A |
| | | G845Rfs*2 | FS del | ShallowDel | | | chr23 | 53227036 | 53227042 | GTAGACC | — |

TABLE 6

| Gene | Accession No. | AA change | Type | Copy # | COSMIC | Mutation Assessor | Chr | Start Pos | End Pos | Ref | Var |
|---|---|---|---|---|---|---|---|---|---|---|---|
| KDM6A | NM_021140.3 | A30V | Missense | Diploid | 1 | Medium | chr23 | 44732886 | 44732886 | C | T |
| | | A1246Pfs*19 | FS del | Diploid | | | chr23 | 44949174 | 44949174 | A | — |
| | | V156del | IF del | ShallowDel | | | chr23 | 44879876 | 44879878 | GGT | — |
| LRP12 | NM_013437.4 | S622L | Missense | Diploid | 1 | Low | chr8 | 105503616 | 105503616 | G | A |
| | | E639K | Missense | Diploid | 2 | Neutral | chr8 | 105503566 | 105503566 | C | T |
| | | V671I | Missense | Gain | 1 | Neutral | chr8 | 105503470 | 105503470 | C | T |
| NCOA6 | NM_001242539.2 | G164E | Missense | Diploid | 1 | Low | chr20 | 33356290 | 33356290 | C | T |
| | | N877I | Missense | Gain | 1 | Low | chr20 | 33337368 | 33337368 | T | A |
| | | N864Y | Missense | Gain | 1 | Neutral | chr20 | 33337408 | 33337408 | T | A |
| | | V1444A | Missense | Diploid | 1 | Neutral | chr20 | 33329729 | 33329729 | A | G |
| | | H832Sfs*47 | FS ins | Gain | | | chr20 | 33337505 | 33337506 | — | G |
| NHS | NM_198270.3 | C360R | Missense | Diploid | | Low | chr23 | 17742451 | 17742451 | T | C |
| | | P1107A | Missense | Diploid | 1 | Low | chr23 | 17745608 | 17745608 | C | G |
| | | D1069H | Missense | Diploid | 2 | Medium | chr23 | 17745494 | 17745494 | G | C |
| RGAG1 | NM_020769.2 | A1015G | Missense | Diploid | 1 | Low | chr23 | 109696889 | 109696889 | C | G |
| | | M858V | Missense | Diploid | 1 | Neutral | chr23 | 109696417 | 109696417 | A | G |
| | | G1053R | Missense | Diploid | 1 | Low | chr23 | 109697002 | 109697002 | G | C |
| SCAF1 | NM_021228.2 | A219Sfs*11 | FS ins | ShallowDel | | | chr19 | 50154294 | 50154295 | — | C |
| | | P211Tfs*19 | FS ins | Diploid | | | chr19 | 50154270 | 50154271 | — | C |
| | | P211Tfs*19 | FS ins | Diploid | | | chr19 | 50154270 | 50154271 | — | C |
| | | A216Pfs*94 | FS del | Diploid | | | chr19 | 50154291 | 50154294 | TGCA | — |

TABLE 7

| Gene | Accession No. | AA change | Type | Copy # | COSMIC | Mutation Assessor | Chr | Start Pos | End Pos | Ref | Var |
|---|---|---|---|---|---|---|---|---|---|---|---|
| SH3TC1 | NM_018986.4 | A375V | Missense | Diploid | 1 | Neutral | chr4 | 8224578 | 8224578 | C | T |
| | | R238Sfs*38 | FS del | Diploid | | | chr4 | 8218768 | 8218768 | G | — |
| | | L180F | Missense | Diploid | 1 | Neutral | chr4 | 8217896 | 8217896 | G | T |
| TBC1D8B | NM_017752.2 | G1059V | Missense | Diploid | 2 | Neutral | chr23 | 106117008 | 106117008 | G | T |
| | | A614T | Missense | ShallowDel | 1 | Medium | chr23 | 106093257 | 106093257 | G | A |
| | | S861* | Nonsense | Gain | 1 | | chr23 | 106109183 | 106109183 | C | G |
| | | Y815F | Missense | Diploid | 3 | Medium | chr23 | 106109045 | 106109045 | A | T |
| | | Y815F | Missense | Diploid | 3 | Medium | chr23 | 106109045 | 106109045 | A | T |
| | | Y815F | Missense | ShallowDel | 3 | Medium | chr23 | 106109045 | 106109045 | A | T |
| TET2 | NM_001127208.2 | Q317K | Missense | ShallowDel | 1 | Low | chr4 | 106156048 | 106156048 | C | A |
| | | K326* | Nonsense | Diploid | 1 | | chr4 | 106156075 | 106156075 | A | T |
| | | L757V | Missense | Diploid | | Neutral | chr4 | 106157368 | 106157368 | C | G |
| | | V449E | Missense | Diploid | | Low | chr4 | 106156445 | 106156445 | T | A |
| | | N1714K | Missense | Diploid | 1 | Medium | chr4 | 106196809 | 106196809 | T | G |
| | | D194E | Missense | Diploid | 1 | Low | chr4 | 106155681 | 106155681 | C | A |
| | | N1390H | Missense | Diploid | 1 | Medium | chr4 | 106190890 | 106190890 | A | C |
| | | R1451Q | Missense | Diploid | 2 | Medium | chr4 | 106193890 | 106193890 | G | A |
| | | M600I | Missense | ShallowDel | 1 | Neutral | chr4 | 106156899 | 106156899 | G | A |
| | | P554S | Missense | ShallowDel | 1 | Neutral | chr4 | 106156759 | 106156759 | C | T |
| TEX13A | NM_001291277.1 | R393S | Missense | Diploid | | Medium | chr23 | 104463697 | 104463697 | C | A |
| | | X199_splice | Splice | Diploid | 2 | | chr23 | 104464282 | 104464282 | C | — |
| | | X199_splice | Splice | Diploid | 2 | | chr23 | 104464282 | 104464282 | C | — |
| | | Y257D | Missense | Diploid | | Low | chr23 | 104464107 | 104464107 | A | C |
| ULK3 | NM_001099436.3 | Q81Sfs*41 | FS del | Diploid | | | chr15 | 75134624 | 75134624 | A | — |
| | | D79H | Missense | Diploid | | Medium | chr15 | 75134629 | 75134629 | C | G |
| | | L77V | Missense | Diploid | | Low | chr15 | 75134635 | 75134635 | C | G |
| WNK3 | NM_001002838.3 | S865* | Nonsense | Diploid | 1 | | chr23 | 54276546 | 54276546 | G | T |
| | | E537G | Missense | Diploid | 1 | Low | chr23 | 54321069 | 54321069 | T | C |
| | | Y589* | Nonsense | Diploid | 1 | | chr23 | 54319687 | 54319687 | A | T |

The correlation between the mutagenesis of the candidate genes and the gender of the patients with kidney cancer was confirmed with respect to each the gender groups. A P-value of less than 0.05 was considered to be statistically significant. The following Tables 8 and 11 list information on the related candidate genes (M0: No distant metastasis, and M1: Distant metastasis).

TABLE 8

| | Gender | | Total No. of patients with identified gene mutations | Fisher's Exact (P-value) | Mutation (%) | Truncating | Mutation type | | | Cytoband | Metastasis | | Metastasis (%) |
|---|---|---|---|---|---|---|---|---|---|---|---|---|---|
| | M | F | | | | | Missense (P) | Missense (D) | In-frame | | M0 | M1 | |
| ACSS3 | 0 | 3 | 3 | 0.042 | 0.72% | 2 | 1 | 0 | 0 | 12q21.31 | 1 | 2 | 66.70% |
| ADAM21 | 0 | 4 | 4 | 0.015 | 0.96% | 0 | 4 | 0 | 0 | 14q24.1 | 4 | 0 | 0.00% |
| AFF2 | 1 | 5 | 6 | 0.022 | 1.44% | 0 | 6 | 0 | 0 | Xq23 | 5 | 1 | 16.70% |
| ALG13 | 0 | 3 | 3 | 0.042 | 0.72% | 1 | 2 | 0 | 0 | Xq23 | 3 | 0 | 0.00% |
| AOC2 | 2 | 2 | 4 | 0.614 | 0.96% | 3 | 1 | 0 | 0 | 17q21 | 4 | 0 | 0.00% |
| AR | 0 | 1 | 1 | 0.35 | 0.24% | 0 | 1 | 0 | 0 | Xq12 | 1 | 0 | 0.00% |
| ARSF | 0 | 1 | 1 | 0.35 | 0.24% | 0 | 1 | 0 | 0 | Xp22.3 | 1 | 0 | 0.00% |
| ASUN | 1 | 2 | 3 | 0.281 | 0.72% | 1 | 2 | 0 | 0 | 12p11.23 | 2 | 1 | 33.30% |
| ASXL2 | 2 | 4 | 6 | 0.19 | 1.44% | 4 | 1 | 0 | 1 | 2p24.1 | 4 | 2 | 33.30% |
| ASXL3 | 7 | 0 | 7 | 0.102 | 1.68% | 0 | 7 | 0 | 0 | 18q12.1 | 4 | 3 | 42.90% |
| AVPR2 | 0 | 2 | 2 | 0.122 | 0.48% | 0 | 2 | 0 | 0 | Xq28 | 2 | 0 | 0.00% |
| BAP1 | 12 | 25 | 37 | <0.001 | 8.87% | 25 | 8 | 3 | 1 | 3p21.1 | 26 | 11 | 29.70% |
| BCOR | 2 | 0 | 2 | 0.544 | 0.48% | 1 | 1 | 0 | 0 | Xq25-q26.1 | 1 | 1 | 50.00% |
| BHLHB9 | 3 | 0 | 3 | 0.555 | 0.72% | 0 | 3 | 0 | 0 | Xq23 | 3 | 0 | 0.00% |
| BRWD3 | 0 | 3 | 3 | 0.042 | 0.72% | 0 | 3 | 0 | 0 | Xq21.1 | 3 | 0 | 0.00% |
| CDCA7 | 0 | 2 | 2 | 0.122 | 0.48% | 0 | 2 | 0 | 0 | 2q31.1 | 2 | 0 | 0.00% |
| CELSR1 | 7 | 0 | 7 | 0.102 | 1.68% | 3 | 4 | 0 | 0 | 22q13.31 | 5 | 2 | 28.60% |
| CFP | 1 | 3 | 4 | 0.126 | 0.96% | 1 | 3 | 0 | 0 | Xp11.4 | 3 | 1 | 25.00% |
| CLN8 | 0 | 2 | 2 | 0.122 | 0.48% | 0 | 2 | 0 | 0 | 8p23 | 2 | 0 | 0.00% |

TABLE 9

| | Gender | | Total No. of patients with identified gene mutations | Fisher's Exact (P-value) | Mutation (%) | Truncating | Mutation type | | | Cytoband | Metastasis | | Metastasis (%) |
|---|---|---|---|---|---|---|---|---|---|---|---|---|---|
| | M | F | | | | | Missense (P) | Missense (D) | In-frame | | M0 | M1 | |
| COL4A5 | 1 | 5 | 6 | 0.022 | 1.44% | 1 | 5 | 0 | 0 | Xq22 | 5 | 1 | 16.70% |
| CPEB1 | 0 | 3 | 3 | 0.042 | 0.72% | 1 | 2 | 0 | 0 | 15q25.2 | 2 | 1 | 33.30% |
| CYLC1 | 0 | 2 | 2 | 0.122 | 0.48% | 0 | 2 | 0 | 0 | Xq21.1 | 2 | 0 | 0.00% |
| DYSF | 2 | 4 | 6 | 0.19 | 1.44% | 2 | 3 | 0 | 1 | 2p13.2 | 4 | 2 | 33.30% |
| ERBB2 | 0 | 4 | 4 | 0.015 | 0.96% | 1 | 3 | 0 | 0 | 17q12 | 4 | 0 | 0.00% |
| FAM47A | 1 | 3 | 4 | 0.126 | 0.96% | 0 | 2 | 0 | 2 | Xp21.1 | 3 | 1 | 25.00% |
| FRMD7 | 4 | 0 | 4 | 0.302 | 0.96% | 2 | 2 | 0 | 0 | Xp22.2 | 3 | 1 | 25.00% |
| FRMPD4 | 4 | 0 | 4 | 0.302 | 0.96% | 3 | 1 | 0 | 0 | Xp22.2 | 4 | 0 | 0.00% |
| GABRQ | 2 | 4 | 6 | 0.19 | 1.44% | 2 | 4 | 0 | 0 | Xq28 | 5 | 1 | 16.70% |
| GPR45 | 0 | 3 | 3 | 0.042 | 0.72% | 1 | 2 | 0 | 0 | 2q12.1 | 2 | 1 | 33.30% |
| HAUS7 | 2 | 0 | 2 | 0.544 | 0.48% | 0 | 2 | 0 | 0 | Xq28 | 1 | 1 | 50.00% |
| HSP90AA1 | 0 | 4 | 4 | 0.015 | 0.96% | 0 | 4 | 0 | 0 | 14q32.31 | 4 | 0 | 0.00% |
| IRAK1 | 0 | 3 | 3 | 0.042 | 0.72% | 1 | 2 | 0 | 0 | Xq28 | 3 | 0 | 0.00% |
| ITIH6 | 0 | 1 | 1 | 0.35 | 0.24% | 0 | 1 | 0 | 0 | Xp11.22-p11.21 | 1 | 0 | 0.00% |
| KDM5C | 3 | 23 | 26 | <0.001 | 6.24% | 18 | 8 | 0 | 0 | Xp11.22-p11.21 | 22 | 4 | 15.40% |
| KDM6A | 0 | 3 | 3 | 0.042 | 0.72% | 1 | 1 | 0 | 1 | Xp11.2 | 3 | 0 | 0.00% |
| LPAR4 | 0 | 2 | 2 | 0.122 | 0.48% | 1 | 1 | 0 | 0 | Xq21.1 | 2 | 0 | 0.00% |
| LRP12 | 0 | 3 | 3 | 0.042 | 0.72% | 0 | 3 | 0 | 0 | 8q22.2 | 3 | 0 | 0.00% |
| MAGEB10 | 0 | 2 | 2 | 0.122 | 0.48% | 0 | 2 | 0 | 0 | Xp21.1 | 2 | 0 | 0.00% |

TABLE 10

|  | Gender M | Gender F | Total No. of patients with identified gene mutations | Fisher's Exact (P-value) | Mutation (%) | Mutation type Truncating | Mutation type Missense (P) | Mutation type Missense (D) | Mutation type In-frame | Cytoband | Metastasis M0 | Metastasis M1 | Metastasis (%) |
|---|---|---|---|---|---|---|---|---|---|---|---|---|---|
| MAGEB16 | 0 | 2 | 2 | 0.122 | 0.48% | 0 | 2 | 0 | 0 | Xp21.1 | 2 | 0 | 0.00% |
| MAGED1 | 2 | 0 | 2 | 0.544 | 0.48% | 0 | 2 | 0 | 0 | Xp11.23 | 2 | 0 | 0.00% |
| MAP3K15 | 1 | 3 | 4 | 0.126 | 0.96% | 2 | 2 | 0 | 0 | Xp22.12 | 3 | 1 | 25.00% |
| MED14 | 4 | 1 | 5 | 0.661 | 1.20% | 1 | 4 | 0 | 0 | Xp11.4 | 5 | 0 | 0.00% |
| NBPF10 | 4 | 4 | 8 | 0.459 | 1.92% | 2 | 6 | 0 | 0 | 1q21.1 | 6 | 2 | 25.00% |
| NCOA6 | 0 | 4 | 4 | 0.015 | 0.96% | 1 | 3 | 0 | 0 | 20q11.22 | 4 | 0 | 0.00% |
| NCOR1P1 |  |  |  |  | Null |  |  |  |  | 20p11.1 |  | Null |  |
| NHS | 0 | 3 | 3 | 0.042 | 0.72% | 0 | 3 | 0 | 0 | Xp22.13 | 3 | 0 | 0.00% |
| NOX1 | 2 | 2 | 4 | 0.614 | 0.96% | 2 | 2 | 0 | 0 | Xq22 | 4 | 0 | 0.00% |
| PABPC3 | 9 | 1 | 10 | 0.176 | 2.40% | 1 | 9 | 0 | 0 | 13q12-q13 | 10 | 0 | 0.00% |
| PHF16(JADE3) | 0 | 2 | 2 | 0.122 | 0.48% | 0 | 2 | 0 | 0 | Xp11.23 | 2 | 0 | 0.00% |
| POTEH-AS1 |  |  |  |  | Null |  |  |  |  | 22q11.1 |  | Null |  |
| PRRG3 | 0 | 2 | 2 | 0.122 | 0.48% | 0 | 2 | 0 | 0 | Xq28 | 2 | 0 | 0.00% |
| RGAG1 | 0 | 3 | 3 | 0.042 | 0.72% | 0 | 3 | 0 | 0 | Xq23 | 3 | 0 | 0.00% |
| SCAF1 | 0 | 4 | 4 | 0.015 | 0.96% | 4 | 0 | 0 | 0 | 19q13.33 | 3 | 1 | 25.00% |
| SCRN1 | 0 | 2 | 2 | 0.122 | 0.48% | 1 | 1 | 0 | 0 | 7p14.3 | 1 | 1 | 50.00% |
| SH3TC1 | 0 | 3 | 3 | 0.042 | 0.72% | 1 | 2 | 0 | 0 | 4p16.1 | 3 | 0 | 0.00% |
| SMC1A | 0 | 2 | 2 | 0.122 | 0.48% | 1 | 1 | 0 | 0 | Xp11.22-p11.21 | 2 | 0 | 0.00% |
| SYTL4 | 0 | 1 | 1 | 0.35 | 0.24% | 0 | 1 | 0 | 0 | Xq21.33 | 1 | 0 | 0.00% |

TABLE 11

|  | Gender M | Gender F | Total No. of patients with identified gene mutations | Fisher's Exact (P-value) | Mutation (%) | Mutation type Truncating | Mutation type Missense (P) | Mutation type Missense (D) | Mutation type In-frame | Cytoband | Metastasis M0 | Metastasis M1 | Metastasis (%) |
|---|---|---|---|---|---|---|---|---|---|---|---|---|---|
| TBC1D8B | 1 | 5 | 6 | 0.022 | 1.44% | 1 | 5 | 0 | 0 | Xq22.3 | 6 | 0 | 0.00% |
| TET2 | 9 | 0 | 9 | 0.03 | 2.16% | 1 | 8 | 0 | 0 | 4q24 | 3 | 6 | 66.70% |
| TEX13A | 0 | 4 | 4 | 0.015 | 0.96% | 2 | 2 | 0 | 0 | Xq22.3 | 4 | 0 | 0.00% |
| TFDP3 | 1 | 2 | 3 | 0.281 | 0.72% | 0 | 3 | 0 | 0 | Xq26.2 | 3 | 0 | 0.00% |
| TRO | 0 | 2 | 2 | 0.122 | 0.48% | 1 | 1 | 0 | 0 | Xp11.22-p11.21 | 2 | 0 | 0.00% |
| ULK3 | 0 | 3 | 3 | 0.042 | 0.72% | 1 | 2 | 0 | 0 | 15q24.1 | 3 | 0 | 0.00% |
| USP51 | 1 | 4 | 5 | 0.53 | 1.20% | 1 | 4 | 0 | 0 | Xp11.21 | 3 | 2 | 40.00% |
| WNK3 | 0 | 3 | 3 | 0.042 | 0.72% | 2 | 1 | 0 | 0 | Xp11.22 | 2 | 1 | 33.30% |
| ZMYM3 | 1 | 1 | 2 | 1 | 0.48% | 0 | 2 | 0 | 0 | Xq13.1 | 2 | 0 | 0.00% |
| ZNF318 | 2 | 5 | 7 | 0.054 | 1.68% | 2 | 5 | 0 | 0 | 6p21.1 | 6 | 1 | 14.30% |
| ZNF449 | 0 | 1 | 1 | 0.35 | 0.24% | 0 | 1 | 0 | 0 | Xq26.3 | 1 | 0 | 0.00% |

From the analysis results, it was confirmed that there were the genes whose P-values were shown to be greater than or equal to 0.05 compared to the other groups even when the genes had mutations in each of the gender groups, and also confirmed that there were the genes whose P-values were shown to be less than 0.05 while the genes had the mutations. Because the mutant genes whose P-values were less than 0.05 compared to the other groups correlated with the certain gender group compared to the other groups, the mutant genes were defined as gender-specific genes. For example, it can be seen that there were a large total number of patients in which AOC2, AR, and ARSF were mutated, but the AOC2, AR, and ARSF mutants had a high P-value of 0.05 or more, there was no correlation between the gender of the patients and the mutations of these genes. On the other hand, it was confirmed that, because the ACSS3, ADAM21, AFF2, ALG13, BAP1, BRWD3, COL4A5, CPEB1, ERBB2, HSP90AA1, IRAK1, KDM5C, KDM6A, LRP12, NCOA6, NHS, RGAG1, SCAF1, SH3TC1, TBC1D8B, TET2, TEX13A, ULK3, and WNK3 genes has a P-value of less than 0.05 in comparison between the groups, there was a correlation between the gender of the patients and the mutagenesis of these genes.

FIG. 1 shows the results of analyzing the correlation between the gender of patients and the mutations of genes. As shown in FIG. 1, it was confirmed that there were a larger number of patients having the mutant genes in the female groups than in the male groups in the case of the ACSS3, ADAM21, AFF2, ALG13, BAP1, BRWD3, COL4A5, CPEB1, ERBB2, HSP90AA1, IRAK1, KDM5C, KDM6A, LRP12, NCOA6, NHS, RGAG1, SCAF1, SH3TC1, TBC1D8B, TEX13A, ULK3, and WNK3 genes, and there were a larger number of patients having the mutant gene in the male groups than in the female groups in the case of the TET2 gene.

From the results, it can be seen that the mutations of ACSS3, ADAM21, AFF2, ALG13, BAP1, BRWD3, COL4A5, CPEB1, ERBB2, HSP90AA1, IRAK1, KDM5C KDM6A, LRP12, NCOA6, NHS, RGAG1, SCAF1, SH3TC1, TBC1D8B, TEX13A, ULK3, and WNK3 were able to be used as the markers specific to the female groups, and that the mutation of TET2 was able to be used as the marker specific to the male groups.

<Example 3> Confirmation of Applicability as Survival-Specific Markers According to Gender It was confirmed whether there were survival-specific mutant genes among the candidate genes according to the gender. The analyses were performed in the same manner as in Example 2. Mutation positions of the respective genes are listed in Table 12.

Kaplan-Meier survival analysis method (Spss 21). The 417 target patients volunteered in Example 1 were divided into surviving patients (270) and dead patients (147), and comparative analyses thereof were performed. The overall survival Kaplan-Meier estimate or the disease-free survival Kaplan-Meier estimate was calculated based on the clinical information (occurrence of events (death or relapse), and observation time) on the patients volunteered in Example 1 using the Kaplan-Meier survival analysis method. The event was defined as 'death' for the overall survival Kaplan-Meier estimate, and the event was defined as 'relapse' for the disease-free survival Kaplan-Meier estimate. To verify whether the mutagenesis in each of the genes correlated with the death of the patients from kidney cancer or the relapse of kidney cancer, the correlation between the mutagenesis and the overall survival Kaplan-Meier estimate, and the correlation between the mutagenesis and the disease-free survival Kaplan-Meier estimate were confirmed, based on the event times of the respective groups obtained in the

TABLE 12

| Gene | Accession No. | AA change | Type | Copy # | COSMIC | Mutation Assessor | Chr | Start Pos | End Pos | Ref | Var |
|---|---|---|---|---|---|---|---|---|---|---|---|
| ACSS3 | NM_024560.3 | R634* | Nonsense | Diploid | 4 | | chr12 | 81647354 | 81647354 | C | T |
| | | X152_splice | Splice | Gain | | | chr12 | 81503485 | 81503485 | T | C |
| | | G268D | Missense | Gain | 1 | Low | chr12 | 81536908 | 81536908 | G | A |
| ALG13 | NM_001099922.2 | P925T | Missense | Diploid | | Low | chr23 | 110987973 | 110987973 | C | A |
| | | L195Pfs*23 | FS del | Diploid | | | chr23 | 110951455 | 110951455 | T | — |
| | | V456E | Missense | Diploid | | Medium | chr23 | 110964871 | 110964871 | T | A |
| ARSF | NM_001201538.1 | I42F | Missense | Diploid | 1 | Medium | chr23 | 2990179 | 2990179 | A | T |
| CFP | NM_001145252.1 | S27L | Missense | Diploid | 2 | Medium | chr23 | 47489070 | 47489070 | G | A |
| | | R359Q | Missense | Diploid | 1 | Low | chr23 | 47485783 | 47485783 | C | T |
| | | E135K | Missense | Diploid | 1 | Low | chr23 | 47487501 | 47487501 | C | T |
| | | E323Gfs*34 | FS ins | Gain | 1 | | chr23 | 47485891 | 47485892 | — | C |
| FAM47A | NM_203408.3 | R505H | Missense | ShallowDel | 3 | Neutral | chr23 | 34148882 | 34148882 | C | T |
| | | E507Q | Missense | ShallowDel | 6 | Low | chr23 | 34148877 | 34148877 | C | G |
| | | L235_H246del | IF del | Diploid | | | chr23 | 34149658 | 34149693 | ATGGGACACTCCAGTCTCTGGAGGCTCCGGGCGGAG | — |
| | | L235_H246del | IF del | Diploid | | | chr23 | 34149658 | 34149693 | ATGGGACACTCCAGTCTCTGGAGGCTCCGGGCGGAG | — |
| KDM6A | NM_021140.3 | A30V | Missense | Diploid | 1 | Medium | chr23 | 44732886 | 44732886 | C | T |
| | | A1246Pfs*19 | FS del | Diploid | | | chr23 | 44949174 | 44949174 | A | — |
| | | V156del | IF del | ShallowDel | | | chr23 | 44879876 | 44879878 | GGT | — |
| PHF16(JADE3) | NM_001074475.2 | K656Q | Missense | Diploid | | Low | chr23 | 46917973 | 46917973 | A | C |
| | | R207W | Missense | ShallowDel | | Medium | chr23 | 46887437 | 46887437 | C | T |
| ZNF449 | NM_152695.5 | F183I | Missense | Diploid | 1 | Low | chr23 | 134483227 | 134483227 | T | A |
| SCRN1 | NM_001145514.1 | D427Y | Missense | Gain | | Medium | chr7 | 29963599 | 29963599 | C | A |
| | | A257Cfs*34 | FS ins | Diploid | | | chr7 | 29980329 | 29980330 | — | C |

An overall survival Kaplan-Meier estimate and a disease-free survival Kaplan-Meier estimate were calculated using a Kaplan-Meier survival analysis method, using a log rank test. A P-value of less than 0.05 was considered to be statistically significant. Cases with alterations in the query genes of the present invention were used as the experimental groups, and a case without alterations in the query genes of the present invention was used as the control. A median months survival refers to a median value when the survival estimates of the patients from the corresponding groups were listed. A gradient of the survival curve obtained by the Kaplan-Meier survival analysis method was determined by the survival estimates.

To check whether the mutagenesis in each of the candidate genes correlated with the survival rate of the patients with kidney cancer, who had a certain gender, the genetic information on the 417 patient with kidney cancer obtained in Example 1 was analyzed. The gender of the patients in which the mutations of the ACSS3, ALG13, ARSF, CFP, FAM47A, KDM6A, PHF16, ZNF449, and SCRN1 genes were identified was listed in Table 13.

TABLE 13

| | Gender group | | Total number of patients with |
|---|---|---|---|
| | M | F | identified gene mutations |
| ACSS3 | 0 | 3 | 3 |
| ALG13 | 0 | 3 | 3 |
| ARSF | 0 | 1 | 1 |
| CFP | 1 | 3 | 4 |
| FAM47A | 1 | 3 | 4 |
| KDM6A | 0 | 3 | 3 |
| PHF16 | 0 | 2 | 2 |
| ZNF449 | 0 | 1 | 1 |
| SCRN1 | 0 | 2 | 2 |

As shown in FIGS. 2 to 10, it can be seen that, because the probability of the null hypothesis being true was shown to be greater than or equal to 99.5% when it is assumed that the mutagenesis of the ACSS3, ALG13, ARSF, CFP, FAM47A, KDM6A, PHF16, ZNF449, and SCRN1 genes correlated with the survival rates of the females of the patients with kidney cancer in comparison between the groups, that is, the probability of the null hypothesis being false was shown to be less than 0.5%, there was the correlation between the mutagenesis of the ACSS3, ALG13, ARSF, CFP, FAM47A, KDM6A, PHF16, ZNF449, and SCRN1 genes and the survival rate of the female patients of the patients with kidney cancer (see information on 'Gender group' and information on 'Total number of patients with identified gene mutations' listed in Table 13).

Some mutant genes whose P-values were shown to be greater than or equal to 0.05, the value of which was considered to be insignificant, when only the correlation between the mutagenesis and the gender was verified in Example 1 had a P-value of less than 0.05, the value of which was considered to be significant, when the correlation between the mutagenesis and the survival rates of the patients with kidney cancer who had a certain gender. For example, the P-value of ARSF was considered to be insignificant only when the correlation between the mutagenesis and the gender was verified in Example 1, but considered to be significant when the correlation between the mutation of ARSF and the survival rates of the patients was compared between the gender groups in this example (see information on 'Gender group' of Table 13 and the P-values shown in FIGS. 2 to 15).

The analysis results of survival of the patients with kidney cancer who had the mutant genes are shown in FIGS. 2 to 15.

From the analysis results, as shown in FIG. 2(A), it was confirmed that at least 50% of the patients with kidney cancer in which the ACSS3 gene was not mutated survived for 80 months or more (blue). On the other hand, it was confirmed that, because at least 50% of the patients with kidney cancer in which the ACSS3 gene was mutated died within 20 months, the patients with kidney cancer in which the ACSS3 gene was mutated had a survival rate lower than the patients with kidney cancer in which the ACSS3 gene was not mutated (red). Referring to FIG. 2(B), it was revealed that at least 50% of the patients with kidney cancer in which the ACSS3 gene was not mutated did not relapse into kidney cancer for 100 months or more (blue), but at least 50% of the patients with kidney cancer relapsed into kidney cancer within 40 months when the ACSS3 gene was mutated (red). Therefore, it can be seen that the mutation of the ACSS3 gene was useful as the marker for predicting the survival rate of the patients with kidney cancer and the relapse of kidney cancer because the patients had a high probability of dying from kidney cancer or relapsing into kidney cancer when the ACSS3 gene was mutated and the gender of the patients with kidney cancer was female.

As shown in FIG. 3, it was confirmed that at least 50% of the patients with kidney cancer in which the ALG13 gene was not mutated survived for 80 months or more (blue). On the other hand, it was confirmed that, because at least 50% of the patients with kidney cancer in which the ALG13 gene was mutated died within 20 months, the patients with kidney cancer in which the ALG13 gene was mutated had a survival rate lower than the patients with kidney cancer in which the ALG13 gene was not mutated (red). Therefore, it can be seen that the mutation of the ALG13 gene was useful as the marker for predicting the survival rate of the patients with kidney cancer because the patients had a high probability of dying from kidney cancer when the ALG13 gene was mutated and the gender of the patients with kidney cancer was female.

As shown in FIG. 4(A), it was confirmed that at least 50% of the patients with kidney cancer in which the ARSF gene was not mutated survived for 80 months or more (blue). On the other hand, it was confirmed that, because at least 50% of the patients with kidney cancer in which the ARSF gene was mutated died within 20 months, the patients with kidney cancer in which the ARSF gene was mutated had a survival rate lower than the patients with kidney cancer in which the ARSF gene was not mutated (red). Referring to FIG. 4(B), it was revealed that at least 50% of the patients with kidney cancer in which the ARSF gene was not mutated did not relapse into kidney cancer for 100 months or more (blue), but at least 50% of the patients with kidney cancer relapsed into kidney cancer within 20 months when the ARSF gene was mutated (red). Therefore, it can be seen that the mutation of the ARSF gene was useful as the marker for predicting the survival rate of the patients with kidney cancer and the relapse of kidney cancer because the patients had a high probability of dying from kidney cancer or relapsing into kidney cancer when the ARSF gene was mutated and the gender of the patients with kidney cancer was female.

As shown in FIG. 5(A), it was confirmed that at least 50% of the patients with kidney cancer in which the CFP gene was not mutated survived for 80 months or more (blue). On the other hand, it was confirmed that, because at least 50% of the patients with kidney cancer in which the CFP gene was mutated died within 20 months, the patients with kidney cancer in which the CFP gene was mutated had a survival rate lower than the patients with kidney cancer in which the CFP gene was not mutated (red). Referring to FIG. 5(B), it was revealed that at least 50% of the patients with kidney cancer in which the CFP gene was not mutated did not relapse into kidney cancer for 100 months or more (blue), but at least 50% of the patients with kidney cancer relapsed into kidney cancer within 40 months when the CFP gene was mutated (red). Therefore, it can be seen that the mutation of the CFP gene was useful as the marker for predicting the survival rate of the patients with kidney cancer and the relapse of kidney cancer because the patients had a high probability of dying from kidney cancer or relapsing into kidney cancer when the CFP gene was mutated and the gender of the patients with kidney cancer was female.

As shown in FIG. 6(A), it was confirmed that at least 50% of the patients with kidney cancer in which the FAM47A gene was not mutated survived for 80 months or more (blue). On the other hand, it was confirmed that, because at least 50% of the patients with kidney cancer in which the FAM47A gene was mutated died within 20 months, the patients with kidney cancer in which the FAM47A gene was mutated had a survival rate lower than the patients with kidney cancer in which the FAM47A gene was not mutated (red). Referring to FIG. 6(B), it was revealed that at least 50% of the patients with kidney cancer in which the FAM47A gene was not mutated did not relapse into kidney cancer for 100 months or more (blue), but at least 50% of the patients with kidney cancer relapsed into kidney cancer within 40 months when the FAM47A gene was mutated (red). Therefore, it can be seen that the mutation of the FAM47A gene was useful as the marker for predicting the survival rate of the patients with kidney cancer and the relapse of kidney cancer because the patients had a high probability of dying from kidney cancer or relapsing into kidney cancer when the FAM47A gene was mutated and the gender of the patients with kidney cancer was female.

As shown in FIG. 7, it was confirmed that at least 50% of the patients with kidney cancer in which the KDM6A gene was not mutated survived for 80 months or more (blue). On the other hand, it was confirmed that, because at least 50% of the patients with kidney cancer in which the KDM6A gene was mutated died within 20 months, the patients with kidney cancer in which the KDM6A gene was mutated had a survival rate lower than the patients with kidney cancer in which the KDM6A gene was not mutated (red). Therefore, it can be seen that the mutation of the KDM6A gene was useful as the marker for predicting the survival rate of the patients with kidney cancer because the patients had a high probability of dying from kidney cancer when the KDM6A gene was mutated and the gender of the patients with kidney cancer was female.

As shown in FIG. 8, it was confirmed that at least 50% of the patients with kidney cancer in which the PHF16 gene was not mutated survived for 80 months or more (blue). On the other hand, it was confirmed that, because at least 50% of the patients with kidney cancer in which the PHF16 gene was mutated died within 40 months, the patients with kidney cancer in which the PHF16 gene was mutated had a survival rate lower than the patients with kidney cancer in which the PHF16 gene was not mutated (red). Therefore, it can be seen that the mutation of the PHF16 gene was useful as the marker for predicting the survival rate of the patients with kidney cancer because the patients had a high probability of dying from kidney cancer when the PHF16 gene was mutated and the gender of the patients with kidney cancer was female.

Referring to FIG. 9, it was revealed that at least 50% of the patients with kidney cancer in which the SCRN1 gene did not relapsed into kidney cancer for 100 months or more (blue), but at least 50% of the patients with kidney cancer relapsed into kidney cancer within 20 months when the SCRN1 gene was mutated (red). Therefore, it can be seen that the mutation of the SCRN1 gene was useful as the marker for predicting the relapse of kidney cancer because the patients had a high probability of relapsing into kidney cancer when the SCRN1 gene was mutated and the gender of the patients with kidney cancer was female.

As shown in FIG. 10(A), it was confirmed that at least 50% of the patients with kidney cancer in which the ZNF449 gene was not mutated survived for 80 months or more (blue). On the other hand, it was confirmed that, because at least 50% of the patients with kidney cancer in which the ZNF449 gene was mutated died within 10 months, the patients with kidney cancer in which the ZNF449 gene was mutated had a survival rate lower than the patients with kidney cancer in which the ZNF449 gene was not mutated (red). Referring to FIG. 10(B), it was revealed that at least 50% of the patients with kidney cancer in which the ZNF449 gene did not relapsed into kidney cancer for 100 months or more (blue), but at least 50% of the patients with kidney cancer relapsed into kidney cancer within 20 months when the ZNF449 gene was mutated (red). Therefore, it can be seen that the mutation of the ZNF449 gene was useful as the marker for predicting the survival rate of the patients with kidney cancer or the relapse of kidney cancer because the patients had a high probability of dying from kidney cancer or relapsing into kidney cancer when the ZNF449 gene was mutated and the gender of the patients with kidney cancer was female.

From the above results, it can be seen that the survival rate of the patients with kidney cancer who had a certain gender was significantly reduced, or the relapse rate of kidney cancer in the patients with kidney cancer was increased when any one gene selected from the group consisting of ACSS3, ALG13, ARSF, CFP, FAM47A, KDM6A, PHF16, ZNF449, and SCRN1 was mutated. Therefore, it can be seen that the prognoses of kidney cancer, particularly the survival of the patients with kidney cancer or the relapse of kidney cancer, were able to be predicted by comparing the gender of the patients to check whether the genes of the present invention were mutated.

<Example 4> Manufacture of Chips Capable of Detecting Genes of Examples 2 and 3

Primer sets for detecting mutations of the genes of Examples 2 and 3 were constructed using Ion AmpliSeq™ Custom and Community Panels (commercially available from Thermo fisher) with reference to the website www dot tools.thermofishercom/content/sfs/manuals/MAN0006735_AmpliSeq_DNA_RNA_LibPrep_UG.pdf. To easily detect the mutations, types of chips were selected and the depth of the chips was enhanced. Specifically, information on a panel to be manufactured was input into Ampliseq.com, and the input information was fed back. Thereafter, the related items were discussed to manufacture a panel equipped with a primer set capable of detecting the mutation. Tables 14 to 21 list the primer sets capable of detecting the mutations of the genes of the present invention.

TABLE 14

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| ACSS3 | chr12 | 31 | GGGATAAGATTGCTATCATCTATGACAGT | 32 | GAAGGCTCTACAATGAGAATGTATGCTAT | 81503404 | 81503433 | 81503537 | 81503566 |
| ACSS3 | chr12 | 33 | TTCAGTCAGATGCTCAGACTTAAATAGATT | 34 | ACAGTCATGTGACTGGGCTTTT | 81536787 | 81536817 | 81536938 | 81536960 |
| ACSS3 | chr12 | 35 | CTCTAGATATAAATGCAACAGAGGAGCAA | 36 | CCATTGACAATGGCAGATAAAGCTG | 81647268 | 81647297 | 81647411 | 81647436 |
| ADAM21 | chr14 | 37 | GGGCTTTCGAGGAGTATTAAAAATAAGT | 38 | TGCTACTTCCTTCTCTGTTAAGCC | 70924606 | 70924634 | 70924735 | 70924759 |
| ADAM21 | chr14 | 39 | GTATTTCTTGTTGTCAACATAGTGGATTCC | 40 | ATGCTGTAGCTGGGAAAGACTG | 70924919 | 70924949 | 70925070 | 70925092 |
| ADAM21 | chr14 | 41 | CTTAAACCAGGGATCATGTCTGCAT | 42 | GTCTTGTTCACACTGCTGTACG | 70925377 | 70925402 | 70925487 | 70925509 |
| ADAM21 | chr14 | 43 | GATGTCTTTTGTGGGAGAGTTCAATG | 44 | GGCCACACACAGTACCATCTTT | 70925885 | 70925911 | 70926037 | 70926059 |
| AFF2 | chrX | 45 | TCACCAGGATAATACCCATCCTTCA | 46 | AGTCTGCATCTTGTTTGGCTGA | 147743623 | 147743648 | 147743775 | 147743797 |
| AFF2 | chrX | 47 | TCGGAGAGCAGCTCTGAGT | 48 | CTGTGGGACAGGCAGATCAT | 148035180 | 148035199 | 148035296 | 148035316 |
| AFF2 | chrX | 49 | GGCTTTGAAGCATAAGTTGTCAACA | 50 | GGGTCATGAAGCTCCACACTTT | 148037399 | 148037424 | 148037550 | 148037572 |
| AFF2 | chrX | 51 | GCCAAATCCAAGGAAATCTGTGGT | 52 | AGAGGTTTTTCAGGTTCTCATGATCTC | 148037805 | 148037829 | 148037952 | 148037979 |
| ALG13 | chrX | 53 | TCCGGATACCTGCATAAGCAAGGAC | 54 | CATCCATTGATGCCTCATTCAAA | 110951367 | 110951389 | 110951515 | 110951541 |
| ALG13 | chrX | 55 | GAAGACTAAGGATTGTGAGTTTGTAGCA | 56 | TCCTGTTGATATTTCTTTACCTTTCTGCT | 110964785 | 110964813 | 110964929 | 110964959 |
| ALG13 | chrX | 57 | TCTTTGTTAGTGATTGCCTCACCAT | 58 | AGTCTCTCCCACATCAAGAGCA | 110987886 | 110987911 | 110988034 | 110988056 |

TABLE 15

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| BAP1 | chr3 | 59 | GTAGGAGAGAAGAAGACTGAGAGCACT | 60 | GTGGAGGCTGAGATTGCAAACTA | 52436693 | 52436720 | 52436840 | 52436863 |
| BAP1 | chr3 | 61 | TTCCAATCAAGAACTTGGCACCT | 62 | GTCGTGGAAGCCACGGACA | 52437065 | 52437088 | 52437218 | 52437237 |
| BAP1 | chr3 | 63 | GCCGTGTCTGTACTCTCATTGC | 64 | CCATCAACGTCTTGGCTGAGAA | 52437674 | 52437696 | 52437808 | 52437830 |

TABLE 15-continued

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| BAP1 | chr3 | 65 | AACCTGGTAGCCTTAGAAAGCTG | 66 | TTGTCCCAGGAGGAAGAAGACCT | 52438439 | 52438462 | 52438588 | 52438611 |
| BAP1 | chr3 | 67 | GGGACTTGGCATAATTGTGATTGT | 68 | ATCCCACAGCCCTCCCAACAAA | 52439134 | 52439158 | 52439248 | 52439270 |
| BAP1 | chr3 | 69 | GCTTCACCACTAGCTTGGGTTT | 70 | GGGAGACTGTGAGCTTTTCTTGG | 52439230 | 52439252 | 52439353 | 52439376 |
| BAP1 | chr3 | 71 | GGACTTGTTGCTGGCTGACTT | 72 | GGGTCTACCCTTTCTCCTCTGA | 52439836 | 52439857 | 52439948 | 52439970 |
| BAP1 | chr3 | 73 | GTATGTTCACGAATCAGAGACAAATGC | 74 | CGACCGCAGGATCAAGTATGAG | 52440173 | 52440200 | 52440325 | 52440347 |
| BAP1 | chr3 | 75 | CAGCCTGGCCTCATACTTGATCG | 76 | CAGGATATCTGCCTCAACCTGAT | 52440317 | 52440339 | 52440440 | 52440464 |
| BAP1 | chr3 | 77 | CATGGTGCCTACCATGGTCAAT | 78 | CCTGAGAAGCAGAATGGCCTTA | 52441178 | 52441200 | 52441291 | 52441313 |
| BAP1 | chr3 | 79 | CGCACTGCACTAAGGCCATT | 80 | GCCAAGGCCCATAATAGCCATG | 52441282 | 52441302 | 52441418 | 52441440 |
| BAP1 | chr3 | 81 | CACACACCTGGCATGGCTATTAA | 82 | CCCATAGTCCTACCTGAGGAGAA | 52441408 | 52441430 | 52441510 | 52441534 |
| BAP1 | chr3 | 83 | CTGAAACCCTTGGTGAAGTCCTA | 84 | TTGGTTTCACAGCTGATACCCA | 52441981 | 52442003 | 52442082 | 52442105 |
| BAP1 | chr3 | 85 | ATCCCACCCTCCAAACAAAGCACTT | 86 | CCCAGCCCTGTATATGGATTTAT | 52442453 | 52442475 | 52442601 | 52442627 |
| BAP1 | chr3 | 87 | GCTGCTGCTTTCTGTGAGATTTT | 88 | GGGTGCAAGTGGAGGAGATCTA | 52443443 | 52443466 | 52443593 | 52443615 |
| BAP1 | chr3 | 89 | CCCTGACATTTGCTCTGAAGGT | 90 | TCGGTAAGAGCCTTTTCTCCCT | 52443570 | 52443592 | 52443710 | 52443732 |
| BAP1 | chr3 | 91 | TCTTACCGAAATCTTCCACGAGC | 92 | AAGATGAATAAGGGCTGGCTGG | 52443724 | 52443747 | 52443875 | 52443897 |
| BAP1 | chrX | 93 | CTTACTGAACACTGTAACACTGGAAAGA | 94 | GTGGGAACAGAGCTAATATTCTCAAGAG | 79948434 | 79948462 | 79948580 | 79948608 |

TABLE 16

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| BRWD3 | chrX | 95 | AGAGGATCCTCAGTGGACACAA | 96 | CTAGAGGAGCTACCAGAGCCAAAC | 79932193 | 79932215 | 79932343 | 79932367 |
| BRWD3 | chrX | 97 | ATTGTTTTTACATGCCATTGCCAGAA | 98 | TTGATGTTAGGCTGAACATGAAAACTTTTT | 79991496 | 79991522 | 79991615 | 79991645 |
| COL4A5 | chrX | 99 | ATTAAATTCTCTGTGGCAAACAA | 100 | TGGGAAACCACGATCACCTTTTTAAGGAC | 107849893 | 107849923 | 107850045 | 107850067 |

TABLE 16 -continued

| Lineitem_Name | Chr | SEQ ID NO Fwd_Primer* | SEQ ID NO Rev_Primer* | Amplicon_Start | Insert_Start | Insert_Stop | Amplicon_Stop |
|---|---|---|---|---|---|---|---|
| COL4A5 | chrX | 101 CAGCTGGACAGAAGGGTGAA | 102 GTGTGTGGTAGCTTAGTAAGAAAGAAGAT | 107909801 | 107909821 | 107909910 | 107909939 |
| COL4A5 | chrX | 103 CAAAAACTGGTTTCTCTCACACCAAT | 104 TGGAGGACCAGCATCTCCTTTA | 107924880 | 107924906 | 107925032 | 107925054 |
| COL4A5 | chrX | 105 CCTCATTCTTTTCCTGTAGGTCCAA | 106 TCTCTCAGACTCAAAGACTTTCCCT | 107929242 | 107929267 | 107929388 | 107929413 |
| COL4A5 | chrX | 107 CCTTGAAAGGCTGTTTGCTATTGT | 108 TCTTGAAGCAAAGTTGCAAACATTATTGA | 107935889 | 107935913 | 107936034 | 107936063 |
| COL4A5 | chrX | 109 CTGCTTGGAAGAGTTTCGTTCAG | 110 CCCTAGCATCTCTGAAGGAAGCT | 107938550 | 107938573 | 107938701 | 107938724 |
| CPEB1 | chr15 | 111 CCCACCTGATCTCGACAGAAGA | 112 TGGCCAATAATGTGCCCTTCTT | 83215186 | 83215208 | 83215335 | 83215357 |
| CPEB1 | chr15 | 113 CACAAGAAAATCCAGTGCCTCAA | 114 AAGTCTGTCCGATCCTTGCTTC | 83221163 | 83221186 | 83221315 | 83221337 |
| CPEB1 | chr15 | 115 CTAACTGAGGGTGCTGGAAACTA | 116 GCTGTTGGCTGCAAAGAAAACT | 83226619 | 83226641 | 83226770 | 83226793 |
| ERBB2 | chr17 | 117 GTTTGAGTGAAGGCATTCATGGTCTT | 118 GATCTCTTCCAGAGTCTCAAACA | 37871434 | 37871457 | 37871582 | 37871608 |
| ERBB2 | chr17 | 119 CAAGAGGGTGGTTCCCAGAATT | 120 GAGTGAAGGGCAATGAAGGGTA | 37875993 | 37876015 | 37876108 | 37876130 |
| ERBB2 | chr17 | 121 GGCTGGCTCCGATGTATTTGAT | 122 CAACGTAGCCATCAGTCTCAGA | 37883628 | 37883650 | 37883751 | 37883773 |

TABLE 17

| Lineitem_Name | Chr | SEQ ID NO Fwd_Primer* | SEQ ID NO Rev_Primer* | Amplicon_Start | Insert_Start | Insert_Stop | Amplicon_Stop |
|---|---|---|---|---|---|---|---|
| HSP90AA1 | chr14 | 123 ATTACATAGTATAAGGCTTACCCAGACCA | 124 CGACAAGTCTGTGAAGGATCTGG | 102548427 | 102548456 | 102548549 | 102548572 |
| HSP90AA1 | chr14 | 125 CCTGATAACTTTCAAAATTTTGCTTTGTTGC | 126 GTCCTTGGAATGACTCAGTGCAT | 102550229 | 102550260 | 102550340 | 102550363 |
| HSP90AA1 | chr14 | 127 CAGACAGAAATTCACTCTGCAATTACATAAAA | 128 CAGGTGAACCTATGGGTCGT | 102551597 | 102551629 | 102551751 | 102551771 |
| HSP90AA1 | chr14 | 129 CCCAAGAAGTTCACACTGAAACC | 130 TGAGACGTTCGCCTTTCAGG | 102552499 | 102552522 | 102552645 | 102552665 |
| IRAK1 | chrX | 131 CGCCTAGGCTCTCGTCACT | 132 CCCGCAGGAGAACTCCTAC | 153278644 | 153278663 | 153278782 | 153278801 |
| IRAK1 | chrX | 133 CCAGGTGTCAGGAGTGCTTT | 134 ACAGGTTTCGTCACCCAAACA | 153283401 | 153283421 | 153283554 | 153283575 |
| KDM5C | chrX | 135 TCCGTACCCTCTTTGGCTCTAG | 136 TGTCTTTCTGCCTGTCTGTAATCAC | 53222382 | 53222404 | 53222516 | 53222541 |

TABLE 17 -continued

| Lineitem_Name | Chr | SEQ ID NO Ion_AmpliSeq_ Fwd_Primer* | SEQ ID NO Ion_AmpliSeq_ Rev_Primer* | Amplicon_Start | Insert_Start | Insert_Stop | Amplicon_Stop |
|---|---|---|---|---|---|---|---|
| KDM5C | chrX | 137 CCAGAAGTGTG CGGATCCTC | 138 AGTTGACTGGC CCTGTGTTG | 53222621 | 53222641 | 53222768 | 53222788 |
| KDM5C | chrX | 139 CCCACACACAC AGATAGAGGTT G | 140 CTGTCCTGGGTA TGGCAGATC | 53223786 | 53223809 | 53223917 | 53223938 |
| KDM5C | chrX | 141 CCATCTGTGTCG AAGCTCCTT | 142 GTTCTCTGCCCA TGTGCAGAT | 53224090 | 53224111 | 53224229 | 53224250 |
| KDM5C | chrX | 143 CTCTTCTGGGTC TCCACTCAAC | 144 CCTAGCCCTGCT GTGGATAAAG | 53225798 | 53225820 | 53225943 | 53225965 |
| KDM5C | chrX | 145 CAGGTTGTTCAT CTGGTCCAGAA | 146 AGTCTTAGCATA GACATGGAGGG AA | 53226986 | 53227009 | 53227102 | 53227127 |
| KDM5C | chrX | 147 GCCTCACTCAG GCAGTTCTTTA | 148 CCTCTGCCTCTA TTCAATACTGCC TA | 53227723 | 53227745 | 53227847 | 53227873 |
| KDM5C | chrX | 149 CTACTGGAGCA CTTGCAGAGAT | 150 GATGATGAGCG CCAGTGTATCA | 53228174 | 53228196 | 53228276 | 53228298 |

TABLE 18

| Lineitem_Name | Chr | SEQ ID NO Ion_AmpliSeq_ Fwd_Primer* | SEQ ID NO Ion_AmpliSeq_ Rev_Primer* | Amplicon_Start | Insert_Start | Insert_Stop | Amplicon_Stop |
|---|---|---|---|---|---|---|---|
| KDM5C | chrX | 151 CCCGAACTTCC ACCAGAATAGG | 152 CCAGAGAAGCT AGACCTGAACC T | 53230683 | 53230705 | 53230807 | 53230830 |
| KDM5C | chrX | 153 CCATCTTGCAGA TAAGCTCCTCA | 154 GAAGCAGGAGG GTTGTAGAGAA G | 53230839 | 53230862 | 53230981 | 53231004 |
| KDM5C | chrX | 155 GCAAAGTTGTA GCCTTGGTTGA CCAT | 156 CAGGAAAATCT CTATCTCAACAG | 53231067 | 53231089 | 53231174 | 53231201 |
| KDM5C | chrX | 157 GAGGTCAGGCT GGCTATCAAAT | 158 CCTGCATGACC AAGGTGTGATT | 53239653 | 53239675 | 53239789 | 53239811 |
| KDM5C | chrX | 159 GGAGCCCACAC TGACTTGATTC | 160 GTACTGTGCCA CATCAATGCAG | 53239811 | 53239833 | 53239963 | 53239985 |
| KDM5C | chrX | 161 ATGCCAGAGATA TCTGCATTGATG T | 162 GTTCCCTAGGCT AAAGAAAATGA CTTAAGA | 53239951 | 53239976 | 53240094 | 53240124 |
| KDM5C | chrX | 163 AGATACTAAATG ATTTGCCTAAGC TCACA | 164 TAGCATTGAGG AAGATGTGACT GTTG | 53240617 | 53240646 | 53240764 | 53240790 |
| KDM5C | chrX | 165 GGGAATGCTTAT TGAAGGGACAA GA | 166 CCTAAGACCTT CCTGGGAGCA A | 53244917 | 53244942 | 53245055 | 53245078 |
| KDM5C | chrX | 167 GTAGCCTCATGG TCATCTTGGT | 168 CCATTTTTCTCT CTCCCAGATAA GGA | 53245003 | 53245025 | 53245151 | 53245177 |
| KDM5C | chrX | 169 TCCCTCCACCTC AAAGCTCTAA TACAAACC | 170 TAATGAGGAGA AGGACAAGGAA | 53246280 | 53246302 | 53246406 | 53246436 |
| KDM5C | chrX | 171 GCAAGGAGCCA ATATTTTTGCCT | 172 CTACAGGCCTA CTCCCTCACATA | 53247043 | 53247066 | 53247194 | 53247217 |
| KDM5C | chrX | 173 ACCACCAGCTC CTAGTCTTCTC | 174 CTTTTGGTGACT TCCGGTCTTACA | 53249997 | 53250019 | 53250144 | 53250168 |

TABLE 18 -continued

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| KDM5C | chrX | 175 | CGATGGGCCTGATTTTCGC | 176 | GCGCCATGAGTCCTTAAGG | 53253960 | 53253979 | 53254115 | 53254134 |
| KDM6A | chrX | 177 | CCAAGCAAGAATTCATGCACGT | 178 | AGACTCATAGTCTGTGTTCACTTTGAAC | 44879794 | 44879816 | 44879938 | 44879966 |
| KDM6A | chrX | 179 | CACTGTTCATTGGGTTCAGGCTA | 180 | AAAAAGGAACAGTCCTATTGGATATAATCC | 44949108 | 44949131 | 44949215 | 44949245 |

TABLE 19

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| LRP12 | chr8 | 181 | ACCTCGGGTACTCTGAGTTGAG | 182 | AAGTTTGTTTTCCGTGGAGTCTGA | 105503375 | 105503397 | 105503522 | 105503546 |
| LRP12 | chr8 | 183 | TCCACGGAAAACAAACTTCTGTGA | 184 | TTCCTATGGCAGGCAGATCAAG | 105503529 | 105503553 | 105503681 | 105503703 |
| NCOA6 | chr20 | 185 | CTGGGAAGTTTGTTAGGATCCGAA | 186 | CAAGGAGAGCTTGAATGTGCCT | 33329645 | 33329669 | 33329793 | 33329815 |
| NCOA6 | chr20 | 187 | CCCAAAATGGCCTGCAGATATG | 188 | GGCCATGGGATGTCTTTCAATG | 33337295 | 33337317 | 33337434 | 33337456 |
| NCOA6 | chr20 | 189 | CTCCACTGAAAGGTGCATTGAAA | 190 | GGTGATCCTGCTACTACAGCAAATAA | 33337420 | 33337443 | 33337568 | 33337594 |
| NCOA6 | chr20 | 191 | GCAGGGCTCAAATGATCAAATAAGC | 192 | TTGGCTCAGAACCGAAGCCAAGA | 33356193 | 33356218 | 33356343 | 33356366 |
| NHS | chrX | 193 | TCCAAGTAAATGAAAATTTGTTTGCCATTT | 194 | GGGATACCCGAGATGGTTTTCC | 17742356 | 17742386 | 17742505 | 17742527 |
| NHS | chrX | 195 | ACAGCAACCCTCTTTAAAAGATGGAA | 196 | TCTCCTACTGTGTTCTGCTTATTATGAGTA | 17745415 | 17745441 | 17745558 | 17745588 |
| NHS | chrX | 197 | ACCGTCATCCACTGCATGTTTT | 198 | CTTAACTTCTTCAGACTTGTTGATGGAC | 17745537 | 17745559 | 17745657 | 17745685 |
| RGAG1 | chrX | 199 | GAATGATGTCATCCATGCCACAA | 200 | AGTGTGCACATGTCTCCAGAAG | 109696331 | 109696354 | 109696483 | 109696505 |
| RGAG1 | chrX | 201 | GTCCACATTGCAAACCAGTGTT | 202 | CATGGGCATCGATCCAGAAACT | 109696809 | 109696831 | 109696949 | 109696971 |
| RGAG1 | chrX | 203 | CCACATCATTTATGAGAGCCTCAGTT | 204 | TGTGGTGTGGACATTGTTCCAG | 109696928 | 109696954 | 109697080 | 109697102 |

TABLE 20

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| SCAF1 | chr19 | 205 | CCATGTGTCCCATTGGCTTCT | 206 | GGGTTCGTGAGCAAAGGAGG | 50145305 | 50145326 | 50145424 | 50145444 |

TABLE 20-continued

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| SCAF1 | chr19 | 207 | CGCTTTAGCTCCGCCTCTC | 208 | ACTAGCGACCCAACTCCGC | 50145405 | 50145424 | 50145555 | 50145574 |
| SCAF1 | chr19 | 209 | GGGACCTCCACTCCAAACTCT | 210 | CTCACCAGGATAAAGGCAGAAGGA | 50148240 | 50148261 | 50148372 | 50148396 |
| SCAF1 | chr19 | 211 | ATGGTCCGCCAGACAGAGA | 212 | GTGCTTCAAGGGAGCCAAGAGT | 50148342 | 50148361 | 50148484 | 50148506 |
| SCAF1 | chr19 | 213 | GCACTTGAGTCTAGCTGTCAGT | 214 | CCGCCATACCTTTATCATTGGG | 50148503 | 50148525 | 50148655 | 50148677 |
| SH3TC1 | chr4 | 215 | CCACAGGCTTCACTCATCACTG | 216 | CAACGCTCACCTTCTTGGATGA | 8217832 | 8217854 | 8217972 | 8217994 |
| SH3TC1 | chr4 | 217 | CAGTGACCACCTCCATCCTTTT | 218 | GGCGGTGAAGAGTCTGTTTCC | 8218658 | 8218680 | 8218804 | 8218825 |
| SH3TC1 | chr4 | 219 | TCTGTCTGTCAAATCAAGGAATGGAAA | 220 | CCTGGCATCCTCCTCAGAAAG | 8224473 | 8224500 | 8224623 | 8224645 |
| TBC1D8B | chrX | 221 | ATGAGATACATCAGCATGCTAATAGAAGTG | 222 | CATATCAGTCATGTGTTCTGTCAGCT | 106093160 | 106093190 | 106093308 | 106093334 |
| TBC1D8B | chrX | 223 | AGCAGACATGGTTTTTAAAATCTTCCAAA | 224 | CAGTCAATCTGATACTGTTCCAAATATGG | 106108946 | 106108975 | 106109091 | 106109120 |
| TBC1D8B | chrX | 225 | CCATATTTGGAACAGTATCAGATTGACTG | 226 | TACCAATTGCAGAGGAGAATTCTTTGAA | 106109092 | 106109121 | 106109238 | 106109266 |
| TBC1D8B | chrX | 227 | TGGAAGGAAACTACATAGCCCTACA | 228 | CAACAGCGATGCAAGAATCTGTT | 106116919 | 106116944 | 106117070 | 106117093 |
| TET2 | chr4 | 229 | TAACTGCAGTGGGCCTGAAAAT | 230 | AGTTCACCATGTGTGTGTTCCA | 106155606 | 106155628 | 106155751 | 106155773 |
| TET2 | chr4 | 231 | CCTGTGATGCTGATGATGCTGATA | 232 | AATTCTTCACCAGACGCTAGCTT | 106155983 | 106156007 | 106156131 | 106156154 |
| TET2 | chr4 | 233 | GGAAAAAGCACTCTGAATGGTGGA | 234 | GCCTTTCAGAAAGCATCGGAGA | 106156363 | 106156387 | 106156514 | 106156537 |

TABLE 21

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| TET2 | chr4 | 235 | AACTGCCAGCAGTTGATGAGAA | 236 | TTACGTTTTAGATGGGATTCCGCT | 106156681 | 106156703 | 106156819 | 106156844 |
| TET2 | chr4 | 237 | CACCAAGCGGAATCCCATCTAA | 238 | AGCTGTGTTGTTTTCTGGGTGTA | 106156816 | 106156838 | 106156956 | 106156979 |
| TET2 | chr4 | 239 | AAACACAACCATCCCAGAGTTCA | 240 | CCATGAAAACATTCTTCCACTTTAGTCTG | 106157285 | 106157308 | 106157430 | 106157459 |
| TET2 | chr4 | 241 | GGGTCACTGCATGTTTGGACTT | 242 | GCAGTGTGAGAACAGACTCAACAG | 106190831 | 106190853 | 106190932 | 106190956 |

TABLE 21 -continued

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| TET2 | chr4 | 243 | AAGTCTCTGACGTGGATGAGTTTG | 244 | GAAAGCTTTTCAGCTGCAGCTT | 106193803 | 106193827 | 106193955 | 106193977 |
| TET2 | chr4 | 245 | AGGTTTGGAAATAGCCAGAGTTTTACA | 246 | ATCTAGAGGTGGCTCCCATGAA | 106196711 | 106196738 | 106196863 | 106196885 |
| TEX13A | chrX | 247 | TCGAGATATACATGCTTCGGTTCTATTTTG | 248 | CTCATCAGCAAAGACCTCCAGTA | 104463605 | 104463635 | 104463756 | 104463779 |
| TEX13A | chrX | 249 | GGGTTCGTGGTTCCAGAGAAAT | 250 | CCTCCATGGAGACCACAGAGAA | 104464028 | 104464050 | 104464156 | 104464178 |
| TEX13A | chrX | 251 | TCTCTCCAGCTTCTCTGTGGT | 252 | CTGCTGGAGGAAAAGGAGCAGA | 104464147 | 104464168 | 104464296 | 104464318 |
| ULK3 | chr15 | 253 | GCCTGAAGAGAGTGTCCCTTCT | 254 | CCAAGAAAAGTCTGAACAAGGCAT | 75134560 | 75134582 | 75134700 | 75134724 |
| WNK3 | chrX | 255 | GCTGAAGAAAGGAGGAGACTGA | 256 | CCTGGCTTCTTCAGTCAATAAGGTAAATAA | 54276466 | 54276489 | 54276610 | 54276640 |
| WNK3 | chrX | 257 | GAAACTTGCTGGTAATGTCCTACTAGT | 258 | GGCAGGAGCTGCATCAGTTATA | 54319571 | 54319598 | 54319722 | 54319744 |
| WNK3 | chrX | 259 | GTGCTGCTGTGGTTTTCTTTGTA | 260 | GGGATTCTCAGTGCAAGTCTATGG | 54321002 | 54321025 | 54321135 | 54321159 |

TABLE 22

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| ARSF | chrX | 261 | GTGCATGACGACAAGCCTAATATTG | 262 | ACGACTGACGAACGTATGACTG | 2990128 | 2990153 | 2990234 | 2990256 |
| CFP | chrX | 263 | GCTGTAGCAGTGCCGGATAT | 264 | ACATGAAGTCCATCAGCTGTCAAG | 47485743 | 47485763 | 47485843 | 47485867 |
| CFP | chrX | 265 | CCGGGATTTCTTGACAGCTGAT | 266 | TGATTCCCTGCTTTGGTCCAATC | 47485835 | 47485857 | 47485940 | 47485963 |
| CFP | chrX | 267 | CCCACTCTGAGGACCTCTGTA | 268 | GAATGGGCAGTGCTCTGGAA | 47487417 | 47487438 | 47487563 | 47487583 |
| CFP | chrX | 269 | GGCAAAGGCAGTGTTGAGAC | 270 | GTGTCCAGGCCCACCACAT | 47488961 | 47488981 | 47489116 | 47489135 |
| FAM47A | chrX | 271 | ACTGGATCTCCGACGAGTGAT | 272 | GAGACTGGAGTGTCCCATCTAAG | 34149619 | 34149640 | 34149760 | 34149783 |
| JADE3 | chrX | 273 | ACGCCATTGCCATGAAAATATGAAC | 274 | TCCACTCTCACTAACCTGATGCA | 46887346 | 46887371 | 46887497 | 46887520 |
| JADE3 | chrX | 275 | CCATTCTAGGAGTGAAGCAAGGA | 276 | GCCATTGGATTTGGCAAACTTG | 46917837 | 46917861 | 46917989 | 46918011 |
| ZNF449 | chrX | 277 | GGAGCTGAACTATGGTGCTACT | 278 | CATTGAGTAATTGGTGTTTCTAACCCAAC | 134483190 | 134483212 | 134483307 | 134483336 |
| SCRN1 | chr7 | 279 | TTTTGCTGGTAATTTAGTAAGGTGGAA | 280 | CCTGGAAGCCATGGAAGAAATCC | 29963511 | 29963539 | 29963658 | 29963681 |

TABLE 22 -continued

| Lineitem_Name | Chr | SEQ ID NO | Ion_AmpliSeq_Fwd_Primer* | SEQ ID NO | Ion_AmpliSeq_Rev_Primer* | Amplicon_Start | Insert_Start | Insert_Stop | Amplicon_Stop |
|---|---|---|---|---|---|---|---|---|---|
| SCRN1 | chr7 | 281 | AGGGTATGAGAAGGAGAATCGTGA | 282 | GAACTCAGGAGTTACGCTCAGA | 29980257 | 29980281 | 29980408 | 29980430 |

To verify whether the mutations of the genes were detected using the constructed primer sets, the gene mutations verified in Example 2 and a DNA test samples derived from wild-type kidney cancer cells were amplified. Specifically, each of the gene mutations and the DNA test samples used as the test sample was amplified using a primer set corresponding to each of the test samples, respectively. Thereafter, the amplified chips were scanned using a scanner and application program, and analyzed using quantitative analysis software.

As a result, it can be seen that the mutations of the genes of Examples 2 and 3 were detected using the primer sets constructed in Example 4. On the other hand, the mutations were not detected in the test samples derived from the kidney cancer cells as the control. As described above, because the mutations of genes selected from a gene group consisting of ACSS3, ADAM21, AFF2, ALG13, BAP1, BRWD3, COL4A5, CPEB1, ERBB2, HSP90AA1, IRAK1, KDM5C, KDM6A, LRP12, NCOA6, NHS, RGAG1, SCAF1, SH3TC1, TBC1D8B, TET2, TEX13A, ULK3, WNK3, ARSF, CFP, FAM47A, PHF16, ZNF449, and SCRN1 were detectable using the primer sets listed in Tables 14 to 22, it was possible to predict the overall survival Kaplan-Meier estimates and disease-free survival Kaplan-Meier estimates of the patients with kidney cancer in which the genes were mutated, thereby effectively designing a therapeutic strategy for kidney cancer.

Although preferred embodiments of the present invention have been shown and described for the purpose of illustration only, it would be appreciated by those skilled in the art that various modifications and changes may be made in these embodiments without departing from the scope of the present invention.

The invention claimed is:

1. A method of providing information required to verify a difference in therapeutic effect against kidney cancer according to the gender of a patient with kidney cancer, the method comprising:

preparing a DNA test sample from a sample of a patient with kidney cancer whose gender is identified;

identifying the presence or absence of a gender specific marker in a DNA test sample;

treating the patient with kidney cancer, in which the gender-specific marker is identified, with any candidate material for treating kidney cancer or healing the patient with kidney cancer using any method; and choosing any candidate material for treating kidney cancer or any method of treating kidney cancer as a therapeutic candidate material or a therapeutic method, which is suitable for the gender group of patients with kidney cancer in which the gender-specific marker is identified, when the any candidate material or the any method is used to treat kidney cancer, wherein the gender specific marker is a mutation of a gene coding for ACSS3, wherein the mutation of a gene coding for ACSS3 is a nonsense mutation 'R634*', a splice mutation 'X152_splice' (where T is substituted with C at position 81503485 on the chromosome), or a missense mutation 'G268D' in the amino acid sequence set forth in SEQ ID NO: 1.

2. The method of claim 1, wherein the patient with kidney cancer is a female.

3. The method of claim 1, wherein the gender-specific marker further comprises a mutation of a gene coding for one selected from the group consisting of ADAM21, ALG13, BRWD3, CPEB1, ERBB2, HSP90AA1, IRAK1, KDM6A, LRP12, NCOA6, NHS, RGAG1, SCAF1, SH3TC1, TET2 TEX13A, ULK3, WNK3, ARSF, CFP, PHF16, ZNF449, and SCRN1.

4. The method of claim 3, wherein the mutation of the gene coding for ADAM21 is at least one mutation selected from the group consisting of N265Y, R408C, T589S, and I161V in the amino acid sequence set forth in SEQ ID NO: 2; the mutation of the gene coding for ALG13 is at least one missense mutation selected from P925T and V456E, or a frameshift deletion (FS del) mutation 'L195Pfs*23' in the amino acid sequence set forth in SEQ ID NO: 4; the mutation of the gene coding for BRWD3 is at least one missense mutation selected from G287A and I1747N in the amino acid sequence set forth in SEQ ID NO: 6; the mutation of the gene coding for CPEB1 is at least one missense mutation selected from S393R and G136V, or a splice mutation 'X499_splice' (where C is substituted with A at position 83215272 on the chromosome) in the amino acid sequence set forth in SEQ ID NO: 8; the mutation of the gene coding for ERBB2 is at least one missense mutation selected from the group consisting of E1114G, 5649T, and V219I, or a frameshift insertion (FS ins) mutation 'N388Qfs*14' in the amino acid sequence set forth in SEQ ID NO: 9; the mutation of the gene coding for HSP90AA1 is at least one missense mutation selected from the group consisting of D512N, H806R, I325T, and L167V in the amino acid sequence set forth in SEQ ID NO: 10; the mutation of the gene coding for IRAK1 is a nonsense mutation 'Q280*', or at least one missense mutation selected from V548M and Q584K in the amino acid sequence set forth in SEQ ID NO: 11; the mutation of the gene coding for KDM6A is a missense mutation 'A30V', an FS mutation 'A1246Pfs*19', or an IF del mutation 'V156del' in the amino acid sequence set forth in SEQ ID NO: 13; the mutation of the gene coding for LRP12 is at least one missense mutation selected from the group consisting of S622L, E639K, and V671I in the amino acid sequence set forth in SEQ ID NO: 14; the mutation of the gene coding for NCOA6 is at least one missense mutation selected from the group consisting of G164E, N877I, N864Y, and V1444A, or an FS ins mutation 'H832Sfs*47' in the amino acid sequence set forth in SEQ ID NO: 15; the mutation of the gene coding for NHS is at least one missense mutation selected from the group consisting of C360R, P1107A, and D1069H in the amino acid sequence set forth in SEQ ID NO: 16; the mutation of the gene coding for RGAG1 is at least one missense mutation selected from the group consisting of A1015G, M858V, and G1053R in the amino acid sequence set forth in SEQ ID NO: 17; the mutation of the gene coding for SCAF1 is at least one FS ins mutation selected from the group consisting of A219Sfs*11, P211Tfs*19, P211Tfs*19, and A216Pfs*94, or an FS del mutation 'A216Pfs*94' in the amino acid sequence set forth in SEQ ID NO: 18; the mutation of the gene coding for SH3TC1 is at least one missense mutation selected from A375V and L180F or an FS del mutation 'R238Sfs*38' in the amino acid sequence set forth in SEQ ID NO: 19; the mutation of the gene coding for TET2 is at least one missense mutation selected from the group consisting of Q317K, L757V, V449E, N1714K, D194E, N1390H, R1451Q, M600I, and P554S, or a nonsense mutation 'K326*' in the amino acid sequence set forth in SEQ ID NO: 21; the mutation of the gene coding for TEX13A is at least one missense mutation selected from R393S and Y257D, or a splice mutation 'X199_splice' (where C at position 104464282 is deleted from the chromosome) in the amino acid sequence set forth in SEQ ID NO: 22; the mutation of the gene coding for ULK3 is an FS del mutation 'Q81Sfs*41' and at least one missense mutation selected from D79H and L77V in the amino acid sequence set forth in SEQ ID NO: 23; the mutation of the gene coding for WNK3 is at least one nonsense mutation selected from S865* and Y589* and a missense mutation 'E537G' in the amino acid sequence set forth in SEQ ID NO: 24; the mutation of the gene coding for ARSF is a missense mutation 'I42F' in the amino acid sequence set forth in SEQ ID NO: 25; the mutation of the gene coding for CFP is at least one missense mutation selected from the group consisting of S27L, R359Q, and E135K, or an FS ins mutation 'E323Gfs*34' in the amino acid sequence set forth in SEQ ID NO: 26; the mutation of the gene coding for PHF16 is at least one missense mutation selected from K656Q and R207W in the amino acid sequence set forth in SEQ ID NO: 28; the mutation of the gene coding for ZNF449 is a missense mutation 'F183I' in the amino acid sequence set forth in SEQ ID NO: 29; and the mutation of the gene coding for SCRN1 is a missense mutation 'D427Y' or an FS ins mutation 'A257Cfs*34' in the amino acid sequence set forth in SEQ ID NO: 30.

5. A method of providing information required to diagnose prognosis of kidney cancer according to the gender of a patient with kidney cancer, the method comprising:

preparing a DNA test sample from a sample of a patient with kidney cancer; identifying the presence or absence of a gender specific maker in a DNA test sample; and judging that the survival rate of the patient with kidney cancer is not good or the relapse rate of kidney cancer in the patient with kidney cancer is high when the gender-specific marker is identified;

wherein the gender specific marker is a mutation of a gene coding for ACSS3, wherein the mutation of a gene coding for ACSS3 is a nonsense mutation 'R634*', a splice mutation 'X152_splice' (where T is substituted with C at position 81503485 on the chromosome), or a missense mutation 'G268D' in the amino acid sequence set forth in SEQ ID NO: 1.

6. The method of claim 5, wherein the gender-specific marker further comprises a mutation of a gene coding for one selected from the group consisting of ALG13, ARSF, CFP, FAM47A, KDM6A, PHF16, ZNF449, and SCRN1,
- wherein the mutation of the gene coding for ALG13 is at least one missense mutation selected from P925T and V456E, or a frameshift deletion (FS del) mutation 'L195Pfs*23' in the amino acid sequence set forth in SEQ ID NO: 4;
- the mutation of the gene coding for ARSF is a missense mutation 'I42F' in the amino acid sequence set forth in SEQ ID NO: 25;
- the mutation of the gene coding for KDM6A is a missense mutation 'A30V', an FS mutation 'A1246Pfs*19', or an IF del mutation 'V156del' in the amino acid sequence set forth in SEQ ID NO: 13;
- the mutation of the gene coding for PHF16 is at least one missense mutation selected from K656Q and R207W in the amino acid sequence set forth in SEQ ID NO: 28;
- the mutation of the gene coding for ZNF449 is a missense mutation 'F183I' in the amino acid sequence set forth in SEQ ID NO: 29; and
- the mutation of the gene coding for SCRN1 is a missense mutation 'D427Y' or an FS ins mutation 'A257Cfs*34' in the amino acid sequence set forth in SEQ ID NO: 30.

* * * * *

UNITED STATES PATENT AND TRADEMARK OFFICE
CERTIFICATE OF CORRECTION

PATENT NO. : 11,243,206 B2
APPLICATION NO. : 15/779108
DATED : February 8, 2022
INVENTOR(S) : Yeong Jin Choi It is certified that error appears in the above-identified patent and that said Letters Patent is hereby corrected as shown below:

In the Claims

Column 283, Line 54 Claim 4:
Delete "5649T"
And replace with -- S649T --

Column 284, Line 51 Claim 4:
Delete "F1831"
And replace with -- F183I --

Column 285, Line 27 Claim 6:
Delete "F1831"
And replace with -- F183I --

Signed and Sealed this
Twenty-sixth Day of July, 2022

Katherine Kelly Vidal
*Director of the United States Patent and Trademark Office*